United States Patent
Wang et al.

(10) Patent No.: US 9,303,072 B2
(45) Date of Patent: *Apr. 5, 2016

(54) METHOD OF STIMULATING AN IMMUNE RESPONSE USING A PSEUDOTYPED LENTIVIRUS

(71) Applicant: CALIFORNIA INSTITUTE OF TECHNOLOGY, Pasadena, CA (US)

(72) Inventors: Pin Wang, Arcadia, CA (US); Lili Yang, Arcadia, CA (US); David Baltimore, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,371

(22) Filed: Nov. 4, 2014

(65) Prior Publication Data

US 2015/0175667 A1 Jun. 25, 2015

Related U.S. Application Data

(60) Division of application No. 13/887,908, filed on May 6, 2013, now Pat. No. 8,906,359, which is a continuation of application No. 12/688,689, filed on Jan. 15, 2010, now Pat. No. 8,715,640, which is a continuation of application No. 11/781,865, filed on Jul. 23, 2007, now Pat. No. 8,329,162.

(60) Provisional application No. 60/920,260, filed on Mar. 27, 2007, provisional application No. 60/832,497, filed on Jul. 21, 2006.

(51) Int. Cl.
| | |
|---|---|
| *A01N 63/00* | (2006.01) |
| *C07K 14/005* | (2006.01) |
| *A61K 31/70* | (2006.01) |
| *A61K 38/17* | (2006.01) |
| *A61K 38/19* | (2006.01) |
| *A61K 38/20* | (2006.01) |
| *A61K 35/76* | (2015.01) |
| *C12N 15/86* | (2006.01) |
| *A61K 39/21* | (2006.01) |
| *C12N 7/00* | (2006.01) |
| *A61K 39/00* | (2006.01) |

(52) U.S. Cl.
CPC ............ *C07K 14/005* (2013.01); *A61K 31/70* (2013.01); *A61K 35/76* (2013.01); *A61K 38/177* (2013.01); *A61K 38/178* (2013.01); *A61K 38/191* (2013.01); *A61K 38/193* (2013.01); *A61K 38/20* (2013.01); *A61K 39/21* (2013.01); *C12N 7/00* (2013.01); *C12N 15/86* (2013.01); *A61K 2039/5256* (2013.01); *C12N 2740/13043* (2013.01); *C12N 2740/13045* (2013.01); *C12N 2740/15041* (2013.01); *C12N 2740/15043* (2013.01); *C12N 2740/15045* (2013.01); *C12N 2770/36122* (2013.01); *C12N 2770/36134* (2013.01); *C12N 2810/609* (2013.01); *C12N 2810/855* (2013.01)

(58) Field of Classification Search
USPC ........................................................ 424/93.2
See application file for complete search history.

(56) References Cited

U.S. PATENT DOCUMENTS

| | | |
|---|---|---|
| 5,168,062 A | 12/1992 | Stinski |
| 5,298,420 A | 3/1994 | Chang |
| 7,323,619 B2 | 1/2008 | Baltimore et al. |
| 7,429,481 B2 | 9/2008 | Bergman et al. |
| 7,455,833 B2 | 11/2008 | Thorpe et al. |
| 7,604,802 B2 | 10/2009 | O'Hagan et al. |
| 7,611,712 B2 | 11/2009 | Karp |
| 7,612,173 B2 | 11/2009 | Abrecht et al. |
| 7,638,133 B2 | 12/2009 | Honda et al. |
| 7,771,979 B2 | 8/2010 | Polo et al. |
| 2001/0007659 A1 | 7/2001 | Wong-staal et al. |
| 2002/0155430 A1 | 10/2002 | Marsco et al. |
| 2003/0059944 A1 | 3/2003 | Lois-caballe et al. |
| 2003/0068821 A1 | 4/2003 | Lois-caballe et al. |
| 2003/0101471 A1 | 5/2003 | Baltimore et al. |
| 2003/0129163 A1 | 7/2003 | Hall et al. |
| 2003/0207438 A1 | 11/2003 | Schauber et al. |
| 2004/0071661 A1 | 4/2004 | Klatzmann et al. |
| 2004/0091853 A1 | 5/2004 | Hazuda et al. |
| 2004/0096823 A1 | 5/2004 | Greene et al. |
| 2005/0003547 A1 | 1/2005 | Spencer et al. |
| 2007/0275873 A1 | 11/2007 | Heidner et al. |
| 2008/0003682 A1 | 1/2008 | Lois-caballe et al. |
| 2008/0019998 A1 | 1/2008 | Wang et al. |
| 2008/0134352 A1 | 6/2008 | Baltimore et al. |
| 2008/0227736 A1 | 9/2008 | Chen et al. |
| 2010/0184206 A1 | 7/2010 | Chen et al. |

FOREIGN PATENT DOCUMENTS

| | | |
|---|---|---|
| WO | WO-96/17072 A2 | 6/1996 |
| WO | WO-00/09730 A2 | 2/2000 |

(Continued)

OTHER PUBLICATIONS

Ageichik et al., Lentivector trargeting to dendritic cells. *Molec. Ther.*, 16(6): 1008-09 (2008).
Alignment for Seq ID No. 11, cited in Non-Final Office Action for U.S. Appl. No. 13/301,545, dated Jan. 6, 2012.
Analyses of Merck's HIV vaccine Step' study. The Medical News, Nov. 12, 2008, Accessed at http://www.new-medical.net/news/2008/11/12/42892.aspx on Nov. 20, 2009.
Apolonia et al., Stable gene transfer to muscle using non-integrating lentiviral vectors. *Molec. Ther.* 15:1947-54 (2007).

(Continued)

*Primary Examiner* — Michael Wilson
(74) *Attorney, Agent, or Firm* — Marshall, Gerstein & Borun LLP

(57) ABSTRACT

Methods and compositions are provided for delivery of a polynucleotide encoding a gene of interest, typically an antigen, to a dendritic cell (DC). The virus envelope comprises a DC-SIGN specific targeting molecule. The methods and related compositions can be used to treat patients suffering from a wide range of conditions, including infection, such as HIV/AIDS, and various types of cancers.

23 Claims, 27 Drawing Sheets

(56) References Cited

FOREIGN PATENT DOCUMENTS

| WO | WO-00/61772 A2 | 10/2000 |
|---|---|---|
| WO | WO-01/16324 | 3/2001 |
| WO | WO-01/16342 A1 | 3/2001 |
| WO | WO-2004/056966 A2 | 7/2004 |
| WO | WO-2004/067710 A2 | 8/2004 |
| WO | WO-2005/118802 A2 | 12/2005 |
| WO | WO-2006/130855 A2 | 12/2006 |
| WO | WO-2008/011636 A2 | 1/2008 |
| WO | WO-2009/076524 A2 | 6/2009 |

OTHER PUBLICATIONS

Bailey et al., Transmission of human immunodeficiency virus type 1 from a patient who developed AIDS to an elite suppressor. *J. Virol.*, 82(15): 7395-410 (2008).
Banchereau et al., Dendritic cells and the control of immunity. *Nature*, 392: 245-52 (1998).
Banchereau et al., Dendritic cells as therapeutic vaccines against cancer. *Nat. Rev. Immunol.*, 5: 296-306 (2005).
Bangham et al., What is required of an HIV vaccine? *Lancet*, 350: 1617-21 (1997).
Barouch et al., Adenovirus vector-based vaccines for human immunodeficiency virus type 1. *Hum. Gene. Ther.*, 16: 149-56 (2005).
Barouch et al., Challenges in the development of an HIV-1 vaccine. *Nat. Rev.*, 455: 613-9 (2008).
Bayer et al., A large U3 deletion causes increased in vivo expression from a nonintegrating lentiviral vector. *Molec. Ther.* 16:1968-76 (2008).
Bear et al., Heparin-binding and patterns of virulence for two recombinant strains of Sindbis virus. *Virology*, 347:183-90 (2006).
Belousova et al., Genetically targeted adenovirus vector directed to CD40-expressing cells, *J. Virol.*, 77: 11367-77 (2003).
Bhardwaj et al., Interactions of viruses with dendritic cells: A double-edged sword. *J. Exp. Med.* 186(6): 795-9 (1997).
Bonifaz et al., Efficient targeting of protein antigen to the dendritic cell receptor DEC-205 in the steady state leads to antigen presentation on major histocompatibility complex class I products and peripheral CD8+ T cell tolerance. *J. Exp. Med.*, 196: 1627-38 (2002).
Bonifaz et al., In vivo targeting of antigens to maturing dendritic cells via the DEC-205 receptor improves T cell vaccination. *J. Exp. Med.*, 199(6): 815-24 (2004).
Branch, A good antisense molecule is hard to find. *TIBS*, 23: 45-50 (1998).
Breckpot et al., Lentiviral vectors for cancer immunotherapy: transforming infectious particles into therapeutics. *Gene Ther.* 14:847-62 (2007).
Burgers et al., The challenges of HIV vaccine development and testing. *Best Practice & Research: Clinical Obstetrics & Gynaecology*, 19(1): 277-91 (2005).
Buschenfelde et al., Generation of tumor-reactive CTL against the tumor-associated antigen HER2 using retrovirally transduced dendritic cells derived from CD341 hemopoietic progenitor cells. *J. Immunol.* 165: 4133-40 (2000).
Butler et al., A quantitative assay for HIV DNA integration in vivo. *Nat. Med.*, 7: 631-4 (2001).
Byrnes et al., Binding of Sindbis virus to cell surface heparan sulfate. *J. Virol.*, 72: 7349-56 (1998).
Byrnes et al., Large-plaque mutants of Sindbis virus show reduced binding to heparan sulfate, heightened viremia, and slower clearance from the circulation. *J. Virol.* 74(20): 644-51 (2000).
Case et al., Stable transduction of quiescent CD34+CD38− human hematopoietic cells by HIV-1-based lentiviral vectors. *Proc. Natl. Acad. Sci. USA*, 96(6): 2988-93 (1999).
Chandrashekran et al., Targeted retroviral transduction of c-kit(+) hematopoietic cells using novel ligand display technology. *Blood*, 104: 2697-703 (2004).
Cheng et al., Mechanism of ad5 vaccine immunity and toxicity: Fiber shaft targeting of dendritic cells. *PLoS Pathog.*, 3:e25 (2007).

Cheong et al., Improved cellular and humoral immune responses in vivo following targeting of HIV Gag to dendritic cells within human anti-human DEC205 monoclonal antibody. *Blood*, 116: 3828-38 (2010).
Chinnasamy et al., Efficient gene transfer to human peripheral blood monocyte-derived dendritic cells using human immunodeficiency virus type 1-based lentiviral vectors. *Hum. Gene Ther.* 11(13): 1901-9 (2000).
Chirila et al., The use of synthetic polymers for delivery of therapeutic antisense oligodeoxynucleotides. *Biomaterials*, 23: 321-42 (2002).
Choi et al., Hybrid HIV/MSCV LTR enhances transgene expression of lentiviral vector in human CD34+ hematopoietic cells. *Stem Cells*, 19: 236-46 (2001).
Chou et al., Expression of chimeric monomer and dimer proteins on the plasma membrane of mammalian cells. *Biotechnol. Bioengin.*, 65(2): 160-9 (1999).
Chu et al., Retroviral vector particles displaying the antigen-binding site of an antibody enable cell-type-specific gene transfer. *J. Virol.*, 69(4): 2659-63 (1995).
Cockrell et al., Gene delivery by lentivirus vectors. *Mol. Biotechnol.* 36:184-204 (2007).
Cohen, Is an effective HIV vaccine feasible? *Science*, 309: 99 (2005).
Collins et al., Gene therapy meets vaccine development. *TRENDS Biotech.*, 22(12): 623-6 (2004).
Cosset et al., Retroviral retargeting by envelopes expressing an N-terminal binding domain, *J. Virol.*, 69(10): 6314-22 (1995).
Coutant et al., Protective antiviral immunity conferred by a nonintegrative lentiviral vector-based vaccine. *Plos ONE* 3:e3973:1-6 (2008).
Cronin et al., Altering the tropism of lentiviral vectors through pseudotyping. *Curr. Gene Ther.*, 5(4): 387-98 (2005).
Dai et al., HIV-I Gag-specific immunity induced by a lentivector-based vaccine directed to dendritic cells. *Proc. Natl. Acad. Sci. USA*, 106:20382-7 (2009).
Dakappagari et al., Internalizing antibodies to the C-type lectins, L-SIGN and DC-SIGN, inhibit viral glycoprotein binding and deliver antigen to human dendritic cells for the induction of T cell responses. *J. Immunol.*, 176: 426-40 (2006).
De Felipe et al., Skipping the co-expression problem: The new 2A "CHYSEL" technology. *Genet. Vaccines Ther.* 2(13): 1-6 (2004).
De Filipe et al., Targeting of proteins derived from self-processing polyproteins containing multiple signal sequences. *Traffic*, 5: 616-26 (2004).
De Gruijl et al., Prolonged maturation and enhanced transduction of dendritic cells migrated from human skin explants after in situ delivery of CD40-targeted adenoviral. *J. Immunol.* 169: 5322-33 (2002).
De Ines et al., Apoptosis of a human melanoma cell line specifically induced by membrane-bound single-chain antibodies. *J. Immunol.* 163: 3948-56 (1999).
Deonarain, Ligand-targeted receptor-mediated vectors for gene delivery. *Exp. Opin. Therapeut. Pat.* 8: 53-69 (1998).
Dimitrov et al., Quantitation of human immunodeficiency virus type 1 infection kinetics. *J. Virol.* 67(4): 2182-90 (1993).
Dimitrov et al., Virus entry: Molecular mechanisms and biomedical applications, *Nat. Rev. Microbiol.* 2: 109-22 (2004).
Dong et al., HIV-specific cytotoxic T cells from long-term survivors select a unique T cell receptor. *J. Exp. Med.* 200(12): 1547-57 (2004).
Drose et al., Bafilomycins and concanamycins as inhibitors of V-ATPases and P-ATPases. *J. Exp. Biol.* 200: 1-8 (1997).
Dullaers et al., Induction of effective therapeutic antitumor immunity by direct in vivo administration of lentiviral vectors. *Gene Ther.* 13: 630-40 (2006).
Engelmayer et al., Vaccinia virus inhibits the maturation of human dendritic cells: A novel mechanism of immune evasion. *J. Immunol.* 163: 6762-8 (1999).
Engering et al., Subset of DC-SIGN dendritic cells in human blood transmits HIV-1 to T lymphocytes. *Blood*, 100(5):1780-6 (2002).
Esslinger et al., Efficient transduction of dendritic cells and induction of a T-cell response by third-generation lentivectors. *Hum. Gene Ther.* 13: 1091-100 (2002).

(56) References Cited

OTHER PUBLICATIONS

Esslinger et al., In vivo administration of a lentiviral vaccine targets DCs and induces efficient CD8(+) T cell responses. *J. Clin. Invest.* 111: 1673-81 (2003).
Evans et al., Human cord blood CD34+CD38– cell transduction via lentivirus-based gene transfer vectors. *Hum. Gene Ther.* 10(9): 1479-89 (1999).
Fielding et al., Inverse targeting of retroviral ventors: Selective gene transfer in a mixed population of hematopoietic and nonhematopoietic cells. *Blood*, 91(5): 1802-9 (1998).
Figdor et al., Dendritic cell immunotherapy: Mapping the way. *Nat. Med.* 10: 475-80 (2004).
Frolov et al., Translation of Sindbis virus mRNA: analysis of sequences downstream of the iniating AUG codon that enhances translation. *J. Virol.* 70(2): 1182-90 (1996).
Gardner et al., Infection of human dendritic cells by a Sindbis virus replicon vector is determined by a single amino acid substitution in the E2 glycoprotein. *J. Virol.* 74:11849-57 (2000).
Geijtenbeek et al., Self- and nonself-recognition by C-type lectins on dendritic cells. *Annu. Rev. Immunol.* 22:33-54 (2004).
Geijtenbeek et al., DC-SIGN, a dendritic cell-specific HIV-1-binding protein that enhances trans-infection of T cells. *Cell*, 100: 587-97 (2000).
Geijtenbeek et al., Identification of DC-SIGN, a novel dendritic cell-specific ICAM-3 receptor that supports primary immune responses. *Cell*, 100: 575-85 (2000).
Gollan et al., Redirecting retroviral tropism by insertion of short, nondisruptive peptide ligands into envelope. *J. Virol.* 76(7): 3558-63 (2002).
Gong et al., Induction of antigen-specific antitumor immunity with adenovirus-transduced dendritic cells. *Gene Ther.* 4: 1023-8 (1997).
Granelli-Piperno et al., Dendritic cells, infected with vesicular stromatitis virus-pseudotyped HIV-1, present viral antigens to CD4+ and CD8+ T cells from HIV-1-infected individuals. *J. Immunol.* 165: 6620-6 (2000).
Gunning et al., A human beta-actin expression vector system directs high-level accumulation of antisense transcripts. *Proc. Natl. Acad. Sci. USA*, 84: 4831-6 (1987).
Gupta et al., Antibody responses against HIV in rhesus macaques following combinations of mucosal and systemic immunizations with chimeric alphavirus-based replicon particles, *AIDS Res., Hum. Retroviruses*, 22(10): 993-7 (2006).
Han et al., Ligand-directed retroviral targeting of human breast cancer cells. *Proc. Natl. Acad. Sci. USA*, 92: 9747-51 (1995).
Hanke et al., Pre-clinical development of a multi-CTL epitope-based DNA prime MVA boost vaccine for AIDS. *Immunol. Lett.* 66: 177-81 (1999).
Hatziioannou et al., Incorporation of fowl plague virus hemagglutinin in murine leukenia virus particles and analysis of the infectivity of the pseudotyped retroviruses. *J. Virol.* 72: 5313 (1998).
Heidner et al., Lethality of PE2 incorporation into Sindbis virus can be suppressed by second-site mutation in E3 and E2. *J. Virol.* 68: 2683-92 (1994).
Heidner et al., The amino-terminal residue of Sindbus virus glycoprotein E2 influences virus maturation, specific infectivity for BHK cells, and virulence for mice. *J. Virol.* 68: 8064-70 (1994).
Iwakuma et al., Self-activating lentiviral ventors with U3 and U5 modifications. *Virology*, 261: 120-32 (1999).
Iwasaki et al., Regulation of adaptive immunity by the innate immune system. *Science*, 327: 291-5 (2010).
Jahn et al., Analysing c-kit internalization using a functional c-kit-EGFP chimera containing the fluorochrome within the extracellular domain. *Oncogene*, 21: 4508-20 (2002).
Jiang et al., Cell-type-specific gene transfer into human cells with retroviral vectors that display single-chain antibodies. *J. Virol.* 72(12): 10148-56 (1998).
Johnson-Saliba et al., Gene therapy: Optimising DNA delivery to the nucleus. *Curr. Drug Targets*, 2(4): 371-99 (2001).

Kahl et al., Human immunodeficiency virus type 1-derived lentivirus vectors pseudotyped with envelope glycoproteins derived from Ross River virus and Semliki Forest virus. *J. Virol.* 79(3): 1421-30 (2004).
Kahl et al., Lentiviral vectors pseudotyped with glycoproteins from Ross River and vesicular stomatitis viruses: Variable transduction related to cell type and culture conditions. *Molec. Ther.* 11(3): 470-82 (2005).
Kamrud et al., Analysus of Venezuelan equine encephalitis replicon particles packages in different coats. *PLoS ONE*, 3(7): e2709 (2008).
Kaplan et al., Induction of antitumor immunity with dendritic cells transduced with adenvirus vector-encoding edogenous tumor-associated antigens, *J. Immunol.*, 163: 699-707 (1999).
Karasuyama et al., Autocrine growth and tumorigenicity of interleukin 2-dependent helper T cells transfected with IL-2 gene. *J. Exp. Med.*, 169: 13-25 (1989).
Keller et al., Overexpression of HOX11 leads to the immortalization of embryonic presursors with both primitive and definitive hematopoietic potential. *Blood*, 92(3): 877-87 (1998).
Kielian et al., Alphavims entry and membrane fusion. *Viruses* 2:796-825 (2010).
Kim et al., Induction of therapeutic antitumor immunity by in vivo administration of a lentiviral vaccine. *Hum. Gene Ther.* 16: 1255-66 (2005).
Kirk et al., Gene-modified dendritic cells for use in tumor vaccines. *Hum. Gene Ther.* 11: 797-803 (2000).
Klimstra et al., Adaptation of Sindbis virus to BHK cells selects for use of heparan sulfate as an attachment receptor. *J. Virol.* 72:7357-66 (1998).
Klimstra et al., DC-SIGN and L-SIGN can act as attachment receptors for alphaviruses and distinguish between mosquito cell- and mammalian cell-derived viruses. *J. Virol.* 77:12022-32 (2003).
Klimstra et al., The furin protease cleavage recognition sequence of Sindbis virus PE2 can mediate virion attachment to cell surface heparan sulfate. *J. Virol.* 73:6299-306 (1999).
Kolokoltsov et al., Efficient functional pseudotyping of oncoretroviral and lentiviral vectors by Venezuelan equine encephalitis virus envelope proteins. *J. Virol.* 79(2): 756-63 (2005).
Korst et al., Active, specific immunotherapy for lung cancer: hurdles and strategies using genetic modification. *Annu. Thor. Surg.* 76: 1319-26 (2003).
Korth et al., Interferon inhibits the replication of HIV-1, SIV, and SHIV chimeric viruses by distinct mechanisms. *Virology*, 247: 265-73 (1998).
Kung et al., A murine leukemia virus (MuLV) long terminal repeat derived from rhesus macaques in the context of a lentivirus vector and MuLV gag sequence results in high-level gene expression in human T lymphocytes. *J. Virol.* 74(8): 3668-81 (2000).
Kwon et al., Determination of infectious retrovirus concentration from colony-forming assay with quantitative analysis. *J. Virol.* 77(10): 5712-20 (2003).
Lavillette et al., Retargeting gene delivery using surface-engineered retroviral vector particles. *Curr. Opin. Biotech.* 12: 461-6 (2001).
Lee et al., A nonneutralizing anti-HIV-1 antibody turns into a neutralizing antibody when expressed on the surface of HIV-1-susceptible cells: A new way to fight HIV. *J. Immunol.* 173: 4618-26 (2004).
Liao et al., Design of trangenes for efficient expression of active chimeric proteins on mammalian cells. *Biotechnol. Bioengin.* 73(4): 313-23 (2001).
Lin et al., Receptor-specific targeting mediated by the coexpression of a targeted murine leukemia virus envelope protein and a binding-defective influenza hemagglutinin protein. *Hum. Gene Ther.* 12(4): 323-32 (2001).
Liu et al., Immune control of an SIV challenge by a T-cell-based vaccine in rhesus monkeys. *Nat. Lett.* 457: 87-91 (2009).
Lois et al., Germline transmission and tissue-specific expression of trangenes delivered by lentiviral vectors. *Science*, 295(5556): 868-72 (2002).
Lori et al., Cellular immunity and DNA vaccines for the treatment of HIV/AIDS. *Curr. Med. Chem. Anti-Infect. Agents*, 3: 31-41 (2004).
Lorimer et al., Targeting retrovirus to cancer cells expressing a mutant EGF receptor by insertion of a single chain antibody variable domain in the envelope glycoprotein receptor binding lobe. *J. Immunol. Meth.* 237: 147-57 (2000).

(56) References Cited

OTHER PUBLICATIONS

Lu et al., Therapeutic dendritic-cell vaccine for chronic HIV-1 infection. *Nat. Med.* 10(12):1359-65 (2004).
Lubong Sabado et al., Directing dendritic cell immunotherapy towards successful cancer treatment. *Immunotherapy,* 2(1): 37-56 (2010).
Lutzko et al., Lentivirus vectors incorporating the immunoglobulin heavy chain enhancer and matrix attachment regions provide position-independent expression in B lymphocytes. *J. Virol.* 77: 7341-51 (2003).
Mangeot et al., Development of minimal lentivirus vectors derived from simian immunodeficiency virus (SIVmac251) as their use for gene transfer into human dendritic cells, *J. Virol.* 74: 8307-15 (2000).
Marozsan et al., Relationships between infectious titer, capsid protein levels, and reverse transcriptase activities of diverse human immunodeficiency virus type 1 isolates. *J. Virol.*, 78(20): 11130-41 (2004).
Matano et al., Targeted infection of a retrovirus bearing a CD4-Env chimera into human cells expressing human immunodeficiency virus type 1. *J. Gen. Virol.* 76: 3165-9 (1995).
Matsuno et al., A life stage of particle-laden rat dendritics in vivo: Their terminal division, active phagocytosis, and translocation from the liver to the draining lymph. *J. Exp. Med.* 183: 1865-78 (1996).
Maurice et al., Efficient gene transfer into human primary blood lymphocytes by surface-engineered lentiviral vectors that display a T cell-activating polypeptide. *Blood,* 99(7): 2342-50 (2002).
McKnight et al., Deduced consensus sequence of Sindbis virus strain AR339: mutations contained in laboratory strains which affect cell culture and in vivo phenotypes. *J. Virol.* 70:1981-9 (1996).
McMichael et al., Escape of human immunodeficiency virus from immune control. *Ann. Rev. Immunol.* 15: 271-96 (1997).
Meissner et al., Development of an inducible pol III transcription system essentially requiring a mutated form of the TATA-binding protein. *Nucl. Acids Res.* 29(8): 1672-82 (2001).
Meyer zum Buschenfelde et al., Generation of tumor-reactive CTL against the tumor-associated antigen HER2 using retrovirally transduced dendritic cells derived from CD34+ hematopoietic profenitor cells. *J. Immunol.* 165: 4311-40 (2000).
Miller et al., Targeted vectors for gene therapy. *FASEB J.* 9(2): 190-9 (1995).
Miyoshi et al., Development of a self-inactivating lentivirus vector. *J. Virol.* 72:8150-7 (1998).
Miyoshi et al., Transduction of human CD34+ cells that mediate long-term engraftment of NOD/SCID mice by HIV vectors. *Science,* 283(5402): 682-6 (1999).
Morizono et al., Antibody-directed targeting of retroviral vectors via cell surface antigens. *Viral,* 75:8016-20 (2001).
Morizono et al., Lentiviral vector retargeting to P-glycoprotein on metastatic melanoma through intravenous injection. *Nat. Med.* 11:346-52 (2005).
Morizono et al., Redirecting lentiviral vectors pesudotyped with Sindbis virus-derived envelope proteins to DC-SIGN by modification of N-linked glycans of envelope proteins. *J. Virol.* 84(14):6923-34 (2010).
Mukhopadhyay et al., A structural perspective of the flavivirus life cycle. *Nature Rev. Microbial.* 3:13-22 (2005).
Narayan et al., Biology and pathogenesis of lentiviruses. *J. Gen. Virol.* 70: 1617-39 (1989).
Navaratnarajah et al., Functional characterization of the Sindbis virus E2 glycoprotein by transposon linker-insertion mutagenesis. *Virology,* 363:134-47 (2007).
Negri et al. Successful immunization with a single injection of non-integrating lentiviral vector. *Mol. Ther.* 15:1716-23 (2007).
Nussenzweig et al., Immune responses: Tails to teach a B cell. *Curr. Biol.* 7: R355-7 (1997).
Nyberg-Hoffman et al., Sensitivity and reproducibility in adenoviral infectious titer determination. *Nat. Med.* 3(7): 808-11 (1997).
Ohno et al., Cell-specific targeting of Sindbis virus vectors displaying IgG-binding domains of protein A. *Nat. Biotechnol.* 15:763-7 (1997).
Palmer et al., Gene therapy for colorectal cancer. *Brit. Med. Bull.* 64: 201-25 (2002).
Papagatsias et al., Activity of different vaccine-associated promoter elements in human dendritic cells. *Immunol. Lett.* 115:117-25 (2008).
Park et al., An essential role for Akt1 in dendritic cell function and tumor immunotherapy. *Nat. Biotechnol.* 24(12): 1581-90 (2006).
Park et al., Five mouse homologues of the human dendritic cell C-type lectin, DC-SIGN. *Intl. Immunol.* 13(10): 1283-90 (2001).
Paule et al., Transcription by RNA polymerase I and III. *Nucl. Acids Res.* 28(6): 1283-98 (2000).
Pauwels, et al., State-of-the-art lentiviral vectors for research use: Risk assessment and biosafety recommendations. *Curr. Gene Ther.* 9:459-74 (2009).
Perri et al., An alphavirus replicon particle chimera derived from Venezuelan equine encephalitis and sindbis viruses is a potent gene-based vaccine delivery vector. *J. Virol.* 77(19): 10394-403 (2003).
Pfeifer et al., Gene therapy: promises and problems. *Annu. Rev. Genomics Hum. Genet.* 2:177-211 (2001).
Philippe et al., Lentiviral vectors with a defective integrase allow efficient and sustained transgene expression in vitro and in vivo. *Proc. Natl. Acad. Sci. USA,* 103:17684-9 (2006).
Pitisuttithum et al., HIV-1 prophylactic vaccine trials in Thailand. *Curr. HIV Res.,* 3(1): 17-30 (2005).
Powlesland et al., Widely divergent biochemical properties of the complete set of mouse DC-SIGN-related proteins. *J. Biol. Chem.* 281: 20440-9 (2006).
Racaniello, Are all virus particles infectious? *Virology blog,* http://www.virology.ws/2011/01/21are-all-virus-particles-infectious/, Jan. 21, 2011.
Ready et al., AIDSVAX flop leaves vaccine field unscathed. *Nat. Med.* 9(4): 376 (2003).
Reed et al., New horizons in adjuvants for vaccine development. *Trends Immunol.* 30:23-32 (2009).
Ribas et al., Cancer immunotherapy using gene-modified dendritic cells. *Curr. Gene Ther.* 2: 57-78 (2000).
Rosenberg et al., Cancer immunotherapy moving beyond current vaccines. *Nat. Med.* 10: 909-15 (2004).
Rowe et al., Immunication with a lentiviral vector stimulates both CD4 and CD8 T cell responses to an ovalbumin trangene. *Molec. Ther.* 13(2): 310-9 (2006).
Russell et al., Sindbis Virus mutations which coordinately affect glycoprotein processing, penetration and virulence in mice. *J. Virol.* 63(4): 1619-29 (1989).
Sanders, No false start for novel pseudotyped vectors. *Curr. Opin. Biotechol.* 13(5): 437-42 (2002).
Sandrin et al., Targeting retroviral and lentiviral vectors. *Curr. Top. Microbiol. Immunol.* 281: 137-78 (2003).
Sastry et al., Titering lentiviral vectors: Comparison of DNA, RNA and marker expression methods. *Gene Ther.* 9: 1155-62 (2002).
Schroers et al., Lentiviral transduction of human dendritic cells. *Meth. Mol. Biol.* 246: 451-9 (2004).
Schuler et al., The use of dendritic cells in cancer immunotherapy. *Curr. Opin. Immunol.* 15: 138-47 (2003).
Schwartz et al., Cloning and functional analysis of multiply spliced mRNA species of human immunodeficiency virus type 1. *J. Virol.* 64(6): 2519-9 (1990).
Sharkey et al., Ross river virus glycoprotein-pseudotyped retroviruses and stable cell lines for their production. *J. Virol.* 75:2653-9 (2001).
Shen et al., Silencing of SOCS1 enhances antigen presentation by dendritic cells and antigen-specific anti-tumor immunity. *Nat. Biotechnol.* 22: 1546-53 (2004).
Shimizu et al., Internalization of kit together with stem cell factor on human fetal liver-derived mast cells: A new protein and RNA synthesis are required for reappearance of kit. *J. Immunol.* 156: 3443-9 (1996).
Shiu et al., Identification of ongoing human immunodeficiency virus type 1 (HIV-1) replication in residual viremia during recombinant HIV-1 poxvirus immunications in patients with clinically undetectable viral loads on durable suppressive highly active antiretroviral therapy. *J. Virol.* 83(19): 9731-42 (2009).

(56) References Cited

OTHER PUBLICATIONS

Shiver et al., Recent advances in the development of HIV-1 vaccines using replication-incompetent adenovirus vectors. *Annu. Rev. Med.* 55:355-72 (2004).
Shoji et al., Current status of delivery systems to improve target efficacy of oligonucleotides. *Curr. Pharm. Des.* 10(7): 785-96 (2004).
Shortman et al., Improving vaccines by targeting antigens to dendritic cells. *Exp. Molec. Med.* 41(2): 61-6 (2009).
Shresta et al., Critical roles for both STAT1-dependent and STAT I-independent pathways in the control of primary dengue virus infection in mice. *J. Immunol.* 175:3946-54 (2005).
Singh et al., Targeting glycan modified OVA to murine DC-SIGN transgenic dendritic cells enhances MHC class I and II presentation. *Molec. Immunol.* 47: 164-74 (2009).
Skehel et al., Receptor binding and membrane fusion in virus entry: The influenza hemagglutinin. *Annu. Rev. Biochem.* 69: 531-69 (2000).
Sloan et al., MHC class I and class II presentation of tumor antigen in retrovirally and adenovirally trasnsduced dendritic cells. *Cancer Gene Ther.* 9(11): 946-50 (2002).
Small et al., Immunotherapy of homone-refractory prostate cancer with antigen-loaded dendritic cells. *J. Clin. Oncol.* 18(23): 2894-903 (2000).
Smit et al., PE2 cleavage mutants of Sindbis virus: Correlation between viral infectivity and pH-dependent membrane fusion activation of the spike heterodimer. *J. Virol.* 75:11196-204 (2001).
Smit et al., Low-pH-dependent fusion of Sindbis virus with receptor-free cholesterol—an sphingolipid-containing liposomes. *J. Virol.* 73(10): 8476-84 (1999).
Somia et al., Generation of targeted retroviral vectors by using single-chain variable fragment—An approach to in vivo gene delivery. *Proc. Natl. Acad. Sci. USA*, 92: 7570-4 (1995).
Song et al., Persistent, antigen-specific, therapeutic antitumor immunity by dendritic cells genetically modified with an adenviral vector to express a model tumor antigen. *Gene Ther.* 7: 2080-6 (2000).
Steinmann et al., Tolerogenic dendritic cells. *Annu. Rev. Immunol.* 21: 685-711 (2003).
Strang et at, Human immunodeficiency virus type 1 vectors with alphavirus envelope glycoproteins produced from stable packaging cells. *J. Virol.* 79:1765-71 (2005).
Strauss et al., The alphaviruses: gene expression, replication, and evolution. *Microbiol. Rev.* 58:491-562 (1994).
Strauss et al., Host-cell receptors for Sindbis virus. *Arch. Virol.* 9: 473-84 (1994).
Stricker et al., The maginot line and AIDS vaccines, *Medical Hypotheses*, 48: 527-9 (1997).
Sutton et al., Human immunodeficiency virus type 1 vectors efficiently transduce human hematopoietic stem cells. *J. Virol.* 72(7): 5781-8 (1998).
Tacken eta l., Dendritic-cell immunotherapy: From ex vivo loading to in vivo targeting. *Nat. Rev. Immunol.* 7: 790-802 (2007).
Takadera et al., Structure of the two promoters of the human *Ick* gene: Differential accumulation of two classes of *Ick* transcripts in T cells. *Mol. Cell. Biol.* 9(5): 2173-80 (1989).
Takahara et al., Functional comparison of the mouse DC-SIGN, SIGNR1, SIGNR3 and Langerin, C-type lectins. *Int. Immunol.* 16: 819-29 (2004).
Tang et al., Molecular links between the E2 envelope glycoprotein and nucleocapsid core in Sindbis virus. *J. Molec. Biol.* 414: 442-59 (2011).
Tarhini et al., Safety and immunogenicity of vaccination with MART-1 (26-35, 27L), gp100 (209-217, 210M), and tyrosinase (368-376, 370D) in adjuvant with PF-3512676 and GM-CSF in metastatic melanoma. *J. Immunother.* 35(4): 359-66 (2012).
Tatsis et al., Adenoviruses as vaccine vectors. *Mol. Ther.* 10: 616-29 (2004).
Temme et al., Efficient transduction and long-term retroviral expression of the melanoma-associated tumor antigen tyrosinase in CD34(+) cord blood-derived dendritic cells. *Gene Ther.* 9: 1551-50 (2002).
Trumpfheller et al., Intensified and protective CD4+ T cell immunity in mice with anti-dendritic cell HIV gag fusion antibody vaccine. *J. Exp. Med.* 1-11 (2006).
Uchida et al., HIV, but not murine leukemia virus, vectors mediate high efficiency gene transfer into freshly isolated G0/G1 human hematopoietic stem cells. *Proc. Natl Acad. Sci. USA*, 95(20): 11939-44 (1998).
Valsesia-Wittmann et al., Modifications in the binding domain of avian retrovirus envelope protein to redirect the host range of retroviral vectors. *J. Virol.* 68(7): 4609-19 (1994).
van Brockhoven et al., Targeting dendritic cells with antigen-containing liposomes: A highly effective procedure for induction of antitumor immunity and for tumor immunotherapy. *Cancer Res.* 64: 4357-65 (2004).
Veljkovic et al., AIDS epidemic at the beginning of the third millennium: Time for a new AIDS vaccine strategy. *Vaccine*, 19: 1855-62 (2001).
Verhoeyen et al., Surface-engineering of lentiviral vectors. *J. Gene Med.* 6: S83-94 (2004).
Verma et al., Gene therapy—promises, problems and prospects, *Nature*, 389(6648): 239-42 (1997).
Waite et al., Inhibition of Sindbis virus release by media of low ionic strength: an electron microscope study. *J. Virol.* 10(3): 537-44 (1972).
Wang et al., High-affinity laminin receptor is a receptor of Sindbis virus in mammalian cells, *J. Virol.* 66: 4992-5001 (1992).
Wang et al., Phase I trial of MART-1 peptide vaccine with incomplete Freund's adjuvant for resected high-risk melanoma. *Clin. Cancer Res.* 5(10): 2756-65 (1999).
Weber et al., Phase I clinical trial with HIV-1 gp160 plasmid vaccine in HIV-1-infected asymptomatic subjects. *Eur. J. Clin. Microbiol. Infect. Dis.* 20: 800-3 (2001).
West et al., Mutations in the endodomain of Sindbis virus glycoprotein E2 define sequences critical for virus assembly. *J. Virol.* 80:4458-68 (2006).
Wigler et al., DNA-mediated transfer of the adenine phosphoribosyltransferase locus into mammalian cells. *Proc. Natl. Acad. Sci. USA*, 76(3): 1373-6 (1979).
Williamsburg BioProcessing Foundation, Reference Materials for Retroviruses and Lentiviruses—Final Report, pp. 1-13, Jun. 5, 2002.
Wu et al., Enhanced breadth of CD4 T-cell immunity by DNA prime adenovirus boost immunication to human immunodeficiency virus Env and Gag immunogens. *J. Virol.*, 79(13): 8024-31 (2005).
Yang et al., Engineered lentivector targeting of dendritic cells for in vivo immunization. *Nat. Biotechnol.* 26:326-34 (2008).
Yang et al., Targeted lentiviral vectors to specific cell types in vivo. *Proc. Natl. Acad. Sci. USA*, 103(31):11479-84 (2006).
Yang et al., Long-term in vivo provision of antigen-specific T cell immunity by programming hematopoietic stem cells. *Proc. Natl. Acad. Sci. USA*, 102: 4518-23 (2005).
Yee et al., The regulation of myogenin gene expression during the embryonic development of the mouse. *Genes Dev.* 7: 1277-89 (1993).
You et al., Targeting dendritic cells to enhance DNA vaccine potency. *Cancer Res.* 61: 3704-11 (2001).
Zarei et al., Transduction of dendritic cells by antigen-encoding lentiviral vectors permits antigen processing and MHC class I-dependent presentation. *J. Allergy Clin. Immunol.* 109: 988-94 (2002).
Zennou et al., HIV-1 genome nuclear import is mediated by a central DNA flap. *Cell*,101:173-85 (2000).
Zhai et al., Antigen-specific tumor vaccines. *J. Immunol.* 156(2): 700-10 (1996).
Zhou et al., Current methods for loading dendritic cells with tumor antigen for the induction of antitumor immunity. *J. Immunol.* 25(4): 289-303 (2002).
Zhou et al., DC-SIGN and immunoregulation. *Cell Mol. Immunol.* 3: 279-83 (2006).
Zimmerman et al., Identification of a host protein essential for assembly of immature HIV-1 capsids. *Lett. Nat.* 415: 88-92 (2002).

(56) References Cited

OTHER PUBLICATIONS

Zufferey et al., Self-inactivating lentivirus vector for safe and efficient in vivo gene delivery. *J. Viral.* 72:9873-80 (1998).

Zufferey et al., Woodchuck hepatitis virus posttranscriptional regulatory element enhances expression of trangenes delivered by retroviral vectors. *J. Virol.* 74(4): 2886-92 (1999).

International Search Report and Written Opinion dated Feb. 29, 2008 for International Application No. PCTR/US2007/074142, filed Jul. 23, 2007.

METHOD OF STIMULATING AN IMMUNE RESPONSE USING A PSEUDOTYPED LENTIVIRUS

CROSS-REFERENCE TO RELATED APPLICATIONS

The present application is a divisional of U.S. application Ser. No. 13/887,908, filed May 6, 2013, now U.S. Pat. No. 8,906,359, which is a continuation of U.S. application Ser. No. 12/688,689, filed Jan. 15, 2010, now U.S. Pat. No. 8,715,640, which is a continuation of U.S. application Ser. No. 11/781,865, filed Jul. 23, 2007, now U.S. Pat. No. 8,329,162, which claims priority under 35 U.S.C. §119(e) to U.S. Provisional Application No. 60/832,497, filed Jul. 21, 2006 and U.S. Provisional Application No. 60/920,260, filed Mar. 27, 2007, each of which is herein incorporated by reference.

STATEMENT REGARDING FEDERALLY SPONSORED R&D

The invention was made with government support under Grant No. AI068978 awarded by the National Institutes of Health. The government has certain rights in the invention.

REFERENCE TO SEQUENCE LISTING

The present application is being filed along with a Sequence Listing in electronic format. The Sequence Listing is provided as a file entitled "SeqList_CALTE-035C1.txt", created Jan. 13, 2010, which is 132,038 bytes in size. The information in the electronic format of the Sequence Listing is incorporated herein by reference in its entirety.

BACKGROUND OF THE INVENTION

The invention relates generally to targeted gene delivery, and more particularly to the use of a recombinant virus comprising a targeting molecule that targets and binds dendritic cells and can thus be used for dendritic cell vaccination.

Immunization is one of the most productive tools in modern medical practice but remains burdened by limitations. Certain infectious diseases such as HIV/AIDS, malaria, and tuberculosis are not currently controlled at all by immunization, while other infectious diseases are controlled by complex immunization regimens. Cancer is a promising target for immunotherapeutic treatments, but clinical outcomes in experimental trials have been disappointing (Rosenberg, S. A. et al. 2004. *Nat. Med.* 10:909-915, which is incorporated herein by reference in its entirety). Novel methods of immunization are needed, for example, to reliably induce anti-tumor immunity.

Dendritic cells (DCs) play critical roles in both innate and adaptive immunity. DCs are specialized antigen-presenting cells with the unique capability to capture and process antigens, migrate from the periphery to a lymphoid organ, and present the antigens to resting T cells in a major histocompatibility complex (MHC)-restricted fashion (Banchereau, J. & Steinman, R. M. 1998. *Nature* 392:245-252; Steinman, R. M., et al. 2003. *Ann Rev Immunol* 21: 685-711, each of which is incorporated herein by reference in its entirety). These cells are derived from bone marrow (BM) and are characterized by dendritic morphology and high mobility. Immature DCs are adept at antigen ingestion and are distributed as sentinels in peripheral tissue throughout the body. However, maturation of DCs is required in order to mount an efficient immune response (Steinman, R. M., et al. 2003. supra). The matured DCs express high levels of MHC-antigen complex and other costimulatory molecules (such as CD40, B7-1, B7-2 and CD1a) (Steinman, R. M. 1991. *Ann Rev Immunol* 9: 271-296, which is incorporated herein by reference in its entirety; Banchereau, J. and R. M. Steinman. 1998. supra). These molecules play key roles in stimulating T cells.

The discovery of the role of DCs as specialized antigen-presenting cells (APCs) has fueled attempts at DC-based immunization/vaccination that involve loading DCs with specific antigens (Banchereau, J. & Palucka, A. K. 2005. *Nat. Rev. Immunol.* 5:296-306; Figdor, C. G. et al. 2004. *Nat. Med.* 10:475-480, each of which is incorporated herein by reference in its entirety). However, all of these attempts involve ex vivo loading of DCs with specific antigens. Ex vivo generated DCs are then administered to the patient. Ex vivo generation of DCs for each patient is extremely labor intensive process.

By contrast, the present invention is directed inter alia to targeting, antigen loading and activation of DCs in vivo, which results in vivo treatment of diseases by generating a beneficial immune response in the patient. The invention thus fulfills a longstanding need for effective and efficient regimes for immunization/vaccination.

SUMMARY OF THE INVENTION

In one aspect of the invention methods of delivering a polynucleotide to a dendritic cell expressing DC-SIGN are provided. In some embodiments the methods comprise transducing the dendritic cell with a recombinant virus, wherein the recombinant virus comprises the polynucleotide to be delivered and a targeting molecule that binds DC-SIGN. In some embodiments the targeting molecule is specific for DC-SIGN.

In some embodiments of the invention, the recombinant virus comprises sequences from a lentivirus genome, such as an HIV genome.

In other embodiments the recombinant virus comprises sequences from a gammaretrovirus genome, such as sequences from a Mouse Stem Cell Virus (MSCV) genome or a Murine Leukemia Virus (MLV) genome.

In some embodiments of the invention, the methods utilize a targeting molecule comprising a viral glycoprotein derived from at least one virus selected from the group of: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus. In more particular embodiments, the targeting molecule comprises a modified viral glycoprotein derived from Sindbis virus (SIN or SVG). In certain embodiments, the targeting molecule is SINmu also known as SVGmu (SEQ ID NO: 11).

In some embodiments, the polynucleotide to be delivered to a dendritic cell comprises at least one of the following: a gene encoding a protein of interest, a gene encoding a siRNA, and a gene encoding a microRNA. The gene encoding a protein of interest may encode an antigen, such as a tumor antigen or an HIV antigen.

The recombinant virus may be produced by transfecting a packaging cell line with a viral vector comprising the polynucleotide to be delivered and a vector comprising a gene encoding the targeting molecule; culturing the transfected packaging cell line; and recovering the recombinant virus from the packaging cell culture. In some embodiments, the packaging cell line is a 293 cell line.

In some embodiments of the invention, the polynucleotide is delivered to a dendritic cell in vitro, while in other embodiments the polynucleotide is delivered to a dendritic cell in a subject in vivo. The subject is typically a mammal, such as a human, mouse or guinea pig.

In another aspect, recombinant virus comprising: a polynucleotide of interest; and a targeting molecule that binds DC-SIGN are provided. In some embodiments the targeting molecule specifically binds DC-SIGN. The recombinant virus may comprise sequences from a lentivirus genome, such as sequences from an HIV genome. In other embodiments the recombinant virus comprises sequences from a gammaretrovirus genome, such as sequences from a Mouse Stem Cell Virus (MSCV) genome or a Murine Leukemia Virus (MLV) genome.

The targeting molecule may comprise a viral glycoprotein derived from at least one virus selected from the group of: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus. In some embodiments the targeting molecule is a viral glycoprotein derived from Sindbis virus. In particular embodiments, the targeting molecule is SVGmu (SEQ ID NO: 11).

The polynucleotide may be, for example, at least one of the following: a gene encoding a protein of interest, a gene encoding a siRNA, and a gene encoding a microRNA of interest. In some embodiments the polynucleotide encodes an antigen, such as a tumor antigen or an HIV antigen.

In another aspect, methods of stimulating an immune response in a mammal are provided. A polynucleotide encoding an antigen to which an immune response is desired is delivered to dendritic cells expressing DC-SIGN by contacting the dendritic cells with a recombinant virus comprising the polynucleotide and a targeting molecule that binds DC-SIGN. In some embodiments the targeting molecule is specific for DC-SIGN and does not bind appreciably to other molecules. In other embodiments the targeting molecule binds preferentially to DC-SIGN.

In a further aspect, vectors encoding targeting molecules that bind DC-SIGN are provided. In some embodiments, the targeting molecule is a modified viral glycoprotein. In further embodiments, the targeting molecule is SVGmu (SEQ ID NO: 11). The targeting molecule specifically binds DC-SIGN in some embodiments. The vector may additionally encode one or more genes of interest, such as a gene encoding an antigen and/or a gene encoding a dendritic cell maturation factor.

In a still further aspect, methods of treating a patient with a disease are provided. A recombinant virus is administered to the patient, where the recombinant virus comprises a polynucleotide encoding an antigen associated with the disease and a targeting molecule that binds DC-SIGN. The targeting molecule may be derived from a viral glycoprotein. In some embodiments, the targeting molecule is SVGmu (SEQ ID NO: 11).

The disease to be treated is generally one for which an antigen is known or can be identified. In some embodiments of the invention, the disease to be treated is cancer. In other embodiments, the disease is HIV/AIDS.

Dendritic cells transduced with a recombinant virus are also provided, where the recombinant virus comprises a polynucleotide of interest and a targeting molecule that binds DC-SIGN. In some embodiments, the targeting molecule comprising a viral glycoprotein derived from at least one virus selected from the group of: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus. In some embodiments, the targeting molecule is SVGmu (SEQ ID NO: 11).

Further, methods of immunizing a mammal by delivering a polynucleotide encoding an antigen to dendritic cells expressing DC-SIGN are also provided in which the dendritic cells are contacted with a recombinant virus comprising a polynucleotide encoding an antigen and a targeting molecule that binds DC-SIGN. In some embodiments, the dendritic cells are contacted with the recombinant virus ex vivo. In other embodiments, the dendritic cells are contacted with the recombinant virus in vivo.

The methods disclosed herein can also be used to stimulate an immune response to a specific antigen in a mammal by delivery of a polynucleotide encoding the antigen to dendritic cells using a recombinant virus comprising the polynucleotide and a targeting molecule that binds DC-SIGN. The immune response may be modulated by providing a further polynucleotide whose expression in the dendritic cell modulates the immune response. For example, a polynucleotide encoding a dendritic maturation factor may be delivered.

BRIEF DESCRIPTION OF THE DRAWINGS

In FIG. 7A, the images show the size of a representative inguinal lymph node close to the injection site compared to that of the equivalent lymph node distant from the injection site. FIG. 7B illustrates the total cell number counts of the indicated lymph nodes in FIG. 7A. FIG. 7C illustrates representative flow cytometric analysis of $CD11c^+$ cells from the two lymph nodes shown in FIG. 7A. The numbers indicate the fraction of $GFP^+$ DC populations FIG. 8 provides a schematic representation of the lentivector encoding the OVA antigen (FOVA) (top) and the lentivector encoding GFP (FUGW) as a control (bottom).

FIG. 16A shows the measured percentage of OVA-specific T cells following immunization with $100\times10^6$ TU of FOVA/SVGmu. FIG. 16B shows the dose responses of OVA-specific T cells following injection of the indicated doses of FOVA/SVGmu.

FIG. 19 illustrates the in vivo the kinetic growth of tumors in a murine E.G7 tumor eradication model. An albino strain of B6 mice were implanted with $5\times10^6$ E.G7 tumor cells stably expressing a firefly luciferase imaging gene (E.G7.luc). A mouse (#1) without tumor implantation was included as a control. Mice bearing tumors were treated without immunization (#2), or with immunization by the injection of $50\times10^6$ TU of FOVA/SVGmu at days 3 and 10 (#3, #4) post tumor challenge. The kinetic growth of the tumors was monitored by live animal imaging using BLI. The p/s/cm$^2$/sr represents photons/s ec/cm$^2$/steri di an.

DETAILED DESCRIPTION OF THE PREFERRED EMBODIMENT

Figure 1:
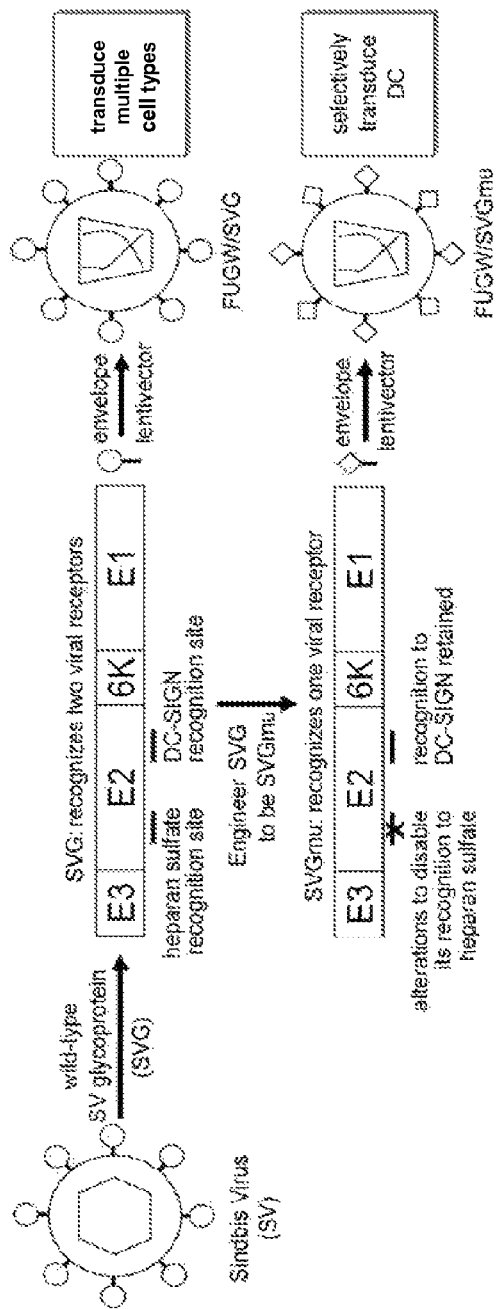
FIG. 1 is a schematic representation of a general strategy to target dendritic cells (DCs) for antigen delivery. Sindbis virus wild-type glycoprotein is mutated at the heparan sulfate binding site to abolish its binding ability. The resulting mutant glycoprotein (SVGmu) binds DC-SIGN but does not bind heparin sulfate. DC-SIGN: Dendritic Cell Specific ICAM-3 (Intracellular Adhesion Molecules 3)-Grabbing Nonintegrin.
Figure 2:
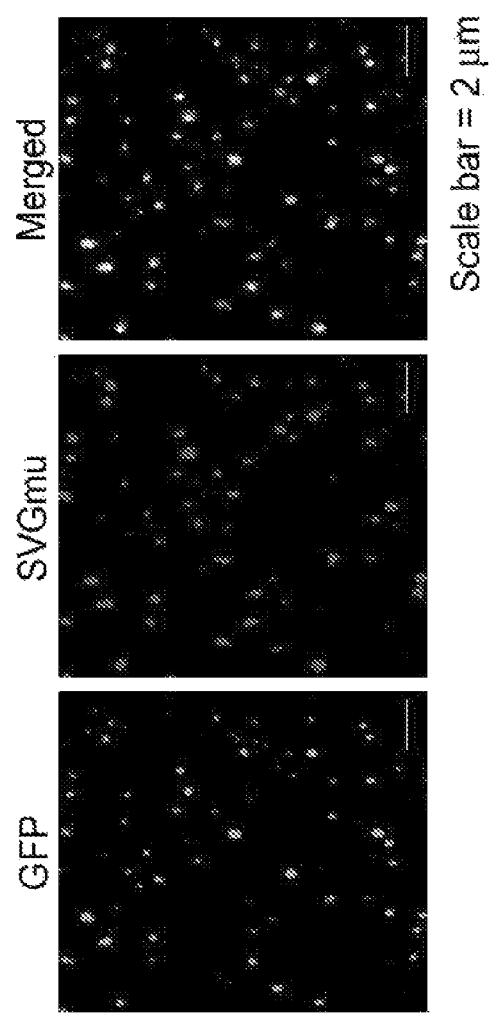
FIG. 2 illustrates laser confocal microscope images of virus particles harvested from virus-producing cells transiently transfected with lentiviral vector, plasmids encoding GFP-vpr and SVGmu, and other necessary packaging constructs. The virus particles are labeled with GFP (green). The surface incorporation of SVGmu was detected by immunostaining with an anti-HA tag antibody (red) to label SVGmu. In the "GFP" slide, viral particles tabled with GFP are green. In the "SVGmu" slide, viral particles with surface incorporation of SVGmu are stained red. In the "Merged" slide, viral particles where only GFP is expressed are green, viral particles where only SVGmu is incorporated into the surface are red, and viral particles expressing both GFP and containing SVGmu are yellow. The overlay of the green and red colors (yellow) indicates the viral particles containing SVGmu, which represent the majority of the total virus particles. The scale bar represents 2 pm.

Genetic engineering has been shown to be an efficient and potent means to convert dendritic cells (DCs) into special immune cells to induce antigen-specific immune responses. A great deal of research involving in vitro manipulation of DCs for vaccination/immunization against cancer, HIV and other diseases has been conducted. However, until now, it has not been possible to specifically and efficiently deliver a gene of interest, such as a gene encoding an antigen, to dendritic cells in vitro and in vivo. The inventors have discovered novel methods and compositions for efficient and specific targeting of DCs in vitro and in vivo. The methods and compositions can be used to induce antigen-specific immune responses, for example for immunotherapy.

Embodiments of the invention include methods and compositions for targeting dendritic cells (DCs) by using a recombinant virus to deliver a polynucleotide to the DCs. This is preferably accomplished through targeting the DC-specific surface molecule DC-SIGN (Dendritic Cell Specific ICAM-3 (Intracellular Adhesion Molecules 3)-Grabbing Nonintegrin; also known as CD209). DC-SIGN is a C-type lectin-like receptor capable of rapid binding and endocytosis of materials (Geijtenbeek, T. B., et al. 2004. *Annu. Rev. Immunol.* 22: 33-54, which is incorporated herein by reference in its entirety). In preferred embodiments, recombinant viruses are enveloped with a designed targeting molecule that is specific in its recognition for DC-SIGN. The polynucleotide can include, but is not limited to, a gene of interest, siRNA(s), and/or microRNA(s). In preferred embodiments, the polynucleotide encodes an antigen. In some embodiments, the recombinant virus delivers more than one gene to DCs. For example, genes encoding two or more antigens could be delivered. The delivery of more than one gene can be achieved, for example, by linking the genes with an Internal Ribosome Entry Site (IRES), and/or with 2A sequences, and driving the expression using a single promoter/enhancer.

As discussed in more detail below, embodiments of the invention are based on the use of recombinant viruses, such as lentiviruses and gammaretroviruses, because these viruses are able to incorporate into their envelope a large number of proteins are found on the surface of virus-producing cells. However, as also discussed below, other types of viruses may be used and the methods modified accordingly. Generally, a packaging cell line is transfected with a viral vector encoding a polynucleotide of interest (typically encoding an antigen), at least one plasmid encoding virus packaging components (such as gag and poll and a targeting molecule that is engineered to bind dendritic cells. In preferred embodiments, the targeting molecule is genetically engineered to specifically bind the DC-SIGN cell surface marker of dendritic cells. During budding of the virus, the targeting molecule, which is expressed in the packaging cell membrane, is incorporated into the viral envelope. As a result, the retroviral particles comprise a core including the polynucleotide of interest and an envelope comprising the targeting molecule on its surface.

The targeting molecule is able to bind DC-SIGN on a dendritic cell, and the virus is able to deliver the gene of interest to the dendritic cell. Without wishing to be bound by theory, it is believed that the binding induces endocytosis, bringing the virus into an endosome, triggering membrane fusion, and allowing the virus core to enter the cytosol. Following reverse transcription and migration of the product to the nucleus, the genome of the virus integrates into the target cell genome, incorporating the polynucleotide of interest into the genome of the target cell. The DC then expresses the polynucleotide of interest (typically encoding an antigen). The antigen is then processed and presented to T and B cells by DCs, generating an antigen-specific immune response. The specific pathway described above is not required so long as the dendritic cell is able to stimulate an antigen-specific immune response.

Embodiments of the present invention include methods and compositions for direct targeting of a gene of interest to DCs both in vitro and in vivo. In some preferred in vivo embodiments, the gene of interest is delivered to DCs without in vitro culture of DCs. For example, the gene of interest may be delivered to DCs via a direct administration of the targeting virus into a living subject. The gene of interest preferably encodes an antigen against which an immune response is desired. Exemplary antigens include: tumor specific antigens, tumor-associated antigens, tissue-specific antigens, bacterial antigens, viral antigens, yeast antigens, fungal antigens, protozoan antigens, parasite antigens, mitogens, and the like. Other antigens will be apparent to one of skill in the art and can be utilized without undue experimentation.

The methods disclosed herein may be readily adopted to utilize targeting molecules that are specific for DCs or that can be manipulated to provide the desired specificity. The targeting molecule is preferably an engineered viral glycoprotein that binds DC-SIGN in dendritic cells and that facilitates delivery of the gene of interest into the dendritic cells. Exemplary targeting molecules include, but are not limited to, glycoproteins derived from the following: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus. The targeting molecule is preferably membrane bound. If necessary, a DC-SIGN-specific targeting molecule that is designed or derived from a viral glycoprotein for use in the recombinant virus can be modified to a membrane bound form.

Any method known in the art can be used to engineer the targeting molecule to provide the desired specificity. Exemplary methods include, but are not limited to, rational protein engineering and DNA shuffling. Generally, to engineer a targeting molecule specific for DCs, a viral glycoprotein that interacts with a dendritic cell-specific surface marker is provided. Preferably, the viral glycoprotein interacts with DC-SIGN. The viral glycoprotein can also interact with at least a second cell surface marker such as, for example, heparin sulfate (HS), which is expressed on cell types other than DCs. The viral glycoprotein is modified such that its ability to interact with the DC-specific surface marker is maintained while its ability to interact with additional cell surface markers is decreased or eliminated. The modification can be a mutation in at least one residue of the viral glycoprotein amino acid sequence. The mutation can be a deletion, addition or substitution of the residue, and it can be carried out by standard methods known in the art. The desired specificity can readily be confirmed. For example, once the viral glycoprotein is modified, it can be used to prepare a recombinant virus by co-transfection with a viral vector containing a reporter gene and at least one plasmid encoding virus packaging components into a packaging cell line. The glycoprotein is incorporated into the viral envelope during budding of the virus. The virus can be used to transfect both a pure population of DCs as well as a mixed population of cells containing DCs, and specificity of the viral transduction of DCs can be confirmed by assaying the cells for expression of the reporter gene in DCs and not to a significant extent in other cell types. If the specificity is not sufficiently stringent (for example, if undesired levels of infection of other cell types is observed), the viral glycoprotein can be modified further and assayed as described until the desired specificity is achieved.

Embodiments of the present invention include the delivery to DCs of DC activators and/or maturation factors in conjunction with antigens. Exemplary DC activators and maturation factors include, but are not limited to, stimulation molecules, cytokines, chemokines, antibodies and other agents such as Flt-3 ligands. For example, the DC maturation factors can include at least one of the following: GM-CSF, IL-2, IL-4, IL-6, IL-7, IL-15, IL-21, IL-23, TNFa, B7.1, B7.2, 4-1BB, CD40 ligand (CD4OL) and drug-inducible CD40 (iCD40) (Hanks, B. A., et al. 2005. *Nat Med* 11:130-137, which is incorporated herein by reference in its entirety).

Embodiments of the present invention also include methods and compositions related to administration of recombinant virus as described above, or DCs infected with recombinant virus, into patients to stimulate antigen-specific immune responses, such as, for example, T cell responses (cellular immune responses) and B cell responses (humoral immune responses). For example, activated CD4 T cells can coordinate and orchestrate the $CD8^+$ cytotoxic T cells and the B cells in an antigen-specific response. In preferred embodiments, the recombinant virus and/or DCs infected with recombinant virus are used to stimulate immune responses for the prevention and treatment of diseases such as, but not limited to, cancer and AIDS/HIV. Any disease can be treated for which an immune response to a particular antigen is beneficial, including, but not limited to, neoplastic disease, infectious disease, and immune-related diseases.

As herein described, studies were conducted that resulted in the discovery of methods and compositions that can be used to direct recombinant viruses to provide genes encoding particular antigens into DCs. The genetic modification of DCs in order to elicit productive immune responses can be used in the prevention and treatment of diseases and provides an effective method of inducing effective T cell immunity as well as strong antibody production. The methods and compositions described herein can provide potent means for immunization with desired antigens. Such immunization can prevent and treat diseases such as, for example, cancer and AIDS/HIV.

DEFINITIONS

Unless defined otherwise, technical and scientific terms used herein have the same meaning as commonly understood by one of ordinary skill in the art to which this invention belongs. See, e.g., Singleton et al., *Dictionary of Microbiology and Molecular Biology 2nd ed*., J. Wiley & Sons (New York, N. Y. 1994); Sambrook et al., *Molecular Cloning, A Laboratory Manual*, Cold Springs Harbor Press (Cold Springs Harbor, N.Y. 1989). Any methods, devices and materials similar or equivalent to those described herein can be used in the practice of this invention.

As used herein, the terms nucleic acid, polynucleotide and nucleotide are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically include nucleic acids composed of bases other than the five biologically occurring bases (adenine, guanine, thymine, cytosine and uracil).

As used herein, a nucleic acid molecule is said to be "isolated" when the nucleic acid molecule is substantially separated from contaminant nucleic acid molecules encoding other polypeptides.

"Immunization" refers to the provision of antigen to a host. In some embodiments, antigen is provided to antigen-presenting cells, such as dendritic cells. As described below, recombinant virus comprising a gene encoding an antigen can be targeted to dendritic cells with an affinity molecule specific to DC-SIGN on dendritic cells. Thus the antigen to which an immune response is desired can be delivered to the dendritic cells. Other methods of immunization are well known in the art.

The term "immunological" or "immune" response is the development of a beneficial humoral (antibody mediated) and/or a cellular (mediated by antigen-specific T cells or their secretion products) response directed against an amyloid peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays (Burke et al., *J. Inf. Dis.* 170, 1110-19 (1994)), by antigen-dependent killing (cytotoxic T lymphocyte assay, Tigges et al., *J. Immunol.* 156, 3901-3910) or by cytokine secretion. The relative contributions of humoral and cellular responses to the protective or therapeutic effect of an immunogen can be distinguished by separately isolating IgG and T-cells from an immunized syngeneic animal and measuring protective or therapeutic effect in a second subject.

An "immunogenic agent" or "immunogen" is capable of inducing an immunological response against itself on administration to a patient, optionally in conjunction with an adjuvant.

The term "adjuvant" refers to a compound that when administered in conjunction with an antigen augments, enhances, and/or boosts the immune response to the antigen, but when administered alone does not generate an immune response to the antigen. An adjuvant can be administered with the recombinant virus of the invention as a single composition, or can be administered before, concurrent with or after administration of the recombinant virus of the invention. Adjuvants can enhance an immune response by several mechanisms including lymphocyte recruitment, stimulation of B and/or T cells, and stimulation of macrophages.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

The term "antibody" is used in the broadest sense and specifically covers human, non-human (e.g. murine), chimeric, and humanized monoclonal antibodies (including full length monoclonal antibodies), polyclonal antibodies, multi-specific antibodies (e.g., bispecific antibodies), single-chain antibodies, and antibody fragments so long as they exhibit the desired biological activity. Typically, fragments compete with the intact antibody from which they were derived for specific binding to an antigen.

The term "epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (see Burke, supra; Tigges, supra).

"Target cells" are any cells to which delivery of a polynucleotide or in which expression of a gene of interest is desired. Preferably, target cells are dendritic cells, particularly dendritic cells that express DC-SIGN.

The term "mammal" is defined as an individual belonging to the class Mammalia and includes, without limitation, humans, domestic and farm animals, and zoo, sports, and pet animals, such as sheep, dogs, horses, cats and cows.

The term "subject" or "patient" includes human and other mammalian subjects that receive either prophylactic or therapeutic treatment.

As used herein, "treatment" is a clinical intervention that may be therapeutic or prophylactic. In therapeutic applications, pharmaceutical compositions or medicants are administered to a patient suspected of, or already suffering from such a disease in an amount sufficient to cure, or at least partially arrest, the symptoms of the disease and its complications. In prophylactic applications, pharmaceutical compositions or medicants are administered to a patient susceptible to, or otherwise at risk of, a particular disease in an amount sufficient to eliminate or reduce the risk or delay the outset of the disease. An amount adequate to accomplish this is defined as a therapeutically- or pharmaceutically-effective dose. Such an amount can be administered as a single dosage or can be administered according to a regimen, whereby it is effective. The amount can cure a disease but, typically, is administered in order to ameliorate the symptoms of a disease, or to effect prophylaxis of a disease or disorder from developing. In both therapeutic and prophylactic regimes, agents are usually administered in several dosages until a sufficient immune response has been achieved. Typically, the immune response is monitored and repeated dosages are given if the immune response starts to fade. "Treatment" need not completely eliminate a disease, nor need it completely prevent a subject from becoming ill with the disease or disorder.

"Tumor," as used herein, refers to all neoplastic cell growth and proliferation, whether malignant or benign, and all pre-cancerous and cancerous cells and tissues.

The term "cancer" refers to a disease or disorder that is characterized by unregulated cell growth. Examples of cancer include, but are not limited to, carcinoma, lymphoma, blastoma and sarcoma. Examples of specific cancers include, but are not limited to, lung cancer, colon cancer, breast cancer, testicular cancer, stomach cancer, pancreatic cancer, ovarian cancer, liver cancer, bladder cancer, colorectal cancer, and prostate cancer. Additional cancers are well known to those of skill in the art and include, but are not limited to: leukemia, lymphoma, cervical cancer, glioma tumors, adenocarcinomas and skin cancer. Exemplary cancers include, but are not limited to, a bladder tumor, breast tumor, prostate tumor, basal cell carcinoma, biliary tract cancer, bladder cancer, bone cancer, brain and CNS cancer (e.g., glioma tumor), cervical cancer, choriocarcinoma, colon and rectum cancer, connective tissue cancer, cancer of the digestive system; endometrial cancer, esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma, neuroblastoma, oral cavity cancer (e.g., lip, tongue, mouth, and pharynx); ovarian cancer; pancreatic cancer, retinoblastoma; rhabdomyosarcoma; rectal cancer, renal cancer, cancer of the respiratory system; sarcoma, skin cancer; stomach cancer, testicular cancer, thyroid cancer; uterine cancer, cancer of the urinary system, as well as other carcinomas and sarcomas. Cancer also includes neoplasias and malignant disorders in mammals that are well known in the art.

A "vector" is a nucleic acid that is capable of transporting another nucleic acid. Vectors may be, for example, plasmids, cosmids or phage. An "expression vector" is a vector that is capable of directing expression of a protein or proteins encoded by one or more genes carried by the vector when it is present in the appropriate environment.

The term "regulatory element" and "expression control element" are used interchangeably and refer to nucleic acid molecules that can influence the transcription and/or translation of an operably linked coding sequence in a particular environment. These terms are used broadly and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals and polyadenylation signals.

The term "transfection" refers to the introduction of a nucleic acid into a host cell.

"Retroviruses" are viruses having an RNA genome.

"Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)), 0 Narayan and Clements J. Gen. Virology 70:1617-1639 (1989), Fields et al. Fundamental Virology Raven Press. (1990), Miyoshi H, Blomer U, Takahashi M, Gage F H, Verma I M. *J Virol.* 72(10):8150-7 (1998), and U.S. Pat. No. 6,013,516.

"Gammaretrovirus" refers to a genus of the retroviridae family. Exemplary gammaretroviruses include, but are not limited to, mouse stem cell virus, murine leukemia virus, feline leukemia virus, feline sarcoma virus, and avian reticuloendotheliosis viruses.

A "hybrid virus" as used herein refers to a virus having components from one or more other viral vectors, including element from non-retroviral vectors, for example, adenoviral-retroviral hybrids. As used herein hybrid vectors having a retroviral component are to be considered within the scope of the retroviruses.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

A "pseudotyped" retrovirus is a retroviral particle having an envelope protein that is from a virus other than the virus from which the RNA genome is derived. The envelope protein can be, for example and without limitation, from a different retrovirus or from a non-retroviral origin. The envelope protein can be a native envelope protein or an envelope protein that is modified, mutated or engineered as described herein. In some embodiments, an envelope protein is a DC-SIGN-specific viral glycoprotein that is derived from a glycoprotein from one of the following: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus.

"Transformation," as defined herein, describes a process by which exogenous DNA enters a target cell. Transformation may rely on any known method for the insertion of foreign nucleic acid sequences into a prokaryotic or eukaryotic host cell and may include, but is not limited to, viral infection, electroporation, heat shock, lipofection, and particle bombardment. "Transformed" cells include stably transformed cells in which the inserted nucleic acid is capable of replication either as an autonomously replicating plasmid or as part of the host chromosome. Also included are cells that transiently express a gene of interest.

A "fusogenic molecule," as described herein, is any molecule that can trigger membrane fusion when present on the surface of a virus and allows a virus core to pass through the membrane and, typically, enter the cytosol of a target cell. Fusogenic molecules can be, for example, viral glycoproteins. Exemplary viral glycoproteins contemplated as fusogenic molecules include, but are not limited to hemagglutinin, mutant hemagglutinin, SIN and viral glycoproteins from the following viruses: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus. Glycoproteins can be native or modified to have desired activity.

By "transgene" is meant any nucleotide sequence, particularly a DNA sequence, that is integrated into one or more chromosomes of a host cell by human intervention, such as by the methods of the present invention. The transgene preferably comprises a "gene of interest."

A "gene of interest" is not limited in any way and may be any nucleic acid, without limitation, that is desired to be delivered to, integrated, transcribed, translated, and/or expressed in a target cell. The gene of interest may encode a functional product, such as a protein or an RNA molecule. Preferably the gene of interest encodes a protein or other molecule, the expression of which is desired in the target cell. The gene of interest is generally operatively linked to other sequences that are useful for obtaining the desired expression of the gene of interest, such as transcriptional regulatory sequences. In some embodiments a gene of interest is preferably one that encodes an antigen to which an immune response is desired. Other genes of interest that may be used in some embodiments are genes that encode dendritic cell activators and/or maturation factors.

A "functional relationship" and "operably linked" mean, with respect to the gene of interest, that the gene is in the correct location and orientation with respect to the promoter and/or enhancer that expression of the gene will be affected when the promoter and/or enhancer is contacted with the appropriate molecules.

"2A sequences" or elements are small peptides introduced as a linker between two proteins, allowing autonomous intraribosomal self-processing of polyproteins (de Felipe. Genetic Vaccines and Ther. 2:13 (2004); deFelipe et al. Traffic 5:616-626 (2004)). The short peptides allow co-expression of multiple proteins from a single vector, such as co-expression of a fusogenic molecule and affinity molecule from the same vector. Thus, in some embodiments polynucleotides encoding the 2A elements are incorporated into a vector between polynucleotides encoding proteins to be expressed.

"DC maturation factors" (also known as "DC activators") are compounds that can induce activation or stimulation of DCs such that DCs facilitate the elicitation of cellular and humoral immune responses. Typical DC maturation factors are known in the art and include, but are not limited to, stimulation molecules, cytokines, chemokines, antibodies and other agents such as Flt-3 ligands (Figdor, C. G., et al. 2004. *Nat Med* 10:475-480; Pulendran, B., et al. 2000. *J Immunol* 165: 566-572; Maraskovsky, E., et al. 2000. *Blood* 96:878-884, each of which is incorporated herein by reference in its entirety). Exemplary DC maturation factors can include, but are not limited to, GM-CSF, IL-2, IL-4, IL-6, IL-7, IL-15, IL-21, IL-23, TNFa, B7.1, B7.2, 4-1BB, CD40 ligand (CD4OL) and drug-inducible CD40 (iCD40).

Targeting Molecules

As discussed above, a targeting molecule is incorporated into a recombinant virus to target the virus to dendritic cells that express DC-SIGN. The targeting molecule preferably also mediates fusion with the cell membrane and efficient transduction and delivery of the desired polynucleotide(s) into the dendritic cell. Thus, the targeting molecule is typically a fusogenic molecule (FM) with the desired binding specificity. The targeting molecule is modified, if necessary, such that it binds to DC-SIGN on dendritic cells. In some embodiments, the targeting molecule specifically binds to DC-SIGN. That is, the targeting molecule preferentially directs the recombinant virus to dendritic cells that express DC-SIGN relative to other cell types. Thus, in some embodiments, targeting molecules are created by eliminating the ability of a FM to bind to other targets, such as hemagglutinin, while retaining the ability to bind DC-SIGN. In other embodiments, the targeting molecule can be modified to eliminate native binding specificity to non-DC-SIGN molecules and components thereof and add or improve binding specificity for DC-SIGN. While some nonspecific binding to other molecules, and thus other cell types, may occur even if the targeting molecule is specific for DC-SIGN, the targeting molecules are modified to have sufficient specificity to avoid undesired side effects, such as side effects that may reduce the desired immune response.

Targeting molecules are generally molecules that are able to pseudotype virus and thus be incorporated in the envelope of recombinant viruses, target dendritic cells and, under the right conditions, induce membrane fusion and allow entry of a gene of interest to the dendritic cells. Preferred targeting molecules are viral glycoproteins. In addition, targeting molecules are preferably resistant to ultracentrifugation to allow concentration, which can be important for in vivo gene delivery.

Targeting molecules preferably induce membrane fusion at a low pH, independently of binding. Thus, in preferred embodiments, targeting molecule-induced membrane fusion occurs once the virus comprising the targeting molecule is inside the endosome of a target cell and the viral core component, including a polynucleotide of interest, is delivered to the cytosol.

In some embodiments a tag sequence is incorporated into a targeting molecule to allow detection of targeting molecule expression and the presence of the targeting molecule in viral particles.

There are two recognized classes of viral fusogens and both can be used as targeting molecules (D. S. Dimitrov, Nature Rev. Microbio. 2, 109 (2004)). The class I fusogens trigger membrane fusion using helical coiled-coil structures whereas the class II fusogens trigger fusion with 13 barrels. These two structures have different mechanics and kinetics (D. S. Dimitrov, Nature Rev. Microbio. 2, 109 (2004)). In some embodiments, class I fusogens are used. In other embodiments, class II fusogens are used. In still other embodiments, both class I and class II fusogens are used.

Some non-limiting examples of surface glycoproteins that may be used as targeting molecules (or as fusogenic molecules in embodiments where the viral binding and fusion functions are separate), either in the wild type or in modified form, include glycoproteins from alphaviruses, such as Semliki Forest virus (SFV), Ross River virus (RRV) and Aura virus (AV), which comprise surface glycoproteins such as E1, E2, and E3. The E2 glycoproteins derived from the Sindbis virus (SIN) and the hemagglutinin (HA) of influenza virus are non-retroviral glycoproteins that specifically bind particular molecules on cell surfaces (heparin sulfate glycosaminoglycan for E2, sialic acid for HA) and can be used to create targeting molecules in some embodiments. Their fusion is relatively independent of binding to receptor molecules, and the activation of fusion is accomplished through acidification in the endosome (Skehel and Wiley, Annu. Rev. Biochem. 69, 531-569 (2000); Smit, J. et al. J. Virol. 73, 8476-8484 (1999)). Moreover, they can tolerate certain genetic modifications and remain efficiently assembled on the retroviral surface (Morizono et al. J. Virol. 75, 8016-8020).

In other embodiments of the invention, surface glycoproteins of Lassa fever virus, Hepatitis B virus, Rabies virus, Borna disease virus, Hantaan virus, or SARS-CoV virus can be utilized as fusion molecules.

In other embodiments of the invention, flavivirus-based surface glycoproteins may be used as the basis for targeting molecules. Like alphaviruses, flaviviruses use the class II fusion molecule to mediate infection (Mukhopadhyay et al. (2005) Rev. Microbio. 3, 13-22). prM (about 165 amino acids) and E (about 495 amino acids) are the glycoproteins of flaviviruses. Also, the ligand-binding pocket for one flavivirus, Dengue virus (DV), has been well-characterized. Of interest, DC-SIGN has been suggested to specifically interact with the carbohydrate residues on the DV E protein to enhance viral entry (Mukhopadhyay et al. (2005) Nat. Rev. Microbio. 3, 13-22). Thus, lentiviruses enveloped only by DV E protein, or by modified DV E protein, can be used to target DCs. The TBE and DV E proteins, as well as other fusion molecules described, may be engineered to provide the desired binding specificity or to be binding deficient and fusion competent if necessary.

In some embodiments, a form of hemagglutinin (HA) from influenza A/fowl plague virus/Rostock/34 (FPV), a class I fusogen, is used (T. Hatziioannou, S. Valsesia-Wittmann, S. J. Russell, F. L. Cosset, J. Virol. 72, 5313 (1998)). In some embodiments, a form of FPV HA is used (A. H. Lin et al., Hum. Gene. Ther. 12, 323 (2001)). HA-mediated fusion is generally considered to be independent of receptor binding (D. Lavillette, S. J. Russell, F. L. Cosset, Curr. Opin. Biotech. 12, 461 (2001)).

In other embodiments, a class II FM is used, preferably the Sindbis virus glycoprotein from the alphavirus family (K. S. Wang, R. J. Kuhn, E. G. Strauss, S. Ou, J. H. Strauss, J. Virol. 66, 4992 (1992)), herein also referred to as SVG. SVG includes two transmembrane proteins (S. Mukhopadhyay, R. J. Kuhn, M. G. Rossmann, Nature Rev. Microbio. 3, 13 (2005)), a first protein responsible for fusion (E1), and a second protein for cell binding (E2). SVG is known to pseudotype both oncoretroviruses and lentiviruses.

As discussed below, in some preferred embodiments a modified SVG that preferentially binds DC-SIGN is utilized. In other embodiments, a binding-deficient and fusion-competent SVG, SVGmu, can be used as the fusogenic molecule in combination with a separate targeting molecule, such as an antibody to DC-SIGN or another dendritic cell specific protein. For example, a SVG fusogenic molecule can be used in which the immunoglobulin G binding domain of protein A (ZZ domain) is incorporated into the E2 protein and one or more additional mutations are made to inactivate the receptor binding sites (K. Morizono et al., Nature Med. 11, 346 (2005)).

The gene encoding the targeting molecule is preferably cloned into an expression vector, such as pcDNA3 (Invitrogen). Packaging cells, such as 293T cells are then co-transfected with the viral vector encoding a gene of interest (typically encoding an antigen), at least one plasmid encoding virus packing components, and a vector for expression of the targeting molecule. If the targeting function is separated from the fusogenic function, one or more vectors encoding an affinity molecule and any associated components is also provided, The targeting molecule is expressed on the membrane of the packaging cell and incorporated into the recombinant virus. Expression of targeting molecules on the packaging cell surface can be analyzed, for example, by FACS.

Based on information obtained, for example from structural studies and molecular modeling, mutagenesis may be employed to generate the mutant forms of glycoproteins that maintain their fusogenic ability but have the desired binding specificity and/or level of binding. Several mutants may be created for each glycoprotein and assayed using the methods described below, or other methods known in the art, to identify FMs with the most desirable characteristics. For example, targeting molecules can be tested for the ability to specifically deliver antigens to dendritic cells by determining their ability to stimulate an immune response without causing undesired side effects in a mammal. The ability to specifically target dendritic cells can also be tested directly, for example, in cell culture as described below.

To select suitable targeting molecules (either wild-type or mutant), viruses bearing the targeting molecule (and an affinity molecule where appropriate) are prepared and tested for their selectivity and/or their ability to facilitate penetration of the target cell membrane. Viruses that display a wild-type glycoprotein can be used as controls for examining titer effects in mutants. Cells expressing the binding partner of the targeting molecule (or affinity molecule, where appropriate) are transduced by the virus using a standard infection assay. After a specified time, for example 48 hours post-transduction, cells can be collected and the percentage of cells infected by the virus comprising the targeting molecule (or affinity molecule and fusogenic molecule) can be determined by, for example, FACS. The selectivity can be scored by calculating the percentage of cells infected by virus. Similarly, the effect of mutations on viral titer can be quantified by dividing the percentage of cells infected by virus comprising a mutant targeting molecule by the percentage of cells infected by virus comprising the corresponding wild type targeting molecule. A preferred mutant will give the best combination of selectivity and infectious titer. Once an targeting molecule is selected, viral concentration assays may be performed to confirm that viruses enveloped by the FM can be concentrated. Viral supernatants are collected and concentrated by ultracentrifugation. The titers of viruses can be determined by limited dilution of viral stock solution and transduction of cells expressing the binding partner of the affinity molecule.

In some embodiments, BlaM-Vpr fusion protein may be utilized to evaluate viral penetration, and thus the efficacy of a fusion molecule (wild-type or mutant). Virus may be prepared, for example, by transient transfection of packaging cells with one or more vectors comprising the viral elements, BlaM-Vpr, and the FM of interest (and an affinity molecule if appropriate). The resulting viruses can be used to infect cells expressing a molecule the targeting molecule (or affinity molecule) specifically binds in the absence or presence of the free inhibitor of binding (such as an antibody). Cells can then be washed with $CO_2$-independent medium and loaded with CCF2 dye (Aurora Bioscience). After incubation at room temperature to allow completion of the cleavage reaction, the cells can be fixed by paraformaldehyde and analyzed by FACS and microscopy. The presence of blue cells indicates the penetration of viruses into the cytoplasm; fewer blue cells would be expected when blocking antibody is added.

To investigate whether penetration is dependent upon a low pH, and select targeting molecules (or fusogenic molecules) with the desired pH dependence, NH$_4$Cl or other compound that alters pH can be added at the infection step (NH$_4$Cl will neutralize the acidic compartments of endosomes). In the case of NH$_4$Cl, the disappearance of blue cells will indicate that penetration of viruses is low pH-dependent.

In addition, to confirm that the activity is pH-dependent, lysosomotropic agents, such as ammonium chloride, chloroquine, concanamycin, bafilomycin A1, monensin, nigericin, etc., may be added into the incubation buffer. These agents can elevate the pH within the endosomal compartments (e.g., Drose and Altendorf, J. Exp. Biol. 200, 1-8, 1997). The inhibitory effect of these agents will reveal the role of pH for viral fusion and entry. The different entry kinetics between viruses displaying different fusogenic molecules may be compared and the most suitable selected for a particular application.

PCR entry assays may be utilized to monitor reverse transcription and thus measure kinetics of viral DNA synthesis as an indication of the kinetics of viral entry. For example, viral particles comprising a particular targeting molecule may be incubated with packaging cells, such as 293T cells, expressing the appropriate cognate for the targeting molecule (or a separate affinity molecule in some embodiments). Either immediately, or after incubation (to allow infection to occur) unbound viruses are removed and aliquots of the cells are analyzed. DNA may then be extracted from these aliquots and semi-quantitative performed using LTR-specific primers. The appearance of LTR-specific DNA products will indicate the success of viral entry and uncoating.

Although the targeting molecule can have both viral binding and fusion functions, in another aspect of the invention, the viral binding and fusion functions are separated into two distinct components. Typically, the recombinant virus comprises both (i) an affinity molecule that mediates viral binding and precisely targets the virus to dendritic cells, and (ii) a distinct fusogenic molecule (FM) that mediates efficient transduction and delivery of the desired polynucleotide into the dendritic cells. The methods disclosed herein may be readily adopted to utilize any of a variety of affinity molecules and fusogenic molecules. In addition to those described herein, other exemplary fusogenic molecules and related methods are described, for example, in U.S. patent application Ser. No. 11/071,785, filed Mar. 2, 2005 (published as U.S. Patent Application Publication 2005-0238626), and in U.S. patent application Ser. No. 11/446,353, filed Jun. 1, 2006 (published as U.S. Patent Application Publication 2007/0020238), each of which is incorporated herein by reference in its entirety.

The affinity molecule is one that binds a dendritic cell surface marker. In preferred embodiments, the affinity molecule binds DC-SIGN with specificity. That is, the binding of the affinity molecule to DC-SIGN is preferably specific enough to avoid undesired side effects due to interaction with markers on other cell types. The affinity molecule can be, for example, an antibody that specifically binds DC-SIGN.

In some preferred embodiments, the fusion molecule is a viral glycoprotein that mediates fusion or otherwise facilitates delivery of the gene of interest to the dendritic cell, preferably in response to the low pH environment of the endosome. The fusion molecule preferably exhibits fast enough kinetics that the viral contents can empty into the cytosol before the degradation of the viral particle. In addition, the fusion molecule can be modified to reduce or eliminate any binding activity and thus reduce or eliminate any non-specific binding. That is, by reducing the binding ability of the fusion molecules, binding of the virus to the target cell is determined predominantly or entirely by the affinity molecule, allowing for high target specificity and reducing undesired effects. Exemplary fusion molecules include, but are not limited to viral glycoproteins derived from one of the following viruses: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus.

The methods disclosed herein can be readily adopted to utilize any of a variety of molecules as targeting molecules, or as fusogenic molecules in combination with affinity molecules. In addition to those described herein, other exemplary molecules and related methods are described, for example, in U.S. Patent Application Publication 2005/0238626 and in U.S. Patent Application Publication 2007/0020238).

Vectors

In a preferred embodiment, one or more vectors are used to introduce polynucleotide sequences into a packaging cell line for the preparation of a recombinant virus as described herein. The vectors can contain polynucleotide sequences encoding the various components of the recombinant virus including the DC-specific targeting molecule, a gene(s) of interest (typically encoding an antigen), and any components necessary for the production of the virus that are not provided by the packaging cell. In some embodiments, vectors containing polynucleotide sequences that encode a DC-specific affinity molecule and a separate fugosenic molecule are substituted for a vector that encodes a DC-specific targeting molecule in the preparation of the virus. Eukaryotic cell expression vectors are well known in the art and are available from a number of commercial sources.

In one aspect of the invention, vectors containing polynucleotide sequences that encode DC maturation factors are also used in the preparation of the virus. These polynucleotides are typically under the control of one or more regulatory elements that direct the expression of the coding sequences in the packaging cell and the target cell, as appropriate. Several lines of evidence have shown the success of DC vaccination is dependent on the maturation state of DCs (Banchereau, J and Palucka, A. K. Nat. Rev. Immunol. 5:296-306 (2005); Schuler, G. et al. Curr. Opin. Immuno 1.15:138-147 (2003); Figdor, C. G. et al. Nat. Med. 10:475-480 (2004), each of which is incorporated herein by reference). Maturation can transform DCs from cells actively involved in antigen capture into cells specialized for T cell priming. In one aspect of the invention, the vector includes genes that encode the stimulatory molecules to trigger the desired DC maturation. Such stimulatory molecules are also referred to as maturation factors or maturation stimulatory factors.

In some embodiments, packaging cells are co-transfected with a viral vector encoding an antigen and one or more additional vectors. For example, in addition to the viral vector encoding an antigen, a second vector preferably carries a gene encoding a targeting molecule that binds dendritic cells, such SVGmu, as described elsewhere in the application. In some preferred embodiments, the targeting molecule encodes a modified viral glycoprotein that is specific for DC-SIGN. The modified viral glycoprotein is preferably one derived from at least one of the following: Sindbis virus, influenza virus, Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus. In some embodiments, the viral vector encoding an antigen also includes a polynucleotide sequence encoding a DC maturation factor. In some embodiments, the polynucleotide sequence encoding a DC maturation factor is contained in a third vector that is co-transfected with the viral vector encoding an antigen and the one or more additional vectors into the packaging cells.

In other embodiments, one or more multicistronic expression vectors are utilized that include two or more of the elements (e.g., the viral genes, gene(s) of interest, the targeting molecule, DC maturation factors) necessary for production of the desired recombinant virus in packaging cells. The use of multicistronic vectors reduces the total number of vectors required and thus avoids the possible difficulties associated with coordinating expression from multiple vectors. In a multicistronic vector the various elements to be expressed are operably linked to one or more promoters (and other expression control elements as necessary). In other embodiments a multicistronic vector comprising a gene of interest, a reporter gene, and viral elements is used. The gene of interest typically encodes an antigen and, optionally, a DC maturation factor. Such a vector may be cotransfected, for example, along with a vector encoding a targeting molecule, or, in some embodiments, a multicistronic vector encoding both an FM and an affinity molecule. In some embodiments the multicistronic vector comprises a gene encoding an antigen, a gene encoding a DC maturation factor and viral elements.

Each component to be expressed in a multicistronic expression vector may be separated, for example, by an IRES element or a viral 2A element, to allow for separate expression of the various proteins from the same promoter. IRES elements and 2A elements are known in the art (U.S. Pat. No. 4,937,190; de Felipe et al. 2004. *Traffic* 5: 616-626, each of which is incorporated herein by reference in its entirety). In one embodiment, oligonucleotides encoding furin cleavage site sequences (RAKR) (Fang et al. 2005. *Nat. Biotech* 23: 584-590, which is incorporated herein by reference in its entirety) linked with 2A-like sequences from foot-and-mouth diseases virus (FMDV), equine rhinitis A virus (ERAV), and thosea asigna virus (TaV) (Szymczak et al. 2004. *Nat. Biotechnol.* 22: 589-594, which is incorporated herein by reference in its entirety) are used to separate genetic elements in a multicistronic vector. The efficacy of a particular multicistronic vector for use in synthesizing the desired recombinant virus can readily be tested by detecting expression of each of the genes using standard protocols.

Generation of the vector(s) can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989. Molecular Cloning: A Laboratory Manual. Cold Spring Harbor Laboratory Press, N.Y.), Coffin et al. (Retroviruses. Cold Spring Harbor Laboratory Press, N.Y. (1997)) and "RNA Viruses: A Practical Approach" (Alan J. Cann, Ed., Oxford University Press, (2000), each of the foregoing which is incorporated herein by reference in its entirety.

The vector(s) may incorporate sequences from the genome of any known organism. The sequences may be incorporated in their native form or may be modified in any way. For example, the sequences may comprise insertions, deletions or substitutions.

Expression control elements that may be used for regulating the expression of the components are known in the art and include, but are not limited to, inducible promoters, constitutive promoters, secretion signals, enhancers and other regulatory elements.

In one embodiment, a vector can include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

The vector(s) may include one or more genes for selectable markers that are effective in a eukaryotic cell, such as a gene for a drug resistance selection marker. This gene encodes a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, or tetracycline, complement auxotrophic deficiencies, or supply critical nutrients withheld from the media. The selectable marker can optionally be present on a separate plasmid and introduced by co-transfection.

Vectors will usually contain a promoter that is recognized by the packaging cell and that is operably linked to the polynucleotide(s) encoding the targeting molecule, viral components, and the like. A promoter is an expression control element formed by a nucleic acid sequence that permits binding of RNA polymerase and transcription to occur. Promoters are untranslated sequences that are located upstream (5') to the start codon of a structural gene (generally within about 100 to 1000 bp) and control the transcription and translation of the antigen-specific polynucleotide sequence to which they are operably linked. Promoters may be inducible or constitutive. The activity of the inducible promoters is induced by the presence or absence of biotic or abiotic factors. Inducible promoters can be a useful tool in genetic engineering because the expression of genes to which they are operably linked can be turned on or off at certain stages of development of an organism or in a particular tissue. Inducible promoters can be grouped as chemically-regulated promoters, and physically-regulated promoters. Typical chemically-regulated promoters include, not are not limited to, alcohol-regulated promoters (e.g. alcohol dehydrogenase I (alcA) gene promoter), tetracycline-regulated promoters (e.g. tetracycline-responsive promoter), steroid-regulated promoter (e.g. rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g. metallothionein gene-based promoters), and pathogenesis-related promoters (e.g. Arabidopsis and maize pathogen-related (PR) protein-based promoters). Typical physically-regulated promoters include, but are not limited to, temperature-regulated promoters (e.g. heat shock promoters), and light-regulated promoters (e.g. soybean SSU promoter). Other exemplary promoters are described elsewhere, for example, in hyper text transfer protocol: //www.patentlens.net/daisy/promoters/768/271.html, which is incorporated herein by reference in its entirety.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. However, heterologous promoters are preferred, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, a-fetoprotein, and insulin). Preferably an enhancer from a eukaryotic cell virus will be used. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors will also contain sequences necessary for the termination of transcription and for stabilizing the mRNA. These sequences are often found in the 5' and, occasionally 3', untranslated regions of eukaryotic or viral DNAs or cDNAs and are well known in the art.

Plasmid vectors containing one or more of the components described above are readily constructed using standard techniques well known in the art.

For analysis to confirm correct sequences in plasmids constructed, the plasmid may be replicated in E. coli, purified, and analyzed by restriction endonuclease digestion, and/or sequenced by conventional methods.

Vectors that provide for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. See Sambrook et al., supra, pp. 16.17-16.22.

Other vectors and methods suitable for adaptation to the expression of the viral polypeptides are well known in the art and are readily adapted to the specific circumstances.

Using the teachings provided herein, one of skill in the art will recognize that the efficacy of a particular expression system can be tested by transforming packaging cells with a vector comprising a gene encoding a reporter protein and measuring the expression using a suitable technique, for example, measuring fluorescence from a green fluorescent protein conjugate. Suitable reporter genes are well known in the art.

Transformation of packaging cells with vectors of the present invention is accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. (2001. Non-Viral Vectors in Cancer Gene Therapy: Principles and Progresses. *Anticancer Drugs*, which is incorporated herein by reference in its entirety). Cationic lipid or salt treatment methods are typically employed, see, for example, Graham et al. (1973. *Virol.* 52:456; Wigler et al. (1979. *Proc. Natl. Acad. Sci. USA* 76:1373-76), each of the foregoing which is incorporated herein by reference in its entirety. The calcium phosphate precipitation method is preferred. However, other methods for introducing the vector into cells may also be used, including nuclear microinjection and bacterial protoplast fusion.

Viral Vector and Packaging Cells

One of the vectors encodes the core virus (the "viral vector"). There are a large number of available viral vectors that are suitable for use with the invention, including those identified for human gene therapy applications, such as those described by Pfeifer and Verma (Pfeifer, A. and I. M. Verma. 2001. *Annu. Rev. Genomics Hum. Genet.* 2:177-211, which is incorporated herein by reference in its entirety). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. Human Immunodeficiency virus (HIV-1)-derived vectors belong to this category. Other examples include lentivirus vectors derived from HIV-2, feline immunodeficiency virus (FIV), equine infectious anemia virus, simian immunodeficiency virus (SIV) and maedi/visna virus.

The viral vector preferably comprises one or more genes encoding components of the recombinant virus as well as one or more genes of interest, such as, for example, an antigen and/or a DC maturation factor. The viral vector may also comprise genetic elements that facilitate expression of the gene of interest in a target cell, such as promoter and enhancer sequences. In order to prevent replication in the target cell, endogenous viral genes required for replication may be removed and provided separately in the packaging cell line.

In a preferred embodiment the viral vector comprises an intact retroviral 5' LTR and a self-inactivating 3' LTR.

Any method known in the art may be used to produce infectious retroviral particles whose genome comprises an RNA copy of the viral vector. To this end, the viral vector (along with other vectors encoding the gene of interest, the DC-specific targeting molecule, etc.) is preferably introduced into a packaging cell line that packages viral genomic RNA based on the viral vector into viral particles.

The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The packaging cell line may stably express the necessary viral proteins. Such a packaging cell line is described, for example, in U.S. Pat. No. 6,218,181, which is incorporated herein by reference in its entirety. Alternatively a packaging cell line may be transiently transfected with plasmids comprising nucleic acid that encodes one or more necessary viral proteins, including the DC-specific targeting molecule (or alternatively, a DC-specific affinity molecule and fusogenic molecule) along with the viral vectors encoding the gene of interest, which typically encodes an antigen and can additionally encode a DC maturation factor.

Viral particles comprising a polynucleotide with the gene of interest and a targeting molecule that is specific for dendritic cells are collected and allowed to infect the target cell. In some preferred embodiments, the virus is pseudotyped to achieve target cell specificity. Methods for pseudotyping are well known in the art and also described herein.

In one embodiment, the recombinant virus used to deliver the gene of interest is a modified lentivirus and the viral vector is based on a lentivirus. As lentiviruses are able to infect both dividing and non-dividing cells, in this embodiment it is not necessary for target cells to be dividing (or to stimulate the target cells to divide).

In another embodiment, the recombinant virus used to deliver the gene of interest is a modified gammaretrovirus and the viral vector is based on a gammaretrovirus.

In another embodiment the vector is based on the murine stem cell virus (MSCV; (Hawley, R. G., et al. (1996) Proc. Natl. Acad. Sci. USA 93:10297-10302; Keller, G., et al. (1998) Blood 92:877-887; Hawley, R. G., et al. (1994) Gene Ther. 1:136-138, each of the foregoing which is incorporated herein by reference in its entirety). The MSCV vector provides long-term stable expression in target cells, particularly hematopoietic precursor cells and their differentiated progeny.

In another embodiment, the vector is based on a modified Moloney virus, for example a Moloney Murine Leukemia Virus. The viral vector can also can be based on a hybrid virus such as that described in Choi, J. K., et al. (2001. *Stem Cells* 19, No. 3, 236-246, which is incorporated herein by reference in its entirety).

A DNA viral vector may be used, including, for example adenovirus-based vectors and adeno-associated virus (AAV)-based vectors. Likewise, retroviral-adenoviral vectors also can be used with the methods of the invention.

Other vectors also can be used for polynucleotide delivery including vectors derived from herpes simplex viruses (HSVs), including amplicon vectors, replication-defective HSV and attenuated HSV (Krisky D M, Marconi P C, Oligino T J, Rouse R J, Fink D J, et al. 1998. Development of herpes simplex virus replication-defective multigene vectors for combination gene therapy applications. *Gene Ther.* 5: 1517-30, which is incorporated herein by reference in its entirety).

Other vectors that have recently been developed for gene therapy uses can also be used with the methods of the invention. Such vectors include those derived from baculoviruses and alpha-viruses. (Jolly D J. 1999. Emerging viral vectors. pp 209-40 in Friedmann T, ed. 1999. The development of human gene therapy. New York: Cold Spring Harbor Lab, which is incorporated herein by reference in its entirety).

In some preferred embodiments, the viral construct comprises sequences from a lentivirus genome, such as the HIV genome or the SIV genome. The viral construct preferably comprises sequences from the 5' and 3' LTRs of a lentivirus. More preferably the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences.

The viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In a preferred embodiment the CMV enhancer/promoter sequence is used.

In some preferred embodiments, the viral construct comprises sequences from a gammaretrovirus genome, such as the mouse stem cell virus (MSCV) genome or the murine leukemia virus (MLV) genome. The viral construct preferably comprises sequences from the 5' and 3' LTRs of a gammaretrovirus. The LTR sequences may be LTR sequences from any gammaretrovirus from any species. For example, they may be LTR sequences from mouse stem cell virus (MSCV), murine leukemia virus (MLV), feline leukemia virus (FLV), feline sarcoma virus (FAV), and avian reticuloendotheliosis viruses (ARV). Preferably the LTR sequences are MSCV and MLV LTR sequences.

In some embodiments, the viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR.

Optionally, the U3 sequence from the gammaretroviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In a preferred embodiment the CMV enhancer/promoter sequence is used.

The viral construct generally comprises a gene that encodes an antigen that is desirably expressed in one or more target cells. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially.

In some embodiments, the gene of interest is in a functional relationship with internal promoter/enhancer regulatory sequences. An "internal" promoter/enhancer is one that is located between the 5' LTR and the 3' LTR sequences in the viral construct and is operably linked to the gene that is desirably expressed.

The internal promoter/enhancer may be any promoter, enhancer or promoter/enhancer combination known to increase expression of a gene with which it is in a functional relationship. A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

The internal promoter/enhancer is preferably selected based on the desired expression pattern of the gene of interest and the specific properties of known promoters/enhancers. Thus, the internal promoter may be a constitutive promoter. Non-limiting examples of constitutive promoters that may be used include the promoter for ubiquitin, CMV (Karasuyama et al. 1989. *J. Exp. Med.* 169:13, which is incorporated herein by reference in its entirety), beta-actin (Gunning et al. 1989. *Proc. Natl. Acad. Sci. USA* 84:4831-4835, which is incorporated herein by reference in its entirety) and pgk (see, for example, Adra et al. 1987. *Gene* 60:65-74; Singer-Sam et al. 1984. *Gene* 32:409-417; and Dobson et al. 1982. *Nucleic Acids Res.* 10:2635-2637, each of the foregoing which is incorporated herein by reference in its entirety).

Alternatively, the promoter may be a tissue specific promoter. In some preferred embodiments, the promoter is a target cell-specific promoter. For example, the promoter can be the dendritic cell-specific promoter CD11c (Masood, R., et al. 2001. *Int J Mol Med* 8:335-343; Somia, N. V., et al. 1995. *Proc Acad Sci USA* 92:7570-7574, each of which is incorporated herein by reference in its entirety.) In addition, promoters may be selected to allow for inducible expression of the gene. A number of systems for inducible expression are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the organism and/or the target cell of interest.

In some embodiments the viral construct preferably comprises at least one RNA Polymerase II or III promoter. The RNA Polymerase II or III promoter is operably linked to the gene of interest and can also be linked to a termination sequence. In addition, more than one RNA Polymerase II or III promoters may be incorporated.

RNA polymerase II and III promoters are well known to one of skill in the art. A suitable range of RNA polymerase III promoters can be found, for example, in Paule and White. *Nucleic Acids Research.*, Vol 28, pp 1283-1298 (2000), which is incorporated herein by reference in its entirety. The definition of RNA polymerase II or III promoters, respectively, also include any synthetic or engineered DNA fragment that can direct RNA polymerase II or III, respectively, to transcribe its downstream RNA coding sequences. Further, the RNA polymerase II or III (Pol II or III) promoter or promoters used as part of the viral vector can be inducible. Any suitable inducible Pol II or III promoter can be used with the methods of the invention. Particularly suited Pol II or III promoters include the tetracycline responsive promoters provided in Ohkawa and Taira *Human Gene Therapy*, Vol. 11, pp 577-585 (2000) and in Meissner et al. *Nucleic Acids Research*, Vol. 29, pp 1672-1682 (2001), each of which is incorporated herein by reference in its entirety.

An internal enhancer may also be present in the viral construct to increase expression of the gene of interest. For example, the CMV enhancer (Karasuyama et al. 1989. *J. Exp. Med.* 169:13, which is incorporated herein by reference in its entirety) may be used. In some embodiments, the CMV enhancer can be used in combination with the chicken 13-actin promoter. One of skill in the art will be able to select the appropriate enhancer based on the desired expression pattern.

The polynucleotide or gene of interest is not limited in any way and includes any nucleic acid that the skilled practitioner desires to have integrated, transcribed, translated, and/or expressed in the target cell. In some embodiments, the polynucleotide can be a gene that encodes an antigen against which an immune response is desired. In some embodiments, the polynucleotide can be a gene encoding a small inhibiting RNA (siRNA) or a microRNA (miRNA) of interest that down-regulates expression of a molecule. For example, the gene encoding an siRNA or a microRNA can be used to down-regulate expression of negative regulators in a cell, including those that inhibit activation or maturation of dendritic cells. siRNAs and microRNAs are known in the art and describe elsewhere (Shen, L. et al. 2004. *Nat Biotech* 22(12): 1546-1553; Zhou, H. et al. 2006. *Biochemical and Biophysical Research Communications* 347:200-207; Song, X-T., et al. 2006. *PLoS Medicine* 3(1):e1; Kobayashi, T. and A. Yoshimura. 2005. *TRENDS in Immunology* 26(4):177-179; Taganov, K., et al. 2007. *Immunity* 26:133-137; Dahlberg, J. E. and E. Lund. 2007. *Sci. STKE* 387:pe25, each of which is incorporated herein by reference in its entirety).

In addition, in some embodiments, the polynucleotide can contain more than one gene of interest, which can be placed in functional relationship with the viral promoter. The gene of interest can encode a protein, a siRNA, or a microRNA. In some embodiments, the polynucleotide to be delivered can comprise multiple genes encoding at least one protein, at least one siRNA, at least one microRNA, or any combinations thereof. For example, the polynucleotide to be delivered can include one or more genes that encode one or more antigens against which an immune response is desired. The one or more antigens can be associated with a single disease or disorder, or the can be associated with multiple diseases and/or disorders. In some embodiments, a gene encoding an immune regulatory protein can be constructed with a primary gene encoding an antigen against which an immune response is desired, and the combination can elicit and regulate the immune response to the desired direction and magnitude. In some embodiments, a gene encoding an siRNA or microRNA can be constructed with a primary gene encoding an antigen against which an immune response is desired, and the combination can regulate the scope of the immune response. (See, for example, embodiments of polynucleotides in FIG. 24*c* and FIG. 24*d*, with accompanying sequences in SEQ ID NO: 9 and SEQ ID NO: 10, respectively.) In some embodiments, a gene encoding a marker protein can be placed after a primary gene of interest to allow for identification of cells that are expressing the desired protein. In one embodiment a fluorescent marker protein, preferably green fluorescent protein (GFP), is incorporated into the construct along with the gene of interest (typically encoding an antigen). If more than one gene is included, internal ribosomal entry site (IRES) sequences, or 2A elements are also preferably included, separating the primary gene of interest from a reporter gene and/or any other gene of interest. The IRES or 2A sequences may facilitate the expression of the reporter gene, or other genes.

The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the target cell. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. 1999. *J. Virol.* 74:3668-3681; Deglon et al. 2000. *Hum. Gene Ther.* 11:179-190, each of which is incorporated herein by reference in its entirety).

A chicken β-globin insulator may also be included in the viral construct. This element has been shown to reduce the chance of silencing the integrated provirus in the target cell due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest.

In a specific embodiment, the viral vector comprises: a cytomegalovirus (CMV) enhancer/promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken beta-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Delivery of the Virus

The virus may be delivered to a target cell in any way that allows the virus to contact the target dendritic cells (DCs) in which delivery of a polynucleotide of interest is desired. In preferred embodiments, a suitable amount of virus is introduced into an animal directly (in vivo), for example though injection into the body. In some preferred embodiments, the viral particles are injected into a mammal's peripheral blood stream. In other preferred embodiments, the viral particles are injected into a mammal through intra-dermal injection, subcutaneous injection, intra-peritoneal cavity injection, or intra-venal injection. The virus may be delivered using a subdermal injection device such the devices disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499, all of which are incorporated by reference in their entirety for all purposes. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively. Depending on the particular circumstances and nature of the target cells, introduction can be carried out through other means including for example, inhalation, or direct contact with epithelial tissues, for example those in the eye, mouth or skin.

In other embodiments, target cells are provided and contacted with the virus in vitro, such as in culture plates. The target cells are typically dendritic cells obtained from a healthy subject or a subject in need of treatment. Preferably, the target cells are dendritic cells obtained from a subject in whom it is desired to stimulate an immune response to an antigen. Methods to obtain cells from a subject are well known in the art. The virus may be suspended in media and added to the wells of a culture plate, tube or other container. The media containing the virus may be added prior to the plating of the cells or after the cells have been plated. Preferably cells are incubated in an appropriate amount of media to provide viability and to allow for suitable concentrations of virus in the media such that infection of the host cell occurs. The cells are preferably incubated with the virus for a sufficient amount of time to allow the virus to infect the cells. Preferably the cells are incubated with virus for at least 1 hour, more preferably at least 5 hours and even more preferably at least 10 hours.

In both in vivo and in vitro delivery embodiments, any concentration of virus that is sufficient to infect the desired target cells may be used, as can be readily determined by the skilled artisan. When the target cell is to be cultured, the concentration of the viral particles is at least 1 PFU/ul, more preferably at least 10 PFU/ul, even more preferably at least 400 PFU/µl and even more preferably at least $1 \times 10^4$ PFU/ul.

In some embodiments, following infection with the virus in vitro, target cells can be introduced (or re-introduced) into an animal. In some embodiments, the cells can be introduced into the dermis, under the dermis, or into the peripheral blood stream. The cells introduced into an animal are preferably cells derived from that animal, to avoid an adverse immune response. Cells also can be used that are derived from a donor animal having a similar immune background. Other cells also can be used, including those designed to avoid an adverse immunogenic response.

The target cells may be analyzed, for example for integration, transcription and/or expression of the polynucleotide or gene(s) of interest, the number of copies of the gene integrated, and the location of the integration. Such analysis may be carried out at any time and may be carried out by any methods known in the art.

Subjects in which a recombinant virus or virus-infected DCs are administered can be analyzed for location of infected cells, expression of the virus-delivered polynucleotide or gene of interest, stimulation of an immune response, and monitored for symptoms associated with a disease or disorder by any methods known in the art.

The methods of infecting cells disclosed above do not depend upon individual-specific characteristics of the cells. As a result, they are readily extended to all mammals. In some embodiments the recombinant virus is delivered to a human or to human dendritic cells. In other embodiments, the recombinant virus is delivered to a mouse or to mouse dendritic cells. In still other embodiments, the recombinant virus is delivered to an animal other than a human or a mouse, or to dendritic cells from an animal other than a human or a mouse.

As discussed above, the recombinant virus can be pseudotyped to confer upon it a broad host range as well as target cell specificity. One of skill in the art would also be aware of appropriate internal promoters to achieve the desired expression of a polynucleotide or gene of interest in a particular animal species. Thus, one of skill in the art will be able to modify the method of infecting dendritic cells derived from any species.

The recombinant virus can be evaluated to determine the specificity of the targeting molecule incorporated into the virus that targets dendritic cells. For example, a mixed population of bone marrow cells can be obtained from a subject and cultured in vitro. The recombinant virus can be administered to the mixed population of bone marrow cells, and expression of a reporter gene incorporated into the virus can be assayed in the cultured cells. In some embodiments, at least about 50%, more preferably at least about 60%, 70%, 80% or 90%, still more preferably at least about 95% of transduced cells in the mixed cell population are dendritic cells that express DC-SIGN.

Therapy

The methods of the present invention can be used to prevent or treat a wide variety of diseases or disorders, particularly those for which activation of an immune response in a patient would be beneficial. Many such diseases are well known in the art. For example, diseases or disorders that are amenable to treatment or prevention by the methods of the present invention include, without limitation, cancers, autoimmune diseases, and infections, including viral, bacterial, fungal and parasitic infections. In embodiments of the invention, a disease is treated by using recombinant viruses to deliver a gene of interest to dendritic cells, wherein expression of the gene produces a disease-specific antigen and leads to stimulation of antigen-specific cellular immune responses and humoral immune responses.

In embodiments of the invention, a recombinant virus is used to deliver polynucleotides encoding an antigen against which an immune response is desired to dendritic cells. In some embodiments, the delivery can be achieved by contacting dendritic cells with the recombinant virus in vitro, whereupon the transduced dendritic cells are provided to a patient. In some embodiments, the delivery can be achieved by delivering the virus to a subject for contact with dendritic cells in vivo. The dendritic cells then stimulate antigen-specific T cells or B cells in a patient to induce cellular and humoral immune responses to the expressed antigen. In such embodiments, a patient that is suffering from a disease or disorder is treated by generating immune cells with a desired specificity.

Any antigen that is associated with a disease or disorder can be delivered to dendritic cells using the recombinant viruses as described herein. An antigen that is associated with the disease or disorder is identified for preparation of a recombinant virus that targets dendritic cells. Antigens associated with many diseases and disorders are well known in the art. An antigen may be previously known to be associated with the disease or disorder, or may be identified by any method known in the art. For example, an antigen to a type of cancer from which a patient is suffering may be known, such as a tumor associated antigen. In one aspect, the invention provides a method to deliver genes encoding tumor antigens and other necessary proteins to DCs in vivo using engineered recombinant lentivirus. In other embodiments, an antigen related to the disease or disorder is identified from the patient to be treated. For example, an antigen associated with a tumor may be identified from the tumor itself by any method known in the art. Tumor associated antigens are not limited in any way and include, for example, antigens that are identified on cancerous cells from the patient to be treated.

Tumor associated antigens are known for a variety of cancers including, for example, prostate cancer and breast cancer. In some breast cancers, for example, the Her-2 receptor is overexpressed on the surface of cancerous cells. Exemplary tumor antigens include, but are not limited to: MAGE, BAGE, RAGE, and NY-ESO, which are nonmutated antigens expressed in the immune-privileged areas of the testes and in a variety of tumor cells; lineage-specific tumor antigens such as the melanocyte-melanoma lineage antigens MART-1/Melan-A, gp100, gp75, mda-7, tyrosinase and tyrosinase-related protein, or the prostate specific membrane antigen (PSMA) and prostate-specific antigen (PSA), which are antigens expressed in normal and neoplastic cells derived from the same tissue; epitope proteins/peptides derived from genes mutated in tumor cells or genes transcribed at different levels in tumor compared to normal cells, such as mutated ras, bcr/ab1 rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; epitope proteins/peptides derived from oncoviral processes, such as human papilloma virus proteins E6 and E7; nonmutated oncofetal proteins with a tumor-selective expression, such as carcinoembryonic antigen and alpha-fetoprotein. A number of tumor associated antigens have been reviewed (see, for example, "Tumor-Antigens Recognized By T-Lymphocytes," Boon T, Cerottini J C, Vandeneynde B, Vanderbruggen P, Vanpel A, Annual Review Of Immunology 12: 337-365, 1994; "A listing of human tumor antigens recognized by T cells," Renkvist N, Castelli C, Robbins P F, Parmiani G. Cancer Immunology Immunotherapy 50: (1) 3-15 Mar. 2001, each of which is incorporated herein by reference in its entirety.)

The antigen can also be an antigen associated with an infectious disease, such as, for example, HIV/AIDS. The antigen can be, for example, gpl 20 (Klimstra, W. B., et al. 2003. *J Virol* 77:12022-12032; Bernard, K. A., et al. 2000. *Virology* 276:93-103; Byrnes, A. P., et al. 1998. *J Virol* 72: 7349-7356, each of which is incorporated herein by reference in its entirety). Other exemplary antigens include, but are not limited to: gag, pol, env, tat, nef and rev (Lieberman, J. et al. 1997. *AIDS Res Hum Retroviruses* 13(5): 383-392; Menendez-Arias, L. et al. 1998. *Viral Immunol* 11(4): 167-181, each of which is incorporated herein by reference in its entirety).

Examples of viral antigens include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSAI c=term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite antigens include, but are not limited to, polypeptides (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Once an antigen has been identified and/or selected, a polynucleotide that encodes the desired antigen is identified. Preferably the polynucleotide comprises a cDNA. The polynucleotides encoding the antigen are preferably introduced into target dendritic cells using a recombinant virus, more preferably a recombinant lentivirus or gammaretrovirus, including a targeting molecule that binds DC-SIGN as described above. The recombinant virus first binds to the dendritic cell membrane by way of the DC-SIGN targeting molecule, and the viral core containing a polynucleotide encoding the antigen subsequently enters the cytosol. The polynucleotide (e.g., one encoding the antigen) is then preferably integrated into the cell's genome and expressed. If contacted ex vivo, the target dendritic cells are then transferred back to the patient, for example by injection, where they interact with immune cells that are capable of generating an immune response against the desired antigen. In preferred embodiments, the recombinant virus is injected into the patient where it transduces the targeted dendritic cells in situ. The dendritic cells then express the particular antigen associated with a disease or disorder to be treated, and the patient is able to mount an effective immune response against the disease or disorder.

In some embodiments, the recombinant virus contains a polynucleotide sequence encoding more than one antigen, and upon transduction of a target dendritic cell, generates immune responses to the multitude of antigens delivered to the cell. In some embodiments, the antigens are related to a single disease or disorder. In other embodiments, the antigens are related to multiple diseases or disorders.

In embodiments of the invention, DC maturation factors that activate and/or stimulate maturation of the DCs are delivered in conjunction with the recombinant virus carrying the polynucleotide or gene of interest. In some embodiments, the DCs are activated by delivery of DC maturation factors prior to delivery of the virus. In some embodiments, the DCs are activated by delivery of DC maturation factors after delivery of the virus. In some embodiments, the DCs are activated by delivery of DC maturation factors simultaneously with delivery of the virus. In some embodiments, DC maturation factors are provided together with administration of the virus. In other embodiments, DC maturation factors are provided separately from administration of the virus.

In certain embodiments, one or more DC maturation factors can be encoded by one or more genes that are contained in the virus and expressed after the virus transducer a dendritic cell. In some embodiments, the one or more genes encoding DC maturation factors can be included in a viral vector encoding an antigen. In further embodiments, the one or more genes encoding DC maturation factors can be included in a viral vector that encodes more than one antigen. In some embodiments, the one or more genes encoding DC maturation factors can be provided in a separate vector that is co-transfected with the viral vector encoding one or more antigens in a packaging cell line.

In some embodiments, the methods of the present invention can be used for adoptive immunotherapy in a patient. As described above, an antigen against which an immune response is desired is identified. A polynucleotide encoding the desired antigen is obtained and packaged into a recombinant virus. Target dendritic cells are obtained from the patient and transduced with a recombinant virus containing a polynucleotide that encodes the desired antigen. The dendritic cells are then transferred back into the patient.

Vaccination

As discussed above, various engineered targeting molecules that bind the DC-SIGN surface dendritic cell marker are contemplated for use in producing recombinant virus that delivers a gene encoding an antigen to DCs. The virus can be used to transduce DCs in vitro or in vivo for prevention of a disease or disorder. For example, the Sindbis virus envelope glycoprotein can be engineered to bind preferentially to DC-SIGN and used to pseudotype a recombinant virus. A gene encoding an antigen against which an immune response is desired, such as for cancer (for example, Mart-1), or another disease/disorder (such as viral infection) may be delivered to DCs using the methods described herein. In some embodiments, multiple genes encoding multiple antigens can be delivered to DCs using the methods described herein, through the use of multiple viral vectors, or, preferably, a multicistronic vector system. The one or more genes for the one or more antigens may be accompanied by genes encoding stimulatory molecules (such as GM-CSF, IL-2, IL-4, IL-6, IL-7, IL-15, IL-21, IL-23, TNFa, B7.1, B7.2, 4-1BB, CD40 ligand (CD4OL), drug-inducible CD40 (iCD40), and the like) and/or a reporter molecule (such as GFP, luciferase and the like) using multiple vectors or, preferably, a multicistronic vector system.

In some embodiments of the invention, human DCs are generated by obtaining CD34a+ human hematopoietic progenitors and using an in vitro culture method as described elsewhere (e.g., Banchereau et al. Cell 106, 271-274 (2001)). Viruses bearing a targeting molecule that binds DC-SIGN are generated comprising a gene encoding an antigen against which an immune response is desired and are used to transduce human DCs. Transduction specificity and efficiency may be quantified by FACS. Maturation of DCs can be characterized by FACS analysis of up-regulation of surface marker such as MHC II.

In other embodiments, virus may be injected in vivo, where it contacts natural DCs and delivers a polynucleotide of interest, typically a gene encoding an antigen. The amount of viral particles is at least $50 \times 10^6$ TU, and can be at least $1 \times 10^7$ TU, at least $2 \times 10^7$ TU, at least $3 \times 10^7$, at least $4 \times 10^7$ TU, or at least $5 \times 10^7$ TU. At selected intervals, DCs from the recipient's lymphoid organs may be used to measure expression, for example, by observing marker expression, such as GFP or luciferase. T cells from lymph nodes and spleens of virus-treated recipients may be measured from the magnitude and durability of response to antigen stimulation. Tissue cells other than DCs, such as epithelial cells and lymphoid cells, may be analyzed for the specificity of in vivo gene delivery.

It is widely agreed that the most effective potential method to end the AIDS epidemic (and other viral diseases) is a vaccine. To date, no vaccination method against HIV has successfully passed a phase III trial. Thus, there is an urgent need for novel and effective vaccination strategies. In some embodiments of the invention, DC vaccination is used. A gene is cloned encoding a viral protein, such as those described above, into a viral vector. Patients are infected with viruses comprising a targeting molecule that binds DC-SIGN in DCs, preferably with specificity such that undesired side effects are avoided. The targeting molecule can be, for example, an engineered Sindbis virus envelope glycoprotein, and the administration of virus can be carried out, for example, by injection. In an animal model, molecularly cloned HIV reporter viruses (NFNSZ-r-HSAS, NL-r-HSAS) and clinical isolates may be used to challenge the animals by tail vein injection. Evidence of infection may be monitored over time in splenocytes, lymph nodes, and peripheral blood. PCR for HIV-gag protein and FACS for HAS in the reporter viruses may be used to test for viral integration and replication. Productive in situ DC vaccination may increase resistance to a HIV challenge. See Examples 17-20.

In some embodiments, dendritic cells transduced with a recombinant virus as described herein are provided for the prevention of or treatment of a disease or disorder. In preferred embodiments, the dendritic cells express an antigen against which an immune response is desired. The antigen is typically one that is not normally expressed in a dendritic cell but is expressed after the target cell is transduced with the recombinant virus containing a polynucleotide encoding the antigen. In some embodiments, the dendritic cells further express a DC maturation factor which is provided to the dendritic cell by a recombinant virus as described herein.

In some aspects of the invention, an adjuvant is administered in conjunction with a recombinant virus of the invention. The adjuvant may be administered with the recombinant virus, before the recombinant virus, or after the recombinant virus.

A variety of adjuvants can be used in combination with the recombinant virus of the invention to elicit an immune response to the antigen encoded to the recombinant virus. Preferred adjuvants augment the intrinsic response to an antigen without causing conformational changes in the antigen that affect the qualitative form of the response. Preferred adjuvants include alum, 3 De-O-acylated monophosphoryl lipid A (MPL) (see GB 2220211). QS21 is a triterpene glycoside or saponin isolated from the bark of the Quillaja Saponaria Molina tree found in South America (see Kensil et al., in *Vaccine Design: The Subunit and Adjuvant Approach* (eds. Powell & Newman, Plenum Press, NY, 1995); U.S. Pat. No. 5,057,540). Other adjuvants are oil in water emulsions (such as squalene or peanut oil), optionally in combination with immune stimulants, such as monophosphoryl lipid A (see Stoute et al., *N. Engi. J. Med.* 336, 86-91 (1997)). Another adjuvant is CpG (*Bioworld Today*, Nov. 15, 1998). Alternatively, AP can be coupled to an adjuvant. For example, a lipopeptide version of AP can be prepared by coupling palmitic acid or other lipids directly to the N-terminus of AP as described for hepatitis B antigen vaccination (Livingston, *J. Immunol.* 159, 1383-1392 (1997)). However, such coupling should not substantially change the conformation of AP so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-al anyl-D-isoglutaminyl-L-alaninel-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Another class of preferred adjuvants is saponin adjuvants, such as Stimulon™ (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

An adjuvant can be administered with the recombinant virus of the invention as a single composition, or can be administered before, concurrent with or after administration of the recombinant virus of the invention. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously. Preferred combinations include alum with MPL, alum with QS21, MPL with QS21, and alum, QS21 and MPL together. Also, Incomplete Freund's ajuvant can be used (Chang et al., *Advanced Drug Delivery Reviews* 32, 173-186 (1998)), optionally in combination with any of alum, QS21, and MPL and all combinations thereof.

Pharmaceutical Compositions and Kits

Also contemplated herein are pharmaceutical compositions and kits containing a recombinant virus provided herein and one or more components. Pharmaceutical compositions can include a recombinant virus provided herein and a pharmaceutical carrier. Kits can include the pharmaceutical compositions and/or combinations provided herein, and one or more components, such as instructions for use, a device for administering a compound to a subject, and a device for administering a compound to a subject.

1. Pharmaceutical Compositions

Provided herein are pharmaceutical compositions containing a virus provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

2. Kits

The recombinant viruses provided herein can be packaged as kits. Kits can optionally include one or more components such as instructions for use, devices, and additional reagents, and components, such as tubes, containers and syringes for practice of the methods. Exemplary kits can include the viruses provided herein, and can optionally include instructions for use, a device for detecting a virus in a subject, a device for administering the virus to a subject, and a device for administering a compound to a subject.

Kits comprising polynucleotides encoding a gene of interest (typically an antigen) are also contemplated herein. In some embodiments, the kit includes at least one plasmid encoding virus packaging components and vector encoding a targeting molecule that is engineered to bind dendritic cells, preferably with specificity. In some embodiments, the kit includes at least one plasmid encoding virus packaging components, a vector encoding a targeting molecule that is engineered to bind dendritic cells and a vector encoding at least one DC maturation factor.

Kits comprising a viral vector encoding a gene of interest (typically an antigen) and optionally, a polynucleotide sequence encoding a DC maturation factor are also contemplated herein. In some embodiments, the kit includes at least one plasmid encoding virus packaging components and vector encoding a targeting molecule that is engineered to bind dendritic cells.

In one example, a kit can contain instructions. Instructions typically include a tangible expression describing the virus and, optionally, other components included in the kit, and methods for administration, including methods for determining the proper state of the subject, the proper dosage amount, and the proper administration method, for administering the virus. Instructions can also include guidance for monitoring the subject over the duration of the treatment time.

Kits provided herein also can include a device for administering a virus to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as a DC activator or stimulator, to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically the device for administering the compound of the kit will be compatible with the desired method of administration of the compound.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

Example 1

Engineering of a DC-Specific Targeting Molecule

Figure 3A:
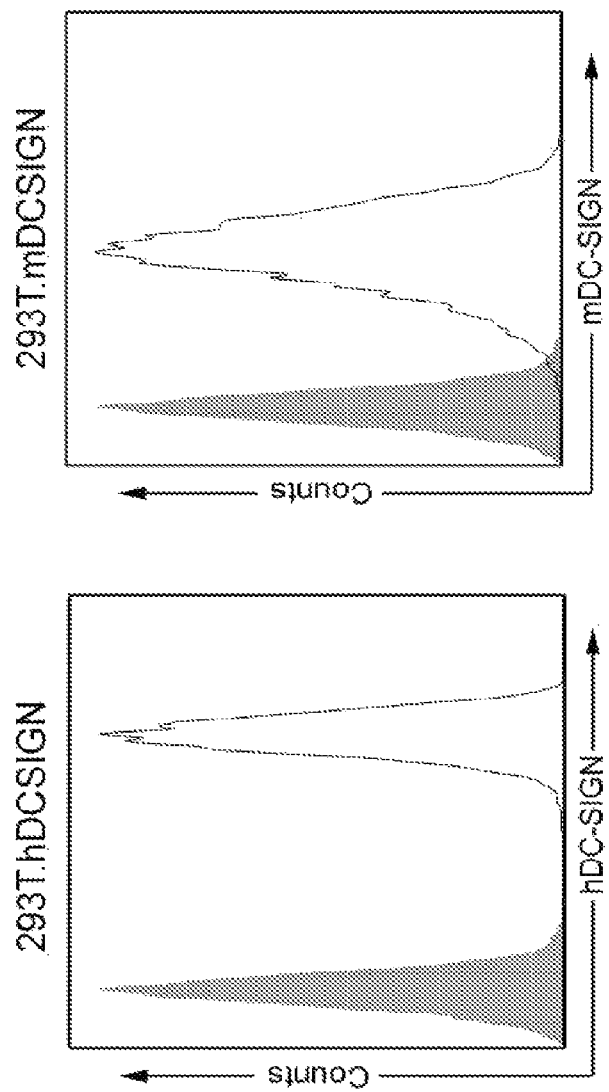
FIG. 3A shows flow cytometric analysis of constructed target cell lines 293T.hDCSIGN expressing human DC-SIGN, and 293T.mDCSIGN expressing murine DC-SIGN. Solid line: expression of DC-SIGN in target cell lines; shaded area: background staining in 293T cells.

Lentiviral vectors can be rationally engineered to make them capable of transducing DCs in a cell-specific manner. Certain subsets of DCs bear on their surface the DC-SIGN protein (Geijtenbeek, T. B., et al. 2000; Geijtenbeek, T. B., et al. 2000, supra), a C-type lectin-like receptor capable of rapid binding and endocytosis of materials (Geijtenbeek, T. B., et al. 2004, supra.), which can be used as a targeting receptor on DCs. Sindbis virus (SV)—a member of the *Alphavirus* genus and the Togaviridae family—is able to infect DCs through DC-SIGN (Klimstra, W. B., et al. 2003. *J. Virol.* 77: 12022-12032, which is incorporated herein by reference in its entirety). However, the canonical viral receptor for the laboratory strain of SV is cell-surface heparan sulfate (HS), which is expressed by many cell types (Strauss, J. H., et al. 1994. *Arch. Virol.* 9: 473-484; Byrnes, A. P., and D. E. Griffin. 1998. *J. Virol.* 72: 7349-7356, each of which is incorporated herein by reference in its entirety). Taking advantage of the physical separation of the two receptor-binding sites on the SV envelope glycoprotein (hereafter designated as SVG), the receptor was engineered to be blind to its canonical binding target HS and to leave intact its ability to interact with DC-SIGN (FIG. 1). Once it is incorporated onto a viral surface, this mutant glycoprotein is able to mediate infection of DCs but not other cells.

The cDNA for wild-type SVG was obtained from the laboratory of Dr. J. H. Strauss laboratory at the California Institute of Technology and cloned into the pcDNA3 vector (Invitrogen) by PCR to generate plasmid pSVG. A ten-residue tag (MYPYDVPDYA) sequence was inserted into E2 protein between amino acids 71 and 74 by PCR mutagenesis to disrupt the HS binding site (Karavans, G., et al. 1998. *Crit Rev Oncol Hemat* 28: 7-30; Lavillete, D., et al. 2001. *Curr Opin Biotech* 12: 461-466; Russell, S. J. and F. L. Cosset. 1999. *J Gene Med* 1: 300-311; Sandrin, V., et al. 2003. *Curr Top Microbiol* 281: 137-178; Verhoeyen, E. and F. L. Cosset. 2004. *J Gene Med* 6: S83-S94, each of which is incorporated herein by reference in its entirety). An available antibody against the inserted tag sequence provided the ability to monitor the expression of the modified SVG. In order to further decrease the HS-specific infection, several critical residues were identified as being involved in binding to HS molecules (Coffin, J. M., et al. 1997. *Retroviruses*. New York: Cold Spring Harbor Laboratory Press; Battini, J. L., et al. 1998. *J Virol* 72:428-435; Valsesiawittmann, S., et al. 1994. *J Virol* 68:4609-4619; Wu, B. W., et al. 2000. *Virology* 269: 7-17; Cosset, F. L., et al. 1995. *J Virol* 69:6314-6322; Kayman, S. C., et al. 1999. *J Virol* 73: 1802-1808; Lorimar, I. A. J. and S. J. Lavictoire. 2000. *J Immunol Methods* 237:147-157; Barnett, A. L., et al. 2001. *Proc Nat Acad Sci USA* 98: 4113-4118; Benedict, C. A., et al. 2002. *Hum Gene Ther* 10:545-557; Gollan, T. J. and M. R. Green. 2002. *J Virol* 76:3558-3563, each of which is incorporated herein by reference in its entirety). Two such residues were mutated into alanines (157KE158 to 157AA158).

An additional deletion was introduced to the E3 glycoprotein of SVG to remove amino acids 61-64. This modified SVG was designated as SVGmu (SEQ ID NO: 11). The cDNA for SVGmu was cloned downstream of the CMV promoter in the pcDNA3 vector (designated as pSVGmu, SEQ ID NO: 3).

Example 2

Preparation of Recombinant Virus Containing the DC-Specific Targeting Molecule

Preparation of the recombinant SVGmu-pseudotyped lentivirus was conducted by standard calcium phosphate-mediated transient transfection of 293T cells with the lentiviral vector FUGW (SEQ ID NO:1) or its derivatives, the packaging constructs encoding gag, pol and rev genes, and pSVGmu (Example 1). FUGW is a self-inactivating lentiviral vector carrying the human ubiquitin-C promoter to drive the expression of a GFP reporter gene (Lois, C., et al. 2002. *Science* 295: 868-872, which is incorporated herein by reference in its entirety). The lentiviral transfer vectors (FUGW and its derivatives) used in these studies are third generation HIV-based lentiviral vectors, in which most of the U3 region of the 3' LTR is deleted, resulting in a self-inactivating 3'-LTR (SIN).

For the transient transfection of 293T cells, 293T cells cultured in 6-cm tissue culture dishes (Coming or BD Biosciences) were transfected with the appropriate lentiviral transfer vector plasmid (5 jig), along with 2.5 [ig each of the envelope plasmid (SVG, SVGmu, Eco, or VSVG) and the packaging plasmids (pMDLg/pRRE and pRSV-Rev). The viral supernatants were harvested 48 and 72 hours post-transfection and filtered through a 0.45-pm filter (Coming). To prepare concentrated viral vectors for in vivo study, the viral supernatants were ultracentrifugated (Optima L-80 K preparative ultracentrifuge, Beckman Coulter) at 50,000×g for 90 min. The pellets were then resuspended in an appropriate volume of cold PBS.

The resultant viruses pseudotyped with SVGmu are hereafter referred to as FUGW/SVGmu. Control viruses enveloped with the wild-type SVG glycoprotein are hereafter referred to as FUGW/SVG.

Example 3

Confocal Imaging of Packaged Recombinant Virus

GFP-vpr-labeled lentivectors were produced as described in Example 2, except with use of FUW lentivector (which does not contain the GFP reporter gene) and with a separate plasmid encoding GFP-vpr (2.5 lug). Fresh viral supernatant was overlaid on polylysine-coated coverslips in a 6-well culture dish and centrifuged at 3,700×g at 4° C. for 2 hours using a Sorvall Legend RT centrifuge. The coverslips were rinsed with cold PBS twice and immunostained by anti-HA-biotin antibody (Miltenyi Biotec) and Cy5-streptavidin (Invitrogen). Fluorescent images were taken by a Zeiss LSM 510 laser scanning confocal microscope equipped with filter sets for fluorescein and Cy5. A plan-apochromat oil immersion objective (63×/1.4) was used for imaging.

FIG. 2 shows the results of the confocal imaging of the recombinant virus produced by the protocol. (The scale bar represents 2 um.) Particles in the "GFP" slide are stained green, particles in the "SVGmu" slide are stained red, and particles in the "Merged" slide are stained green where only GFP is expressed, red where only SVGmu is expressed, and yellow/yellow-orange where GFP and SVGmu are both expressed. Over 90% of the GFP-labeled particles contained SVGmu. Thus, the production of lentiviral particles displaying SVGmu was confirmed through confocal imaging.

Example 4

Preparation of DC-Sign Cell Lines

To facilitate the study of targeted transduction, DC-SIGN cell lines expressing human DC-SIGN (hereafter referred to as 293T.hDCSIGN) and murine DC-SIGN (hereafter referred to as 293T.mDCSIGN) were constructed. The 293T.hDC-SIGN and 293T.mDCSIGN cell lines were generated by stable transduction of parental 293T cells with a VSVG-pseudotyped lentivector. The cDNAs for human DC-SIGN and murine DC-SIGN were amplified from plasmids pUNO-hDCSIGN1Aa and pUNO-mDCSIGN (InvivoGene) and cloned downstream of the human ubiquitin-C promoter in the lentiviral plasmid FUW to generate FUW-hDCSIGN (SEQ ID NO: 5) and FUW-mDCSIGN (SEQ ID NO: 6), respectively. The lentivectors were then pseudotyped with VSVG and used to transduce 293T cells. The resulting cells were subjected to antibody staining (anti-human DC-SIGN antibody from BD Biosciences and anti-murine DC-SIGN from eBioscience) and cell sorting to yield a uniform population of DC-SIGN$^+$ 293T.hDCSIGN and mDC-SIGN$^+$ 293T.mDC-SIGN cell lines Flow cytometry showed that DC-SIGN was expressed in virtually all of the 293T.hDCSIGN and 293T.mDCSIGN cells of the cell lines (FIG. 3A). In each diagram, the solid lines (unfilled area) represents expression of DC-SIGN in the 293T DC-SIGN cell lines, and the shaded area represents the background staining of non-transduced 293T cells.

Example 5

Evaluation of the DC-Sign Specific Recombinant Virus by Transduction of DC-Sign Cell Lines To assess the transduction efficiency and specificity of FUGW/SVG or FUGW/SVGmu (Example 2), the viruses were used to transduce the 293T.hDCSIGN and 293T.mDC-SIGN cell lines (Example 4). Transduction efficiency was measured by GFP expression within the cell lines.

Figure 3B:
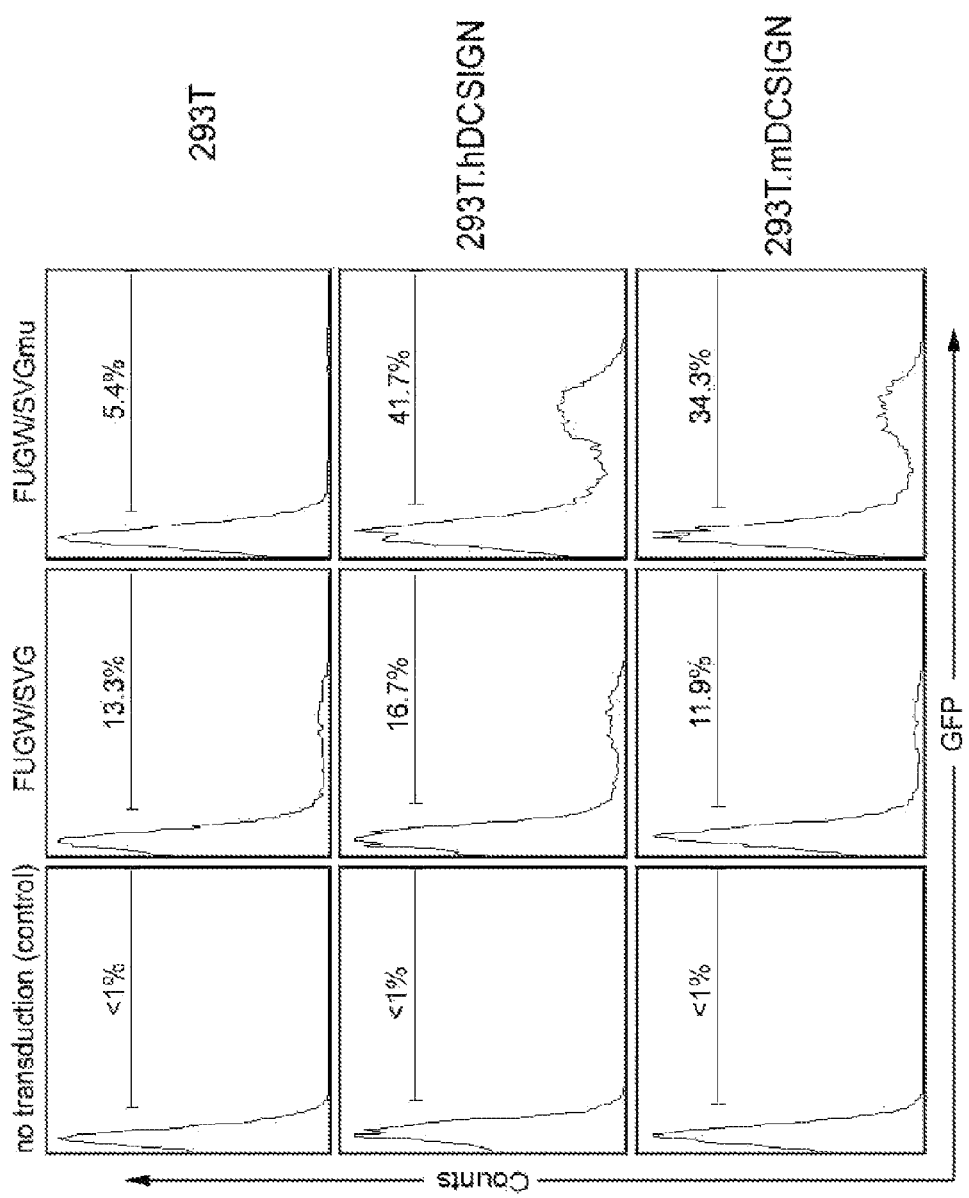
FIG. 3B shows flow cytometry results for detection of GFP expressed in 293T cells transduced with lentivector enveloped with wild-type Sindbis glycoprotein (FUGW/SVG) or mutant Sindbis glycoprotein (FUGW/SVGmu). One milliliter of fresh viral supernatants of FUGW/SVG and FUGW/SVGmu were used to transduce 293T cells ($2 \times 10^5$) expressing human DC-SIGN (293T.hDCSIGN) or murine DC-SIGN (293T.mDCSIGN). The parental 293T cells lacking the expression of DC-SIGN were included as controls. As illustrated, lentivector enveloped with the mutant Sindbis virus glycoprotein (SVGmu) is able to specifically transduce 293T cells expressing human or mouse DC-SIGN. The specific transduction titer of FUGW/SVGmu was estimated to be approximately $1 \times 10^6$ TU/ml for 293T.hDC-SIGN and approximately $0.8 \times 10^6$ TU/ml for 293T.mDC-SIGN.

Target cells (293T.hDCSIGN, 293T.mDCSIGN, or 293T cells; 0.2×10$^6$ per well) were seeded in a 24-well culture dish (Coming or BD Biosciences) and spin-infected with viral supernatants (1 ml per well) at 2,500 rpm and 30° C. for 90 min by using a Sorvall Legend centrifuge. Subsequently, the supernatants were replaced with fresh culture medium and incubated for 3 days at 37° C. with 5% of $CO_2$. The percentage of GFP$^+$ cells was measured by flow cytometry. The transduction titer was determined by the dilution ranges that exhibited a linear response Flow cytometry showed that FUGW/SVG (containing the wild-type SVG envelope glycoprotein) had similar transduction efficiency (11-16% transduction) towards the three target cell lines (293T, 293T.hDCSIGN, and 293T.mDCSIGN) (FIG. 3B). This indicates that that SVG has broad specificity and the presence of DC-SIGN on the cell surface does not markedly alter the transduction ability of a SVG-pseudotyped lentiviral vector. In contrast, the FUGW/SVGmu vector (containing the mutant SVG envelope glycoprotein) could specifically transduce 293T.hDCSIGN and 293T.mDCSIGN cells with a 42% and 34% transduction efficiency, respectively, but not the 293T cells (FIG. 3B). These results demonstrate that a pseudotyped lentiviral vector displaying SVGmu can specifically transduce cells expressing either human or murine DC-SIGN. Furthermore, the mutant SVG gave more efficient transduction of DC-SIGN-expressing cells than of wild type SVG.

The stable integration of the FUGW lentiviral vector in the transduced cells was confirmed by PCR analysis of the genomic integration of the GFP reporter gene. To demonstrate that the specific transduction was mediated by DC-SIGN, the addition of soluble anti-human DC-SIGN antibody to the FUGW/SVGmu viral supernatant before its exposure to 293T.hDCSIGN cells reduced the transduction efficiency (data not shown). The specific titer of FUGW/SVGmu for 293T.mDCSIGN was estimated to be 1×10$^6$ TU (Transduction Units)/ml. The titer of FUGW/SVGmu for 293T.hDC-SIGN was estimated to be 1-2×10$^6$ TU/ml.

Example 6

Evaluation of the Recombinant Virus In Vitro

To investigate the specificity of the engineered lentivector for transduction of dendritic cells (DCs) expressing DC-SIGN, total bone marrow (BM) cells were isolated from mice and transduced directly with the FUGW/SVGmu viral vector (Example 2). A protocol to generate mouse DCs from progenitors grown in BM cultures was adapted for use in the experiment (Buchholz, C. J., et al. 1998. *Nat Biotech* 16:951-954, which is incorporated herein by reference in its entirety).

Total bone marrow cells were harvested from B6 female mouse (Charles River Breeding Laboratories), and BMDCs were generated as described elsewhere (Yang, L. and D. Baltimore. 2005. *Proc. Natl. Acad. Sci. USA* 102: 4518-4523, which is incorporated herein by reference in its entirety). Either total BM cells or BMDCs were plated in a 24-well culture dish (2×10$^6$ cells per well), and spin-infected with viral supernatant (1 ml per well) at 2,500 rpm and 30° C. for 90 min using a Sorvall RT7 centrifuge. After the spin, the supernatant was removed and replaced with fresh RPMI medium containing 10% FBS and GM-CSF (1:20 J558L conditioned medium). The cells were cultured for 3 days and were analyzed for GFP expression using flow cytometry.

Figure 4A:
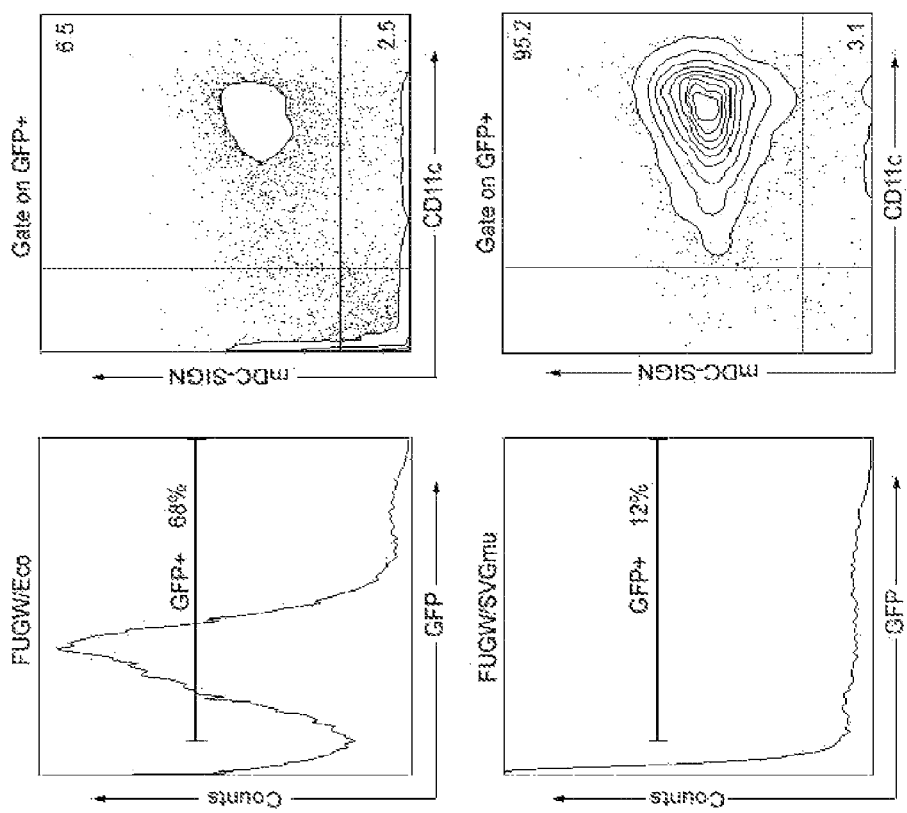
FIG. 4A shows flow cytometry results that illustrate the ability of the FUGW lentivirus enveloped with the mutant Sindbis glycoprotein (FUGW/SVGmu) to specifically transduce mouse dendritic cells expressing DC-SIGN in a primary mixed bone marrow culture. Whole bone marrow cells isolated from B6 mice were exposed to the fresh viral supernatant of FUGW/SVGmu. The FUGW lentivector pseudotyped with the ecotropic glycoprotein (FUGW/Eco) was included as a non-targeting control. Surface antigens of the GFP-positive cells were assessed by staining with anti-CD11c and anti-DC-SIGN antibodies.

The BM cells isolated from mice were transduced directly with either FUGW/SVGmu viral vector or with a control vector. For the control, an ecotropic murine leukemia virus glycoprotein (Eco)-enveloped lentivector (FUGW/Eco) was used; vector enveloped with Eco can infect rodent cells with a broad specificity. Three days post-infection, the transduction efficiency was analyzed by flow cytometry (FIG. 4A). Approximately 9% of the cells in the mixed BM cultures were DCs (as indicated by the expression of CD11c), of which most (approximately 80%) were DC-SIGN high (data not shown). It was observed that 12% of the total BM cells were GFP positive (GFP$^+$) upon FUGW/SVGmu transduction (FIG. 4A). When gated on GFP$^+$ cells, it was observed that up to 95% of the transduced cells were DC-SIGN and CD11c double-positive (DC-SIGN$^+$CD11c$^+$), indicating that FUGW/SVGmu specifically transduces DCs expressing DC-SIGN and not other cell types in the bone marrow. In contrast, although 68% of total BM cells were GFP-positive after exposure to FUGW/Eco, only 9% of the transduced cells were DCs, within which 6.5% were DC-SIGN$^+$.

Figure 4B:
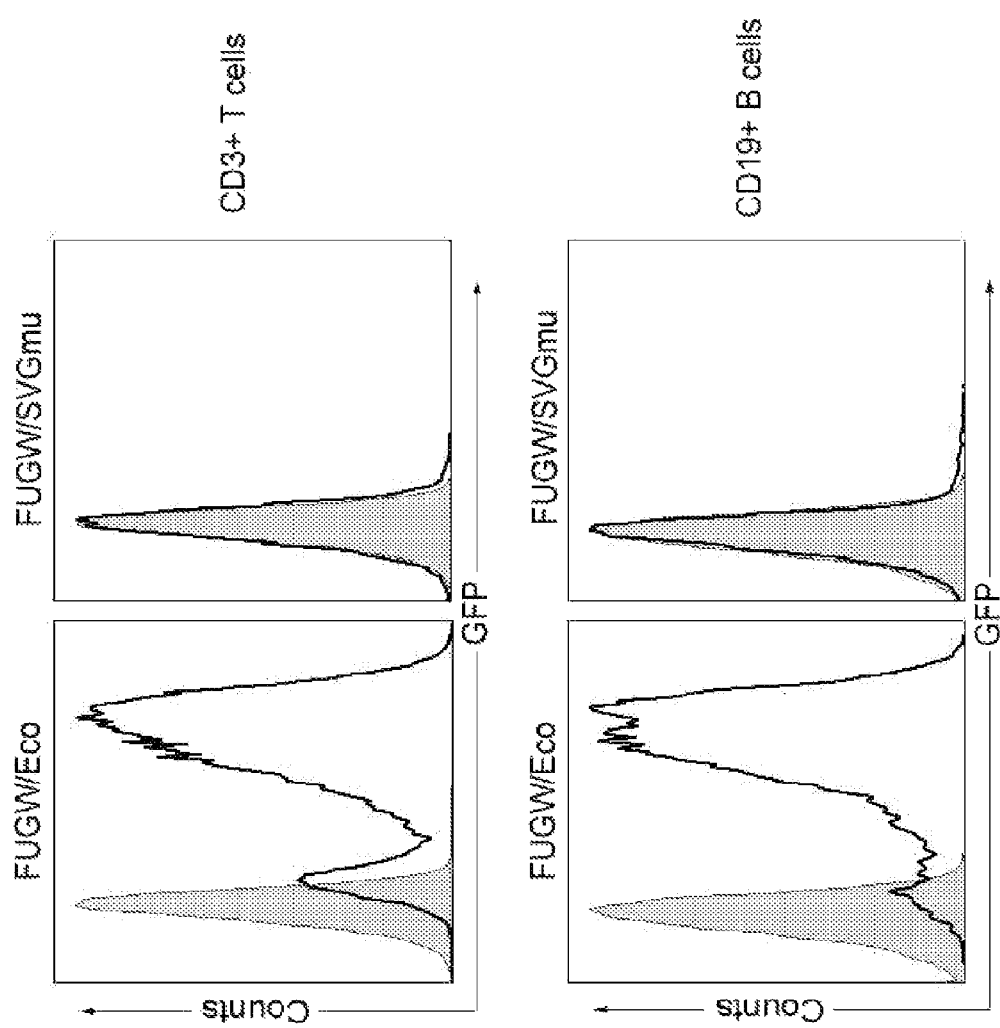
FIG. 4B shows flow cytometry results indicating that FUGW lentivirus enveloped with the mutant Sindbis glycoprotein (FUGW/SVGmu) does not transduce other cell types including primary T cells ($CD3^+$, top panel) and B cells ($CD19^\pm$, bottom panel). Primary $CD3^+$ T cells and $CD19^+$ B cells were isolated from the mouse spleen and transduced with the fresh viral supernatant of either the targeting FUGW/SVGmu or non-targeting FUGW/Eco vector. GFP expression was analyzed by flow cytometry. Solid line: cells exposed to indicated lentiviral vector; shaded area: cells without transduction (as a negative control).

The stable transduction of FUGW/SVGmu was verified by Alu PCR analysis (Butler, S. L., et al. 2001. *Nat. Med.* 7: 631-634, which is incorporated herein by reference in its entirety) of the genomic integration of the LTR of the lentivector backbone. In addition, we used FUGW/SVGmu to transduce primary T and B cells harvested from mouse spleen and virtually no transduction was detected (FIG. 4B), indicating remarkable transduction specificity.

Figure 5:
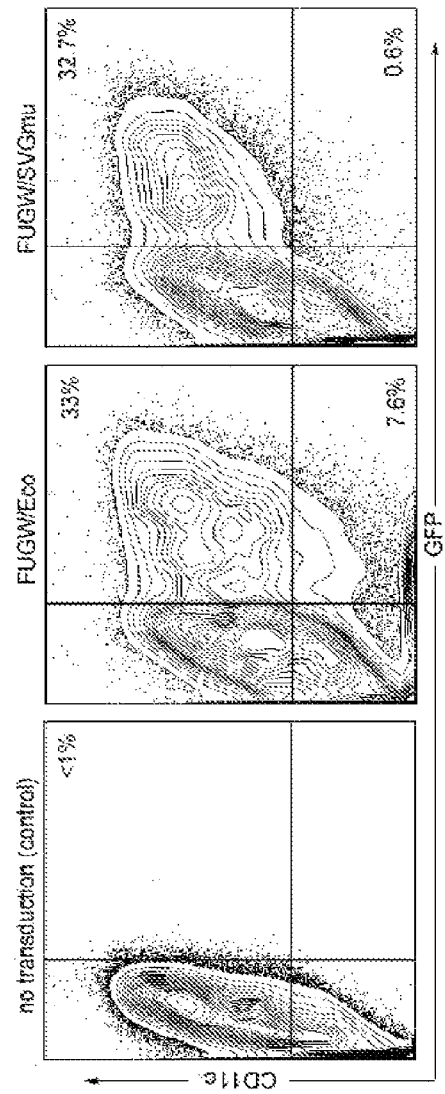
FIG. 5 shows flow cytometry results that illustrate the ability of the FUGW lentivirus enveloped with the mutant Sindbis glycoprotein (FUGW/SVGmu) to specifically transduce bone marrow-derived DCs (BMDCs). BMDCs were generated by culturing freshly isolated bone marrow cells in the presence of cytokine GM-CSF for 6 days. The cells were then transduced with the fresh viral supernatant of either the targeting FUGW/SVGmu or non-targeting FUGW/Eco vector. GFP and CD11c expression were measured by flow cytometry.

The efficiency of the lentivector bearing SVGmu to transduce in vitro-cultured, bone marrow (BM)-derived DCs (BMDCs) was also tested. Bone marrow (BM)-derived DCs (BMDCs) were generated as described above by culturing in the presence of granulocyte-macrophage colony-stimulating factor (GM-CSF) for 6 days. The cells were then exposed to either the FUGW/SVGmu or FUGW/Eco lentivector. Flow cytometry of the BMDCs on day 3 post-transduction showed that FUGW/Eco transduced both CD11c$^+$ DCs (33%) and CD11c$^-$ cells (7.6%) (FIG. 5), which is consistent with the wide tropism of Eco. On the contrary, FUGW/SGVmu only transduced CD11c⁺ DCs (32.7%), and no GFP⁺ cells were detected among the CD11c⁻ cells (FIG. 5), indicating that FUGW/SVGmu can specifically modify BMDCs.

These results thus collectively demonstrate that the engineered recombinant lentivectors bearing SVGmu can specifically transduce DCs in vitro and that the targeted transduction is correlated with the expression of DC-SIGN on the surface of DCs.

Example 7

Effect of Recombinant Virus on Activation of Dendritic Cells In Vitro

The recombinant lentivirus was further examined to determine whether it could specifically target, transduce and activate DCs into mature DCs. The surface up-regulation of the co-stimulatory molecule B7.2 (CD86) and the MHC class II molecule I-A$^b$, which are considered to be signatures of DC activation (Steinman, R. M., et al. 2003. *Annu. Rev. Immunol.* 21: 685-711, which is incorporated herein by reference in its entirety), was measured in DCs exposed to recombinant virus. BMDCs were generated and infected with FUGW/SVGmu as described in Example 6. LPS at a concentration of 1 µg/ml was also added overnight for further activation of transduced BMDCs.

Figure 6:
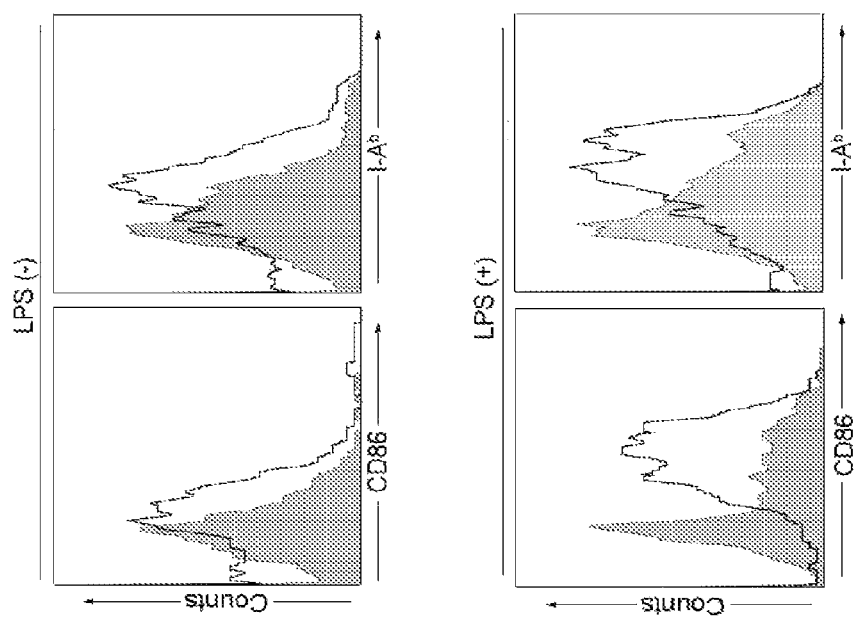
FIG. 6 shows activation of BMDCs after targeted transduction with FUGW/SVGmu. DC activation was assessed by analyzing the surface expression of CD86 and I-$A^b$ using flow cytometry. The addition of LPS (1 Kg/ml) overnight was used as a synergistic stimulator for the activation of transduced BMDCs. Shaded area: GFP negative (untransduced); solid line: GFP positive (transduced).

Flow cytometry of BMDCs 3 days post-transduction showed that treatment with FUGW/SVGmu elevated the expression of DC activation markers, CD86 and I-A$^b$, on GFP positive DCs, as compared to GFP negative DCs (FIG. 6, top panel). The shaded area indicates GFP negative (untransduced) cells, and the solid line (unfilled area) indicates GFP positive (transduced) cells. It was observed that the targeted transduction of BMDCs synergized with lipopolysaccharide (LPS) treatment to further mature DCs (FIG. 6, bottom panel). This indicates that the targeted transduction can either work alone or in combination with other DC maturation factors to induce DC activation.

Example 8

Targeting of Dendritic Cells In Vivo by Recombinant Virus

The proof of whether this methodology can be used for vaccination can be examined by in vivo experimentation. To test whether engineered lentivectors bearing SVGmu could target DCs in vivo, the recombinant and concentrated lentivector FUGW/SVGmu (50×10⁶ TU resuspended in 200 IA PBS) was injected subcutaneously into the left flank of the C57BL/6 female mice (B6, Charles River Breeding Laboratories) close to an inguinal lymph node (within 1 cm range). The left inguinal lymph node and the equivalent lymph node at the opposite site were isolated for size examination on day 3 post-injection. The cells were harvested from these nodes and their total numbers were counted. The percentage of GFP⁺ DCs was analyzed by flow cytometry on cells stained with anti-CD11c antibody (BD Biosciences).

Figure 7A:
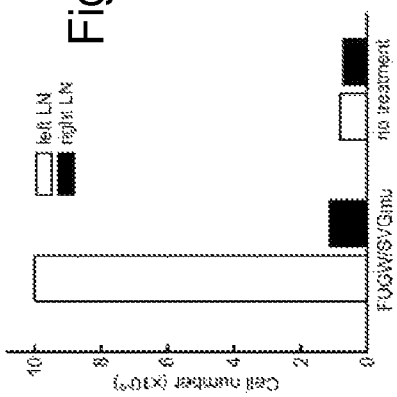
FIG. 7A, FIG. 7B and FIG. 7C illustrate targeting of DCs in vivo using FUGW/SVGmu lentivirus. B6 mice were injected with $50\times10^6$ TU of FUGW/SVGmu and analyzed 3 days later. Non-immunized mice were included as a control.
Figure 7B:
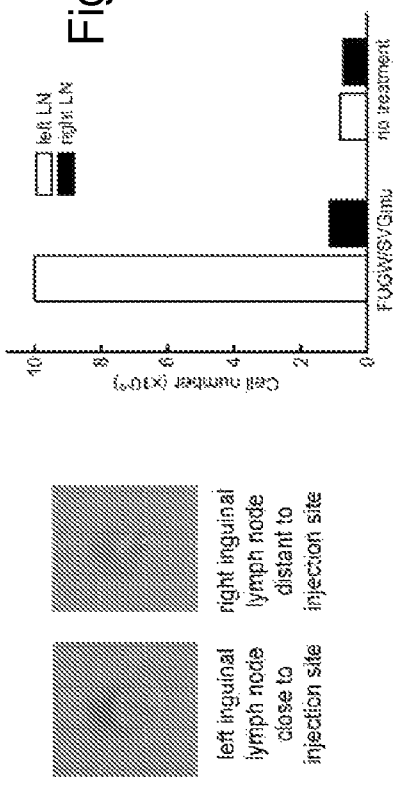

On day 3, a significant enlargement of the left inguinal lymph node close to the injection site was observed (FIG. 7A, left image), and the cell number in this lymph node increased more than 10-fold, compared with the equivalent lymph node at the opposite side or lymph nodes from a naïve mouse (FIG. 7B). This indicates that vector administration can enhance trafficking and proliferation of lymphocytes in a nearby lymph node.

Figure 7C:
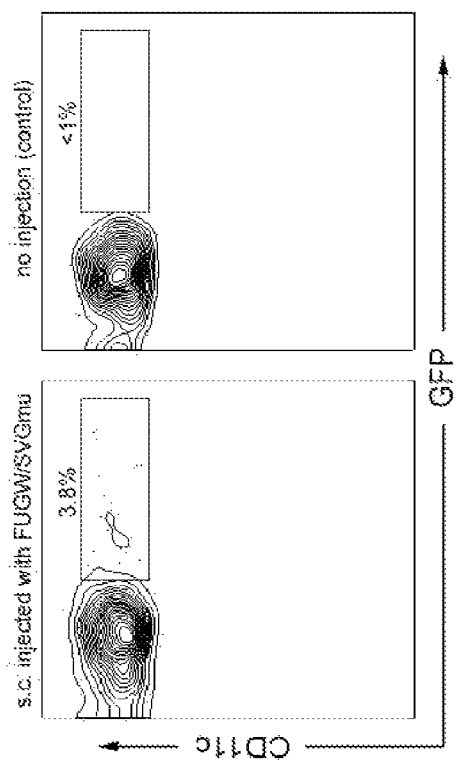

Flow cytometry indicated that approximately 3.8% of the total CD11c⁺ cells in the left inguinal lymph node cells were GFP⁺ DCs (FIG. 7C), which appear to have migrated from the injection site. This is considered a remarkably large effect from one subcutaneous injection of vector and demonstrates that the recombinant virus is effectively infecting DCs in vivo.

Example 9

Evaluation of the Specificity of Recombinant Virus by In Vivo Transduction

Figure 22A:
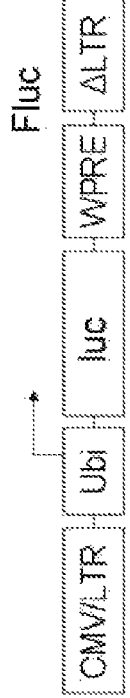
FIG. 22A provides a schematic representation of a DC-targeted lentivector encoding an imaging gene firefly luciferase (Luc), designated as Fluc/SVGmu.

To examine the in vivo specificity of the DC-targeted lentivector, a lentiviral vector encoding a firefly luciferase was constructed. The cDNA of firefly luciferase was amplified from pGL4.2LucP (Promega) and cloned into FUGW (Lois, C. et al. 2002. supra.) to replace GFP, yielding the construct Fluc (SEQ ID NO: 4) (FIG. 22A). The luciferase reporter gene was then used to visualize the in vivo transduction of the tissue cells using standard protocols of bioluminescence imaging (BLI).

Figure 22B:
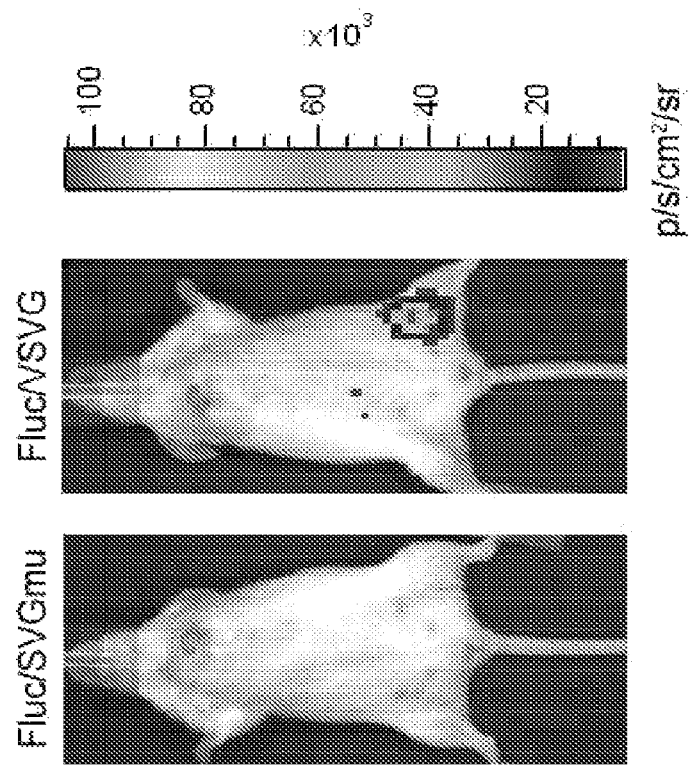
FIG. 22B illustrates bioluminescence imaging of mice injected subcutaneously with $50\times10^6$ TU of either the DC-targeting Fluc/SVGmu lentivector (shown in FIG. 25A) or a non-targeting Fluc/VSVG lentivector. The representative image was obtained at day 30 post-injection using IVIS200® (Xenogen).

The recombinant lentivector (hereafter referred to as Fluc/SVGmu) was injected subcutaneously at the left flank of the mouse. In another mouse, a lentivector pseudotyped with vesicular stomatitis viral glycoprotein (hereafter referred to as Fluc/VSVG) was injected as a non-specific vector control. Vector-treated mice were then imaged non-invasively using BLI. Fluc/VSVG-treated mice had a strong and permanent signal at the injection site, indicating that non-specific tissues were transduced to express luciferase (FIG. 22B). This is consistent with the fact that VSVG-enveloped virus has broad specificity. In contrast, no significant signal was detected at the injection site of Fluc/SVGmu-treated mice (FIG. 22B), indicating that the lentivector bearing SVGmu had a relatively stringent target specificity. At no time was luminescence signal able to be detected in the targeted mice, likely due to the rare and sparse distribution of the DCs, which is beyond the sensitivity of the current BLI method.

After one month, the mice injected with Fluc/SVGmu were subjected to biodistribution analysis by quantitative RT-PCR and no detectable copy of the lentivector was observed in all isolated organs (heart, liver, spleen, kidney, gonad, lung, skin, lymph node), verifying the lack of non-specific infection in the animals and thus the specificity of the targeted vector for DCs.

Example 10

In Vitro Antigen Delivery by Recombinant Virus

Figure 8:
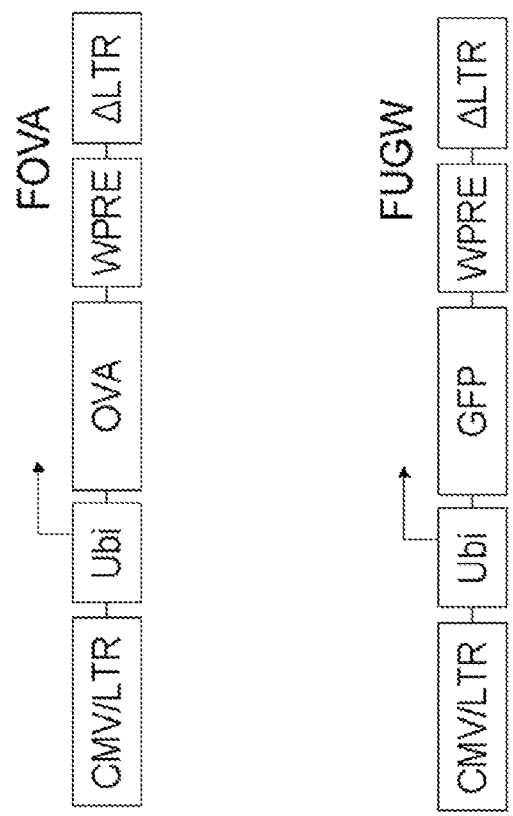

To determine whether the targeted transduction of DCs by a recombinant lentivector could be used to effectively deliver antigen genes to DCs for stimulation of antigen-specific CD8⁺ and CD4⁺ T cell responses, a lentivector expressing the model antigen, chicken ovalbumin (OVA), was constructed. In C57BL/6J (B6) mice, OVA is a well-characterized target antigen for the CD8⁺ T-cell receptor OT1, which specifically binds OVA257-269 (designated as OVAp), and for the CD4⁺ T-cell receptor OT2, which specifically binds OVA323_339 (designated as OVAp*) (Yang, L. and D. Baltimore. 2005. *Proc. Natl. Acad. Sci. USA* 102: 4518-4523, which is incorporated by reference in its entirety). The lentivector expressing OVA (FOVA (SEQ ID NO:2), FIG. 8, top) was constructed from FUGW (FIG. 8, bottom) by replacing the GFP with the cDNA of chicken ovalbumin.

The BMDCs (Example 6) were transduced on day 6 of culture with either recombinant lentivirus FOVA/SVGmu or control recombinant lentivirus FUGW/SVGmu (encoding a non-relevant reporter gene GFP). The day 6 BMDCs were spin-infected with viral supernatant, and cultured for an additional 3 days. On day 9, the non-adherent cells were collected and re-cultured in RPMI medium containing 10% FBS, GM-CSF (1:20 J558L conditional medium), and 1 pg/ml LPS (Sigma). On day 10, the cells were collected and used for T cell stimulation. The modified BMDCs were designated as DC/FOVA and DC/FUGW, depending on the lentivector used for transduction. In parallel, non-adherent cells were collected from non-transduced day 9 BMDC culture, and were re-cultured in the same medium (RPMI containing 10% FBS, GM-CSF and LPS). On day 10, the cells were collected and loaded with either OVAp (OVA257-269, specifically bound by OT1 T-cell receptors, hereafter referred to as DC/OVAp) or OVAp* ($OVA_{323-339}$, specifically bound by OT2 T-cell receptors, hereafter referred to as DC/OVAp*), and used as positive controls for T cell stimulation. To examine the ability of vector-transduced BMDCs to process and present the transgenic OVA antigen, spleen cells were collected from the OT1 and OT2 transgenic mice and cultured with the lentivector-transduced BMDCs, or BMDCs loaded with either OVAp or OVAp*, at the indicated ratio. Three days later, the supernatant was collected and assayed for IFN-y production using ELISA and the cells were collected and analyzed for their surface activation markers using flow cytometry. T cell proliferation was assayed using [$^3$H] thymidine incorporation.

Figure 9:
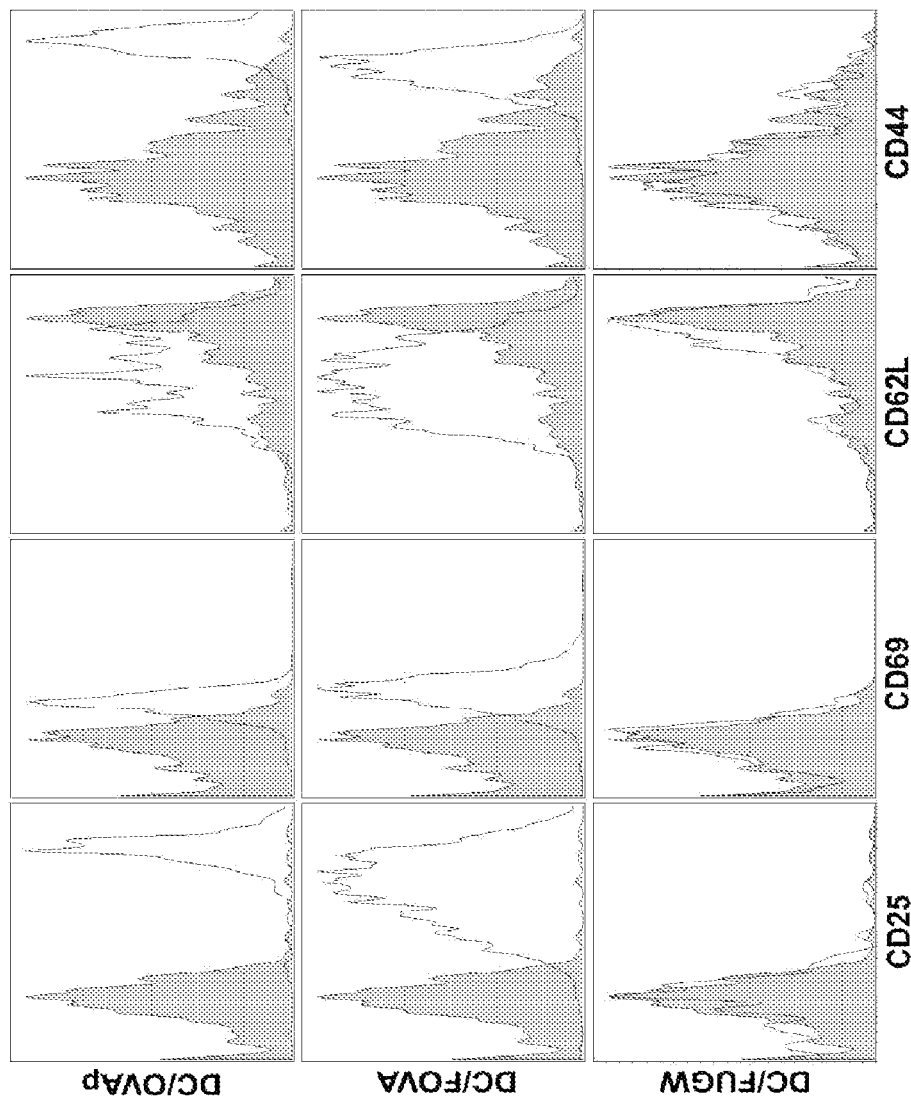
FIG. 9 illustrates in vitro stimulation of $CD8^+$ OT1 T cells by dendritic cells that were transduced with the FOVA/SVGmu (DC/FOVA) or FUGW/SVGmu lentivector (DC/FUGW), or by non-transduced BMDCs pulsed with OVAp peptide (SIINFEKL) (DC/OVAp). Patterns of surface activation markers of OT1 T cells cocultured with BMDCs were assessed by antibody staining for CD25, CD69, CD62L, and CD44. Shaded area: naïve OT1 T cells harvested from transgenic animals; solid line: OT1 T cells cocultured with indicated BMDCs.
Figure 10B:
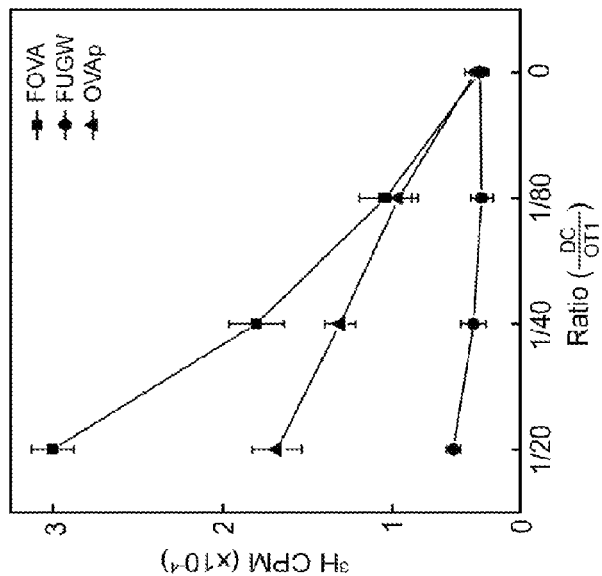
FIG. 10B illustrates the proliferative responses of treated OT1 T cells from FIG. 10A measured by a [$^3$H] thymidine incorporation assay for 12 hours.
Figure 10A:
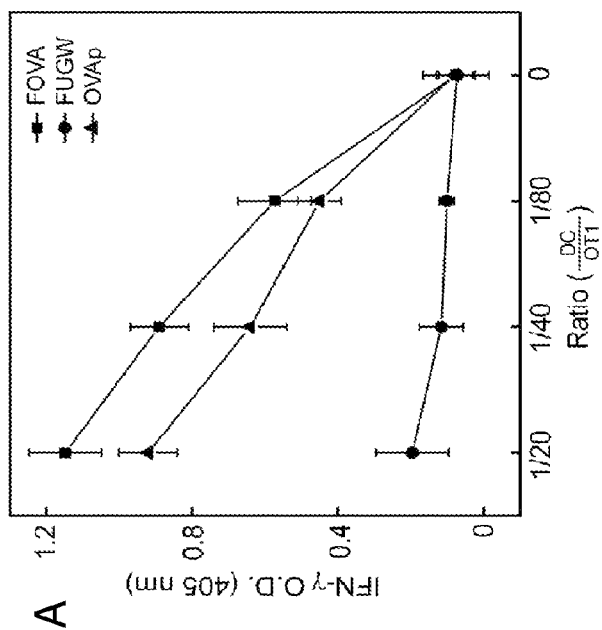
FIG. 10A illustrates the measurement of IFN-y by ELISA in OT1 T cells mixed with various dilutions of BMDCs transduced with FOVA/SVGmu (.), FUGW/SVGmu (P), or pulsed with OVAp peptide (•) and cultured for 3 days.

After a three-day coculture with varying ratios of DC/FOVA to transgenic T cells, OT1 T cells responded vigorously as measured by the release of IFN-y (FIG. 10A) and T cell proliferation (FIG. 10B). As expected, no obvious OVA response was detected using DC/FUGW (FIGS. 10A and 10B). It was also observed that the transgenic expression of OVA was even more efficient than peptide-loading for stimulation of an OT1 T cell response, which is consistent with the notion that MHC class I favors the presentation of endogenously produced peptides. Flow cytometry showed that the activated OT1 T cells exhibited the typical effector cytotoxic T cell phenotype ($CD25^{\pm}CD69^{\pm}CD62L^{\mathit{low}}CD44^{h1}g^h$) after stimulation by either DC/FOVA or DC/OVAp (FIG. 9).

Figure 11:
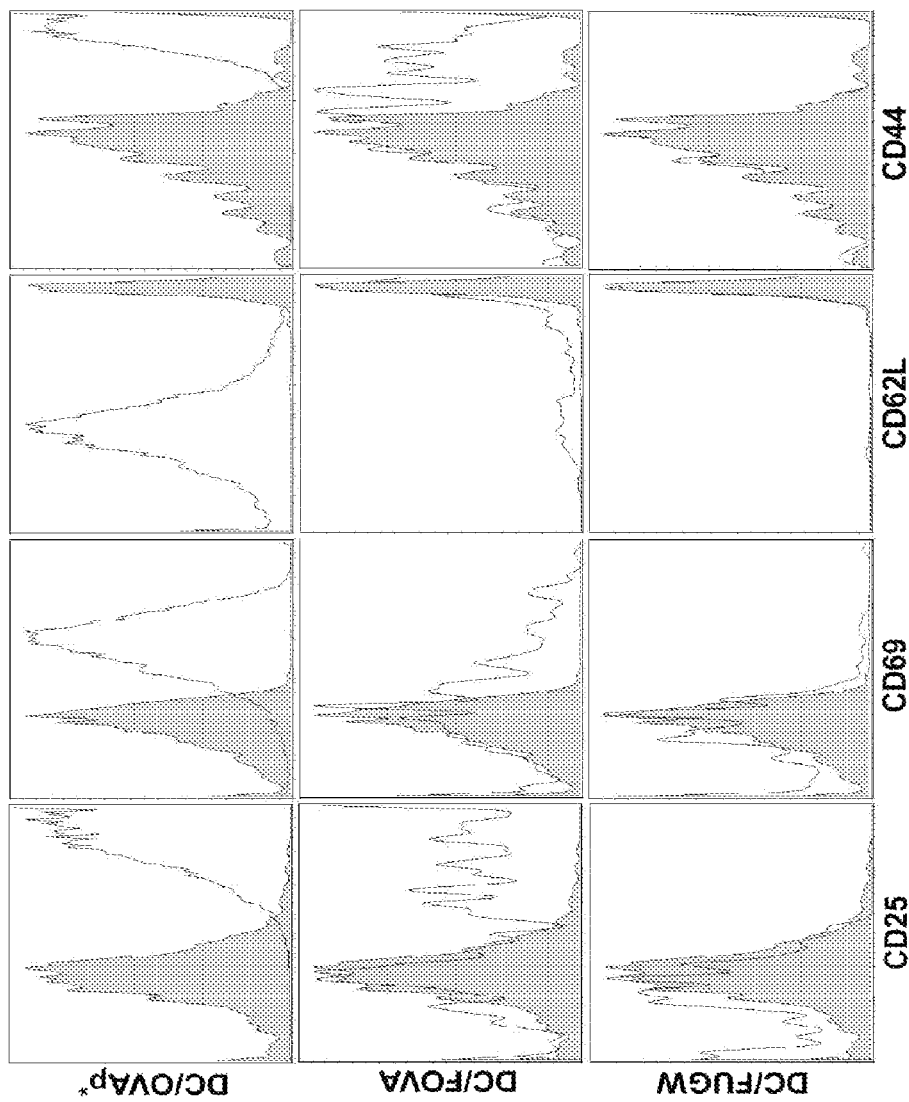
FIG. 11 illustrates in vitro stimulation of $CD4^+$ OT2 T cells by dendritic cells that were transduced with the FOVA/SVGmu (DC/FOVA) or FUGW/SVGmu lentivector (DC/FUGW), or by non-transduced BMDCs pulsed with OVAp* peptide (ISQAVHAAHAEINEAGR) (DC/OVAp*). Patterns of surface activation markers of OT2 transgenic T cells cocultured with BMDCs were assessed by antibody staining for CD25, CD69, CD62L, and CD44. Shaded area: naïve OT2 T cells harvested from transgenic animals; solid line: OT2 T cells cocultured with BMDCs.
Figure 12:
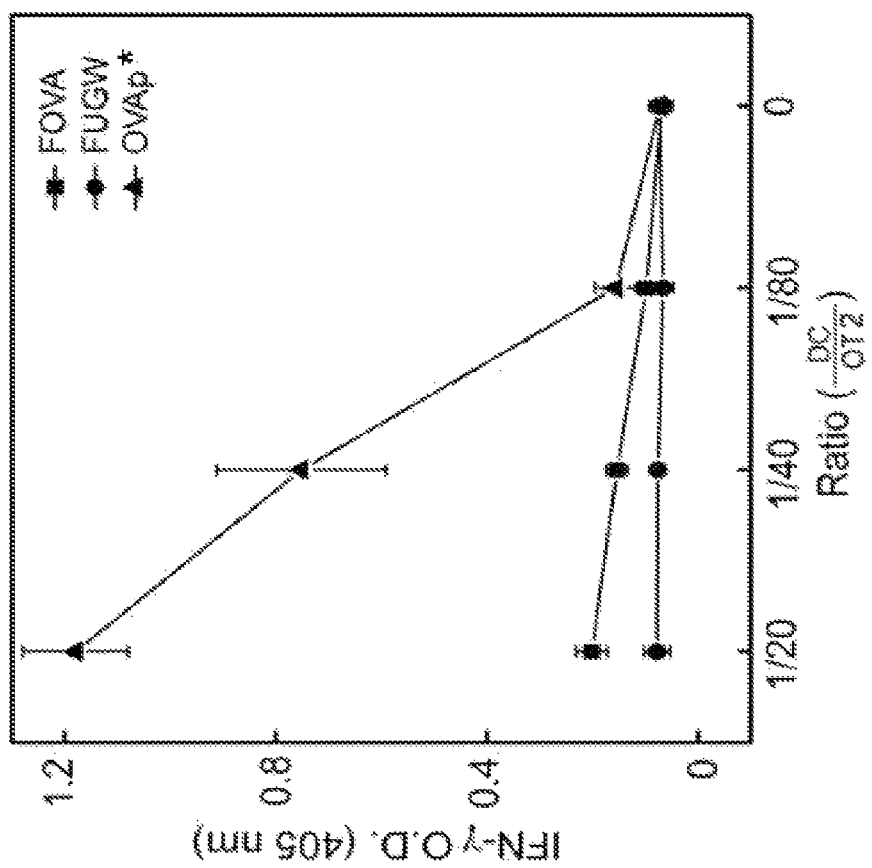
FIG. 12 illustrates the measurement of IFN-y by ELISA in OT2 T cells mixed with various dilutions of BMDCs transduced with FOVA/SVGmu (a), FUGW/SVGmu (.), or pulsed with OVAp* peptide (•) and cultured for 3 days.

When the DCs were co-cultured with OT2 $CD4^+$ T cells, T cell activation was also observed, as indicated by changes in the surface markers (FIG. 11) and the production of IFN-y (FIG. 12). However, stimulation of $CD4^+$ cells was not as pronounced as that of $CD8^+$ cells, presumably due to the less efficient presentation of endogenous antigen peptides to the MHC class II molecules. By modifying the cellular localization of OVA antigen to direct it to MHC class H presentation pathway, an enhancement of CD4 stimulation was achieved that was even better than that of peptide-pulsed DCs (data not shown).

These results show that the method of DC targeting through lentivector infection can effectively deliver antigens to DCs and stimulate both $CD8^+$ and $CD4^+$ T cell responses.

Example 11

In Vivo Antigen Delivery by Recombinant Virus

To determine if DCs targeted with lentivectors could activate antigen-specific T cells in vivo, a method of T-cell receptor (TCR) gene transfer into murine hematopoietic stem cells (HSCs) was used to generate antigen-specific and TCR-engineered T cells in mice, as described elsewhere (Yang, L. and D. Baltimore, D. 2005. supra.). A tricistronic retroviral vector MIG-0T1 co-expressing OT1 TCRa and TCRi3, along with the GFP marker (FIG. 13A) was constructed.

Briefly, B6 female mice (Charles River Breedling Laboratories) were treated with 250 p,g of 5-flurouracil (Sigma). Five days later, bone marrow (BM) cells enriched with HSCs were harvested from the tibia and femur and cultured in a 24-well culture plate ($2 \times 10^6$ cells per well) in BM culture medium (RPMI containing 10% FBS, 2 Ong/ml rmIL-3, 5 Ong/m1 rmIL-6 and 5 Ong/ml rmSCF (PeproTech)). On day 1 and day 2 of the culture, the cells were spin-infected with the MIG-0T1 retroviral vector pseudotyped with Eco (2 ml viral supernatant per well) at 2,500 rpm and 30° C. for 90 min. After each spin, the supernatant was removed and replaced with fresh BM culture medium. On day 3, the transduced BM cells were collected and transferred into B6 recipient mice receiving 1,200 rads of total body irradiation. Eight weeks post-transfer, the mice were used for the in vivo immunization study. Each mouse received one dose of subcutaneous injection of $10 \times 10^6$ TU of targeting lentivector. Seven days later, spleen and lymph node cells were harvested and analyzed for the presence of OT1 T cells and their surface activation markers using flow cytometry.

Figures 13A, 13B:
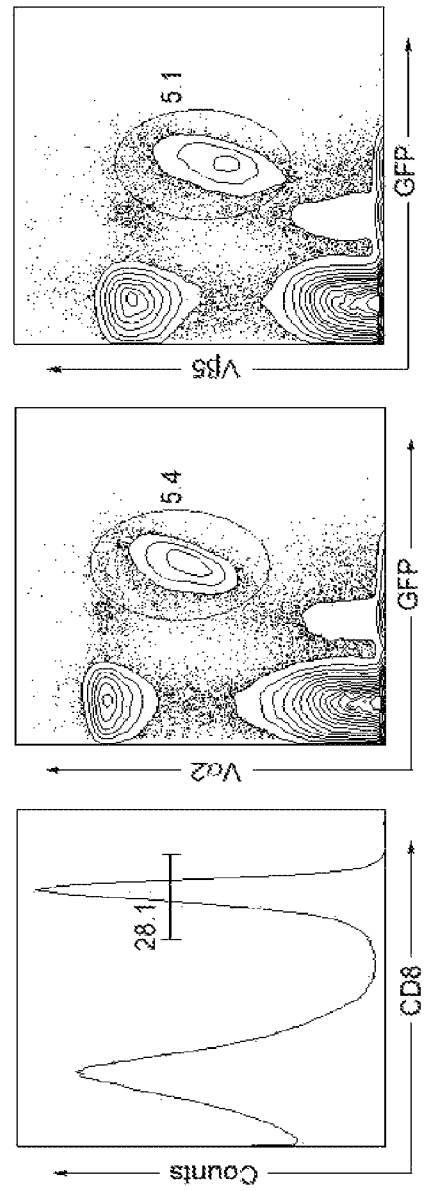
FIG. 13A provides a schematic representation of the retroviral vector MIG-0T1 used for genetic modification of murine hematopoietic stem cells (HSCs).
FIG. 13B illustrates how $CD8^+$ OT1 T cells derived from the MIG-0T1-modified HSCs in reconstituted mice were identified by the co-expression of GFP and TCR Va2 or V135. HSCs from B6 mice were infected with MIG-0T1 pseudotyped with Eco (MIG-OT1/Eco) and transferred into irradiated B6 recipient mice. Eight weeks post-transfer, the $CD8^+$ OT1 T cells were identified by flow cytometry.
Figure 14A:
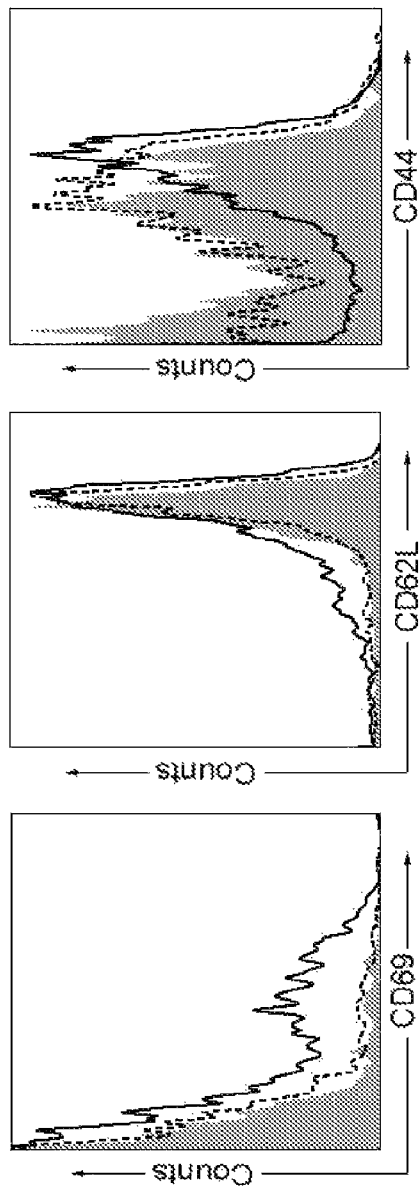
FIG. 14A illustrates assessment of patterns of surface activation markers on $GFP^\pm OT1^+$ T cells isolated from the spleens of reconstituted and immunized mice. Mice reconstituted by MIG-0T1 modified HSCs were immunized by direct subcutaneous injection of $10\times10^6$ TU of either FOVA/SVGmu or FUGW/SVGmu (as a control) and analyzed seven days later. Detection of surface staining for CD69, CD62L and CD44 was conducted. Solid line: $GFP^\pm OT1^+$ T cells from FOVA/SVGmu-immunized mice; dotted line: $GFP^+ OT1^+$ T cells from control FUGW/SVGmu-immunized mice; shaded area: $GFP^\pm OT1^+$ T cells from non-immunized mice.
Figure 14B:
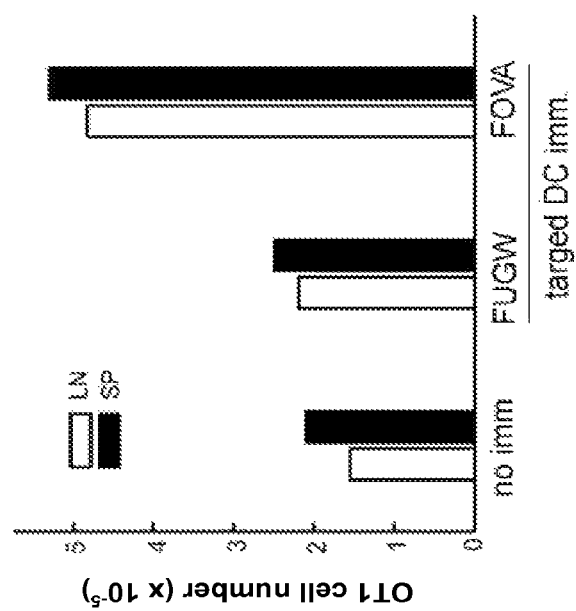
FIG. 14B illustrates the total number of OT 1 cells harvested from lymph nodes (LN, □) or spleens (SP, ■) of non-immunized mice (no imm) or mice immunized with FUGW/SVGmu or FOVA/SVGmu.

Eight weeks post-transfer, analysis of the peripheral T cells of the reconstituted mice showed that approximately 5% of the $CD8^+$ T cells were $GFP^+OT1^+$ (FIG. 13B). Some of the reconstituted mice were immunized via subcutaneous injection of the same dose ($10 \times 10^6$ TU) of either FOVA/SVGmu (Example 10) or FUGW/SVGmu (Example 2). Analysis of $GFP^+OT1^+$ T cells harvested from peripheral lymphoid organs 7 days later showed that the targeted DC immunization by FOVA/SVGmu doubled the number of OT1 T cells as compared to the control mice, which were either not immunized or immunized with FUGW/SVGmu (FIG. 14B). The $GFP^+OT1^+$ T cells derived from FOVA/SVGmu-immunized mice exhibited an effector memory phenotype ($CD69^{16w}CD62^{hi}g^hCD44^{hI}g^h$), indicating these cells have gone through a productive immune response (FIG. 14A).

These results demonstrate that a recombinant lentivector bearing surface SVGmu can target DCs in vivo to efficiently stimulate antigen-specific T cells and induce a strong immune response.

Example 12

Induction of In Vivo CTL and Antibody Responses by Direct Administration of Recombinant Virus Studies were conducted on the efficacy of the in vivo DC targeting for inducing an antigen-specific $CD8^+$ cytotoxic T lymphocyte (CTL) response and antibody response through the administration of the targeting lentivector to naïve, wild-type mice.

Wild-type B6 mice (Charles River Breeding Laboratories) were given a single injection of targeting lentivector ($50+10^6$ TU of FUGW/SVG or FOVA/SVGmu) subcutaneously on the right flank at the indicated dose. On day 7 and day 14 post-immunization, blood was collected from the immunized mice through tail bleeding, and the serum anti-OVA IgG was measured using ELISA. On day 14, spleen and lymph node cells were harvested and analyzed for the presence of OVA-specific T cells and their surface activation markers using flow cytometry.

Figure 15:
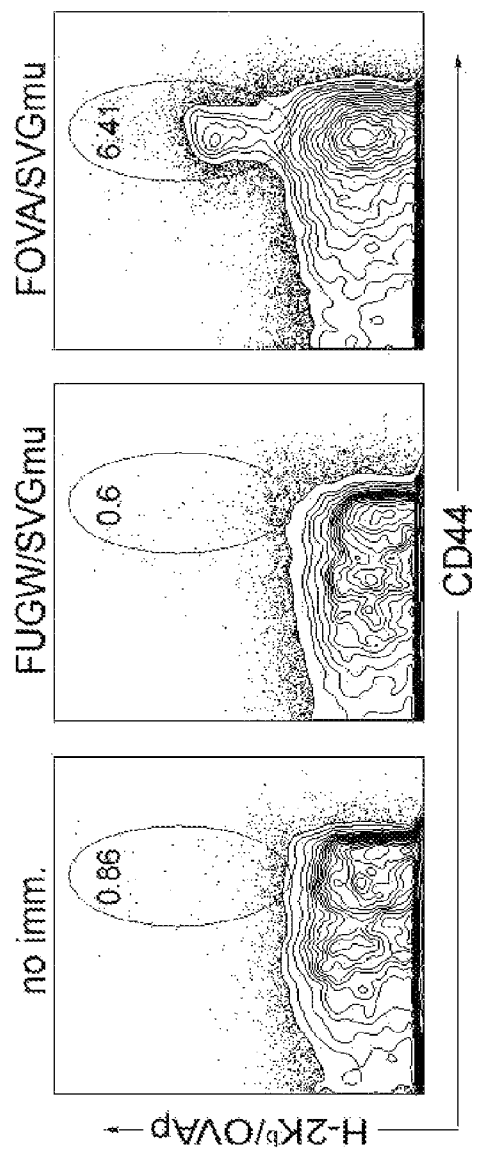
FIG. 15 illustrates in vivo stimulation of antigen specific T cell and antibody responses in wild-type mice following a subcutaneous injection of the DC-targeting lentivector FOVA/SVGmu. B6 mice were immunized subcutaneously with $50\times10^6$ TU of either FOVA/SVGmu or FUGW/SVGmu (as a control). Mice without immunization (no imm.) were included as a negative control. Fourteen days post-immunization, spleen cells were harvested and analyzed for the presence of OVA-specific T cells measured by $H-2K^b$-SIIN-FEKL-PE tetramer and CD44 staining. Indicated percentages are the percent of total $CD8^+$ T cells.
Figure 17A:
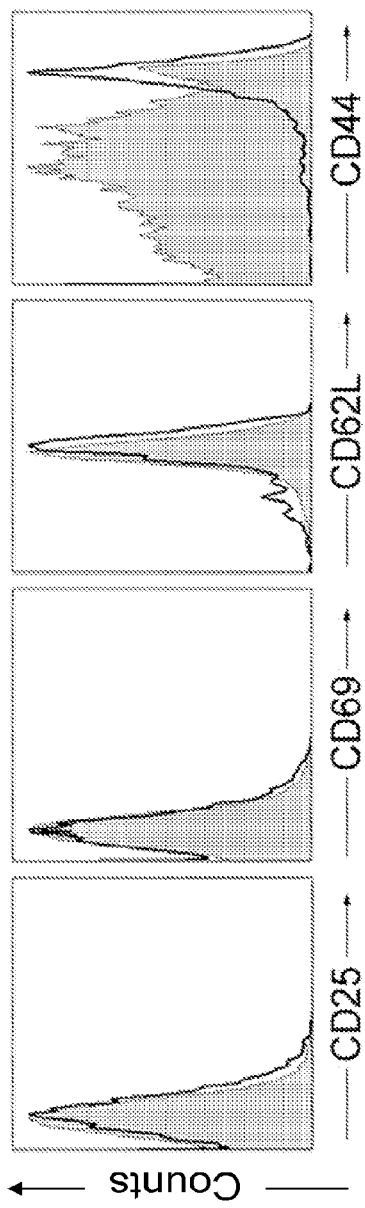
FIG. 17A illustrates the patterns of surface activation markers of OVA-specific $CD8^+$ T cells (identified as tetramer positive cells) isolated from FOVA/SVGmu immunized mice 2 weeks post-injection. The surface activation markers were assessed by antibody staining for CD25, CD69, CD62L and CD44. Solid line: tetramer+CD8+ T cells from FOVA/SVGmu-immunized mice; shaded area: naïve CD8+ T cells from non-immunized mice.
Figure 23:
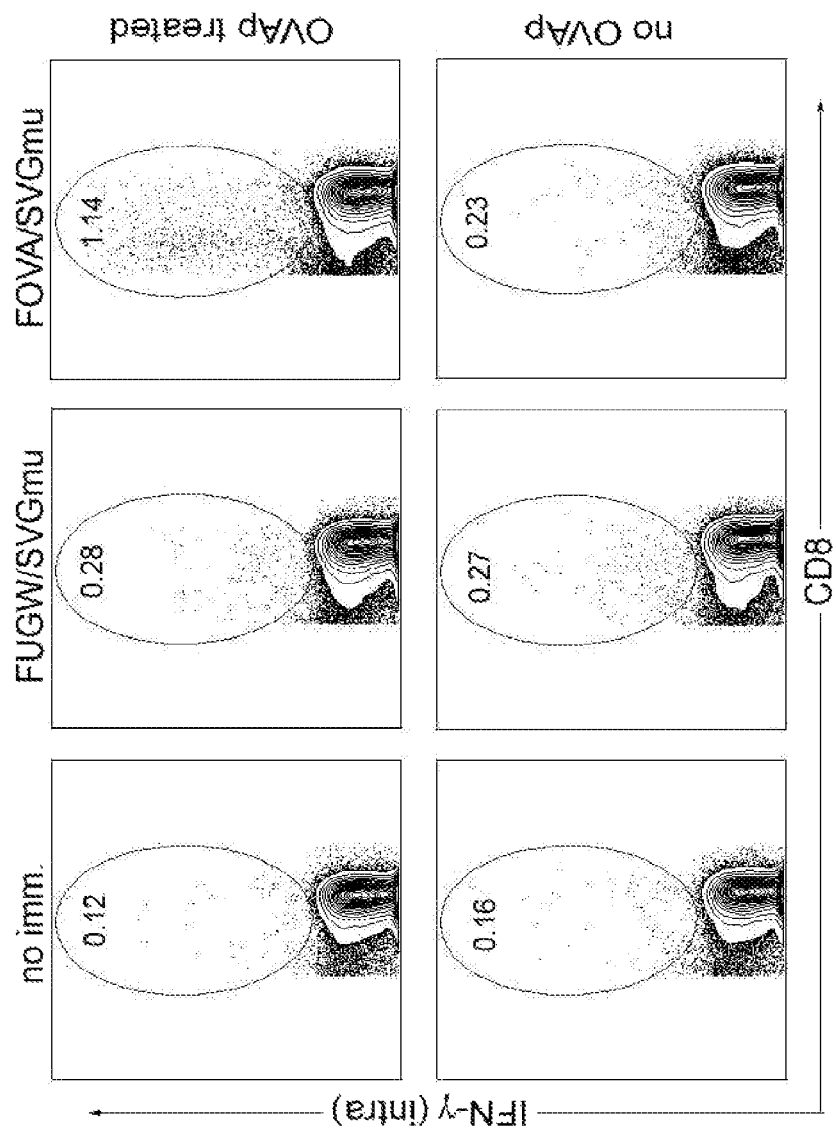
FIG. 23 illustrates that administration of a single dose of recombinant DC-specific lentivector FOVA/SVGmu can generate IFN-y+CD8+ T cells in B6 mice. Naive B6 mice are immunized by subcutaneous injection of $50\times10^6$ TU of FOVA/SVGmu lentivector, or the same dose of FUGW/SVGmu as a control. The non-immunized B6 mice (no imm.) were included as a negative control. Two weeks later, spleen cells were harvested from the experimental mice, and were analyzed for intracellular IFN-y production using flow cytometry with or without OVAp peptide restimulation. Indicated percentages are the percent of IFN-y+CD8+ T cells of the total CD8+ T cells.

The presence of OVA-specific T cells was measured by measuring cytokine secretion and tetramer staining. At day 14 post-injection, T cells harvested from peripheral lymphoid organs were analyzed. Lentivector targeting to native DCs was able to elicit OVA-responsive $CD8^+$ T cells in both the lymph node (data not shown) and spleen (FIG. 23). Administration of a single dose of recombinant FOVA/SVGmu was sufficient to generate CD8+ T cells, which could be primed to secrete IFN-γ upon OVAp restimulation (FIG. 23). Administration of the control vector FUGW/SVGmu failed to generate any OVAp-specific responses (FIG. 23). To further evaluate the magnitude of responses, the OVAp-specific CD8+ T cells was measured by MHC class I tetramer staining. A high frequency of OVAp-specific T cells (>6%) was obtained following a single dose injection (FIG. 15); no tetramer-positive cells were detected in the mice treated with FUGW/SVGmu (FIG. 15). The data generated by tetramer quantitation correlated well with the analysis of CD8+ effector cells assayed by intracellular IFN-γ staining (FIG. 23). Phenotype analysis of these OVAp-positive T cells showed that these cells displayed the surface characteristics of effector memory T cells ($CD25^{1n/}CD69^{1n/}CD62L^{hi}g^{h}CD44^{hi}g^{h}$) (FIG. 17A).

Figures 16A, 16B:
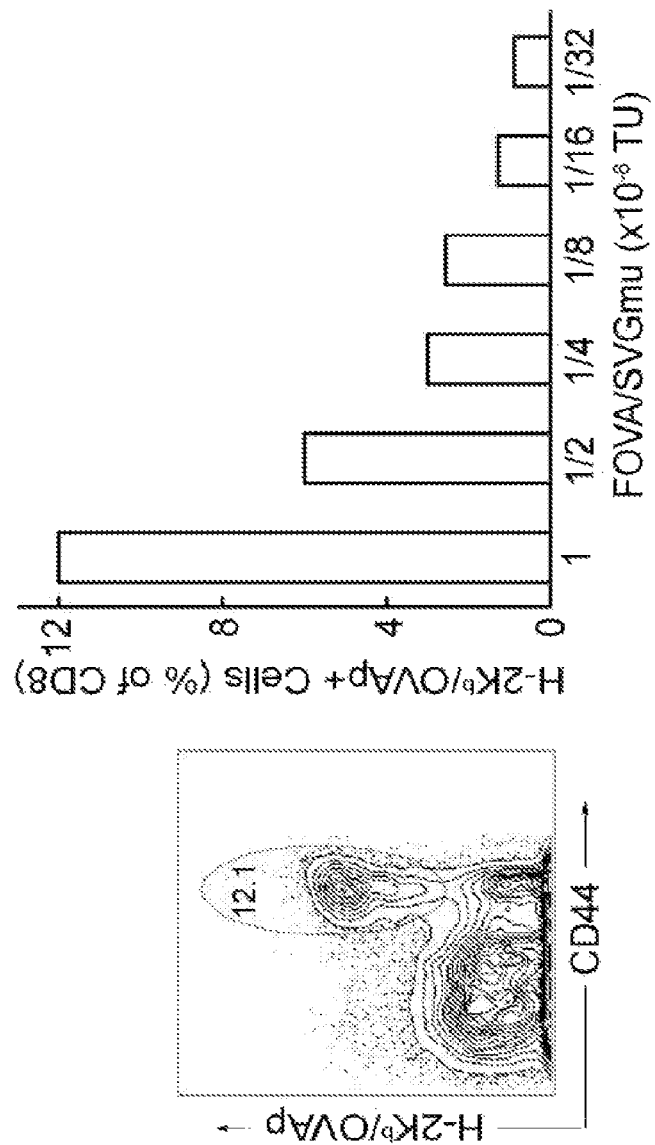
FIG. 16A and FIG. 16B illustrate in vivo OVA-specific T cell responses seen in mice receiving different subcutaneous doses of FOVA/SVGmu. OVA-specific T cells were identified by tetramer staining as in FIG. 17.

To investigate the dose response of lentivector administration, doses of FOVA/SVGmu ranging from $100\times10^6$ TU to $3\times10^6$ TU were injected subcutaneously and OVAp-specific T cells in the spleen were measured at day 14 post-injection. An exceptionally high frequency (12%) of OVAp-specific CD8+ T cells was detected at the dose of $100\times10^6$ TU (FIG. 16A). The percentage of OVAp-specific cells correlated proportionately with the amount of recombinant vector administered (FIG. 16B). A plateau in the dose response was not achieved with the doses that were tested, indicating that further enhancement can be achieved by increasing the amount of vector injected and/or the frequency of injection.

Figure 17B:
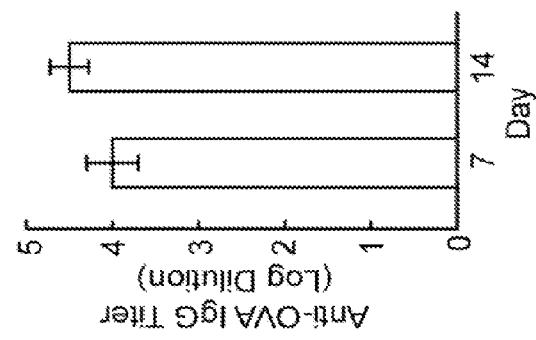
FIG. 17B illustrates the OVA-specific serum IgG titer of B6 mice following immunization with $50\times10^6$ TU FOVA/SVGmu. Sera were collected on day 7 and day 14 post-immunization and were analyzed for the titer of OVA-specific IgG using ELISA at serial 10× dilutions, starting at 1:100. The titer values were determined by the highest dilution at which the optical density was 2× standard derivations higher than that of the baseline serum at the equivalent dilution.

Further, the serum IgG levels specific for OVA in mice were examined on the 7th and 14th days after immunization with FOVA/SVGmu ($50\times10^6$ TU). The IgG serum titer was 1:10,000 on day 7 and 1:30,000 on day 14 (FIG. 17B). This is a rather impressive antibody response for a single dose injection without additional adjuvant or other stimuli, indicating that targeted lentivector immunization can also elicit significant B cell secretion of antigen-specific antibodies.

These results show that in vivo administration of a DC-targeting lentivector can induce both cellular and humoral immune responses against the delivered antigen.

Example 13

Generation of Anti-Tumor Immunity

Preventive Protection

The anti-tumor immunity generated after an in vivo administration of DC-targeted lentivector was evaluated. An E.G7 tumor model (Wang, L. and D. Baltimore. 2005. supra.) was used in which OVA serves as the tumor antigen.

The tumor cell lines EL4 (C57BL/6J, H-2", thymoma) and E.G7 (EL4 cells stably expressing one copy of chicken OVA cDNA) were used for the tumor challenge of mice. For the tumor protection experiment, B6 mice (Charles River Breeding Laboratories) received a single injection of $50\times10^6$ TU of the targeting lentivector (FOVA/SVGmu or FUGW/SVGmu) on the right flank. Two weeks later, $5\times10^6$ EL4 or E.G7 cells were injected subcutaneously into the left flank of the mice. Tumor size was measured every other day using fine calipers and was shown as the product of the two largest perpendicular diameters a×b (mm$^2$). The mice were killed when the tumors reached 400 mm$^2$.

Figure 18:
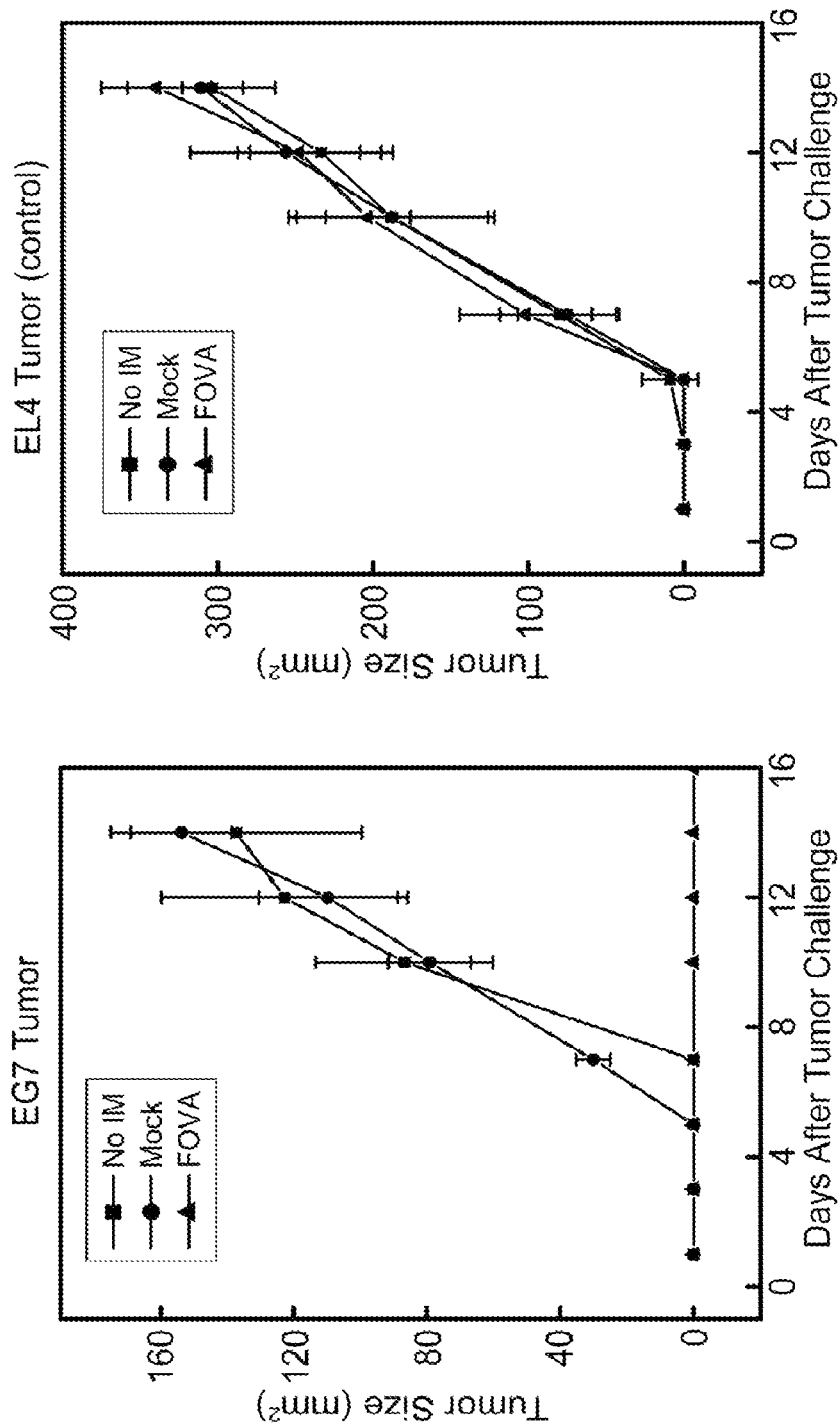
FIG. 18 illustrates tumor size as a function of time in a murine E.G7 tumor model. B6 mice were immunized with subcutaneous injection of $50\times10^6$ TU of either FOVA/SVGmu (A) or mock vector FUW/SVGmu (.). No immunization (■) was included as a control. Four mice were included in each group. At day 14 post-immunization, the mice were challenged with $5\times10^6$ of either E.G7 tumor cells (expressing the OVA antigen, left panel) or the parental EL4 tumor cells (lacking the OVA antigen, as a control, right panel) subcutaneously. Tumor growth was measured with a fine caliper and is shown as the product of the two largest perpendicular diameters ($mm^2$).

Vaccination with $50\times10^6$ TU FOVA/SVGmu completely protected the mice from the E.G7 tumor challenge (FIG. 18, left), while tumors grew rapidly in mice receiving a mock vaccination with a lentivector lacking the OVA transgene (FIG. 18, left). This protection was OVA-specific because the vaccinated mice grew control EL4 tumors that lack expression of OVA (FIG. 18, right), regardless of the lentivector used for immunization.

Example 14

Generation of Anti-Tumor Immunity

Tumor Treatment

The anti-tumor immunity generated after an in vivo administration of DC-targeted lentivector was evaluated where tumor cells were introduced prior to administration of the lentivector. The steps of tumor injection and lentivector administration were reversed relative to that in Example 13 to test whether an established tumor could be eliminated, in a test of "therapeutic vaccination". To this end, E.G7 tumor cells expressing the firefly luciferase gene (E.G7.luc) were used to challenge mice, allowing close monitoring of tumor growth kinetics in live animals using BLI. To facilitate imaging, an albino strain of B6 mice (The Jackson Laboratory) was used. These mice lack pigmentation and therefore have low background absorption of the luminescence signal. Injection of these mice with $100\times10^6$ TU of FOVA/SVGmu (Example 10) showed a similar response to that observed in canonical B6 mice (FIG. 21). E.G7.luc tumor cells ($5\times10^6$) were implanted subcutaneously in the albino B6 mice. The mice were immunized by FOVA/SVGmu ($50\times10^6$ TU per mice per time) twice on days 3 and 10 post-tumor challenge via subcutaneous injection. The experiment was repeated three times with a representative experiment shown in FIGS. 19 and 20.

Figure 19:
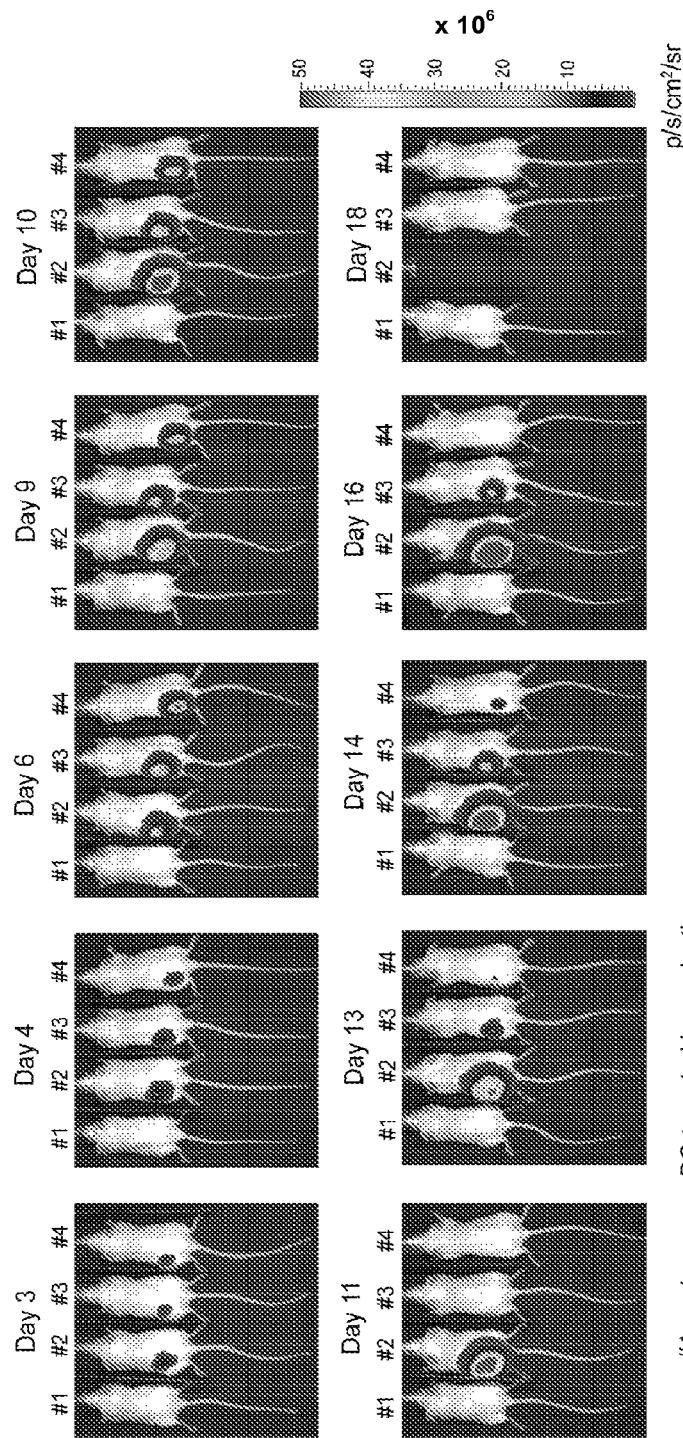
Figure 20:
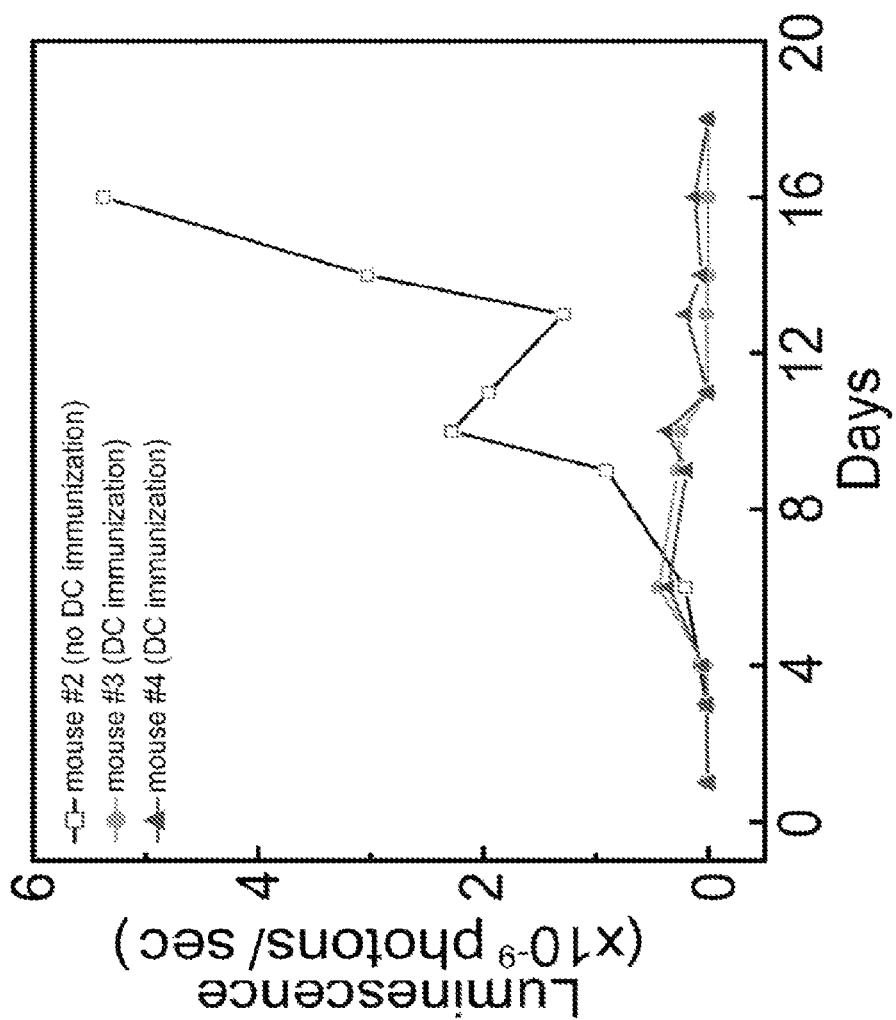
FIG. 20 shows the quantitation of luminescence signals generated by the E.G7 tumors in FIG. 19. (□) for mouse #2; (to) for mouse #3; (A) for mouse #4.
Figure 21:
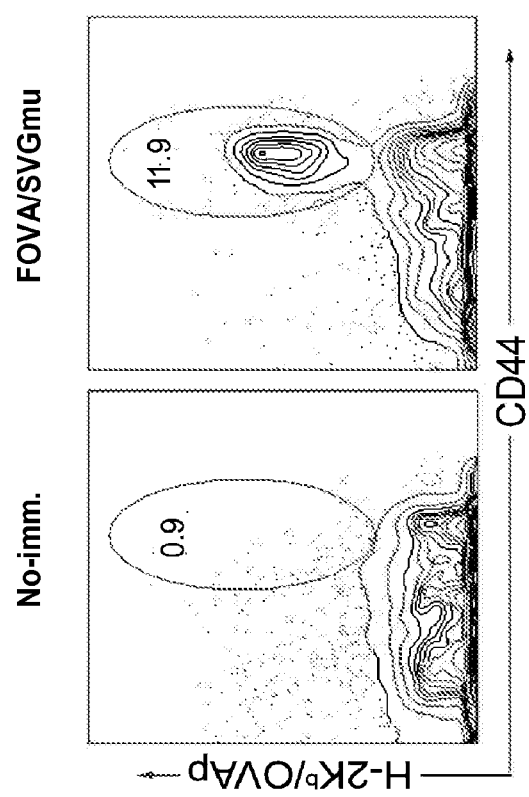
FIG. 21 illustrates the percentage of OVA-specific T cells present following immunization with $100\times10^6$ TU of FOVA/SVGmu in the albino strain of B6 mice. Albino B6 mice were immunized subcutaneously with $50\times10^6$ TU of FOVA/SVGmu. Mice without immunization (no imm.) were included as a negative control. Fourteen days post-immunization, spleen cells were harvested and analyzed for the presence of OVA-specific T cells measured by H-2K$^b$-SIINFEKL-PE tetramer and CD44 staining. Indicated percentages are the percent of total CD8+ T cells.

The mice receiving the DC-targeting lentivector immunization showed a decline of tumor growth starting at day 9, followed by tumor regression and a reduction of luminescence below the detection level on day 11 (FIGS. 19 and 20). Although minimal tumor recurrence was observed from day 12 to day 16, mice treated with FOVA/SVGmu were free of disease at the end of day 18 and thereafter; no tumor relapse was observed for as long as the experiment ran (>60 days). In contrast, tumors grew progressively in the mice receiving no treatment and the mice had to be removed from the experiment after day 16 due to the large size of the tumors. It was a interesting to note that tumor regression was observed starting at 7 days after the lentivector immunization. The timing of tumor regression correlates well with the kinetics of an antigen-specific immune response induced by vaccination.

Example 15

In Vitro Delivery of Antigen and Maturation Factory by a Recombinant Virus

The success of DC vaccination can depend on the maturation state of DCs (Banchereau, J. and A. K. Palucka. 2005. *Nat Rev Immunol* 5:296-306; Schuler, G., et al. 2003. *Curr Opin Immunol* 15: 138-147; Figdor, C. G., et al. 2004. *Nat Med* 10: 475-480, each of which is incorporated herein by reference in its entirety). Therefore, genes can be included in the lentiviral vectors that encode the stimulatory molecules to trigger the desired DC-maturation. Cytokines that can be used include, but are not limited to, GM-CSF, IL-4, TNFa, IL-6, and the like. In some embodiments, the maturation agent that is used is the CD40 ligand (CD4OL), which is typically expressed on CD4 T cells and serves as a ligand for the CD40 receptor on DCs (Matano, T., et al. 1995. *J Gen Virol* 76:

3165-3169; Nguyen, T. H., et al. 1998. *Hum Gene Ther* 9: 2469-2479, each of which is incorporated herein by reference in its entirety). To further manipulate DCs to be a potent vaccine for therapy, a drug-inducible CD40 receptor (iCD40) is adapted into the gene delivery system in some embodiments. As described elsewhere, iCD40 was designed and consists of a cytoplasmic domain of CD40 fused to ligand-binding domains and a membrane-targeting sequence (Hanks, B. A., et al. 2005. *Nat Med* 11: 130-137, which is herein incorporated by reference in its entirety). When iCD40 is expressed, maturation and activation of DCs is regulated with a lipid-permeable, dimerizing drug.

Figure 24:
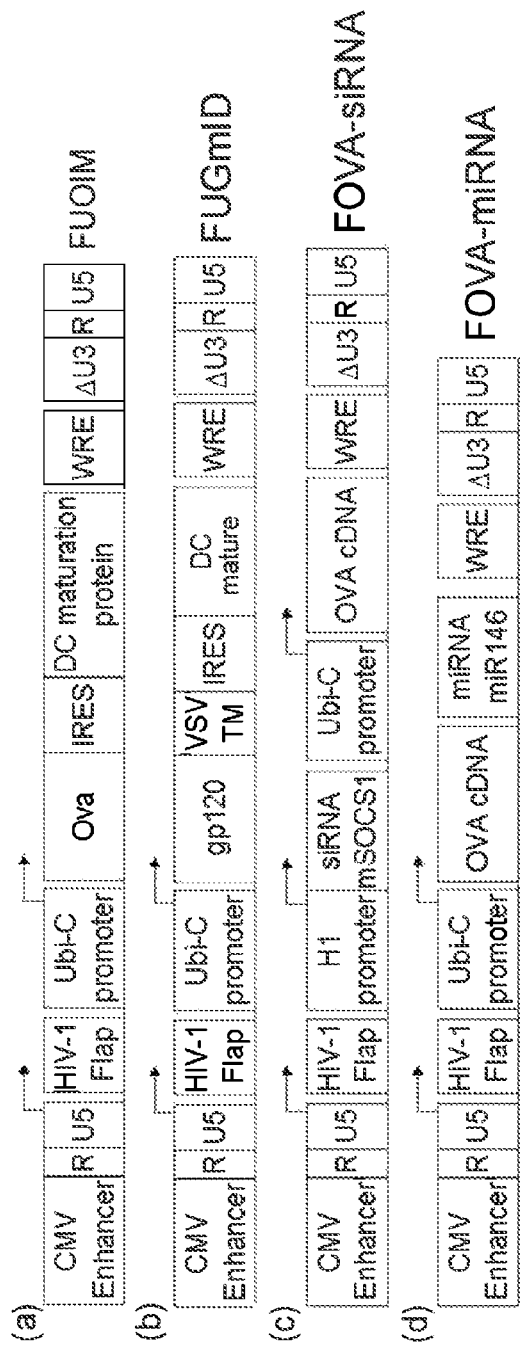
FIG. 24 illustrates a schematic representation of lentiviral constructs for preparation of DC-targeting recombinant viruses.

To examine the effect of including DC maturation factors, the cDNAs for ovalbumin (OVA, as described in Example 10), GM-CSF, IL-4, TNFa, IL-6 and CD4OL are obtained. The iCD40 is constructed as described elsewhere (Hanks, B. A., et al. 2005. supra). Using IRES and 2A-like sequences, multicistronic lentiviral vectors capable of efficiently translating up to four proteins are constructed. This system is adapted to construct lentiviral vectors co-expressing the following genes: OVA and a maturation factor molecule (GM-CSF, IL-4, TNFa, IL-6, CD4OL or iCD40) (FIG. 24*a*, labeled as "FUOIM"). An exemplary vector sequence is provided by SEQ ID NO: 7. SVGmu-enveloped lentiviruses are prepared (as described in Example 2), and the lentiviruses are transduced • in vitro into cultured mouse BMDCs (generated as described in Example 6) to specifically deliver these genes into the cells. Maturation of BMDCs is measured by FACS analysis for up-regulation of several key molecules that have essential roles in the process of T cell stimulation. Typical representative markers are ICAM-1 (CD54), B7.1 (CD80), MHC class I, MHC class II and endogenous CD40. BMDCs transduced with lentiviruses encoding only OVA and GFP genes serve as controls for the experiment. It is observed that up-regulation of maturation markers is achieved when iCD40-modified DCs are exposed to an effective amount of dimeric drug AP20187.

In addition, two characteristic features of matured DCs are the reduced capacity for endocytosis and the improved potential for T cell activation. The uptake of FITC-tagged dextran is used to quantify the endocytosis of transduced DCs. The mature DCs are also used to stimulate T cells expressing OT1 T cell receptors (TCRs) (as described in Example 10), in order to evaluate their capacity to mount an immune response. It is observed that when iCD40-modified DCs are exposed to an effective amount of dimeric drug AP20187, the uptake of FITC-tagged dextran is reduced relative to that of non-iCD40-modified DCs. Furthermore, it is observed that after coculture with varying ratios of iCD40-modified DCs (treated with the dimeric drug) to transgenic T cells, OT1 T cells respond more vigorously as measured by the release of IFN-y and T cell proliferation than do those co-cultured with non-iCD40-modified DCs.

Longevity of DCs is another parameter that determines T-cell-dependent immunity. The effects of stimulator molecules on DC survival using an in vitro serum-starvation assay will be compared using the method as described in Hanks et al. (Hanks, B. A., et al. 2005. supra).

If necessary, two maturation factor molecules can be delivered by lentiviral vector to targeted DCs, as the vector configuration has the capacity to express four proteins.

Example 16

In Vivo Delivery of Antigen and Maturation Factors by a Recombinant Virus

Recombinant viruses packaged with FUOIM lentiviral vector (SEQ ID NO: 7) are prepared as described in Example 15. The viruses are administered to naive B6 mice to deliver OVA antigen and maturation factor molecules to DCs, and induction of immunity to graded doses of viruses is evaluated as described in Example 11.

It is observed that the targeted DC immunization by iCD40-containing lentiviruses increases the number of OVA responsive T cells as compared to the control mice, which are either not immunized, immunized with a non-OVA containing lentivirus (e.g. FUGW/SVGmu), or immunized with non-iCD40 containing lentivirus (e.g. FOVA/SVGmu).

In addition, the resistance of the animals to a tumor challenge is assessed with the iCD40-containing lentivectors, as described in Example 13. The mice are injected with the following lentivectors in the tumor challenge experiment: FUOIM/SVGmu, FOVA/SVGmu, or FUGW/SVGmu. The following cell lines are used for tumor challenge: EL4 (C57BL/6J, H-2$^{1)}$, thymoma) and E.G7 ((EL4 cells stably expressing one copy of chicken OVA cDNA). It is observed that the mice receiving immunization by the DC-targeting lentivectors FUOIM/SVGmu and FOVA/SVGmu are protected from the tumor challenge. In contrast, it is observed that tumors grow rapidly in mice receiving a mock vaccination with a lentivector lacking the OVA transgene (FUGW/SVGmu). This protection is OVA-specific because the vaccinated mice grow control EL4 tumors that lack expression of OVA, regardless of the lentivector used for immunization.

Finally, the potential of this method to eradicate an established tumor is assessed with the iCD40-containing lentivectors, as described in Example 14. The following lentivectors are used for immunization in the experiment: FUOIM/SVGmu and FOVA/SVGmu. The following cell lines are used for tumor treatment: EL4 and E.G7. It is observed that the tumor cell-injected mice receiving immunization by the DC-targeting lentivectors (FUOIM/SVGmu and FOVA/SVGmu) show a decline of tumor growth, followed by tumor regression and a reduction of luminescence below the detection level. Further, no tumor relapse is observed for as long as the experiment runs (>60 days). In contrast, tumors grow progressively in the mice receiving no treatment.

Example 17

HIV/AIDS Antigen Presentation by Recombinant Virus In Vitro

Figure 25:
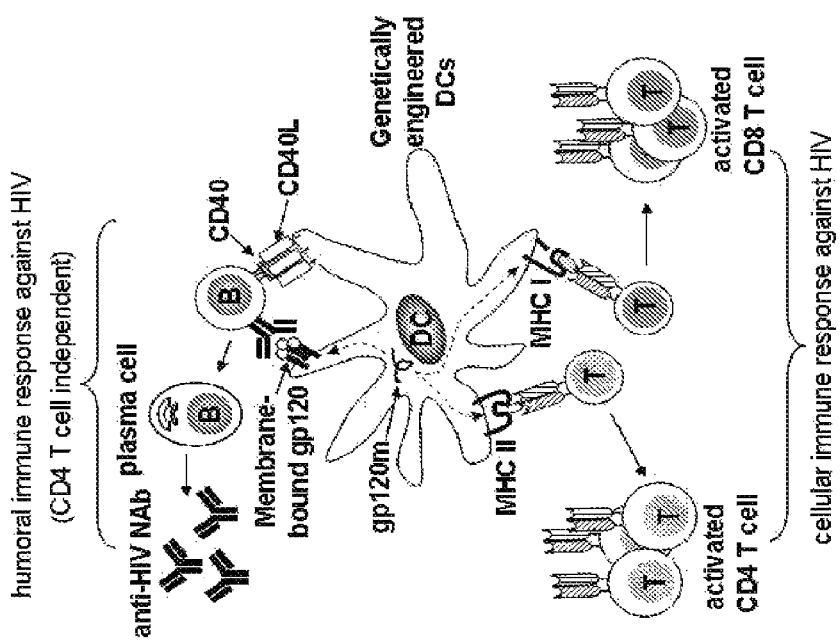
FIG. 25 shows a schematic representation of an embodiment of in situ vaccination against HIV/AIDS.

To treat HIV/AIDS, "dual-functional" DCs are generated based on the described gene delivery strategy. The "dual functional" DCs are efficacious at both eliciting neutralizing antibodies (Nabs) and inducing T cell immunity (FIG. 25). To efficiently elicit NAbs, a gene encoding chimeric membrane-bound gp120 (gp120 m) is delivered to DCs. Gp120 is an envelope glycoprotein for HIV and is considered to be the most potent immunogen (Klimstra, W. B., et al. 2003. *J Virol* 77:12022-12032; Bernard, K. A., et al. 2000. *Virology* 276: 93-103; Byrnes, A. P., et al. 1998. *J Virol* 72: 7349-7356, each of which is incorporated herein by reference in its entirety). As described else here, gp1 20 fused with the transmembrane domain of the vesicular stomatitis virus glycoprotein can be expressed on the cell surface in a trimeric form, mimicking the mature trimer on the HIV virion surface (Klimstra, W. B., et al. 1998. *J Virol* 72: 7357-7366, which is incorporated herein by reference in its entirety). This form of immunogen will be displayed on the DC's surface. In addition to surface expression, the DCs can also present epitope peptides derived from gpl 20 in MHC restricted fashion to T cells.

Since HIV infection can significantly impair DC function through the depletion of CD4 T cells, it is desirable to engineer DCs that function independently of T cells. Expression of CD4OL or iCD40 can result in maturation and activation of DCs in the absence of CD4 T cells. Thus, the engineered CD4OL or iCD40, as described in Example 16, which functions as a maturation and stimulatory molecule, is incorporated into the DC-targeting virus.

The lentiviral construct for genetically modifying DCs is illustrated in FIG. 24b and is labeled as FUGmID (SEQ ID NO: 8). Codon-optimized cDNAs for gp120 from NIH AIDS Research & Reference Reagent Program are obtained. The codon-optimized sequence can achieve exceptionally high levels of gene expression outside of the context of the HIV-I genome. The construct is prepared by fusion of gp120 with the transmembrane domain of the vesicular stomatitis virus glycoprotein.

In vitro assays are conducted to assess the efficacy of gene-modified DCs to elicit NAbs. $CD19^+$ B cells are isolated from the spleens of naive B6 mice using anti-CD19 microbeads (MiHenyi Biotech, Auburn, Calif.) and co-cultured with modified DCs in the presence of IL-4 and IL-6. The lentiviral vector FUmGID is co-transfected with SVGmu in cell lines to prepare the FUmGID/SVGmu virus, as described in Example 2. The resultant viruses are transduced into bone marrow-derived DCs (BMDCs). The transduced DCs are be irradiated (3,000 rad) and used as antigen presenting cells (APCs) in co-culture with B cells. The time course of the proliferation of B cells in response to transduced BMDCs is measured. It is observed that B cells proliferate to a greater extent in co-culture with transduced BMDCs than those that are co-cultured with mock-transduced BMDCs.

To investigate the effect of genetically modified DCs on the differentiation of B cells into specific immunoglobulin-secreting cells, the co-culture method as previously described is employed with the exception that the DCs are not irradiated. After 14 days, the titer of various isotypes of HIV-specific antibody in culture supernatants is determined by ELISA using recombinant gpI20 (available from NIB: AIDS Research & Reference Reagent Program) as the antigen. Expression of the various isotypes of HIV-specific antibody are greater in B-cells co-cultured with transduced BMDCs than in those cocultured with mock-transduced BMDCs.

To assess the efficacy of the genetically modified DCs to activate T cells in vitro, $CD3^+$ T cells are isolated from naive B6 mice and co-cultured with lentivirus-infected and irradiated DCs. The time course of T cell proliferation is measured. T cell proliferation is found to be greater in T cell cultures co-cultured with transduced and irradiated DCs than in those co-cultured with mock-transduced DCs.

The results are expected to collectively demonstrate that BMDCs transduced with the FUmGID/SVGmu lentivector is effective in both stimulation of B-cells to produce neutralizing antibodies (Nabs) and in inducing T cell immunity against HIV/AIDS.

Example 18

HIV/AIDS Antigen Presentation by Recombinant Virus In Vivo

To evaluate the activation of B cells in vivo, B6 mice are immunized by subcutaneous injection with the recombinant lentiviruses prepared as described in Example 17. Controls include mice injected with lentiviruses encoding antigens alone, lentiviruses encoding maturation molecules alone, and naive mice without any treatment. Two weeks after virus injection, serum antibodies against HIV are measured by ELISA. The antibody titer is found to be higher in those mice injected with the FUmGID/SVGmu virus as well as in those injected with lentivirus encoding antigens alone. In contrast, antibody titer is relatively low in those mice immunized with lentivirus encoding maturation molecules alone and in naïve mice.

For in vivo activation of T cells, the recombinant viruses described are injected into B6 mice. Seven days later, T cells are isolated, and their proliferation and cytokine secretion, after in vitro restimulation with genetically modified DCs, is measured as described in Example 12. The durability of the effector T cell responses is also monitored. Lentivector targeting to native DCs is able to elicit HIV-responsive T cells in both the lymph node and spleen. Administration of recombinant FUmGID/SVGmu is sufficient to generate T cells which secrete IFN-y. In contrast, administration of a mock control vector (e.g. FUGW/SVGmu) fails to elicit an HIV-specific response.

Example 19

In Situ HIV/AIDS Vaccination by Recombinant Virus

Protection Against HIV Challenge

In order to test in situ DC vaccination approach to deal with HIV, a new mouse model of HIV pathogenesis involving human/mouse chimeras is developed. As described elsewhere, the $RAG2^{-/-}y_c^{-/-}$ mouse can be reconstituted with a human adaptive immune system (Strauss, J. H., et al. 1994. Archives of Virology 9:473-484, which is incorporated herein by reference in its entirety). The $RAG2^{4-}y_c^{-/-}$ mice lack B, T, and NK cells (Morizono, K., et al. 2001. J Virol 75: 8016-8020, which is incorporated herein by reference in its entirety). Injection of $CD34^+$ human cord blood into the liver of one-day old partially-irradiated mice leads to the generation and maturation of functionally diverse human DCs, B cells, and T cells with human MHC restriction. Additionally, this model directs the development of primary and secondary lymphoid organs, and the production of a functional $CD8^+$ T cell immune response against a viral challenge. Furthermore, the observation of the Ig isotype switching from IgM to IgG indicates the existence of functional $CD4^+$ T cell immunity.

To determine the effectiveness of preventive protection against HIV by DC-targeted immunization, the human/mouse chimeras are administered recombinant viruses enveloped with SVGmu by injection. The recombinant viruses encode gp120 m antigen (Example 17) in conjunction with a maturation stimulator (for example, CD4OL or iCD40 as in Example 15), and they are prepared and concentrated as described in Example 2. The immunized mice are then inoculated with HIV according to methods well known in the art, such as, for example, via intraperitoneal or intravenous routes. Since the reconstituted mice maintain human CD4 T cells, the animals are challenged with molecularly cloned HIV reporter viruses, NFNSX-r-HSAS (CCR5-tropic), NL-r-HSAS (CXCR4-tropic) and clinical isolates (Baenziger, et al. 2006. Proc Natl Acad Sci USA 103:15951-15956, which is incorporated herein by reference in its entirety). The replication-competent reporter viruses also contain the heat-stable antigen (HSA) in the vpr region. Further, to establish a productive infection prior to inoculation, infected syngeneic peripheral blood mononuclear cells (PBMCs) are injected into the peritoneal space of the reconstituted human/mouse chimera.

Evidence of HIV infection is monitored over time in spleens, lymph nodes, PBMCs, and peripheral blood. FACS for HSA in the HIV reporter viruses is used to test for HIV viral integration and replication. HIV viral load is also measured from plasma using RT-PCR. Through evaluation of HIV infection by these methods, it is observed that productive in situ DC vaccination makes the immunized mice more resistant to the HIV challenge than those which are not immunized.

Example 20

In Situ HIV/AIDS Vaccination by Recombinant Virus

Clearance of HIV Infection

To test the ability of the in situ DC vaccination approach to clear an active HIV infection, human/mouse chimeras are first challenged with molecularly cloned HIV reporter virus, NFNSX-r-HSAS (CCR5-tropic), as described in Example 19. Active HIV infection is monitored by FACS analysis of HSA expression in human CD4 T cells. Once successful HIV infection is confirmed, the engineered recombinant viruses (Example 19) are injected into animals via subcutaneous injection or by an optimal route determined by one of skill in the art (for example, s.c., i.d., i.v. or i.p.). The HIV viral load is then monitored by RT-PCR, and peripheral CD4 counts are followed. It is observed that DC vaccination is able to lower HIV viral load and to clear an established HIV infection in immunized mice compared to non-vaccinated controls.

Highly active antiretroviral therapy (HAART), utilizing a three-drug strategy, has significantly improved AIDS morbidity and mortality. The strategy outlined above can be adapted to this paradigm by simultaneously transducing DC cells in vivo with engineered recombinant viruses. In conjunction with HAART, the above studies are repeated to evaluate the ability to prevent or reduce infection after HIV challenge (Example 19) and to clear an active HIV infection.

Example 21

Treatment of a Malignant Tumor in a Human Using a Recombinant Virus

A human patient is diagnosed with a malignant tumor. The patient is administered a suitable amount of recombinant virus containing a gene that encodes an antigen specific for the tumor and enveloped with a DC-SIGN specific targeting molecule, such as, for example, SVGmu. The virus optionally contains a gene encoding a DC maturation factor, as described in Example 15. The virus is administered by weekly intravenous injection for the duration of treatment. At periodic times during and after the treatment regimen, tumor burden is assessed by magnetic resonance imaging (MRI). Significant reductions in tumor size are found as treatment progresses.

Example 22

Prevention of Tumor Formation in a Human Using a Recombinant Virus

A group of human patients is administered a suitable amount of recombinant virus containing at least one gene encoding an antigen that is commonly and specifically associated with tumor cells and optionally containing a gene encoding a DC maturation factor, as described in Example 15. The virus is enveloped with a DC-SIGN specific targeting molecule, such as, for example, SVGmu (Example 2). Patients in the experimental group and in a control group are monitored periodically for tumor growth. It is observed that the incidence of malignant tumor formation is lower in patients to whom the virus is administered than in the control group.

Example 23

Treatment of AIDS/HIV in a Human Using a Recombinant Virus

A human patient is diagnosed with HIV/AIDS. The patient is administered a suitable amount of recombinant virus containing a gene that encodes Gp120 (Example 17) and enveloped with a DC-SIGN specific targeting molecule, such as, for example, SVGmu (Example 2). The virus optionally contains a gene encoding a DC maturation factor, as described in Example 15. The virus is administered by weekly intravenous injection for the duration of treatment. At periodic times during and after the treatment regimen, HIV viral load is assessed by measuring antibodies in the patient's blood against HIV using ELISA. The patient's T-cell count is also evaluated. It is observed that a significant reduction in HIV viral load is achieved as treatment progresses. Furthermore, it is observed that the patient's T-cell count stops decreasing as treatment progresses.

Example 24

Prevention of HIV/AIDS in a Human Using a Recombinant Virus

A group of human patients considered at risk for HIV infection is administered a suitable amount of recombinant virus containing a gene encoding GP120 (Example 17) and optionally containing a gene encoding a DC maturation factor, as described in Example 15. The virus is enveloped with a DC-SIGN specific targeting molecule, such as, for example, SVGmu (Example 2). Patients in the experimental group and in a control group are tested every 6 months for HIV infection and if positive, monitored for HIV viral load and T-cell counts. In positively infected patients within the vaccinated group, it is observed that HIV viral load stays low and T-cell counts remain high relative to the positively-infected patients of the control group.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

What is claimed is:

1. A method of stimulating an antigen-specific immune response in a mammal comprising: administering to said mammal a recombinant replication deficient lentivirus pseudotyped with a modified E2 alphavirus glycoprotein that transduces dendritic cells more efficiently compared to other cell types, wherein the lentivirus comprises an exogenous polynucleotide encoding an antigen associated with a disease, and wherein said lentivirus is administered in an amount sufficient to stimulate an immune response to said antigen.

2. The method of claim 1 wherein the immune response is an antibody response or antigen-specific T-cell response or both.

3. The method of claim 2 wherein the immune response is an antigen-specific T-cell response.

4. The method of claim 3 wherein the antigen-specific T-cell response is a CD8+ T-cell response.

5. The method of claim 1 wherein the virus envelope further comprises an E1 alphavirus glycoprotein.

6. The method of claim 1 wherein the E2 glycoprotein is produced from the nucleic acid sequence of SEQ ID NO: 3 or comprises the amino acid sequence of SEQ ID NO: 11.

7. The method of claim 1 wherein the lentivirus comprises an HIV vector, a MSCV vector or an MLV vector.

8. The method of claim 1 wherein the replication deficient lentivirus further comprises one or more additional polynucleotides of interest.

9. The method of claim 1 wherein the replication deficient lentivirus further comprises a polynucleotide encoding a second antigen associated with a disease.

10. The method of claim 1 wherein the mammal is a human.

11. The method of claim 1 wherein the antigen is a tumor associated antigen, viral antigen, bacterial antigen, fungal antigen, protozoan parasite antigen, helminth parasite antigen, or ectoparasite antigen.

12. The method according to claim 11 wherein the antigen is Her-2 receptor, MAGE, BAGE, RAGE, NY-ESO, MART-1/Melan-A, gp100, gp75, mda-7, tyrosinase, tyrosinase-related protein, prostate specific membrane antigen (PSMA), prostate-specific antigen (PSA), ras, bcr/ab1, Her2/neu, p53, cytochrome P450 1B1, N-acetylglucosaminyltransferase-V, human papilloma virus protein E6, human papilloma virus protein E7, carcinoembryonic antigen and alpha-fetoprotein, gp120, an adenovirus polypeptide, an alphavirus polypeptide, a calicivirus polypeptide, calicivirus capsid antigen, a coronavirus polypeptide, s distemper virus polypeptide, an Ebola virus polypeptide, an enterovirus polypeptide, a flavivirus polypeptides, a hepatitis virus (AE) polypeptide, a hepatitis B core antigen, a hepatitis or surface antigen, a herpesvirus polypeptide, a herpes simplex virus glycoptrotein, a varicella zoster virus glycoprotein, an immunodeficiency virus polypeptide, a human immunodeficiency virus envelope protein, a human immunodeficiency virus protease, an infectious peritonitis virus polypeptide, an influenza virus polypeptide, an influenza A hemagglutinin, an influenza A neuraminidase, an influenza A nucleoprotein, a leukemia virus polypeptide, a Marburg virus polypeptide, an orthomyxovirus polypeptide, a papilloma virus polypeptide, a parainfluenza virus polypeptide, a parainfluenza virus hemagglutinin, aparainfluenza virus neuraminidase, a paramyxovirus polypeptide, a parvovirus polypeptide, a pestivirus polypeptide, a picorna virus polypeptidea poliovirus capsid polypeptide, a pox virus polypeptide, a vaccinia virus polypeptide, a rabies virus polypeptide, a rabies virus glycoprotein G, a reovirus polypeptide, a retrovirus polypeptide, a rotavirus polypeptide, an *Absidia* polypeptide, an *Acremonium* polypeptide, an *Alternaria* polypeptide, an *Aspergillus* polypeptide, a *Basidiobolus* polypeptide, a *Bipolaris* polypeptide, a *Blastomyces* polypeptide, a *Candida* polypeptide, a *Coccidioides* polypeptide, a *Conidiobolus* polypeptide, a *Cryptococcus* polypeptide, a *Curvalaria* polypeptide, an *Epidermophyton* polypeptide, an *Exophiala* polypeptide, an *Geotrichum* polypeptide, a *Histoplasma* polypeptide, a *Madurella* polypeptide, a *Malassezia* polypeptide, a *Microsporum* polypeptide, a *Moniliella* polypeptide, a *Mortierella* polypeptide, a *Mucor* polypeptide, a *Paecilomyces* polypeptide, a *Penicillium* polypeptide, a *Phialemonium* polypeptide, a *Phialophora* polypeptide, a *Prototheca* polypeptide, a *Pseudallescheria* polypeptide, a *Pseudomicrodochium* polypeptide, a *Pythium* polypeptide, a *Rhinosporidium* polypeptide, a *Rhizopus* polypeptide, a *Scolecobasidium* polypeptide, a *Sporothrix* polypeptide, a *Stemphylium* polypeptide, a *Trichophyton* polypeptide, a *Trichosporon* polypeptide, and a *Xylohypha* polypeptide, a *Babesia* polypeptide, a *Balantidium* polypeptide, a *Besnoitia* polypeptide, a *Cryptosporidium* polypeptide, an *Eimeria* polypeptide, an *Encephalitozoon* polypeptide, an *Entamoeba* polypeptide, a *Giardia* polypeptide, a *Hammondia* polypeptide, a *Hepatozoon* polypeptide, an *Isospora* polypeptide, a *Leishmania* polypeptide, a *Microsporidia* polypeptide, a *Neospora* polypeptide, a *Nosema* polypeptide, a *Pentatrichomonas* polypeptide, a *Plasmodium* polypeptide, *P. falciparum* circumsporozoite (PfCSP), sporozoite surface protein 2 (PfSSP2), carboxyl terminus of liver state antigen 1 (PfLSA1 c-term), exported protein 1 (PfExp-1), a *Pneumocystis* polypeptide, a *Sarcocystis* polypeptide, a *Schistosoma* polypeptide, *Ta heileria* polypeptide, a *Toxoplasma* polypeptide, a *Trypanosoma* polypeptide, an *Acanthocheilonema* polypeptide, an *Aelurostrongylus* polypeptide, an *Ancylostoma* polypeptide, an *Angiostrongylus* polypeptide, an *Ascaris* polypeptide, a *Brugia* polypeptide, a *Bunostomum* polypeptide, a *Capillaria* polypeptide, a *Chabertia* polypeptide, a *Cooperia* polypeptide, a *Crenosoma* polypeptide, a *Dictyocaulus* polypeptide, a *Dioctophyme* polypeptide, a *Dipetalonema* polypeptide, a *Diphyllobothrium* polypeptide, a *Diplydium* polypeptide, a *Dirofilaria* polypeptide, a *Dracunculus* polypeptide, an *Enterobius* polypeptide, a *Filaroides* polypeptide, a *Haemonchus* polypeptide, a *Lagochilascaris* polypeptide, a *Loa* polypeptide, a *Mansonella* polypeptide, a *Muellerius* polypeptide, a *Nanophyetus* polypeptide, a *Necator* polypeptide, a *Nematodirus* polypeptide, an *Oesophagostomum* polypeptide, an *Onchocerca* polypeptide, an *Opisthorchis* polypeptide, an *Ostertagia* polypeptide, a *Parafilaria* polypeptide, a *Paragonimus* polypeptide, a *Parascaris* polypeptide, a *Physaloptera* polypeptide, a *Protostrongylus* polypeptide, a *Setaria* polypeptide, a *Spirocerca* polypeptide, a *Spirometra* polypeptide, a *Stephanofilaria* polypeptide, a *Strongyloides* polypeptide, a *Strongylus* polypeptide, a *Thelazia* polypeptide, a *Toxascaris* polypeptide, a *Toxocara* polypeptide, a *Trichinella* polypeptide, a *Trichostrongylus* polypeptide, a *Trichuris* polypeptide, an *Uncinaria* polypeptide, a *Wuchereria* polypeptide, a flea polypeptide, a tick polypeptide, a hard tick polypeptide, a soft tick polypeptide, a fly polypeptide, a midge polypeptide, a mosquito polypeptide, a sand fly polypeptide, a black fly polypeptide, a horse fly polypeptide, a horn fly polypeptide, a deer fly polypeptide, a tsetse fly polypeptide, a stable fly polypeptide, a myiasis-causing fly polypeptide, a biting gnat polypeptide, an ant polypeptide, a spider polypeptide, a lice polypeptide, a mite polypeptide, a true bug polypeptide, a bed bug polypeptide, and a kissing bug polypeptide.

13. The method of claim 1 wherein the lentivirus further comprises a nucleotide sequence encoding a maturation factor.

14. The method of claim 13 wherein the maturation factor is selected from the group consisting of GM-CSF, IL-2, IL-4, IL-6, IL-7, IL-15, IL-21, IL-23, TNFα, B7.1, B7.2, 4-1BB, CD40 ligand (CD40L) and drug-inducible CD40 (iCD40).

15. The method of claim 1 wherein the replication deficient lentivirus is administered subcutaneously or intradermally.

16. The method of claim 1 wherein the E2 alphavirus glycoprotein is a Sindbis virus glycoprotein.

17. The method of claim 16 wherein the replication deficient lentivirus is administered subcutaneously or intradermally.

18. The method of claim 16 wherein the lentivirus comprises an HIV vector, a MSCV vector or an MLV vector.

19. The method of claim 16 wherein the replication deficient lentivirus further comprises a polynucleotide encoding a second antigen associated with a disease.

20. The method of claim 16 wherein the mammal is a human.

21. The method of claim 16 wherein the antigen is a tumor associated antigen, viral antigen, bacterial antigen, fungal antigen, protozoan parasite antigen, helminth parasite antigen, or ectoparasite antigen.

22. The method according to claim 21 wherein the antigen is Her-2 receptor, MAGE, BAGE, RAGE, NY-ESO, MART-1/Melan-A, gp100, gp75, mda-7, tyrosinase, tyrosinase-related protein, prostate specific membrane antigen (PSMA), prostate-specific antigen (PSA), ras, bcr/ab1, Her2/neu, p53, cytochrome P450 1B1, N-acetylglucosaminyltransferase-V, human papilloma virus protein E6, human papilloma virus protein E7, carcinoembryonic antigen and alpha-fetoprotein, gp120, an adenovirus polypeptide, an alphavirus polypeptide, a calicivirus polypeptide, calicivirus capsid antigen, a coronavirus polypeptide, s distemper virus polypeptide, an Ebola virus polypeptide, an enterovirus polypeptide, a flavivirus polypeptides, a hepatitis virus (AE) polypeptide, a hepatitis B core antigen, a hepatitis or surface antigen, a herpesvirus polypeptide, a herpes simplex virus glycoptrotein, a varicella zoster virus glycoprotein, an immunodeficiency virus polypeptide, a human immunodeficiency virus envelope protein, a human immunodeficiency virus protease, an infectious peritonitis virus polypeptide, an influenza virus polypeptide, an influenza A hemagglutinin, an influenza A neuraminidase, an influenza A nucleoprotein, a leukemia virus polypeptide, a Marburg virus polypeptide, an orthomyxovirus polypeptide, a papilloma virus polypeptide, a parainfluenza virus polypeptide, a parainfluenza virus hemagglutinin, aparainfluenza virus neuraminidase, a paramyxovirus polypeptide, a parvovirus polypeptide, a pestivirus polypeptide, a picorna virus polypeptidea poliovirus capsid polypeptide, a pox virus polypeptide, a vaccinia virus polypeptide, a rabies virus polypeptide, a rabies virus glycoprotein G, a reovirus polypeptide, a retrovirus polypeptide, a rotavirus polypeptide, an *Absidia* polypeptide, an *Acremonium* polypeptide, an *Alternaria* polypeptide, an *Aspergillus* polypeptide, a *Basidiobolus* polypeptide, a *Bipolaris* polypeptide, a *Blastomyces* polypeptide, a *Candida* polypeptide, a *Coccidioides* polypeptide, a *Conidiobolus* polypeptide, a *Cryptococcus* polypeptide, a *Curvalaria* polypeptide, an *Epidermophyton* polypeptide, an *Exophiala* polypeptide, an *Geotrichum* polypeptide, a *Histoplasma* polypeptide, a *Madurella* polypeptide, a *Malassezia* polypeptide, a *Microsporum* polypeptide, a *Moniliella* polypeptide, a *Mortierella* polypeptide, a *Mucor* polypeptide, a *Paecilomyces* polypeptide, a *Penicillium* polypeptide, a *Phialemonium* polypeptide, a *Phialophora* polypeptide, a *Prototheca* polypeptide, a *Pseudallescheria* polypeptide, a *Pseudomicrodochium* polypeptide, a *Pythium* polypeptide, a *Rhinosporidium* polypeptide, a *Rhizopus* polypeptide, a *Scolecobasidium* polypeptide, a *Sporothrix* polypeptide, a *Stemphylium* polypeptide, a *Trichophyton* polypeptide, a *Trichosporon* polypeptide, and a *Xylohypha* polypeptide, a *Babesia* polypeptide, a *Balantidium* polypeptide, a *Besnoitia* polypeptide, a *Cryptosporidium* polypeptide, an *Eimeria* polypeptide, an *Encephalitozoon* polypeptide, an *Entamoeba* polypeptide, a *Giardia* polypeptide, a *Hammondia* polypeptide, a *Hepatozoon* polypeptide, an *Isospora* polypeptide, a *Leishmania* polypeptide, a *Microsporidia* polypeptide, a *Neospora* polypeptide, a *Nosema* polypeptide, a *Pentatrichomonas* polypeptide, a *Plasmodium* polypeptide, *P. falciparum* circumsporozoite (PfCSP), sporozoite surface protein 2 (PfSSP2), carboxyl terminus of liver state antigen 1 (PfLSA1 c-term), exported protein 1 (PfExp-1), a *Pneumocystis* polypeptide, a *Sarcocystis* polypeptide, a *Schistosoma* polypeptide, *Ta heileria* polypeptide, a *Toxoplasma* polypeptide, a *Trypanosoma* polypeptide, an *Acanthocheilonema* polypeptide, an *Aelurostrongylus* polypeptide, an *Ancylostoma* polypeptide, an *Angiostrongylus* polypeptide, an *Ascaris* polypeptide, a *Brugia* polypeptide, a *Bunostomum* polypeptide, a *Capillaria* polypeptide, a *Chabertia* polypeptide, a *Cooperia* polypeptide, a *Crenosoma* polypeptide, a *Dictyocaulus* polypeptide, a *Dioctophyme* polypeptide, a *Dipetalonema* polypeptide, a *Diphyllobothrium* polypeptide, a *Diplydium* polypeptide, a *Dirofilaria* polypeptide, a *Dracunculus* polypeptide, an *Enterobius* polypeptide, a *Filaroides* polypeptide, a *Haemonchus* polypeptide, a *Lagochilascaris* polypeptide, a *Loa* polypeptide, a *Mansonella* polypeptide, a *Muellerius* polypeptide, a *Nanophyetus* polypeptide, a *Necator* polypeptide, a *Nematodirus* polypeptide, an *Oesophagostomum* polypeptide, an *Onchocerca* polypeptide, an *Opisthorchis* polypeptide, ab *Ostertagia* polypeptide, a *Parafilaria* polypeptide, a *Paragonimus* polypeptide, a *Parascaris* polypeptide, a *Physaloptera* polypeptide, a *Protostrongylus* polypeptide, a *Setaria* polypeptide, a *Spirocerca* polypeptide, a *Spirometra* polypeptide, a *Stephanofilaria* polypeptide, a *Strongyloides* polypeptide, a *Strongylus* polypeptide, a *Thelazia* polypeptide, a *Toxascaris* polypeptide, a *Toxocara* polypeptide, a *Trichinella* polypeptide, a *Trichostrongylus* polypeptide, a *Trichuris* polypeptide, an *Uncinaria* polypeptide, a *Wuchereria* polypeptide, a flea polypeptide, a tick polypeptide, a hard tick polypeptide, a soft tick polypeptide, a fly polypeptide, a midge polypeptide, a mosquito polypeptide, a sand fly polypeptide, a black fly polypeptide, a horse fly polypeptide, a horn fly polypeptide, a deer fly polypeptide, a tsetse fly polypeptide, a stable fly polypeptide, a myiasis-causing fly polypeptide, a biting gnat polypeptide, an ant polypeptide, a spider polypeptide, a lice polypeptide, a mite polypeptide, a true bug polypeptide, a bed bug polypeptide, and a kissing bug polypeptide.

23. The method of claim 16 wherein the lentivirus further comprises a nucleotide sequence encoding a maturation factor.

* * * * *

SEQUENCE LISTING

```
<160> NUMBER OF SEQ ID NOS: 11

<210> SEQ ID NO 1
<211> LENGTH: 9941
<212> TYPE: DNA
<213> ORGANISM: Artificial Sequence
<220> FEATURE:
<223> OTHER INFORMATION: Constructed plasmid vector
```

<400> SEQUENCE: 1

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg cccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctgggatt     1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
```

```
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg cgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtgggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct tcgtggccg ccgggccgct    3060
cggtgggacg gaagcgtgtg gagagaccgc caagggctgt agtctgggtc cgcgagcaag    3120
gttgccctga actgggggtt gggggagcg cacaaaatgg cggctgttcc cgagtcttga    3180
atggaagacg cttgtaaggc gggctgtgag gtcgttgaaa caaggtgggg gcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgagggagg    3600
gataagtgag gcgtcagttt ctttggtcgg ttttatgtac ctatcttctt aagtagctga    3660
agctccggtt ttgaactatg cgctcggggt tggcgagtgt gttttgtgaa gtttttttagg    3720
cacctttttga aatgtaatca tttgggtcaa tatgtaattt tcagtgttag actagtaaag    3780
cttctgcagg tcgactctag aaaattgtcc gctaaattct ggccgttttt ggctttttttg    3840
ttagacagga tccccgggta ccggtcgcca ccatggtgag caagggcgag gagctgttca    3900
ccggggtggt gcccatcctg gtcgagctgg acggcgacgt aaacggccac aagttcagcg    3960
tgtccggcga gggcgagggc gatgccacct acggcaagct gaccctgaag ttcatctgca    4020
ccaccggcaa gctgcccgtg ccctggccca ccctcgtgac caccctgacc tacggcgtgc    4080
agtgcttcag ccgctacccc gaccacatga agcagcacga cttcttcaag tccgccatgc    4140
ccgaaggcta cgtccaggag cgcaccatct tcttcaagga cgacggcaac tacaagaccc    4200
gcgccgaggt gaagttcgag ggcgacaccc tggtgaaccg catcgagctg aagggcatcg    4260
acttcaagga ggacggcaac atcctggggc acaagctgga gtacaactac aacagccaca    4320
acgtctatat catggccgac aagcagaaga acggcatcaa ggtgaacttc aagatccgcc    4380
acaacatcga ggacggcagc gtgcagctcg ccgaccacta ccagcagaac ccccccatcg    4440
gcgacggccc cgtgctgctg cccgacaacc actacctgag cacccagtcc gccctgagca    4500
aagaccccaa cgagaagcgc gatcacatgg tcctgctgga gttcgtgacc gccgccggga    4560
tcactctcgg catggacgag ctgtacaagt aaagcggccg cgactctaga attcgatatc    4620
aagcttatcg ataatcaacc tctggattac aaaatttgtg aaagattgac tggtattctt    4680
```

```
aactatgttg ctccttttac gctatgtgga tacgctgctt taatgccttt gtatcatgct   4740
attgcttccc gtatggcttt cattttctcc tccttgtata aatcctggtt gctgtctctt   4800
tatgaggagt tgtggcccgt tgtcaggcaa cgtggcgtgg tgtgcactgt gtttgctgac   4860
gcaaccccca ctggttgggg cattgccacc acctgtcagc tcctttccgg gactttcgct   4920 ttcccctcc ctattgccac ggcggaactc atcgccgcct gccttgcccg ctgctggaca    4980
ggggctcggt gttgggcac tgacaattcc gtggtgttgt cggggaaatc atcgtccttt    5040
ccttggctgc tcgcctgtgt tgccacctgg attctgcgcg ggacgtcctt ctgctacgtc   5100
ccttcggccc tcaatccagc ggaccttcct tcccgcggcc tgctgccggc tctgcggcct   5160
cttccgcgtc ttcgccttcg ccctcagacg agtcggatct cccttggc cgcctcccg     5220 catcgatacc gtcgacctcg agacctagaa aaacatggag caatcacaag tagcaataca   5280
gcagctacca atgctgattg tgcctggcta gaagcacaag aggaggagga ggtgggtttt    5340
ccagtcacac ctcaggtacc tttaagacca atgacttaca aggcagctgt agatcttagc   5400
cactttttaa aagaaaaggg gggactggaa gggctaattc actcccaacg aagacaagat   5460
atccttgatc tgtggatcta ccacacacaa ggctacttcc ctgattggca gaactacaca   5520
ccagggccag ggatcagata tccactgacc tttggatggt gctacaagct agtaccagtt   5580
gagcaagaga aggtagaaga agccaatgaa ggagagaaca cccgcttgtt acaccctgtg   5640
agcctgcatg ggatggatga cccggagaga gaagtattag agtggaggtt tgacagccgc   5700
ctagcatttc atcacatggc ccgagagctg catccggact gtactgggtc tctctggtta   5760
gaccagatct gagcctggga gctctctggc taactaggga acccactgct taagcctcaa   5820
taaagcttgc cttgagtgct tcaagtagtg tgtgcccgtc tgttgtgtga ctctggtaac   5880
tagagatccc tcagaccctt ttagtcagtg tggaaaatct ctagcagggc cgtttaaac    5940 ccgctgatca gcctcgactg tgccttctag ttgccagcca tctgttgttt gccctccc    6000 cgtgccttcc ttgaccctgg aaggtgccac tcccactgtc ctttcctaat aaaatgagga   6060
aattgcatcg cattgtctga gtaggtgtca ttctattctg ggggtgggg tgggcagga    6120 cagcaagggg gaggattggg aagacaatag caggcatgct ggggatgcgg tgggctctat   6180
ggcttctgag gcggaaagaa ccagctgggg ctctaggggg tatccccacg cgccctgtag   6240
cggcgcatta agcgcggcgg gtgtggtggt tacgcgcagc gtgaccgcta cacttgccag   6300
cgccctagcg cccgctcctt tcgctttctt cccttccttt ctcgccacgt tcgccggctt   6360
tccccgtcaa gctctaaatc ggggctccc tttagggttc cgatttagtg ctttacggca   6420
cctcgacccc aaaaaacttg attagggtga tggttcacgt agtgggccat cgccctgata   6480
gacggttttt cgccctttga cgttggagtc acgttctttt aatagtggac tcttgttcca   6540
aactggaaca cactcaacc ctatctcggt ctattctttt gatttataag ggattttgcc    6600
gatttcggcc tattggttaa aaaatgagct gatttaacaa aaatttaacg cgaattaatt    6660
ctgtggaatg tgtgtcagtt agggtgtgga aagtccccag gctccccagc aggcagaagt   6720
atgcaaagca tgcatctcaa ttagtcagca accaggtgtg gaaagtcccc aggctcccca   6780
gcaggcagaa gtatgcaaag catgcatctc aattagtcag caaccatagt cccgccccta   6840
actccgccca tcccgcccct aactccgccc agttccgccc attctccgcc ccatggctga   6900 ctaattttt ttatttatgc agaggccgag gccgcctctg cctctgagct attccagaag    6960
tagtgaggag gcttttttgg aggcctaggc ttttgcaaaa agctcccggg agcttgtata   7020
```

```
tccattttcg gatctgatca gcacgtgttg acaattaatc atcggcatag tatatcggca    7080
tagtataata cgacaaggtg aggaactaaa ccatggccaa gttgaccagt gccgttccgg    7140
tgctcaccgc gcgcgacgtc gccggagcgg tcgagttctg gaccgaccgg ctcgggttct    7200
cccgggactt cgtggaggac gacttcgccg gtgtggtccg ggacgacgtg accctgttca    7260
tcagcgcggt ccaggaccag gtggtgccgg acaacaccct ggcctgggtg tgggtgcgcg    7320
gcctggacga gctgtacgcc gagtggtcgg aggtcgtgtc cacgaacttc cgggacgcct    7380
ccgggccggc catgaccgag atcggcgagc agccgtgggg gcgggagttc gccctgcgcg    7440
acccggccgg caactgcgtg cacttcgtgg ccgaggagca ggactgacac gtgctacgag    7500
atttcgattc caccgccgcc ttctatgaaa ggttgggctt cggaatcgtt ttccgggacg    7560
ccggctggat gatcctccag cgcgggatc tcatgctgga gttcttcgcc caccccaact    7620
tgtttattgc agcttataat ggttacaaat aaagcaatag catcacaaat ttcacaaata    7680
aagcattttt ttcactgcat tctagttgtg gtttgtccaa actcatcaat gtatcttatc    7740
atgtctgtat accgtcgacc tctagctaga gcttggcgta atcatggtca tagctgtttc    7800
ctgtgtgaaa ttgttatccg ctcacaattc cacacaacat acgagccgga agcataaagt    7860
gtaaagcctg gggtgcctaa tgagtgagct aactcacatt aattgcgttg cgctcactgc    7920
ccgcttttcc agtcgggaaac ctgtcgtgcc agctgcatta atgaatcggc caacgcgcgg    7980
ggagaggcgg tttgcgtatt gggcgctctt ccgcttcctc gctcactgac tcgctgcgct    8040
cggtcgttcg gctgcggcga gcggtatcag ctcactcaaa ggcggtaata cggttatcca    8100
cagaatcagg ggataacgca ggaaagaaca tgtgagcaaa aggccagcaa aaggccagga    8160
accgtaaaaa ggccgcgttg ctggcgtttt tccataggct ccgcccccct gacgagcatc    8220
acaaaaatcg acgctcaagt cagaggtggc gaaacccgac aggactataa agataccagg    8280
cgtttccccc tggaagctcc ctcgtgcgct ctcctgttcc gaccctgccg cttaccggat    8340
acctgtccgc ctttctccct tcgggaagcg tggcgctttc tcatagctca cgctgtaggt    8400
atctcagttc ggtgtaggtc gttcgctcca agctgggctg tgtgcacgaa ccccccgttc    8460
agcccgaccg ctgcgcctta tccggtaact atcgtcttga gtccaacccg gtaagacacg    8520
acttatcgcc actggcagca gccactggta acaggattag cagagcgagg tatgtaggcg    8580
gtgctacaga gttcttgaag tggtggccta actacggcta cactagaaga acagtatttg    8640
gtatctgcgc tctgctgaag ccagttacct tcggaaaaag agttggtagc tcttgatccg    8700
gcaaacaaac caccgctggt agcggtggtt tttttgtttg caagcagcag attacgcgca    8760
gaaaaaaagg atctcaagaa gatcctttga tcttttctac ggggtctgac gctcagtgga    8820
acgaaaactc acgttaaggg attttggtca tgagattatc aaaaaggatc ttcacctaga    8880
tccttttaaa ttaaaaatga agttttaaat caatctaaag tatatatgag taaacttggt    8940
ctgacagtta ccaatgctta atcagtgagg cacctatctc agcgatctgt ctatttcgtt    9000
catccatagt tgcctgactc cccgtcgtgt agataactac gatacgggag ggcttaccat    9060
ctggccccag tgctgcaatg ataccgcgag acccacgctc accggctcca gatttatcag    9120
caataaacca gccagccgga agggccgagc gcagaagtgg tcctgcaact ttatccgcct    9180
ccatccagtc tattaattgt tgccgggaag ctagagtaag tagttcgcca gttaatagtt    9240
tgcgcaacgt tgttgccatt gctacaggca tcgtggtgtc acgctcgtcg tttggtatgg    9300
cttcattcag ctccggttcc caacgatcaa ggcgagttac atgatccccc atgttgtgca    9360
aaaaagcggt tagctccttc ggtcctccga tcgttgtcag aagtaagttg gccgcagtgt    9420
```

-continued

```
tatcactcat ggttatggca gcactgcata attctcttac tgtcatgcca tccgtaagat    9480
gcttttctgt gactggtgag tactcaacca agtcattctg agaatagtgt atgcggcgac    9540
cgagttgctc ttgcccggcg tcaatacggg ataataccgc gccacatagc agaactttaa    9600
aagtgctcat cattggaaaa cgttcttcgg ggcgaaaact ctcaaggatc ttaccgctgt    9660
tgagatccag ttcgatgtaa cccactcgtg cacccaactg atcttcagca tcttttactt    9720
tcaccagcgt ttctgggtga gcaaaaacag gaaggcaaaa tgccgcaaaa aagggaataa    9780
gggcgacacg gaaatgttga atactcatac tcttcctttt tcaatattat tgaagcattt    9840 atcaggggtta ttgtctcatg agcggataca tatttgaatg tatttagaaa aataaacaaa    9900
taggggttcc gcgcacattt ccccgaaaag tgccacctga c                       9941
```

<210> SEQ ID NO 2
<211> LENGTH: 9206
<212> TYPE: DNA
<213> ORGANISM: Artificial Sequence
<220> FEATURE:
<223> OTHER INFORMATION: Constructed plasmid vector

<400> SEQUENCE: 2

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa atttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagaccctt tagtcagtgt ggaaaatctc tagcagtggc    1020
gcccgaacag ggacttgaaa gcgaaaggga accagagga gctctctcga cgcaggactc    1080
ggcttgctga gcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga gaacttagat cattatata atacagtagc aaccctctat tgtgtgcatc    1440
aaaggataga gataaaagac accaaggaag ctttagacaa gatagaggaa gagcaaaaca    1500
```

```
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggg att   1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattga tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
cgggcgcccc cctcctcacg gcgagcgctg ccacgtcaga cgaagggcgc aggagcgttc   2700
ctgatccttc cgcccggacg ctcaggacag cggcccgctg ctcataagac tcggccttag   2760
aaccccagta tcagcagaag gacattttag gacgggactt gggtgactct agggcactgg   2820 ttttcttttcc agagagcgga acaggcgagg aaaagtagtc ccttctcggc gattctgcgg   2880
agggatctcc gtggggcggt aacgccgat gattatataa ggacgcgccg ggtgtggcac   2940
agctagttcc gtcgcagccg ggatttgggt cgcggttctt gtttgtggat cgctgtgatc   3000
gtcacttggt gagttgcggg ctgctgggct ggccggggct ttcgtggccg ccgggccgct   3060
cggtgggacg gaagcgtgtg gagagaccgc caagggctgt agtctgggtc cgcgagcaag   3120
gttgccctga actgggggtt gggggggagcg cacaaaatgg cggctgttcc cgagtcttga   3180
atggaagacg cttgtaaggc gggctgtgag gtcgttgaaa caaggtgggg ggcatggtgg   3240
gcggcaagaa cccaaggtct tgaggccttc gctaatgcgg gaaagctctt attcgggtga   3300
gatgggctgg ggcaccatct ggggaccctg acgtgaagtt tgtcactgac tggagaactc   3360
gggtttgtcg tctggttgcg ggggcggcag ttatgcggtg ccgttgggca gtgcacccgt   3420
acctttggga gcgcgcgcct cgtcgtgtcg tgacgtcacc cgttctgttg cttataatg   3480 cagggtgggg ccacctgccg gtaggtgtgc ggtaggctt tctccgtcgc aggacgcagg   3540
gttcgggcct agggtaggct ctcctgaatc gacaggcgcc ggacctctgg tgagggagg   3600 gataagtgag gcgtcagttt cttttggtcgg ttttatgtac ctatcttctt aagtagctga   3660
agctccggtt ttgaactatg cgctcgggt tggcgagtgt gttttgtgaa gttttttagg   3720 cacctttga aatgtaatca tttgggtcaa tatgtaattt tcagtgttag actagtaaag   3780
cttctgcagg tcgactctag aaaattgtcc gctaaattct ggccgttttt ggcttttttg   3840
ttagacagga tccgttaacc tcgagggcgc gccgaattcg atatcaagct tatcgataat   3900
```

```
caacctctgg attacaaaat ttgtgaaaga ttgactggta ttcttaacta tgttgctcct    3960
tttacgctat gtggatacgc tgctttaatg cctttgtatc atgctattgc ttcccgtatg    4020
gctttcattt tctcctcctt gtataaatcc tggttgctgt ctctttatga ggagttgtgg    4080
cccgttgtca ggcaacgtgg cgtggtgtgc actgtgtttg ctgacgcaac ccccactggt    4140
tggggcattg ccaccacctg tcagctcctt tccgggactt tcgctttccc cctccctatt    4200
gccacggcgg aactcatcgc cgcctgcctt gcccgctgct ggacagggc tcggctgttg      4260
ggcactgaca attccgtggt gttgtcgggg aaatcatcgt cctttccttg gctgctcgcc    4320
tgtgttgcca cctggattct cgcgggacg tccttctgct acgtcccttc ggccctcaat      4380
ccagcggacc ttccttcccg cggcctgctg ccggctctgc ggcctcttcc gcgtcttcgc    4440
cttcgccctc agacgagtcg gatctccctt gggccgcct cccgcatcg ataccgtcga       4500
cctcgagacc tagaaaaaca tggagcaatc acaagtagca atacagcagc taccaatgct    4560
gattgtgcct ggctagaagc acaagaggag gaggaggtgg gttttccagt cacacctcag    4620
gtacctttaa gaccaatgac ttacaaggca gctgtagatc ttagccactt tttaaaagaa    4680
aaggggggac tggaagggct aattcactcc caacgaagac aagatatcct tgatctgtgg    4740
atctaccaca cacaaggcta cttccctgat tggcagaact acacaccagg gccagggatc    4800
agatatccac tgacctttgg atggtgctac aagctagtac cagttgagca agagaaggta    4860
gaagaagcca atgaaggaga aacacccgc ttgttacacc ctgtgagcct gcatgggatg      4920
gatgacccgg agagagaagt attagagtgg aggtttgaca gccgcctagc atttcatcac    4980
atggcccgag agctgcatcc ggactgtact gggtctctct ggttagacca gatctgagcc    5040
tgggagctct ctggctaact agggaaccca ctgcttaagc ctcaataaag cttgccttga    5100
gtgcttcaag tagtgtgtgc ccgtctgttg tgtgactctg gtaactagag atccctcaga    5160
ccctttagt cagtgtggaa aatctctagc agggcccgtt taaacccgct gatcagcctc      5220
gactgtgcct tctagttgcc agccatctgt tgtttgcccc tcccccgtgc cttccttgac    5280
cctggaaggt gccactccca ctgtcctttc ctaataaaat gaggaaattg catcgcattg    5340
tctgagtagg tgtcattcta ttctgggggg tggggtgggg caggacagca agggggagga    5400
ttgggaagac aatagcaggc atgctgggga tgcggtgggc tctatggctt ctgaggcgga    5460
aagaaccagc tggggctcta gggggtatcc ccacgcgccc tgtagcggcg cattaagcgc    5520
ggcgggtgtg gtggttacgc gcagcgtgac cgctacactt gccagcgccc tagcgcccgc    5580
tcctttcgct ttcttccctt cctttctcgc cacgttcgcc ggctttcccc gtcaagctct    5640
aaatcggggg ctccctttag ggttccgatt tagtgcttta cggcacctcg accccaaaaa    5700
acttgattag ggtgatggtt cacgtagtgg gccatcgccc tgatagacgg ttttcgccc     5760
tttgacgttg gagtccacgt tctttaatag tggactcttg ttccaaactg gaacaacact    5820
caaccctatc tcggtctatt cttttgattt ataagggatt ttgccgattt cggcctattg    5880
gttaaaaaat gagctgattt aacaaaaatt taacgcgaat taattctgtg aatgtgtgt     5940
cagttagggt gtggaaagtc ccaggctcc ccagcaggca gaagtatgca aagcatgcat      6000
ctcaattagt cagcaaccag gtgtggaaag tccccaggct ccccagcagg cagaagtatg    6060
caaagcatgc atctcaatta gtcagcaacc atagtcccgc cctaactccg cccatcccg      6120
cccctaactc cgcccagttc cgcccattct ccgccccatg ctgactaat tttttttatt     6180
tatgcagagg ccgaggccgc ctctgcctct gagctattcc agaagtagtg aggaggcttt    6240
```

```
tttggaggcc taggcttttg caaaaagctc ccgggagctt gtatatccat tttcggatct    6300
gatcagcacg tgttgacaat taatcatcgg catagtatat cggcatagta taatacgaca    6360
aggtgaggaa ctaaaccatg ccaagttga ccagtgccgt tccggtgctc accgcgcgcg    6420
acgtcgccgg agcggtcgag ttctggaccg accggctcgg gttctcccgg gacttcgtgg    6480
aggacgactt cgccggtgtg gtccgggacg acgtgaccct gttcatcagc gcggtccagg    6540
accaggtggt gccggacaac accctggcct gggtgtgggt gcgcggcctg gacgagctgt    6600
acgccgagtg gtcggaggtc gtgtccacga acttccggga cgcctccggg ccggccatga    6660
ccgagatcgg cgagcagccg tggggcgggg agttcgccct gcgcgacccg gccggcaact    6720
gcgtgcactt cgtggccgag gagcaggact gacacgtgct acgagatttc gattccaccg    6780
ccgccttcta tgaaaggttg gcttcggaa tcgttttccg gacgccggc tggatgatcc    6840
tccagcgcgg ggatctcatg ctggagttct tcgcccaccc caacttgttt attgcagctt    6900
ataatggtta caaataaagc aatagcatca caaatttcac aaataaagca ttttttttcac   6960
tgcattctag ttgtggtttg tccaaactca tcaatgtatc ttatcatgtc tgtataccgt    7020
cgacctctag ctagagcttg gcgtaatcat ggtcatagct gtttcctgtg tgaaattgtt    7080
atccgctcac aattccacac aacatacgag ccggaagcat aaagtgtaaa gcctggggtg    7140
cctaatgagt gagctaactc acattaattg cgttgcgctc actgcccgct ttccagtcgg    7200
gaaacctgtc gtgccagctg cattaatgaa tcggccaacg cgcggggaga ggcggtttgc    7260
gtattgggcg ctcttccgct tcctcgctca ctgactcgct gcgctcggtc gttcggctgc    7320
ggcgagcggt atcagctcac tcaaaggcgg taatacggtt atccacagaa tcaggggata    7380
acgcaggaaa gaacatgtga gcaaaaggcc agcaaaaggc caggaaccgt aaaaaggccg    7440
cgttgctggc gttttccat aggctccgcc cccctgacga gcatcacaaa aatcgacgct    7500
caagtcagag gtggcgaaac ccgacaggac tataaagata ccaggcgttt ccccctggaa    7560
gctccctcgt gcgctctcct gttccgaccc tgccgcttac cggatacctg tccgcctttc    7620
tcccttcggg aagcgtggcg ctttctcata gctcacgctg taggtatctc agttcggtgt    7680
aggtcgttcg ctccaagctg ggctgtgtgc acgaacccc cgttcagccc gaccgctgcg    7740
ccttatccgg taactatcgt cttgagtcca acccggtaag acacgactta tcgccactgg    7800
cagcagccac tggtaacagg attagcagag cgaggtatgt aggcggtgct acagagttct    7860
tgaagtggtg gcctaactac ggctacacta agaacagt atttggtatc tgcgctctgc    7920
tgaagccagt taccttcgga aaagagttg gtagctcttg atccggcaaa caaaccaccg    7980
ctggtagcgg tggttttttt gtttgcaagc agcagattac gcgcagaaaa aaaggatctc    8040
aagaagatcc tttgatcttt tctacggggt ctgacgctca gtggaacgaa aactcacgtt    8100
aagggatttt ggtcatgaga ttatcaaaaa ggatcttcac ctagatcctt ttaaattaaa    8160
aatgaagttt taaatcaatc taagtatat atgagtaaac ttggtctgac agttaccaat    8220
gcttaatcag tgaggcacct atctcagcga tctgtctatt tcgttcatcc atagttgcct    8280
gactccccgt cgtgtagata actacgatac gggagggctt accatctggc cccagtgctg    8340
caatgatacc gcgagaccca cgctcaccgg ctccagattt atcagcaata aaccagccag    8400
ccggaagggc cgagcgcaga agtggtcctg caactttatc cgcctccatc cagtctatta    8460
attgttgccg ggaagctaga gtaagtagtt cgccagttaa tagtttgcgc aacgttgttg    8520
ccattgctac aggcatcgtg gtgtcacgct cgtcgtttgg tatggcttca ttcagctccg    8580
gttcccaacg atcaaggcga gttacatgat cccccatgtt gtgcaaaaaa gcggttagct    8640
```

```
ccttcggtcc tccgatcgtt gtcagaagta agttggccgc agtgttatca ctcatggtta    8700
tggcagcact gcataattct cttactgtca tgccatccgt aagatgcttt tctgtgactg    8760
gtgagtactc aaccaagtca ttctgagaat agtgtatgcg gcgaccgagt tgctcttgcc    8820
cggcgtcaat acgggataat accgcgccac atagcagaac tttaaaagtg ctcatcattg    8880
gaaaacgttc ttcggggcga aaactctcaa ggatcttacc gctgttgaga tccagttcga    8940
tgtaacccac tcgtgcaccc aactgatctt cagcatcttt tactttcacc agcgtttctg    9000
ggtgagcaaa acaggaagg caaaatgccg caaaaaggg aataagggcg cacggaaat      9060 gttgaatact catactcttc cttttcaat attattgaag catttatcag ggttattgtc     9120
tcatgagcgg atacatattt gaatgtattt agaaaaataa acaaataggg gttccgcgca    9180
catttccccg aaaagtgcca cctgac                                         9206
```

<210> SEQ ID NO 3  
<211> LENGTH: 8435  
<212> TYPE: DNA  
<213> ORGANISM: Artificial Sequence  
<220> FEATURE:  
<223> OTHER INFORMATION: Constructed plasmid vector

<400> SEQUENCE: 3

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg ggatttcca agtctccacc ccattgacgt     600
caatgggagt ttgttttggc accaaaatca acgggacttt ccaaaatgtc gtaacaactg     660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagctta agcttggatc cgccgccacc atgtccgcag caccactggt   1140
cacggcaatg tgtttgctcg gaaatgtgag cttcccatgc gaccgccgc ccacatgcta    1200 tacccgcgaa ccttccagag ccctcgcat ccttgaagag aacgtgaacc atgaggccta    1260
cgataccctg ctcaatgcca tattgcggtg cggatcgtct ggcagcgtca ttgacgactt    1320
taccctgacc agcccctact ggggcacatg ctcgtactgc caccatactg taccgtgctt    1380
cagccctgtt aagatcgagc aggtctggga cgaagcggac gataacacca tacgcatacA   1440
```

```
gacttccgcc cagtttggat acgaccaaag cggagcagca agcgcaaaca agtaccgcta    1500
catgtcgctt aagctgatgt acccatacga tgttccagat tacgctaccg ttaaagaagg    1560
caccatggat gacatcaaga ttagcacctc aggaccgtgt agaaggctta gctacaaagg    1620
atactttctc ctcgcaaaat gccctccagg ggacagcgta acggttagca tagtgagtag    1680
caactcagca acgtcatgta cactggcccg caagataaaa ccaaaattcg tgggacggga    1740
aaaatatgat ctacctcccg ttcacggtaa aaaaattcct tgcacagtgt acgaccgtct    1800
ggccgctaca actgcaggct acatcactat gcacaggccg agaccgcacg cttatacatc    1860
ctacctggaa gaatcatcag ggaaagttta cgcaaagccg ccatctggga gaacattac     1920 gtatgagtgc aagtgcggcg actacaagac cggaaccgtt tcgacccgca ccgaaatcac    1980
tggttgcacc gccatcaagc agtgcgtcgc ctataagagc gaccaaacga agtgggtctt    2040
caactcaccg gacttgatca gacatgacga ccacacggcc caagggaaat tgcatttgcc    2100
tttcaagttg atcccgagta cctgcatggt ccctgttgcc cacgcgccga atgtaataca    2160
tggctttaaa cacatcagcc tccaattaga tacagaccac ttgacattgc tcaccaccag    2220
gagactaggg gcaaacccgg aaccaaccac tgaatggatc gtcggaaaga cggtcagaaa    2280
cttcaccgtc gaccgagatg gcctggaata catatgggga aatcatgagc cagtgagggt    2340
ctatgcccaa gagtcagcac caggagaccc tcacggatgg ccacacgaaa tagtacagca    2400
ttactaccat cgccatcctg tgtacaccat cttagccgtc gcatcagcta ccgtggcgat    2460
gatgattggc gtaactgttg cagtgttatg tgcctgtaaa gcgcgccgtg agtgcctgac    2520
gccatacgcc ctgccccaa acgccgtaat cccaacttcg ctggcactct tgtgctgcgt    2580
taggtcggcc aatgctgaaa cgttcaccga gaccatgagt tacttgtggt cgaacagtca    2640
gccgttcttc tgggtccagt tgtgcatacc tttggccgct ttcatcgttc taatgcgctg    2700
ctgctcctgc tgcctgcctt ttttagtggt tgccggcgcc tacctggcga aggtagacgc    2760
ctacgaacat gcgaccactg ttccaaatgt gccacagata ccgtataagg cacttgttga    2820
aagggcaggg tatgccccgc tcaatttgga gatcactgtc atgtcctcgg aggttttgcc    2880
ttccaccaac caagagtaca ttacctgcaa attccaccact gtggtcccct ccccaaaaat    2940
caaatgctgc ggctccttgg aatgtcagcc ggccgctcat gcaggctata cctgcaaggt    3000
cttcggaggg gtctacccct ttatgtgggg aggagcgcaa tgttttttgcg acagtgagaa    3060 cagccagatg agtgaggcgt acgtcgaatt gtcagcagat tgcgcgtctg accacgcgca    3120
ggcgattaag gtgcacactg ccgcgatgaa agtaggactg cgtattgtgt acgggaacac    3180
taccagtttc ctagatgtgt acgtgaacgg agtcacacca ggaacgtcta aagacttgaa    3240
agtcatagct ggaccaattt cagcatcgtt tacgccattc gatcataagg tcgttatcca    3300
tcgcggcctg gtgtacaact atgacttccc ggaatatgga gcgatgaaac caggagcgtt    3360
tggagacatt caagctacct ccttgactag caaggatctc atcgccagca cagacattag    3420
gctactcaag ccttccgcca gaacgtgca tgtcccgtac acgcaggcct catcaggatt    3480
tgagatgtgg aaaaacaact caggccgccc actgcaggaa accgcacctt tcgggtgtaa    3540
gattgcagta aatcgctcc gagcggtgga ctgttcatac gggaacattc ccatttctat     3600
tgacatcccg aacgctgcct ttatcaggac atcagatgca ccactggtct caacagtcaa    3660
atgtgaagtc agtgagtgca cttattcagc agacttcggc gggatggcca ccctgcagta    3720
tgtatccgac cgcgaaggtc aatgcccgt acattcgcat tcgagcacag caactctcca     3780
agagtcgaca gtacatgtcc tggagaaagg agcggtgaca gtacactta gcaccgcgag     3840
```

```
tccacaggcg aactttatcg tatcgctgtg tgggaagaag acaacatgca atgcagaatg    3900
taaaccacca gctgaccata tcgtgagcac cccgcacaaa aatgaccaag aatttcaagc    3960
cgccatctca aaaacatcat ggagttggct gtttgccctt ttcggcggcg cctcgtcgct    4020
attaattata ggacttatga ttttttgcttg cagcatgatg ctgactagca cacgaagatg    4080
aggatccgaa ttggccgctt cccttttagtg agggttaatg cttcgagcag acatgataag    4140
atacattgat gagtttggac aaaccacaac tagaatgcag tgaaaaaaat gctttatttg    4200
tgaaatttgt gatgctattg ctttatttgt aaccattata agctgcaata aacaagttaa    4260
caacaacaat tgcattcatt ttatgtttca ggttcagggg gagatgtggg aggtttttta    4320
aagcaagtaa aacctctaca aatgtggtaa aatccgataa ggatcgatcc gggctggcgt    4380
aatagcgaag aggcccgcac cgatcgccct tcccaacagt tgcgcagcct gaatggcgaa    4440
tggacgcgcc ctgtagcggc gcattaagcg cggcgggtgt ggtggttacg cgcagcgtga    4500
ccgctacact tgccagcgcc ctagcgcccg ctcctttcgc tttcttccct tcctttctcg    4560
ccacgttcgc cggctttccc cgtcaagctc taaatcgggg gctcccttta gggttccgat    4620
ttagagcttt acggcacctc gaccgcaaaa aacttgattt gggtgatggt tcacgtagtg    4680
ggccatcgcc ctgatagacg gttttttcgcc ctttgacgtt ggagtccacg ttctttaata    4740
gtggactctt gttccaaact ggaacaacac tcaaccctat ctcggtctat tcttttgatt    4800
tataagggat tttgccgatt tcggcctatt ggttaaaaaa tgagctgatt taacaaatat    4860
ttaacgcgaa ttttaacaaa atattaacgt ttacaatttc gcctgatgcg gtattttctc    4920
cttacgcatc tgtgcggtat ttcacaccgc atacgcggat ctgcgcagca ccatggcctg    4980
aaataacctc tgaaagagga acttggttag gtaccttctg aggcggaaag aaccagctgt    5040
ggaatgtgtg tcagttaggg tgtggaaagt ccccaggctc cccagcaggc agaagtatgc    5100
aaagcatgca tctcaattag tcagcaacca ggtgtggaaa gtcccaggc tccccagcag    5160 gcagaagtat gcaaagcatg catctcaatt agtcagcaac catagtcccg cccctaactc    5220
cgcccatccc gcccctaact ccgcccagtt ccgcccattc tccgcccat ggctgactaa    5280 tttttttat ttatgcagag gccgaggccg cctcggcctc tgagctattc cagaagtagt    5340
gaggaggctt ttttggaggc ctaggctttt gcaaaaagct tgattcttct gacacaacag    5400
tctcgaactt aaggctagag ccaccatgat tgaacaagat ggattgcacg caggttctcc    5460
ggccgcttgg gtggagaggc tattcggcta tgactgggca caacagacaa tcggctgctc    5520
tgatgccgcc gtgttccggc tgtcagcgca ggggcgcccg gttcttttg tcaagaccga    5580 cctgtccggt gccctgaatg aactgcagga cgaggcagcg cggctatcgt ggctggccac    5640
gacgggcgtt ccttgcgcag ctgtgctcga cgttgtcact gaagcgggaa gggactggct    5700
gctattgggc gaagtgccgg ggcaggatct cctgtcatct caccttgctc ctgccgagaa    5760
agtatccatc atggctgatg caatgcggcg gctgcatacg cttgatccgg ctacctgccc    5820
attcgaccac caagcgaaac atcgcatcga gcgagcacgt actcggatgg aagccggtct    5880
tgtcgatcag gatgatctgg acgaagagca tcagggctcgc gccagccg aactgttcgc    5940 caggctcaag gcgcgcatgc ccgacggcga ggatctcgtc gtgacccatg gcgatgcctg    6000
cttgccgaat atcatggtgg aaaatggccg cttttctgga ttcatcgact gtggccggct    6060
gggtgtggcg gaccgctatc aggacatagc gttggctacc cgtgatattg ctgaagagct    6120
tggcggcgaa tgggctgacc gcttcctcgt gctttacggt atcgccgctc ccgattcgca    6180
```

```
gcgcatcgcc ttctatcgcc ttcttgacga gttcttctga gcgggactct ggggttcgaa    6240
atgaccgacc aagcgacgcc caacctgcca tcacgatggc cgcaataaaa tatctttatt    6300
ttcattacat ctgtgtgttg gttttttgtg tgaatcgata gcgataagga tccgcgtatg    6360
gtgcactctc agtacaatct gctctgatgc cgcatagtta agccagcccc gacacccgcc    6420
aacacccgct gacgcgccct gacgggcttg tctgctcccg gcatccgctt acagacaagc    6480
tgtgaccgtc tccgggagct gcatgtgtca gaggttttca ccgtcatcac cgaaacgcgc    6540
gagacgaaag ggcctcgtga tacgcctatt tttataggtt aatgtcatga taataatggt    6600
ttcttagacg tcaggtggca cttttcgggg aaatgtgcgc ggaacccct a tttgtttatt    6660 tttctaaata cattcaaata tgtatccgct catgagacaa taaccctgat aaatgcttca    6720
ataatattga aaaggaaga gtatgagtat tcaacatttc cgtgtcgccc ttattccctt    6780
ttttgcggca ttttgccttc ctgttttgc tcacccagaa acgctggtga agtaaaaga    6840 tgctgaagat cagttgggtg cacgagtggg ttacatcgaa ctggatctca acagcggtaa    6900
gatccttgag agttttcgcc ccgaagaacg ttttccaatg atgagcactt ttaaagttct    6960
gctatgtggc gcggtattat cccgtattga cgccgggcaa gagcaactcg gtcgccgcat    7020
acactattct cagaatgact tggttgagta ctcaccagtc acagaaaagc atcttacgga    7080
tggcatgaca gtaagagaat tatgcagtgc tgccataacc atgagtgata acactgcggc    7140
caacttactt ctgacaacga tcggaggacc gaaggagcta accgcttttt tgcacaacat    7200
gggggatcat gtaactcgcc ttgatcgttg ggaaccggag ctgaatgaag ccataccaaa    7260
cgacgagcgt gacaccacga tgcctgtagc aatggcaaca acgttgcgca aactattaac    7320
tggcgaacta cttactctag cttcccggca acaattaata gactggatgg aggcggataa    7380
agttgcagga ccacttctgc gctcggccct tccggctggc tggtttattg ctgataaatc    7440
tggagccggt gagcgtgggt ctcgcggtat cattgcagca ctggggccag atggtaagcc    7500
ctcccgtatc gtagttatct acacgacggg gagtcaggca actatggatg aacgaaatag    7560
acagatcgct gagataggtg cctcactgat taagcattgg taactgtcag accaagttta    7620
ctcatatata ctttagattg atttaaaact tcatttttaa tttaaaagga tctaggtgaa    7680
gatccttttt gataatctca tgaccaaaat cccttaacgt gagttttcgt tccactgagc    7740
gtcagacccc gtagaaaaga tcaaaggatc ttcttgagat cctttttttc tgcgcgtaat    7800
ctgctgcttg caaacaaaaa aaccaccgct accagcggtg gtttgtttgc cggatcaaga    7860
gctaccaact ctttttccga aggtaactgg cttcagcaga gcgcagatac caaatactgt    7920
ccttctagtg tagccgtagt taggccacca cttcaagaac tctgtagcac cgcctacata    7980
cctcgctctg ctaatcctgt taccagtggc tgctgccagt ggcgataagt cgtgtcttac    8040
cgggttggac tcaagacgat agttaccgga taaggcgcag cggtcgggct gaacggggggg   8100 ttcgtgcaca cagcccagct tggagcgaac gacctacacc gaactgagat acctacagcg    8160
tgagctatga gaaagcgcca cgcttcccga agggagaaag gcggacaggt atccggtaag    8220
cggcagggtc ggaacaggag agcgcacgag ggagcttcca gggggaaacg cctggtatct    8280
ttatagtcct gtcgggtttc gccacctctg acttgagcgt cgatttttgt gatgctcgtc    8340
aggggggcgg agcctatgga aaaacgccag caacgcggcc ttttacggtt cctggccttt    8400
ttgctggcct tttgctcaca tggctcgaca gatct                               8435
```

<210> SEQ ID NO 4
<211> LENGTH: 11092

<212> TYPE: DNA
<213> ORGANISM: Artificial Sequence
<220> FEATURE:
<223> OTHER INFORMATION: Constructed plasmid vector

<400> SEQUENCE: 4

```
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt cgcgctgctt cgcgatgtac ggccagatat acgcgttgac   240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca atagggactt   420
tccattgacg tcaatgggtg gagtatttac ggtaaactgc ccacttggca gtacatcaag   480
tgtatcatat gccaagtacg ccccctattg acgtcaatga cggtaaatgg cccgcctggc   540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagaccctt  tagtcagtgt ggaaaatctc tagcagtggc  1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa  1140
ttttgactag cggaggctag aaggagagag atgggtgcga gagcgtcagt attaagcggg  1200
ggagaattag atcgcgatgg gaaaaaattc ggttaaggcc agggggaaag aaaaaatata  1260
aattaaaaca tatagtatgg gcaagcaggg agctagaacg attcgcagtt aatcctggcc  1320
tgttagaaac atcagaaggc tgtagacaaa tactgggaca gctacaacca tcccttcaga  1380
caggatcaga agaacttaga tcattatata atacagtagc aaccctctat tgtgtgcatc  1440
aaaggataga gataaagac accaaggaag ctttagacaa gatagaggaa gagcaaaaca   1500
aaagtaagac caccgcacag caagcggccg ctgatcttca gacctggagg aggagatatg  1560
agggacaatt ggagaagtga attatataaa tataaagtag taaaaattga accattagga  1620
gtagcaccca ccaaggcaaa gaagagtg tgcagagag aaaaaagagc agtgggaata  1680
ggagctttgt tccttgggtt cttgggagca gcaggaagca ctatgggcgc agcgtcaatg  1740
acgctgacgg tacaggccag acaattattg tctggtatag tgcagcagca gaacaatttg  1800
ctgagggcta ttgaggcgca acagcatctg ttgcaactca cagtctgggg catcaagcag  1860
ctccaggcaa gaatcctggc tgtggaaaga tacctaaagg atcaacagct cctggggatt  1920
tggggttgct ctggaaaact catttgcacc actgctgtgc cttggaatgc tagttggagt  1980
aataaatctc tggaacagat ttggaatcac acgacctgga tggagtggga cagagaaatt  2040
aacaattaca caagcttaat acactcctta attgaagaat cgcaaaacca gcaagaaaag  2100
aatgaacaag aattattgga attagataaa tgggcaagtt tgtggaattg gtttaacata  2160
```

```
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt ggggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420 accttttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt ctttggtcgg ttttatgtac ctatcttctt aagtagctga    3660
agctccggtt ttgaactatg cgctcggggt tggcgagtgt gttttgtgaa gttttttagg    3720
caccttttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tctggcctcg gcggccaagc ttggcaatcc ggtactgttg gtaaagccac    3900
catggaagat gccaaaaaca ttaagaaggg cccagcgcca ttctacccac tcgaagacgg    3960
gaccgccggc gagcagctgc acaaagccat gaagcgctac gccctggtgc ccggcaccat    4020
cgcctttacc gacgcacata tcgaggtgga cattacctac gccgagtact tcgagatgag    4080
cgttcggctg gcagaagcta tgaagcgcta tgggctgaat acaaaccatc ggatcgtggt    4140
gtgcagcgag aatagcttgc agttcttcat gcccgtgttg ggtgccctgt tcatcggtgt    4200
ggctgtggcc ccagctaacg acatctacaa cgagcgcgag ctgctgaaca gcatgggcat    4260
cagccagccc accgtcgtat tcgtgagcaa gaaagggctg caaaagatcc tcaacgtgca    4320
aaagaagcta ccgatcatac aaaagatcat catcatggat agcaagaccg actaccaggg    4380
cttccaaagc atgtacacct tcgtgacttc ccatttgcca cccggcttca acgagtacga    4440
cttcgtgccc gagagcttcg accgggacaa aaccatcgcc ctgatcatga acagtagtgg    4500
cagtaccgga ttgcccaagg gcgtagccct accgcaccgc accgcttgtg tccgattcag    4560
```

```
tcatgcccgc gaccccatct tcggcaacca gatcatcccc gacaccgcta tcctcagcgt    4620
ggtgccattt caccacggct tcggcatgtt caccacgctg ggctacttga tctgcggctt    4680
tcgggtcgtg ctcatgtacc gcttcgagga ggagctattc ttgcgcagct tgcaagacta    4740
taagattcaa tctgccctgc tggtgcccac actatttagc ttcttcgcta agagcactct    4800
catcgacaag tacgacctaa gcaacttgca cgagatcgcc agcggcgggg cgccgctcag    4860
caaggaggta ggtgaggccg tggccaaacg cttccaccta ccaggcatcc gccagggcta    4920
cggcctgaca gaaacaacca gcgccattct gatcaccccc gaaggggacg acaagcctgg    4980
cgcagtaggc aaggtggtgc ccttcttcga ggctaaggtg gtggacttgg acaccggtaa    5040
gacactgggt gtgaaccagc gcggcgagct gtgcgtccgt ggccccatga tcatgagcgg    5100
ctacgttaac aaccccgagg ctacaaacgc tctcatcgac aaggacggct ggctgcacag    5160
cggcgacatc gcctactggg acgaggacga gcacttcttc atcgtggacc ggctgaagag    5220
cctgatcaaa tacaagggct accaggtagc cccagccgaa ctggagagca tcctgctgca    5280
acaccccaac atcttcgacg ccggggtcgc cggcctgccc gacgacgatg ccggcgagct    5340
gcccgccgca gtcgtcgtgc tggaacacgg taaaaccatg accgagaagg agatcgtgga    5400
ctatgtggcc agccaggtta caaccgccaa gaagctgcgc ggtggtgttg tgttcgtgga    5460
cgaggtgcct aaaggactga ccggcaagtt ggacgcccgc aagatccgcg agattctcat    5520
taaggccaag aagggcggca agatcgccgt gaattctgct tgcaagaact ggttcagtag    5580
cttaagccac tttgtgatcc accttaacag ccacggcttc cctccgagg tggaggagca    5640 ggccgccggc accctgccca tgagctgcgc ccaggagagc ggcatggata cacccctgc    5700 tgcttgcgcc agcgccagga tcaacgtcta actgcagtct agaacctcga gggcgcgccg    5760
aattcgatat caagcttatc gataatcaac ctctggatta caaaatttgt gaaagattga    5820
ctggtattct taactatgtt gctccttta cgctatgtgg atacgctgct ttaatgcctt    5880
tgtatcatgc tattgcttcc cgtatggctt tcattttctc ctccttgtat aaatcctggt    5940
tgctgtctct ttatgaggag ttgtggcccg ttgtcaggca acgtggcgtg gtgtgcactg    6000
tgtttgctga cgcaacccc actggttggg gcattgccac cacctgtcag ctcctttccg    6060
ggactttcgc tttccccctc cctattgcca cggcggaact catcgccgcc tgccttgccc    6120
gctgctggac aggggctcgg ctgttgggca ctgacaattc cgtggtgttg tcggggaaat    6180
catcgtcctt ccttggctg ctcgcctgtg ttgccacctg gattctgcgc gggacgtcct    6240
tctgctacgt cccttcggcc ctcaatccag cggaccttcc ttcccgcggc ctgctgccgg    6300
ctctgcggcc tcttccgcgt cttcgccttc gccctcagac gagtcggatc tccctttggg    6360
ccgcctcccc gcatcgatac cgtcgacctc gagacctaga aaaacatgga gcaatcacaa    6420
gtagcaatac agcagctacc aatgctgatt gtgcctggct agaagcacaa gaggaggagg    6480
aggtgggttt tccagtcaca cctcaggtac ctttaagacc aatgacttac aaggcagctg    6540
tagatcttag ccactttta aagaaaaagg ggggactgga agggctaatt cactcccaac    6600
gaagacaaga tatccttgat ctgtggatct accacacaca aggctacttc cctgattggc    6660
agaactacac accagggcca gggatcagat atccactgac ctttggatgg tgctacaagc    6720
tagtaccagt tgagcaagag aaggtagaag aagccaatga aggagagaac acccgcttgt    6780
tacaccctgt gagcctgcat gggatggatg acccggagag agaagtatta gagtggaggt    6840
ttgacagccg cctagcattt catcacatgg cccgagagct gcatccggac tgtactgggt    6900
```

| | |
|---|---|
| ctctctggtt agaccagatc tgagcctggg agctctctgg ctaactaggg aacccactgc | 6960 |
| ttaagcctca ataaagcttg ccttgagtgc ttcaagtagt gtgtgcccgt ctgttgtgtg | 7020 |
| actctggtaa ctagagatcc ctcagaccct tttagtcagt gtggaaaatc tctagcaggg | 7080 |
| cccgtttaaa cccgctgatc agcctcgact gtgccttcta gttgccagcc atctgttgtt | 7140 |
| tgcccctccc ccgtgccttc cttgaccctg gaaggtgcca ctcccactgt cctttcctaa | 7200 |
| taaaatgagg aaattgcatc gcattgtctg agtaggtgtc attctattct gggggtgggg | 7260 |
| gtggggcagg acagcaaggg ggaggattgg gaagacaata gcaggcatgc tggggatgcg | 7320 |
| gtgggctcta tggcttctga ggcggaaaga accagctggg gctctagggg gtatccccac | 7380 |
| gcgccctgta gcggcgcatt aagcgcggcg ggtgtggtgg ttacgcgcag cgtgaccgct | 7440 |
| acacttgcca gcgccctagc gcccgctcct ttcgctttct tcccttcctt tctcgccacg | 7500 |
| ttcgccggct ttccccgtca gctctaaat cgggggctcc ctttagggtt ccgatttagt | 7560 |
| gctttacggc acctcgaccc caaaaaactt gattagggtg atggttcacg tagtgggcca | 7620 |
| tcgccctgat agacggtttt tcgccctttg acgttggagt ccacgttctt taatagtgga | 7680 |
| ctcttgttcc aaactggaac aacactcaac cctatctcgg tctattcttt tgatttataa | 7740 |
| gggattttgc cgatttcggc ctattggtta aaaaatgagc tgatttaaca aaaatttaac | 7800 |
| gcgaattaat tctgtggaat gtgtgtcagt tagggtgtgg aaagtcccca ggctccccag | 7860 |
| caggcagaag tatgcaaagc atgcatctca attagtcagc aaccaggtgt ggaaagtccc | 7920 |
| caggctcccc agcaggcaga agtatgcaaa gcatgcatct caattagtca gcaaccatag | 7980 |
| tcccgcccct aactccgccc atcccgcccc taactccgcc cagttccgcc cattctccgc | 8040 |
| cccatggctg actaattttt tttatttatg cagaggccga ggccgcctct gcctctgagc | 8100 |
| tattccagaa gtagtgagga ggcttttttg gaggcctagg cttttgcaaa aagctcccgg | 8160 |
| gagcttgtat atccattttc ggatctgatc agcacgtgtt gacaattaat catcggcata | 8220 |
| gtatatcggc atagtataat acgacaaggt gaggaactaa accatggcca agttgaccag | 8280 |
| tgccgttccg gtgctcaccg cgcgcgacgt cgccggagcg gtcgagttct ggaccgaccg | 8340 |
| gctcgggttc tcccgggact tcgtggagga cgacttcgcc ggtgtggtcc gggacgacgt | 8400 |
| gaccctgttc atcagcgcgg tccaggacca ggtggtgccg gacaacaccc tggcctgggt | 8460 |
| gtgggtgcgc ggcctggacg agctgtacgc cgagtggtcg gaggtcgtgt ccacgaactt | 8520 |
| ccgggacgcc tccgggccgg ccatgaccga gatcggcgag cagccgtggg ggcgggagtt | 8580 |
| cgccctgcgc gacccggccg gcaactgcgt gcacttcgtg gccgaggagc aggactgaca | 8640 |
| cgtgctacga gatttcgatt ccaccgccgc cttctatgaa aggttgggct tcggaatcgt | 8700 |
| tttccgggac gccggctgga tgatcctcca gcgcggggat ctcatgctgg agttcttcgc | 8760 |
| ccaccccaac ttgtttattg cagcttataa tggttacaaa taaagcaata gcatcacaaa | 8820 |
| tttcacaaat aaagcatttt tttcactgca ttctagttgt ggtttgtcca aactcatcaa | 8880 |
| tgtatcttat catgtctgta taccgtcgac ctctagctag agcttggcgt aatcatggtc | 8940 |
| atagctgttt cctgtgtgaa attgttatcc gctcacaatt ccacacaaca tacgagccgg | 9000 |
| aagcataaag tgtaaagcct ggggtgccta atgagtgagc taactcacat taattgcgtt | 9060 |
| gcgctcactg cccgctttcc agtcgggaaa cctgtcgtgc cagctgcatt aatgaatcgg | 9120 |
| ccaacgcgcg gggagaggcg gtttgcgtat tgggcgctct tccgcttcct cgctcactga | 9180 |
| ctcgctgcgc tcggtcgttc ggctgcggcg agcggtatca gctcactcaa aggcggtaat | 9240 |
| acggttatcc acagaatcag gggataacgc aggaaagaac atgtgagcaa aaggccagca | 9300 |

```
aaaggccagg aaccgtaaaa aggccgcgtt gctggcgttt ttccataggc tccgccccc    9360 tgacgagcat cacaaaaatc gacgctcaag tcagaggtgg cgaaacccga caggactata   9420
aagataccag gcgtttcccc ctggaagctc cctcgtgcgc tctcctgttc cgaccctgcc   9480
gcttaccgga tacctgtccg cctttctccc ttcgggaagc gtggcgcttt ctcatagctc   9540
acgctgtagg tatctcagtt cggtgtaggt cgttcgctcc aagctgggct gtgtgcacga   9600
accccccgtt cagcccgacc gctgcgcctt atccggtaac tatcgtcttg agtccaaccc   9660
ggtaagacac gacttatcgc cactggcagc agccactggt aacaggatta gcagagcgag   9720
gtatgtaggc ggtgctacag agttcttgaa gtggtggcct aactacggct acactagaag   9780
aacagtattt ggtatctgcg ctctgctgaa gccagttacc ttcggaaaaa gagttggtag   9840
ctcttgatcc ggcaaacaaa ccaccgctgg tagcggtggt ttttttgttt gcaagcagca   9900
gattacgcgc agaaaaaaag gatctcaaga agatcctttg atcttttcta cggggtctga   9960
cgctcagtgg aacgaaaact cacgttaagg gattttggtc atgagattat caaaaaggat  10020
cttcacctag atccttttaa attaaaaatg aagttttaaa tcaatctaaa gtatatatga  10080
gtaaacttgg tctgacagtt accaatgctt aatcagtgag gcacctatct cagcgatctg  10140
tctatttcgt tcatccatag ttgcctgact ccccgtcgtg tagataacta cgatacggga  10200
gggcttacca tctggcccca gtgctgcaat gataccgcga gacccacgct caccggctcc  10260
agatttatca gcaataaacc agccagccgg aagggccgag cgcagaagtg gtcctgcaac  10320
tttatccgcc tccatccagt ctattaattg ttgccgggaa gctagagtaa gtagttcgcc  10380
agttaatagt ttgcgcaacg ttgttgccat tgctacaggc atcgtggtgt cacgctcgtc  10440
gtttggtatg gcttcattca gctccggttc ccaacgatca aggcgagtta catgatcccc  10500
catgttgtgc aaaaaagcgg ttagctcctt cggtcctccg atcgttgtca gaagtaagtt  10560
ggccgcagtg ttatcactca tggttatggc agcactgcat aattctctta ctgtcatgcc  10620
atccgtaaga tgcttttctg tgactggtga gtactcaacc aagtcattct gagaatagtg  10680
tatgcggcga ccgagttgct cttgcccggc gtcaatacgg gataataccg cgccacatag  10740
cagaacttta aaagtgctca tcattggaaa acgttcttcg gggcgaaaac tctcaaggat  10800
cttaccgctg ttgagatcca gttcgatgta acccactcgt gcacccaact gatcttcagc  10860
atcttttact ttcaccagcg tttctgggtg agcaaaaaca ggaaggcaaa atgccgcaaa  10920
aaagggaata agggcgacac ggaaatgttg aatactcata ctcttccttt ttcaatatta  10980
ttgaagcatt tatcagggtt attgtctcat gagcggatac atatttgaat gtatttagaa  11040
aaataaacaa ataggggttc cgcgcacatt tccccgaaaa gtgccacctg ac          11092
```

<210> SEQ ID NO 5
<211> LENGTH: 10401
<212> TYPE: DNA
<213> ORGANISM: Artificial Sequence
<220> FEATURE:
<223> OTHER INFORMATION: Constructed plasmid vector

<400> SEQUENCE: 5

```
gtcgacggat cgggagatct cccgatcccc tatggtgcac tctcagtaca atctgctctg     60
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
```

```
attgattatt gactagttat taatagtaat caattacggg gtcattagtt catagcccat      300
atatggagtt ccgcgttaca taacttacgg taaatggccc gcctggctga ccgcccaacg      360
accccggccc attgacgtca ataatgacgt atgttcccat agtaacgcca atagggactt      420
tccattgacg tcaatgggtg gagtatttac ggtaaactgc ccacttggca gtacatcaag      480
tgtatcatat gccaagtacg cccccctattg acgtcaatga cggtaaatgg cccgcctggc     540
attatgccca gtacatgacc ttatgggact ttcctacttg gcagtacatc tacgtattag      600
tcatcgctat taccatggtg atgcggtttt ggcagtacat caatgggcgt ggatagcggt      660
ttgactcacg gggatttcca agtctccacc ccattgacgt caatgggagt ttgttttggc      720
accaaaatca acgggacttt ccaaaatgtc gtaacaactc cgccccattg acgcaaatgg      780
gcggtaggcg tgtacggtgg gaggtctata taagcagcgc gttttgcctg tactgggtct      840
ctctggttag accagatctg agcctgggag ctctctggct aactagggaa cccactgctt      900
aagcctcaat aaagcttgcc ttgagtgctt caagtagtgt gtgcccgtct gttgtgtgac      960
tctggtaact agagatccct cagacccttt tagtcagtgt ggaaaatctc tagcagtggc     1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa     1140
ttttgactag cggaggctag aaggagagag atgggtgcga gagcgtcagt attaagcggg     1200
ggagaattag atcgcgatgg gaaaaaattc ggttaaggcc agggggaaag aaaaaatata     1260
aattaaaaca tatagtatgg gcaagcaggg agctagaacg attcgcagtt aatcctggcc     1320
tgttagaaac atcagaaggc tgtagacaaa tactgggaca gctacaacca tcccttcaga     1380
caggatcaga agaacttaga tcattatata atacagtagc aaccctctat tgtgtgcatc     1440
aaaggataga gataaaagac accaaggaag ctttagacaa gatagaggaa gagcaaaaca     1500
aaagtaagac caccgcacag caagcggccg ctgatcttca gacctggagg aggagatatg     1560
agggacaatt ggagaagtga attatataaa tataaagtag taaaaattga accattagga     1620
gtagcaccca ccaaggcaaa gagaagagtg gtgcagagag aaaaaagagc agtgggaata     1680
ggagctttgt tccttgggtt cttgggagca gcaggaagca ctatgggcgc agcgtcaatg     1740
acgctgacgg tacaggccag acaattattg tctggtatag tgcagcagca gaacaatttg     1800
ctgagggcta ttgaggcgca acagcatctg ttgcaactca cagtctgggg catcaagcag     1860
ctccaggcaa gaatcctggc tgtggaaaga tacctaaagg atcaacagct cctggggatt     1920
tggggttgct ctggaaaact catttgcacc actgctgtgc cttggaatgc tagttggagt     1980
aataaatctc tggaacagat ttggaatcac acgacctgga tggagtggga cagagaaatt     2040
aacaattaca caagcttaat acactcctta attgaagaat cgcaaaacca gcaagaaaag     2100
aatgaacaag aattattgga attagataaa tgggcaagtt tgtggaattg gtttaacata     2160
acaaattggc tgtggtatat aaaattattc ataatgatag taggaggctt ggtaggttta     2220
agaatagttt ttgctgtact ttctatagtg aatagagtta ggcagggata ttcaccatta     2280
tcgtttcaga cccacctccc aaccccgagg ggacccgaca ggcccgaagg aatagaagaa     2340
gaaggtggag agagagacag agacagatcc attcgattag tgaacggatc ggcactgcgt     2400
gcgccaattc tgcagacaaa tggcagtatt catccacaat tttaaaagaa aagggggat      2460 tggggggtac agtgcagggg aaagaatagt agacataata gcaacagaca tacaaactaa     2520
agaattacaa aaacaaatta caaaaattca aaattttcgg gttattaca gggacagcag     2580 agatccagtt tggttaatta agggtgcagc ggcctccgcg ccgggttttg gcgcctcccg     2640
```

```
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820 ttttcttttcc agagagcgga acaggcgagg aaaagtagtc ccttctcggc gattctgcgg    2880
agggatctcc gtgggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt cttttggtcgg ttttatgtac ctatcttctt aagtagctga    3660
agctccggtt ttgaactatg cgctcggggt tggcgagtgt gttttgtgaa gttttttagg    3720
caccttttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tccatgagtg actccaagga accaagactg cagcagctgg gcctcctgga    3900
ggaggaacag ctgagaggcc ttggattccg acagactcga ggatacaaga gcttagcagg    3960
gtgtcttggc catggtcccc tggtgctgca actcctctcc ttcacgctct tggctgggct    4020
ccttgtccaa gtgtccaagg tccccagctc cataagtcag gaacaatcca ggcaagacgc    4080
gatctaccag aacctgaccc agcttaaagc tgcagtgggt gagctctcag agaaatccaa    4140
gctgcaggag atctaccagg agctgacccg actgaaggct gcagtgggtg agcttccaga    4200
gaaatctaag ctgcaggaga tctaccagga gctgacccga ctgaaggctg cagtgggtga    4260
gcttccagag aaatctaagc tgcaggagat ctaccaggag ctgacctggc tgaaggctgc    4320
agtgggtgag cttccagaga aatctaagat gcaggagatc taccaggagc tgactcggct    4380
gaaggctgca gtgggtgagc ttccagagaa atctaagcag caggagatct accaggagct    4440
gacccggctg aaggctgcag tgggtgagct tccagagaaa tctaagcagc aggagatcta    4500
ccaggagctg acccggctga aggctgcagt gggtgagctt ccagagaaat ctaagcagca    4560
ggagatctac caggagctga cccagctgaa ggctgcagtg gaacgccgtgt gccacccctg    4620 tccctgggaa tggacattct tccaaggaaa ctgttacttc atgtctaact cccagcggaa    4680
ctggcacgac tccatcaccg cctgcaaaga agtggggggcc cagctcgtcg taatcaaaag    4740
tgctgaggag cagaacttcc tacagctgca gtcttccaga agtaaccgct tcacctggat    4800
gggactttca gatctaaatc aggaaggcac gtggcaatgg gtggacggct cacctctgtt    4860
gcccagcttc aagcagtatt ggaacagagg agagcccaac aacgttgggg aggaagactg    4920
cgcggaattt agtggcaatg gctggaacga cgacaaatgt aatcttgcca aattctggat    4980
```

```
ctgcaaaaag tccgcagcct cctgctccag ggatgaagaa cagtttcttt ctccagcccc   5040
tgccacccca aacccccctc ctgcgtagga attcgatatc aagcttatcg ataatcaacc   5100
tctggattac aaaatttgtg aaagattgac tggtattctt aactatgttg ctccttttac   5160
gctatgtgga tacgctgctt taatgccttt gtatcatgct attgcttccc gtatggcttt   5220
cattttctcc tccttgtata atcctggtt gctgtctctt tatgaggagt tgtggcccgt    5280
tgtcaggcaa cgtggcgtgg tgtgcactgt gtttgctgac gcaaccccca ctggttgggg   5340
cattgccacc acctgtcagc tccttttcgg gactttcgct ttccccctcc ctattgccac   5400
ggcggaactc atcgccgcct gccttgcccg ctgctggaca ggggctcggc tgttgggcac   5460
tgacaattcc gtggtgttgt cggggaaatc atcgtccttt ccttggctgc tcgcctgtgt   5520
tgccacctgg attctgcgcg gacgtcctt ctgctacgtc ccttcggccc tcaatccagc    5580
ggaccttcct tcccgcggcc tgctgccggc tctgcggcct cttccgcgtc ttcgccttcg   5640
ccctcagacg agtcggatct cccttggc cgcctcccg catcgatacc gtcgacctcg      5700
agacctagaa aaacatggag caatcacaag tagcaataca gcagctacca atgctgattg   5760
tgcctggcta gaagcacaag aggaggagga ggtgggtttt ccagtcacac ctcaggtacc   5820
tttaagacca atgacttaca aggcagctgt agatcttagc cacttttaa aagaaaaggg    5880 gggactggaa gggctaattc actcccaacg aagacaagat atccttgatc tgtggatcta   5940
ccacacacaa ggctacttcc ctgattggca gaactacaca ccagggccag ggatcagata   6000
tccactgacc tttggatggt gctacaagct agtaccagtt gagcaagaga aggtagaaga   6060
agccaatgaa ggagagaaca cccgcttgtt acaccctgtg agcctgcatg ggatggatga   6120
cccggagaga gaagtattag agtggaggtt tgacagccgc ctagcatttc atcacatggc   6180
ccgagagctg catccggact gtactgggtc tctctggtta gaccagatct gagcctggga   6240
gctctctggc taactaggga acccactgct taagcctcaa taaagcttgc cttgagtgct   6300
tcaagtagtg tgtgcccgtc tgttgtgtga ctctggtaac tagagatccc tcagaccctt   6360
ttagtcagtg tggaaaatct ctagcagggc ccgtttaaac ccgctgatca gcctcgactg   6420
tgccttctag ttgccagcca tctgttgttt gcccctcccc cgtgccttcc ttgaccctgg   6480
aaggtgccac tcccactgtc ctttcctaat aaaatgagga aattgcatcg cattgtctga   6540
gtaggtgtca ttctattctg ggggtgggg tggcagga cagcaaggg gaggattggg        6600 aagacaatag caggcatgct ggggatgcgg tgggctctat ggcttctgag gcggaaagaa   6660
ccagctgggg ctctaggggg tatccccacg cgccctgtag cggcgcatta agcgcggcgg   6720
gtgtggtggt tacgcgcagc gtgaccgcta cacttgccag cgccctagcg cccgctcctt   6780
tcgctttctt cccttccttt ctcgccacgt tcgccggctt tccccgtcaa gctctaaatc   6840 ggggggctccc tttagggttc cgatttagtg ctttacggca cctcgacccc aaaaaacttg   6900
attagggtga tggttcacgt agtgggccat cgccctgata cggtttttt cgccctttga    6960 cgttggagtc cacgttcttt aatagtggac tcttgttcca actggaaca acactcaacc    7020 ctatctcggt ctattctttt gatttataag ggattttgcc gatttcggcc tattggttaa   7080
aaaatgagct gatttaacaa aaatttaacg cgaattaatt ctgtgaatg tgtgtcagtt    7140 agggtgtgga aagtccccag gctcccagc aggcagaagt atgcaaagca tgcatctcaa    7200
ttagtcagca accaggtgtg gaaagtcccc aggctcccca gcaggcagaa gtatgcaaag   7260
catgcatctc aattagtcag caaccatagt cccgccccta actccgccca tcccgcccct   7320
aactccgccc agttccgccc attctccgcc ccatggctga ctaattttt ttatttatgc    7380
```

```
agaggccgag gccgcctctg cctctgagct attccagaag tagtgaggag gcttttttgg   7440
aggcctaggc ttttgcaaaa agctcccggg agcttgtata tccattttcg gatctgatca   7500
gcacgtgttg acaattaatc atcggcatag tatatcggca tagtataata cgacaaggtg   7560
aggaactaaa ccatggccaa gttgaccagt gccgttccgg tgctcaccgc gcgcgacgtc   7620
gccggagcgg tcgagttctg gaccgaccgg ctcgggttct cccgggactt cgtggaggac   7680
gacttcgccg gtgtggtccg ggacgacgtg accctgttca tcagcgcggt ccaggaccag   7740
gtggtgccgg acaacaccct ggcctgggtg tgggtgcgcg gcctggacga gctgtacgcc   7800
gagtggtcgg aggtcgtgtc cacgaacttc cgggacgcct ccgggccggc catgaccgag   7860
atcggcgagc agccgtgggg gcgggagttc gccctgcgcg acccggccgg caactgcgtg   7920
cacttcgtgg ccgaggagca ggactgacac gtgctacgag atttcgattc caccgccgcc   7980
ttctatgaaa ggttgggctt cggaatcgtt ttccgggacg ccggctggat gatcctccag   8040
cgcggggatc tcatgctgga gttcttcgcc cacccaact tgtttattgc agcttataat   8100
ggttacaaat aaagcaatag catcacaaat ttcacaaata aagcattttt ttcactgcat   8160
tctagttgtg gtttgtccaa actcatcaat gtatcttatc atgtctgtat accgtcgacc   8220
tctagctaga gcttggcgta atcatggtca tagctgtttc ctgtgtgaaa ttgttatccg   8280
ctcacaattc cacacaacat acgagccgga agcataaagt gtaaagcctg gggtgcctaa   8340
tgagtgagct aactcacatt aattgcgttg cgctcactgc ccgctttcca gtcgggaaac   8400
ctgtcgtgcc agctgcatta tgaatcggc caacgcgcgg ggagaggcgg tttgcgtatt   8460
gggcgctctt ccgcttcctc gctcactgac tcgctgcgct cggtcgttcg gctgcggcga   8520
gcggtatcag ctcactcaaa ggcggtaata cggttatcca cagaatcagg ggataacgca   8580
ggaaagaaca tgtgagcaaa aggccagcaa aaggccagga accgtaaaaa ggccgcgttg   8640
ctggcgtttt tccataggct ccgcccccct gacgagcatc acaaaaatcg acgctcaagt   8700
cagaggtggc gaaacccgac aggactataa agataccagg cgtttccccc tggaagctcc   8760
ctcgtgcgct ctcctgttcc gaccctgccg cttaccggat acctgtccgc ctttctccct   8820
tcgggaagcg tggcgctttc tcatagctca cgctgtaggt atctcagttc ggtgtaggtc   8880
gttcgctcca agctgggctg tgtgcacgaa ccccccgttc agcccgaccg ctgcgcctta   8940
tccggtaact atcgtcttga gtccaacccg gtaagcacg acttatcgcc actggcagca   9000
gccactggta acaggattag cagagcgagg tatgtaggcg gtgctacaga gttcttgaag   9060
tggtggccta actacggcta cactagaaga acagtatttg gtatctgcgc tctgctgaag   9120
ccagttacct tcggaaaaag agttggtagc tcttgatccg gcaaacaaac caccgctggt   9180
agcggtggtt tttttgtttg caagcagcag attacgcgca gaaaaaaagg atctcaagaa   9240
gatcctttga tcttttctac ggggtctgac gctcagtgga acgaaaactc acgttaaggg   9300
attttggtca tgagattatc aaaaaggatc ttcacctaga tccttttaaa ttaaaaatga   9360
agttttaaat caatctaaag tatatatgag taaacttggt ctgacagtta ccaatgctta   9420
atcagtgagg cacctatctc agcgatctgt ctatttcgtt catccatagt tgcctgactc   9480
cccgtcgtgt agataactac gatacgggag ggcttaccat ctggccccag tgctgcaatg   9540
ataccgcgag acccacgctc accggctcca gatttatcag caataaacca gccagccgga   9600
agggccgagc gcagaagtgg tcctgcaact ttatccgcct ccatccagtc tattaattgt   9660
tgccgggaag ctagagtaag tagttcgcca gttaatagtt tgcgcaacgt tgttgccatt   9720
```

```
gctacaggca tcgtggtgtc acgctcgtcg tttggtatgg cttcattcag ctccggttcc    9780
caacgatcaa ggcgagttac atgatccccc atgttgtgca aaaaagcggt tagctccttc    9840
ggtcctccga tcgttgtcag aagtaagttg gccgcagtgt tatcactcat ggttatggca    9900
gcactgcata attctcttac tgtcatgcca tccgtaagat gcttttctgt gactggtgag    9960
tactcaacca agtcattctg agaatagtgt atgcggcgac cgagttgctc ttgcccggcg    10020
tcaatacggg ataataccgc gccacatagc agaactttaa aagtgctcat cattggaaaa    10080
cgttcttcgg ggcgaaaact ctcaaggatc ttaccgctgt tgagatccag ttcgatgtaa    10140
cccactcgtg cacccaactg atcttcagca tcttttactt tcaccagcgt ttctgggtga    10200
gcaaaaacag gaaggcaaaa tgccgcaaaa aagggaataa gggcgacacg gaaatgttga    10260
atactcatac tcttccttt tcaatattat tgaagcattt atcagggtta ttgtctcatg    10320
agcggataca tatttgaatg tatttagaaa aataaacaaa taggggttcc gcgcacattt    10380
ccccgaaaag tgccacctga c    10401
```

<210> SEQ ID NO 6
<211> LENGTH: 9903
<212> TYPE: DNA
<213> ORGANISM: Artificial Sequence
<220> FEATURE:
<223> OTHER INFORMATION: Constructed plasmid vector

<400> SEQUENCE: 6

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
```

```
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tgcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt cttttggtcgg ttttatgtac ctatcttctt aagtagctga    3660
agctccggtt ttgaactatg cgctcggggt tggcgagtgt gttttgtgaa gttttttagg    3720
```

```
caccttttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tccatgagtg attctaagga aatgggaag aggcagcttc gccctctgga    3900
tgaggaactg ctgacatcca gccacaccag gcactccatc aaaggctttg gcttccaaac   3960
aaattctgga ttcagtagct tcacagggtg cctggtccac agtcaagtcc ccttggcact   4020
gcaggtgctc ttcctagctg tttgttctgt gctgctggtt gtcatccttg tcaaagtcta   4080
caaaataccc agttctcagg aagaaaacaa tcagatgaat gtctaccaag aactgaccca   4140
gttgaaggct ggcgtagatc gactgtgccg ctcctgcccc tgggactgga cgcacttcca   4200
aggaagctgt tacttcttct ctgtgggccca gaagtcctgg aatgattctg ccactgcctg   4260
ccacaatgtg ggggctcaac ttgtggtcat caagagtgat gaagagcaga actttctaca   4320
acaaacttct aagaagagag gctacacttg gatggggctc attgacatga gcaaggagtc   4380
tacatggtac tgggtagatg gttcacctct gactctcagt ttcatgaagt attggagtaa   4440
aggagaacct aacaacctgg gagaggaaga ctgtgcagag ttcagagatg acggctggaa   4500
tgacaccaaa tgtactaaca agaaaattctg gatctgcaaa aagctttcaa cttcctgccc   4560
tagcaagtga gaattcgata tcaagcttat cgataatcaa cctctggatt acaaaatttg   4620
tgaaagattg actggtattc ttaactatgt tgctcctttt acgctatgtg gatacgctgc   4680
tttaatgcct ttgtatcatg ctattgcttc ccgtatggct ttcattttct cctccttgta   4740
taaatcctgg ttgctgtctc tttatgagga gttgtggccc gttgtcaggc aacgtggcgt   4800
ggtgtgcact gtgtttgctg acgcaacccc cactggttgg ggcattgcca ccacctgtca   4860
gctcctttcc gggactttcg ctttccccct ccctattgcc acggcggaac tcatcgccgc   4920
ctgccttgcc cgctgctgga caggggctcg gctgttgggc actgacaatt ccgtggtgtt   4980
gtcggggaaa tcatcgtcct tccttggct gctcgcctgt gttgccacct ggattctgcg   5040
cgggacgtcc ttctgctacg tcccttcggc cctcaatcca gcggaccttc cttcccgcgg   5100
cctgctgccg gctctgcggc ctcttccgcg tcttcgcctt cgccctcaga cgagtcggat   5160
ctccctttgg gccgcctccc cgcatcgata ccgtcgacct cgagacctag aaaaacatgg   5220
agcaatcaca agtagcaata cagcagctac caatgctgat tgtgcctggc tagaagcaca   5280
agaggaggag gaggtggggtt ttccagtcac acctcaggta cctttaagac caatgactta   5340
caaggcagct gtagatctta gccacttttt aaaagaaaag ggggactgg aagggctaat   5400
tcactcccaa cgaagacaag atatccttga tctgtggatc taccacacac aaggctactt   5460
ccctgattgg cagaactaca caccagggcc agggatcaga tatccactga cctttggatg   5520
gtgctacaag ctagtaccag ttgagcaaga gaaggtagaa gaagccaatg aaggagagaa   5580
cacccgcttg ttacaccctg tgagcctgca tgggatggat gacccggaga gagaagtatt   5640
agagtggagg tttgacagcc gcctagcatt tcatcacatg gcccgagagc tgcatccgga   5700
ctgtactggg tctctctggt tagaccagat ctgagcctgg gagctctctg gctaactagg   5760
gaacccactg cttaagcctc aataaagctt gccttgagtg cttcaagtag tgtgtgcccg   5820
tctgttgtgt gactctggta actagagatc cctcagaccc ttttagtcag tgtggaaaat   5880
ctctagcagg gcccgtttaa acccgctgat cagcctcgac tgtgccttct agttgccagc   5940
catctgttgt ttgcccctcc cccgtgcctt ccttgaccct ggaaggtgcc actcccactg   6000
tcctttccta ataaaatgag gaaattgcat cgcattgtct gagtaggtgt cattctattc   6060
tggggggtgg ggtggggcag gacagcaagg gggaggattg ggaagacaat agcaggcatg   6120
```

```
ctggggatgc ggtgggctct atggcttctg aggcggaaag aaccagctgg ggctctaggg    6180
ggtatcccca cgcgccctgt agcggcgcat taagcgcggc gggtgtggtg gttacgcgca    6240
gcgtgaccgc tacacttgcc agcgccctag cgcccgctcc tttcgctttc ttcccttcct    6300
ttctcgccac gttcgccggc tttccccgtc aagctctaaa tcggggctc  cctttagggt    6360 tccgatttag tgctttacgg cacctcgacc ccaaaaaact tgattagggt gatggttcac    6420
gtagtgggcc atcgccctga tagacggttt ttcgcccttt gacgttggag tccacgttct    6480
ttaatagtgg actcttgttc caaactggaa caacactcaa ccctatctcg gtctattctt    6540
ttgatttata agggattttg ccgatttcgg cctattggtt aaaaaatgag ctgatttaac    6600
aaaaatttaa cgcgaattaa ttctgtggaa tgtgtgtcag ttagggtgtg aaagtcccc    6660 aggctcccca gcaggcagaa gtatgcaaag catgcatctc aattagtcag caaccaggtg    6720
tggaaagtcc ccaggctccc cagcaggcag aagtatgcaa agcatgcatc tcaattagtc    6780
agcaaccata gtcccgcccc taactccgcc catcccgccc ctaactccgc ccagttccgc    6840
ccattctccg ccccatggct gactaatttt ttttatttat gcagaggccg aggccgcctc    6900
tgcctctgag ctattccaga agtagtgagg aggcttttt ggaggcctag gcttttgcaa    6960
aaagctcccg ggagcttgta tatccatttt cggatctgat cagcacgtgt tgacaattaa    7020
tcatcggcat agtatatcgg catagtataa tacgacaagg tgaggaacta aaccatggcc    7080
aagttgacca gtgccgttcc ggtgctcacc gcgcgcgacg tcgccggagc ggtcgagttc    7140
tggaccgacc ggctcgggtt ctcccgggac ttcgtggagg acgacttcgc cggtgtggtc    7200
cgggacgacg tgaccctgtt catcagcgcg gtccaggacc aggtggtgcc ggacaacacc    7260
ctggcctggg tgtgggtgcg cggcctggac gagctgtacg ccgagtggtc ggaggtcgtg    7320
tccacgaact tccgggacgc ctccgggccg gccatgaccg agatcggcga gcagccgtgg    7380
gggcgggagt tcgccctgcg cgaccccgcc ggcaactgcg tgcacttcgt ggccgaggag    7440
caggactgac acgtgctacg agatttcgat tccaccgccg ccttctatga aaggttgggc    7500
ttcggaatcg ttttccggga cgccggctgg atgatcctcc agcgcgggga tctcatgctg    7560
gagttcttcg cccaccccaa cttgtttatt gcagcttata atggttacaa ataaagcaat    7620
agcatcacaa atttcacaaa taaagcattt ttttcactgc attctagttg tggtttgtcc    7680
aaactcatca atgtatctta tcatgtctgt ataccgtcga cctctagcta gagcttggcg    7740
taatcatggt catagctgtt tcctgtgtga aattgttatc cgctcacaat tccacacaac    7800
atacgagccg gaagcataaa gtgtaaagcc tggggtgcct aatgagtgag ctaactcaca    7860
ttaattgcgt tgcgctcact gcccgctttc cagtcgggaa acctgtcgtg ccagctgcat    7920
taatgaatcg gccaacgcgc ggggagaggc ggtttgcgta ttgggcgctc ttccgcttcc    7980
tcgctcactg actcgctgcg ctcggtcgtt cggctgcggc gagcggtatc agctcactca    8040
aaggcggtaa tacggttatc cacagaatca ggggataacg caggaaagaa catgtgagca    8100
aaaggccagc aaaaggccag gaaccgtaaa aaggccgcgt tgctggcgtt tttccatagg    8160
ctccgccccc ctgacgagca tcacaaaaat cgacgctcaa gtcagaggtg gcgaaacccg    8220
acaggactat aaagatacca ggcgtttccc cctggaagct ccctcgtgcg ctctcctgtt    8280
ccgaccctgc cgcttaccgg atacctgtcc gcctttctcc cttcgggaag cgtggcgctt    8340
tctcatagct cacgctgtag gtatctcagt tcggtgtagg tcgttcgctc caagctgggc    8400
tgtgtgcacg aaccccccgt tcagcccgac cgctgcgcct tatccggtaa ctatcgtctt    8460
```

| | |
|---|---|
| gagtccaacc cggtaagaca cgacttatcg ccactggcag cagccactgg taacaggatt | 8520 |
| agcagagcga ggtatgtagg cggtgctaca gagttcttga agtggtggcc taactacggc | 8580 |
| tacactagaa gaacagtatt tggtatctgc gctctgctga agccagttac cttcggaaaa | 8640 |
| agagttggta gctcttgatc cggcaaacaa accaccgctg gtagcggtgg ttttttttgtt | 8700 |
| tgcaagcagc agattacgcg cagaaaaaaa ggatctcaag aagatccttt gatcttttct | 8760 |
| acggggtctg acgctcagtg gaacgaaaac tcacgttaag gattttggt catgagatta | 8820 |
| tcaaaaagga tcttcaccta gatccttta aattaaaaat gaagttttaa atcaatctaa | 8880 |
| agtatatatg agtaaacttg gtctgacagt taccaatgct taatcagtga ggcacctatc | 8940 |
| tcagcgatct gtctatttcg ttcatccata gttgcctgac tccccgtcgt gtagataact | 9000 |
| acgatacggg agggcttacc atctggcccc agtgctgcaa tgataccgcg agacccacgc | 9060 |
| tcaccggctc cagatttatc agcaataaac cagccagccg gaagggccga gcgcagaagt | 9120 |
| ggtcctgcaa ctttatccgc ctccatccag tctattaatt gttgccggga agctagagta | 9180 |
| agtagttcgc cagttaatag tttgcgcaac gttgttgcca ttgctacagg catcgtggtg | 9240 |
| tcacgctcgt cgtttggtat ggcttcattc agctccggtt cccaacgatc aaggcgagtt | 9300 |
| acatgatccc ccatgttgtg caaaaaagcg gttagctcct tcggtcctcc gatcgttgtc | 9360 |
| agaagtaagt tggccgcagt gttatcactc atggttatgg cagcactgca taattctctt | 9420 |
| actgtcatgc catccgtaag atgcttttct gtgactggtg agtactcaac caagtcattc | 9480 |
| tgagaatagt gtatgcggcg accgagttgc tcttgcccgg cgtcaatacg ggataatacc | 9540 |
| gcgccacata gcagaacttt aaaagtgctc atcattggaa acgttcttc ggggcgaaaa | 9600 |
| ctctcaagga tcttaccgct gttgagatcc agttcgatgt aacccactcg tgcacccaac | 9660 |
| tgatcttcag catcttttac tttcaccagc gtttctgggt gagcaaaaac aggaaggcaa | 9720 |
| aatgccgcaa aaaagggaat aagggcgaca cggaaatgtt gaatactcat actcttcctt | 9780 |
| tttcaatatt attgaagcat ttatcagggt tattgtctca tgagcggata catatttgaa | 9840 |
| tgtatttaga aaaataaaca ataggggtt ccgcgcacat ttccccgaaa agtgccacct | 9900 |
| gac | 9903 |

<210> SEQ ID NO 7
<211> LENGTH: 11586
<212> TYPE: DNA
<213> ORGANISM: Artificial Sequence
<220> FEATURE:
<223> OTHER INFORMATION: Constructed plasmid vector
<220> FEATURE:
<221> NAME/KEY: misc_feature
<222> LOCATION: (3907)..(3907)
<223> OTHER INFORMATION: n=a, t, c or g

<400> SEQUENCE: 7

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |

```
tgtatcatat gccaagtacg cccctattg acgtcaatga cggtaaatgg cccgcctggc    540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taagcagcgc gttttgcctg tactgggtct   840
ctctggttag accagatctg agcctgggag ctctctggct aactagggaa cccactgctt   900
aagcctcaat aaagcttgcc ttgagtgctt caagtagtgt gtgcccgtct gttgtgtgac   960
tctggtaact agagatccct cagacccttt tagtcagtgt ggaaaatctc tagcagtggc   1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga gaacttaga tcattatata atacagtagc aaccctctat tgtgtgcatc     1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggatt    1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagacag agacagatcc attcgattag tgaacggatc ggcactgcgt    2400
gcgccaattc tgcagacaaa tggcagtatt catccacaat tttaaaagaa aagggggat     2460 tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta agggtgcagc ggcctccgcg ccgggttttg gcgcctcccg   2640
cgggcgcccc cctcctcacg gcgagcgctg ccacgtcaga cgaagggcgc aggagcgttc   2700
ctgatccttc cgcccggacg ctcaggacag cggcccgctg ctcataagac tcggccttag   2760
aaccccagta tcagcagaag gacatttag gacgggactt gggtgactct agggcactgg    2820
```

```
ttttctttcc agagagcgga acaggcgagg aaaagtagtc ccttctcggc gattctgcgg    2880
agggatctcc gtgggggcgt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggcc ttcgtggccg ccgggccgct    3060
cggtgggacg gaagcgtgtg gagagaccgc caagggctgt agtctgggtc cgcgagcaag    3120
gttgccctga actgggggtt ggggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt cttttggtcgg ttttatgtac ctatcttctt aagtagctga    3660
agctccggtt ttgaactatg cgctcggggt tggcgagtgt gttttgtgaa gttttttagg    3720
cacctttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tctctcgagg ttaacgaatt caaagacaac tcagagttca ccatgggctc    3900
catcggngca gcaagcatgg aattttgttt tgatgtattc aaggagctca agtccacca     3960
tgccaatgag aacatcttct actgccccat tgccatcatg tcagctctag ccatggtata    4020
cctgggtgca aaagacagca ccaggacaca aataaataag gttgttcgct ttgataaact    4080
tccaggattc ggagacagta ttgaagctca gtgtggcaca tctgtaaacg ttcactcttc    4140
acttagagac atcctcaacc aaatcaccaa accaatgat gtttattcgt tcagccttgc     4200
cagtagactt tatgctgaag agagataccc aatcctgcca gaatacttgc agtgtgtgaa    4260
ggaactgtat agaggaggct tggaacctat caactttcaa acagctgcag atcaagccag    4320
agagctcatc aattcctggg tagaaagtca gacaaatgga attatcagaa atgtccttca    4380
gccaagctcc gtggattctc aaactgcaat ggttctggtt aatgccattg tcttcaaagg    4440
actgtgggag aaaacattta aggatgaaga cacacaagca atgcctttca gagtgactga    4500
gcaagaaagc aaacctgtgc agatgatgta ccagattggt ttatttagag tggcatcaat    4560
ggcttctgag aaaatgaaga tcctggagct tccatttgcc agtgggacaa tgagcatgtt    4620
ggtgctgttg cctgatgaag tctcaggcct tgagcagctt gagagtataa tcaactttga    4680
aaaactgact gaatggacca gttctaatgt tatggaagag aggaagatca agtgtactt     4740
acctcgcatg aagatggagg aaaaatacaa cctcacatct gtcttaatgg ctatgggcat    4800
tactgacgtg tttagctctt cagccaatct gtctggcatc tcctcagcag agagcctgaa    4860
gatatctcaa gctgtccatg cagcacatgc agaaatcaat gaagcaggca gagaggtggt    4920
agggtcagca gaggctggag tggatgctgc aagcgtctct gaagaattta gggctgacca    4980
tccattcctc ttctgtatca agcacatcgc aaccaacgcc gttctcttct ttggcagatg    5040
tgtttcccct aaaaagaag aaagctgaaa aactctgtcc cttccaacaa gacccagagc    5100
actgtagtat caggggtaaa atgaaaagta tgttctctgc tgcatccaga cttcataaaa    5160
gctggagctt aatctagact cgagcggccg ccactgtgct ggatatctgc agaattccgc    5220
```

```
ccctctccct cccccccccc taacgttact ggccgaagcc gcttggaata aggccggtgt    5280
gcgtttgtct atatgttatt ttccaccata ttgccgtctt ttggcaatgt gagggcccgg    5340
aaacctggcc ctgtcttctt gacgagcatt cctagggctc tttcccctct cgccaaagga    5400
atgcaaggtc tgttgaatgt cgtgaaggaa gcagttcctc tggaagcttc ttgaagacaa    5460
acaacgtctg tagcgaccct tgcaggcag cggaaccccc cacctggcga caggtgcctc     5520
tgcggccaaa agccacgtgt ataagataca cctgcaaagg cggcacaacc ccagtgccac    5580
gttgtgagtt ggatagttgt ggaaagagtc aaatggctct cctcaagcgt attcaacaag    5640
gggctgaagg atgcccagaa ggtacccat tgtatgggat ctgatctggg gcctcggtgc      5700
acatgcttta catgtgttta gtcgaggtta aaaaacgtct aggcccccg aaccacgggg     5760 acgtggtttt cctttgaaaa acacgatgat aatatggcca caaccatgtg gctgcagaat    5820
ttacttttcc tgggcattgt ggtctacagc ctctcagcac ccacccgctc acccatcact    5880
gtcacccggc cttggaagca gtagaggcc atcaaagaag ccctgaacct cctggatgac     5940
atgcctgtca cgttgaatga agaggtagaa gtcgtctcta acgagttctc cttcaagaag    6000
ctaacatgtg tgcagacccg cctgaagata ttcgagcagg gtctacgggg caatttcacc    6060
aaactcaagg gcgccttgaa catgacagcc agctactacc agacatactg ccccccaact    6120
ccggaaacgg actgtgaaac acaagttacc acctatgcgg atttcataga cagccttaaa    6180 accttttctga ctgatatccc ctttgaatgc aaaaaaccag gccaaaaatg agtcgaaacc    6240
tcgagggcgc gccgaattcg atatcaagct tatcgataat caacctctgg attacaaaat    6300
ttgtgaaaga ttgactggta ttcttaacta tgttgctcct tttacgctat gtggatacgc    6360
tgctttaatg cctttgtatc atgctattgc ttcccgtatg gctttcattt tctcctcctt    6420
gtataaatcc tggttgctgt ctctttatga ggagttgtgg cccgttgtca ggcaacgtgg    6480
cgtggtgtgc actgtgtttg ctgacgcaac ccccactggt tggggcattg ccaccacctg    6540
tcagctcctt tccgggactt tcgctttccc cctccctatt gccacggcgg aactcatcgc    6600
cgcctgcctt gcccgctgct ggacaggggc tcggctgttg ggcactgaca attccgtggt    6660
gttgtcgggg aaatcatcgt cctttccttg gctgctcgcc tgtgttgcca cctggattct    6720
gcgcgggacg tccttctgct acgtcccttc ggccctcaat ccagcggacc ttccttcccg    6780
cggcctgctg ccggctctgc ggcctcttcc gcgtcttcgc cttcgccctc agacgagtcg    6840
gatctcccct tgggccgcct ccccgcatcg ataccgtcga cctcgagacc tagaaaaaca    6900
tggagcaatc acaagtagca atacagcagc taccaatgct gattgtgcct ggctagaagc    6960
acaagaggag gaggaggtgg gttttccagt cacacctcag gtacctttaa gaccaatgac    7020
ttacaaggca gctgtagatc ttagccactt ttttaaagaa aagggggggac tggaagggct    7080 aattcactcc caacgaagac aagatatcct tgatctgtgg atctaccaca cacaaggcta    7140
cttccctgat tggcagaact acacaccagg gccagggatc agatatccac tgacctttgg    7200
atggtgctac aagctagtac cagttgagca agagaaggta gaagaagcca atgaaggaga    7260
gaacacccgc ttgttacacc ctgtgagcct gcatgggatg gatgacccgg agagagaagt    7320
attagagtgg aggtttgaca gccgcctagc atttcatcac atggcccgag agctgcatcc    7380
ggactgtact gggtctctct ggttagacca gatctgagcc tgggagctct ctggctaact    7440
agggaaccca ctgcttaagc ctcaataaag cttgccttga gtgcttcaag tagtgtgtgc    7500
ccgtctgttg tgtgactctg gtaactagag atccctcaga cccttttagt cagtgtggaa    7560
```

```
aatctctagc agggcccgtt taaacccgct gatcagcctc gactgtgcct tctagttgcc    7620
agccatctgt tgtttgcccc tccccgtgc cttccttgac cctggaaggt gccactccca     7680
ctgtcctttc ctaataaaat gaggaaattg catcgcattg tctgagtagg tgtcattcta    7740
ttctgggggg tggggtgggg caggacagca agggggagga ttgggaagac aatagcaggc    7800
atgctgggga tgcggtgggc tctatggctt ctgaggcgga agaaccagc tggggctcta     7860 gggggtatcc ccacgcgccc tgtagcgcg cattaagcgc ggcgggtgtg gtggttacgc     7920
gcagcgtgac cgctacactt gccagcgccc tagcgcccgc tcctttcgct ttcttccctt    7980
cctttctcgc cacgttcgcc ggctttcccc gtcaagctct aaatcggggg ctcccttag     8040 ggttccgatt tagtgcttta cggcacctcg accccaaaaa acttgattag ggtgatggtt    8100
cacgtagtgg gccatcgccc tgatagacgg ttttcgccc tttgacgttg gagtccacgt     8160
tctttaatag tggactcttg ttccaaactg gaacaacact caaccctatc tcggtctatt    8220
cttttgattt ataagggatt ttgccgattt cggcctattg gttaaaaaat gagctgattt    8280
aacaaaaatt taacgcgaat taattctgtg gaatgtgtgt cagttagggt gtggaaagtc    8340
cccaggctcc ccagcaggca gaagtatgca aagcatgcat ctcaattagt cagcaaccag    8400
gtgtggaaag tccccaggct ccccagcagg cagaagtatg caaagcatgc atctcaatta    8460
gtcagcaacc atagtcccgc ccctaactcc gcccatcccg ccctaactc gcccagttc     8520 cgcccattct ccgccccatg gctgactaat ttttttatt tatgcagagg ccgaggccgc    8580
ctctgcctct gagctattcc agaagtagtg aggaggcttt tttggaggcc taggcttttg    8640
caaaaagctc ccgggagctt gtatatccat tttcggatct gatcagcacg tgttgacaat    8700
taatcatcgg catagtatat cggcatagta taatacgaca aggtgaggaa ctaaaccatg    8760
gccaagttga ccagtgccgt tccggtgctc accgcgcgcg acgtcgccgg agcggtcgag    8820
ttctggaccg accggctcgg gttctcccgg gacttcgtgg aggacgactt cgccggtgtg    8880
gtccgggacg acgtgaccct gttcatcagc gcggtccagg accaggtggt gccggacaac    8940
accctggcct gggtgtgggt gcgcggcctg gacgagctgt acgccgagtg gtcggaggtc    9000
gtgtccacga acttccggga cgcctccggg ccggccatga ccgagatcgg cgagcagccg    9060 tggggggcggg agttcgccct gcgcgacccg gccggcaact gcgtgcactt cgtggccgag    9120
gagcaggact gacacgtgct acgagatttc gattccaccg ccgccttcta tgaaaggttg    9180
ggcttcggaa tcgttttccg gacgccggc tggatgatcc tccagcgcgg ggatctcatg     9240
ctggagttct tcgcccaccc caacttgttt attgcagctt ataatggtta caaataaagc    9300
aatagcatca caaatttcac aaataaagca tttttttcac tgcattctag ttgtggtttg    9360
tccaaactca tcaatgtatc ttatcatgtc tgtataccgt cgacctctag ctagagcttg    9420
gcgtaatcat ggtcatagct gtttcctgtg tgaaattgtt atccgctcac aattccacac    9480
aacatacgag ccggaagcat aaagtgtaaa gcctggggtg cctaatgagt gagctaactc    9540
acattaattg cgttgcgctc actgcccgct ttccagtcgg gaaacctgtc gtgccagctg    9600
cattaatgaa tcggccaacg cgcggggaga ggcggtttgc gtattgggcg ctcttccgct    9660
tcctcgctca ctgactcgct gcgctcggtc gttcggctgc ggcgagcggt atcagctcac    9720
tcaaaggcgg taatacggtt atccacagaa tcaggggata acgcaggaaa gaacatgtga    9780
gcaaaaggcc agcaaaaggc caggaaccgt aaaaaggccg cgttgctggc gtttttccat    9840
aggctccgcc ccctgacga gcatcacaaa aatcgacgct caagtcagag gtggcgaaac     9900
ccgacaggac tataaagata ccaggcgttt ccccctggaa gctccctcgt gcgctctcct    9960
```

```
gttccgaccc tgccgcttac cggatacctg tccgcctttc tcccttcggg aagcgtggcg   10020 cttttctcata gctcacgctg taggtatctc agttcggtgt aggtcgttcg ctccaagctg   10080
ggctgtgtgc acgaaccccc cgttcagccc gaccgctgcg ccttatccgg taactatcgt   10140
cttgagtcca acccgtaag acacgactta tcgccactgg cagcagccac tggtaacagg   10200
attagcagag cgaggtatgt aggcggtgct acagagttct tgaagtggtg gcctaactac   10260
ggctacacta agaacagt atttggtatc tgcgctctgc tgaagccagt taccttcgga   10320
aaaagagttg gtagctcttg atccggcaaa caaaccaccg ctggtagcgg tggttttttt   10380
gtttgcaagc agcagattac gcgcagaaaa aaaggatctc aagaagatcc tttgatcttt   10440
tctacggggt ctgacgctca gtggaacgaa aactcacgtt aagggatttt ggtcatgaga   10500
ttatcaaaaa ggatcttcac ctagatcctt ttaaattaaa aatgaagttt taaatcaatc   10560
taaagtatat atgagtaaac ttggtctgac agttaccaat gcttaatcag tgaggcacct   10620
atctcagcga tctgtctatt tcgttcatcc atagttgcct gactccccgt cgtgtagata   10680
actacgatac gggagggctt accatctggc cccagtgctg caatgatacc gcgagaccca   10740
cgctcaccgg ctccagattt atcagcaata aaccagccag ccggaagggc cgagcgcaga   10800
agtggtcctg caactttatc cgcctccatc cagtctatta attgttgccg ggaagctaga   10860
gtaagtagtt cgccagttaa tagtttgcgc aacgttgttg ccattgctac aggcatcgtg   10920
gtgtcacgct cgtcgtttgg tatggcttca ttcagctccg gttcccaacg atcaaggcga   10980
gttacatgat cccccatgtt gtgcaaaaaa gcggttagct ccttcggtcc tccgatcgtt   11040
gtcagaagta agttggccgc agtgttatca ctcatggtta tggcagcact gcataattct   11100
cttactgtca tgccatccgt aagatgcttt tctgtgactg gtgagtactc aaccaagtca   11160
ttctgagaat agtgtatgcg gcgaccgagt tgctcttgcc cggcgtcaat acgggataat   11220
accgcgccac atagcagaac tttaaaagtg ctcatcattg gaaaacgttc ttcggggcga   11280
aaactctcaa ggatcttacc gctgttgaga tccagttcga tgtaacccac tcgtgcaccc   11340
aactgatctt cagcatcttt tactttcacc agcgtttctg ggtgagcaaa aacaggaagg   11400
caaaatgccg caaaaaaggg aataagggcg acacggaaat gttgaatact catactcttc   11460 cttttttcaat attattgaag catttatcag ggttattgtc tcatgagcgg atacatattt   11520
gaatgtattt agaaaaataa acaaataggg gttccgcgca catttccccg aaaagtgcca   11580
cctgac                                                                11586
```

<210> SEQ ID NO 8
<211> LENGTH: 11893
<212> TYPE: DNA
<213> ORGANISM: Artificial Sequence
<220> FEATURE:
<223> OTHER INFORMATION: Constructed plasmid vector

<400> SEQUENCE: 8

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
```

| | |
|---|---|
| accccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg cccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |
| aaagtaagac caccgcacag caagcggccg ctgatcttca gacctggagg aggagatatg | 1560 |
| agggacaatt ggagaagtga attatataaa tataaagtag taaaaattga accattagga | 1620 |
| gtagcaccca ccaaggcaaa gagaagagtg gtgcagagag aaaaaagagc agtgggaata | 1680 |
| ggagctttgt tccttgggtt cttgggagca gcaggaagca ctatgggcgc agcgtcaatg | 1740 |
| acgctgacgg tacaggccag acaattattg tctggtatag tgcagcagca gaacaatttg | 1800 |
| ctgagggcta ttgaggcgca acagcatctg ttgcaactca cagtctgggg catcaagcag | 1860 |
| ctccaggcaa gaatcctggc tgtggaaaga tacctaaagg atcaacagct cctgggatt | 1920 |
| tggggttgct ctggaaaact catttgcacc actgctgtgc cttggaatgc tagttggagt | 1980 |
| aataaatctc tggaacagat ttggaatcac acgacctgga tggagtggga cagagaaatt | 2040 |
| aacaattaca caagcttaat acactcctta attgaagaat cgcaaaacca gcaagaaaag | 2100 |
| aatgaacaag aattattgga attagataaa tgggcaagtt tgtggaattg gtttaacata | 2160 |
| acaaattggc tgtggtatat aaaattattc ataatgatag taggaggctt ggtaggttta | 2220 |
| agaatagttt ttgctgtact ttctatagtg aatagagtta ggcagggata ttcaccatta | 2280 |
| tcgtttcaga cccacctccc aaccccgagg ggacccgaca ggcccgaagg aatagaagaa | 2340 |
| gaaggtggag agagagacag agacagatcc attcgattag tgaacggatc ggcactgcgt | 2400 |
| gcgccaattc tgcagacaaa tggcagtatt catccacaat tttaaaagaa aagggggat | 2460 |
| tgggggtac agtgcagggg aaagaatagt agacataata gcaacagaca tacaaactaa | 2520 |
| agaattacaa aaacaaatta caaaaattca aaattttcgg gtttattaca gggacagcag | 2580 |
| agatccagtt tggttaatta agggtgcagc ggcctccgcg ccgggttttg gcgcctcccg | 2640 |
| cgggcgcccc cctcctcacg cgcagcgctg ccacgtcaga cgaagggcgc aggagcgttc | 2700 |
| ctgatccttc cgcccggacg ctcaggacag cggcccgctg ctcataagac tcggccttag | 2760 |

```
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt gaacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt gggggagcg cacaaaatgg cggctgttcc cgagtcttga    3180
atggaagacg cttgtaaggc gggctgtgag gtcgttgaaa caaggtgggg ggcatggtgg    3240
gcggcaagaa cccaaggtct tgaggccttc gctaatgcgg gaaagctctt attcgggtga    3300
gatgggctgg ggcaccatct ggggaccctg acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg gcttataatg    3480
cagggtgggg ccacctgccg gtaggtgtgc ggtaggcttt tctccgtcgc aggacgcagg    3540
gttcgggcct agggtaggct ctcctgaatc gacaggcgcc ggacctctgg tgaggggagg    3600
gataagtgag gcgtcagttt cttggtcgg ttttatgtac ctatcttctt aagtagctga    3660
agctccggtt ttgaactatg cgctcggggt tggcgagtgt gttttgtgaa gttttttagg    3720 cacctttga aatgtaatca tttgggtcaa tatgtaattt tcagtgttag actagtaaag    3780
cttctgcagg tcgactctag aaaattgtcc gctaaattct ggccgttttt ggcttttttg    3840
ttagacagga tctctcgagg ttaacgaatt catgcccatg gggtctctgc aaccgctggc    3900
caccttgtac ctgctgggga tgctggtcgc ttccgtgcta gcctggggca acctgtgggt    3960
gaccgtgtac tacggcgtgc ccgtgtggaa ggaggccaag accaccctgt tctgcgccag    4020
cgacgccaag agctacgaga aggaggtgca caacgtgtgg gccacccacg cctgcgtgcc    4080
caccgacccc aaccccagg agatcgtgct gggcaacgtg accgagaact tcaacatgtg    4140
gaagaacgac atggtggacc agatgcacga ggacatcatc agcctgtggg accagagcct    4200
gaagccctgc gtgaagctga ccccctgtg cgtgaccctg aactgcaccg aggtgaacgt    4260
gacccgcaac gtgaacaaca gcgtggtgaa caacaccacc aacgtgaaca acagcatgaa    4320
cggcgacatg aagaactgca gcttcaacat caccaccgag ctgaaggaca agaagaagaa    4380
cgtgtacgcc ctgttctaca agctggacat cgtgagcctg aacgagaccg acgacagcga    4440
gaccggcaac agcagcaagt actaccgcct gatcaactgc aacaccagcg ccctgaccca    4500
ggcctgcccc aaggtgagct tcgaccccat ccccatccac tactgcgccc ccgccggcta    4560
cgccatcctg aagtgcaaca caagaccctt caacggcacc ggccctgcc acaacgtgag    4620 caccgtgcag tgcacccacg gcatcaagcc cgtggtgagc acccagctgc tgctgaacgg    4680
cagcctggcc gaggagggca tcatcatccg cagcgagaac ctgaccaaca cgtcaagac    4740 catcatcgtg cacctgaacc gcagcatcga gatcgtgtgc gtgcgcccca acaacaacac    4800
ccgccagagc atccgcatcg gcccccggcca gaccttctac gccaccggcg acatcatcgg    4860
cgacatccgc caggcccact gcaacatcag ccgcaccaac tggaccaaga ccctgcgcga    4920
ggtgcgcaac aagctgcgcg agcacttccc caacaagaac atcaccttca gcccagcag    4980 cggcggcgac ctggagatca ccaccccacag cttcaactgc cgcggcgagt tcttctactg    5040
caacaccagc ggcctgttca gcatcaacta caccgagaac aacaccgacg gcacccccat    5100
```

```
cacccctgccc tgccgcatcc gccagatcat caacatgtgg caggaggtgg gccgcgccat    5160
gtacgccccc cccatcgagg gcaacatcgc ctgcaagagc gacatcaccg gcctgctgct    5220
ggtgcgcgac ggcggcagca ccaacgacag caccaacaac aacaccgaga tcttccgccc    5280
cgccggcggc gacatgcgcg caactggcg cagcgagctg tacaagtaca aggtggtgga    5340
gatcaagccc ctgggcatcg cccccaccgt gtctattgcc tcttttttct ttatcatagg    5400
gttaatcatt ggactattct tggttctccg agttggtatc catctttgca ttaaattaaa    5460
gcacaccaag aaaagacaga tttatacaga catagagatg aaccgacttg gaaagtaaga    5520
attccgcccc tctccctccc cccccctaa cgttactggc cgaagccgct tggaataagg    5580
ccggtgtgcg tttgtctata tgttattttc caccatattg ccgtcttttg gcaatgtgag    5640
ggcccggaaa cctggccctg tcttcttgac gagcattcct agggggtcttt ccctctcgc    5700 caaaggaatg caaggtctgt tgaatgtcgt gaaggaagca gttcctctgg aagcttcttg    5760
aagacaaaca acgtctgtag cgacccttttg caggcagcgg aaccccccac ctggcgacag    5820
gtgcctctgc ggccaaaagc cacgtgtata agatacacct gcaaaggcgg cacaaccccca    5880 gtgccacgtt gtgagttgga tagttgtgga aagagtcaaa tggctctcct caagcgtatt    5940
caacaagggg ctgaaggatg cccagaaggt accccattgt atgggatctg atctggggcc    6000
tcggtgcaca tgctttacat gtgtttagtc gaggttaaaa aacgtctagg ccccccgaac    6060
cacggggacg tggttttcct ttgaaaaaca cgatgataat atggccacaa ccatgtggct    6120
gcagaattta cttttcctgg gcattgtggt ctacagcctc tcagcaccca cccgctcacc    6180
catcactgtc acccggcctt ggaagcatgt agaggccatc aaagaagccc tgaacctcct    6240
ggatgacatg cctgtcacgt tgaatgaaga ggtagaagtc gtctctaacg agttctcctt    6300
caagaagcta acatgtgtgc agacccgcct gaagatattc gagcagggtc tacggggcaa    6360
tttcaccaaa ctcaagggcg ccttgaacat gacagccagc tactaccaga catactgccc    6420
cccaactccg gaaacggact gtgaaacaca agttaccacc tatgcggatt tcatagacag    6480
ccttaaaacc tttctgactg atatcccctt tgaatgcaaa aaaccaggcc aaaaatgagt    6540
cgaaacctcg agggcgcgcc gaattcgata tcaagcttat cgataatcaa cctctggatt    6600
acaaaatttg tgaaagattg actggtattc ttaactatgt tgctcctttt acgctatgtg    6660
gatacgctgc tttaatgcct ttgtatcatg ctattgcttc ccgtatggct ttcattttct    6720
cctccttgta taaatcctgg ttgctgtctc tttatgagga gttgtggccc gttgtcaggc    6780
aacgtggcgt ggtgtgcact gtgtttgctg acgcaacccc cactggttgg ggcattgcca    6840
ccacctgtca gctcctttcc gggactttcg ctttcccccct ccctattgcc acggcggaac    6900
tcatcgccgc ctgccttgcc cgctgctgga caggggctcg gctgttgggc actgacaatt    6960
ccgtggtgtt gtcggggaaa tcatcgtcct ttccttggct gctcgcctgt gttgccacct    7020
ggattctgcg cgggacgtcc ttctgctacg tcccttcggc cctcaatcca gcggaccttc    7080
cttcccgcgg cctgctgccg gctctgcggc ctcttccgcg tcttcgcctt cgccctcaga    7140
cgagtcggat ctccctttgg gccgcctccc cgcatcgata ccgtcgacct cgagacctag    7200
aaaaacatgg agcaatcaca agtagcaata cagcagctac caatgctgat tgtgcctggc    7260
tagaagcaca agaggaggag gaggtgggtt ttccagtcac acctcaggta cctttaagac    7320
caatgactta caaggcagct gtagatctta gccactttttt aaaagaaaag ggggactgg    7380 aagggctaat tcactcccaa cgaagacaag atatccttga tctgtggatc taccacacac    7440
aaggctactt ccctgattgg cagaactaca caccagggcc aggggatcaga tatccactga    7500
```

-continued

```
cctttggatg gtgctacaag ctagtaccag ttgagcaaga gaaggtagaa gaagccaatg    7560
aaggagagaa cacccgcttg ttacaccctg tgagcctgca tgggatggat gacccggaga    7620
gagaagtatt agagtggagg tttgacagcc gcctagcatt tcatcacatg gcccgagagc    7680
tgcatccgga ctgtactggg tctctctggt tagaccagat ctgagcctgg gagctctctg    7740
gctaactagg gaacccactg cttaagcctc aataaagctt gccttgagtg cttcaagtag    7800
tgtgtgcccg tctgttgtgt gactctggta actagagatc cctcagaccc ttttagtcag    7860
tgtggaaaat ctctagcagg gcccgtttaa acccgctgat cagcctcgac tgtgccttct    7920
agttgccagc catctgttgt ttgccccctcc cccgtgcctt ccttgaccct ggaaggtgcc    7980
actcccactg tcctttccta ataaaatgag gaaattgcat cgcattgtct gagtaggtgt    8040
cattctattc tggggggtgg ggtggggcag gacagcaagg gggaggattg gaagacaat     8100 agcaggcatg ctggggatgc ggtgggctct atggcttctg aggcggaaag aaccagctgg    8160
ggctctaggg ggtatcccca cgcgcccgt agcggcgcat taagcgcggc gggtgtggtg     8220
gttacgcgca gcgtgaccgc tacacttgcc agcgccctag cgcccgctcc tttcgctttc    8280
ttcccttcct ttctcgccac gttcgccggc tttccccgtc aagctctaaa tcggggctc     8340 cctttagggt tccgatttag tgctttacgg cacctcgacc ccaaaaaact tgattagggt    8400
gatggttcac gtagtgggcc atcgccctga tagacggttt ttcgcccttt gacgttggag    8460
tccacgttct ttaatagtgg actcttgttc caaactggaa caacactcaa ccctatctcg    8520
gtctattctt ttgatttata agggattttg ccgatttcgg cctattggtt aaaaaatgag    8580
ctgatttaac aaaaatttaa cgcgaattaa ttctgtggaa tgtgtgtcag ttagggtgtg    8640
gaaagtcccc aggctcccca gcaggcagaa gtatgcaaag catgcatctc aattagtcag    8700
caaccaggtg tggaaagtcc ccaggctccc cagcaggcag aagtatgcaa agcatgcatc    8760
tcaattagtc agcaaccata gtcccgcccc taactccgcc catccgccc ctaactccgc      8820 ccagttccgc ccattctccg ccccatggct gactaatttt ttttatttat gcagaggccg    8880
aggccgcctc tgcctctgag ctattccaga agtagtgagg aggcttttt ggaggcctag     8940 gcttttgcaa aaagctcccg ggagcttgta tatccatttt cggatctgat cagcacgtgt    9000
tgacaattaa tcatcggcat agtatatcgg catagtataa tacgacaagg tgaggaacta    9060
aaccatggcc aagttgacca gtgccgttcc ggtgctcacc gcgcgcgacg tcgccggagc    9120
ggtcgagttc tggaccgacc ggctcgggtt ctcccgggac ttcgtggagg acgacttcgc    9180
cggtgtggtc cgggacgacg tgaccctgtt catcagcgcg gtccaggacc aggtggtgcc    9240
ggacaacacc ctggcctggg tgtgggtgcg cggcctggac gagctgtacg ccgagtggtc    9300
ggaggtcgtg tccacgaact tccgggacgc ctccgggccg gccatgaccg agatcggcga    9360
gcagccgtgg gggcgggagt tcgccctgcg cgacccggcc ggcaactgcg tgcacttcgt    9420
ggccgaggag caggactgac acgtgctacg agatttcgat tccaccgccg ccttctatga    9480
aaggttgggc ttcggaatcg ttttccggga cgccggctgg atgatcctcc agcgcgggga    9540
tctcatgctg gagttcttcg cccacccca cttgtttatt gcagcttata atggttacaa    9600
ataaagcaat agcatcacaa atttcacaaa taaagcattt ttttcactgc attctagttg    9660
tggtttgtcc aaactcatca atgtatctta tcatgtctgt ataccgtcga cctctagcta    9720
gagcttggcg taatcatggt catagctgtt tcctgtgtga attgttatc cgctcacaat     9780 tccacacaac atacgagccg gaagcataaa gtgtaaagcc tggggtgcct aatgagtgag    9840
```

```
ctaactcaca ttaattgcgt tgcgctcact gcccgctttc cagtcgggaa acctgtcgtg    9900
ccagctgcat taatgaatcg gccaacgcgc ggggagaggc ggtttgcgta ttgggcgctc    9960
ttccgcttcc tcgctcactg actcgctgcg ctcggtcgtt cggctgcggc gagcggtatc   10020
agctcactca aaggcggtaa tacggttatc cacagaatca ggggataacg caggaaagaa   10080
catgtgagca aaaggccagc aaaaggccag gaaccgtaaa aaggccgcgt tgctggcgtt   10140
tttccatagg ctccgccccc ctgacgagca tcacaaaaat cgacgctcaa gtcagaggtg   10200
gcgaaacccg acaggactat aaagatacca ggcgtttccc cctggaagct ccctcgtgcg   10260
ctctcctgtt ccgaccctgc cgcttaccgg atacctgtcc gcctttctcc cttcgggaag   10320
cgtggcgctt tctcatagct cacgctgtag gtatctcagt tcggtgtagg tcgttcgctc   10380
caagctgggc tgtgtgcacg aaccccccgt tcagcccgac cgctgcgcct tatccggtaa   10440
ctatcgtctt gagtccaacc cggtaagaca cgacttatcg ccactggcag cagccactgg   10500
taacaggatt agcagagcga ggtatgtagg cggtgctaca gagttcttga agtggtggcc   10560
taactacggc tacactagaa gaacagtatt tggtatctgc gctctgctga agccagttac   10620
cttcggaaaa agagttggta gctcttgatc cggcaaacaa accaccgctg gtagcggtgg   10680
ttttttgtt tgcaagcagc agattacgcg cagaaaaaaa ggatctcaag aagatccttt   10740
gatcttttct acggggtctg acgctcagtg gaacgaaaac tcacgttaag ggattttggt   10800
catgagatta tcaaaaagga tcttcaccta gatccttta aattaaaaat gaagttttaa   10860
atcaatctaa agtatatatg agtaaacttg gtctgacagt taccaatgct taatcagtga   10920
ggcacctatc tcagcgatct gtctatttcg ttcatccata gttgcctgac tccccgtcgt   10980
gtagataact acgatacggg agggcttacc atctggcccc agtgctgcaa tgataccgcg   11040
agacccacgc tcaccggctc cagatttatc agcaataaac cagccagccg aagggccga   11100
gcgcagaagt ggtcctgcaa ctttatccgc ctccatccag tctattaatt gttgccggga   11160
agctagagta agtagttcgc cagttaatag tttgcgcaac gttgttgcca ttgctacagg   11220
catcgtggtg tcacgctcgt cgtttggtat ggcttcattc agctccggtt cccaacgatc   11280
aaggcgagtt acatgatccc ccatgttgtg caaaaaagcg gttagctcct tcggtcctcc   11340
gatcgttgtc agaagtaagt tggccgcagt gttatcactc atggttatgg cagcactgca   11400
taattctctt actgtcatgc catccgtaag atgcttttct gtgactggtg agtactcaac   11460
caagtcattc tgagaatagt gtatgcggcg accgagttgc tcttgcccgg cgtcaatacg   11520
ggataatacc gcgccacata gcagaacttt aaaagtgctc atcattggaa aacgttcttc   11580
ggggcgaaaa ctctcaagga tcttaccgct gttgagatcc agttcgatgt aacccactcg   11640
tgcacccaac tgatcttcag catcttttac tttcaccagc gtttctgggt gagcaaaaac   11700
aggaaggcaa aatgccgcaa aaaagggaat aagggcgaca cggaaatgtt gaatactcat   11760
actcttcctt tttcaatatt attgaagcat ttatcagggt tattgtctca tgagcggata   11820
catatttgaa tgtatttaga aaaataaaca ataggggtt ccgcgcacat tccccgaaa    11880
agtgccacct gac                                                     11893

<210> SEQ ID NO 9
<211> LENGTH: 9569
<212> TYPE: DNA
<213> ORGANISM: Artificial Sequence
<220> FEATURE:
<223> OTHER INFORMATION: Constructed plasmid vector
<220> FEATURE:
<221> NAME/KEY: misc_feature
```

<222> LOCATION: (4189)..(4189)
<223> OTHER INFORMATION: n=a, t, c or g

<400> SEQUENCE: 9

| | | | | | |
|---|---|---|---|---|---|
| gtcgacggat | cgggagatct | cccgatcccc | tatggtgcac | tctcagtaca | atctgctctg | 60 |
| atgccgcata | gttaagccag | tatctgctcc | ctgcttgtgt | gttggaggtc | gctgagtagt | 120 |
| gcgcgagcaa | aatttaagct | acaacaaggc | aaggcttgac | cgacaattgc | atgaagaatc | 180 |
| tgcttagggt | taggcgtttt | gcgctgcttc | gcgatgtacg | ggccagatat | acgcgttgac | 240 |
| attgattatt | gactagttat | taatagtaat | caattacggg | gtcattagtt | catagcccat | 300 |
| atatggagtt | ccgcgttaca | taacttacgg | taaatggccc | gcctggctga | ccgcccaacg | 360 |
| acccccgccc | attgacgtca | ataatgacgt | atgttcccat | agtaacgcca | atagggactt | 420 |
| tccattgacg | tcaatgggtg | gagtatttac | ggtaaactgc | ccacttggca | gtacatcaag | 480 |
| tgtatcatat | gccaagtacg | ccccctattg | acgtcaatga | cggtaaatgg | cccgcctggc | 540 |
| attatgccca | gtacatgacc | ttatgggact | ttcctacttg | gcagtacatc | tacgtattag | 600 |
| tcatcgctat | taccatggtg | atgcggtttt | ggcagtacat | caatgggcgt | ggatagcggt | 660 |
| ttgactcacg | gggatttcca | agtctccacc | ccattgacgt | caatgggagt | ttgttttggc | 720 |
| accaaaatca | acgggacttt | ccaaaatgtc | gtaacaactc | cgccccattg | acgcaaatgg | 780 |
| gcggtaggcg | tgtacggtgg | gaggtctata | taagcagcgc | gttttgcctg | tactgggtct | 840 |
| ctctggttag | accagatctg | agcctgggag | ctctctggct | aactagggaa | cccactgctt | 900 |
| aagcctcaat | aaagcttgcc | ttgagtgctt | caagtagtgt | gtgcccgtct | gttgtgtgac | 960 |
| tctggtaact | agagatccct | cagacccttt | tagtcagtgt | ggaaaatctc | tagcagtggc | 1020 |
| gcccgaacag | ggacttgaaa | gcgaaaggga | aaccagagga | gctctctcga | cgcaggactc | 1080 |
| ggcttgctga | agcgcgcacg | gcaagaggcg | aggggcggcg | actggtgagt | acgccaaaaa | 1140 |
| ttttgactag | cggaggctag | aaggagagag | atgggtgcga | gagcgtcagt | attaagcggg | 1200 |
| ggagaattag | atcgcgatgg | gaaaaaattc | ggttaaggcc | aggggggaaag | aaaaaatata | 1260 |
| aattaaaaca | tatagtatgg | gcaagcaggg | agctagaacg | attcgcagtt | aatcctggcc | 1320 |
| tgttagaaac | atcagaaggc | tgtagacaaa | tactgggaca | gctacaacca | tcccttcaga | 1380 |
| caggatcaga | agaacttaga | tcattatata | atacagtagc | aaccctctat | tgtgtgcatc | 1440 |
| aaaggataga | gataaaagac | accaaggaag | ctttagacaa | gatagaggaa | gagcaaaaca | 1500 |
| aaagtaagac | caccgcacag | caagcggccg | ccgcgctga | tcttcagacc | tggaggagga | 1560 |
| gatatgaggg | acaattggag | aagtgaatta | tataaatata | aagtagtaaa | aattgaacca | 1620 |
| ttaggagtag | cacccaccaa | ggcaaagaga | agagtggtgc | agagagaaaa | aagagcagtg | 1680 |
| ggaataggag | ctttgttcct | tgggttcttg | ggagcagcag | gaagcactat | gggcgcagcg | 1740 |
| tcaatgacgc | tgacggtaca | ggccagacaa | ttattgtctg | gtatagtgca | gcagcagaac | 1800 |
| aatttgctga | gggctattga | ggcgcaacag | catctgttgc | aactcacagt | ctggggcatc | 1860 |
| aagcagctcc | aggcaagaat | cctggctgtg | gaaagatacc | taaaggatca | acagctcctg | 1920 |
| gggatttggg | gttgctctgg | aaaactcatt | tgcaccactg | ctgtgccttg | gaatgctagt | 1980 |
| tggagtaata | aatctctgga | acagatttgg | aatcacacga | cctggatgga | gtgggacaga | 2040 |
| gaaattaaca | attacacaag | cttaatacac | tccttaattg | aagaatcgca | aaaccagcaa | 2100 |
| gaaaagaatg | aacaagaatt | attggaatta | gataaatggg | caagtttgtg | gaattggttt | 2160 |
| aacataacaa | attggctgtg | gtatataaaa | ttattcataa | tgatagtagg | aggcttggta | 2220 |

```
ggtttaagaa tagtttttgc tgtactttct atagtgaata gagttaggca gggatattca    2280
ccattatcgt ttcagaccca cctcccaacc ccgaggggac ccgacaggcc cgaaggaata    2340
gaagaagaag gtggagagag agacagagac agatccattc gattagtgaa cggatcggca    2400
ctgcgtgcgc caattctgca gacaaatggc agtattcatc cacaatttta aaagaaaagg    2460
ggggattggg gggtacagtg caggggaaag aatagtagac ataatagcaa cagacataca    2520
aactaaagaa ttacaaaaac aaattacaaa aattcaaaat tttcgggttt attacaggga    2580
cagcagagat ccagtttggt tagtaccggg cccggtgctt tgctctgagc cagcccacca    2640
gtttggaatg actccttttt atgacttgaa ttttcaagta taaagtctag tgctaaattt    2700
aatttgaaca actgtatagt ttttgctggt tgggggaagg aaaaaaaatg gtggcagtgt    2760 tttttttcaga attagaagtg aaatgaaaat tgttgtgtgt gaggatttct aatgacatgt    2820
ggtggttgca tactgagtga agccggtgag cattctgcca tgtcacccccc tcgtgctcag    2880 taatgtactt tacagaaatc ctaaactcaa aagattgata taaaccatgc ttcttgtgta    2940
tatccggtct cttctctggg tagtctcact cagcctgcat ttctgccagg gcccgctcta    3000
gaactagtgg atcccccggg ctgcaggaat tcgaacgctg acgtcatcaa cccgctccaa    3060
ggaatcgcgg gcccagtgtc actaggcggg aacacccagc gcgcgtgcgc cctggcagga    3120
agatggctgt gagggacagg ggagtggcgc cctgcaatat ttgcatgtcg ctatgtgttc    3180
tgggaaatca ccataaacgt gaaatgtctt tggatttggg aatcttataa gttctgtatg    3240
agaccacaga tccccctacc tgagttcctt ccccttcaag agagggaag gaactcaggt     3300 agttttttaag cttatcgata ccgtcgacct cgaggtcgac ggtatcgata agctcgcttc    3360
acgagattcc agcaggtcga gggacctaat aacttcgtat agcatacatt atacgaagtt    3420
atattaaggg ttccaagctt aagcggccgc gtggataacc gtattaccgc catgcattag    3480
ttattaatag taatcaatta cggggtcatt agttcatagc ccatatatgg agttccgcgt    3540
tacataactt acggtaaatg gcccgcctgg ctgaccgccc aacgaccccc gcccattgac    3600
gtcaataatg acgtatgttc ccatagtaac gccaatagg acttttccat tgacgtcaatg     3660 ggtggagtat ttacggtaaa ctgcccactt ggcagtacat caagtgtatc atatgccaag    3720
tacgccccct attgacgtca atgacggtaa atggcccgcc tggcattatg cccagtacat    3780
gaccttatgg gactttccta cttggcagta catctacgta ttagtcatcg ctattaccat    3840
ggtgatgcgg ttttggcagt acatcaatgg gcgtggatag cggtttgact cacggggatt    3900
tccaagtctc caccccattg acgtcaatgg gagtttgttt tggcaccaaa atcaacggga    3960
ctttccaaaa tgtcgtaaca actccgcccc attgacgcaa atgggcggta ggcgtgtacg    4020
gtgggaggtc tatataagca gagctggttt agtgaaccgt cagatccgct agcgctaccg    4080
gatcacaagt ttgtacaaaa aagcaggctc tttaaaggaa ccaattcagt cgactggatc    4140
cggtaccgaa ttcaaagaca actcagagtt caccatgggc tccatcggng cagcaagcat    4200
ggaattttgt tttgatgtat tcaaggagct caaagtccac catgccaatg agaacatctt    4260
ctactgcccc attgccatca tgtcagctct agccatggta tacctgggtg caaaagacag    4320
caccaggaca caaataaata aggttgttcg ctttgataaa cttccaggat tcggagcag    4380 tattgaagct cagtgtggca catctgtaaa cgttcactct tcacttagag acatcctcaa    4440
ccaaatcacc aaaccaaatg atgtttattc gttcagcctt gccagtagac tttatgctga    4500
agagagatac ccaatcctgc cagaatactt gcagtgtgtg aaggaactgt atagaggagg    4560
cttggaacct atcaacttc aaacagctgc agatcaagcc agagagctca tcaattcctg    4620
```

```
ggtagaaagt cagacaaatg gaattatcag aaatgtcctt cagccaagct ccgtggattc    4680
tcaaactgca atggttctgg ttaatgccat tgtcttcaaa ggactgtggg agaaaacatt    4740
taaggatgaa gacacacaag caatgccttt cagagtgact gagcaagaaa gcaaacctgt    4800
gcagatgatg taccagattg gtttatttag agtggcatca atggcttctg agaaaatgaa    4860
gatcctggag cttccatttg ccagtgggac aatgagcatg ttggtgctgt tgcctgatga    4920
agtctcaggc cttgagcagc ttgagagtat aatcaacttt gaaaaactga ctgaatggac    4980
cagttctaat gttatggaag agaggaagat caaagtgtac ttacctcgca tgaagatgga    5040
ggaaaaatac aacctcacat ctgtcttaat ggctatgggc attactgacg tgtttagctc    5100
ttcagccaat ctgtctggca tctcctcagc agagagcctg aagatatctc aagctgtcca    5160
tgcagcacat gcagaaatca tgaagcagg cagagaggtg gtagggtcag cagaggctgg    5220
agtggatgct gcaagcgtct ctgaagaatt tagggctgac catccattcc tcttctgtat    5280
caagcacatc gcaaccaacg ccgttctctt ctttggcaga tgtgtttccc cttaaaaaga    5340
agaaagctga aaaactctgt cccttccaac aagacccaga gcactgtagt atcaggggta    5400
aaatgaaaag tatgttctct gctgcatcca gacttcataa agctggagc ttaatctaga    5460 ctcgagcggc cgccactgtg ctggatatct gcagaattcg cggccgcact cgagatatct    5520
agacccagct tcttgtaca aagtggtgat aattcgtcga gggacctaat aacttcgtat    5580
agcatacatt atacgaagtt atacatgttt aagggttccg gttccactag gtacaattcg    5640
atatcaagct tatcgataat caacctctgg attacaaaat ttgtgaaaga ttgactggta    5700
ttcttaacta tgttgctcct tttacgctat gtggatacgc tgctttaatg cctttgtatc    5760
atgctattgc ttcccgtatg gctttcattt tctcctcctt gtataaatcc tggttgctgt    5820
ctctttatga ggagttgtgg cccgttgtca ggcaacgtgg cgtggtgtgc actgtgtttg    5880
ctgacgcaac ccccactggt tggggcattg ccaccacctg tcagctcctt ccgggactt    5940 tcgctttccc cctccctatt gccacggcgg aactcatcgc cgcctgcctt gcccgctgct    6000
ggacaggggc tcggctgttg ggcactgaca attccgtggt gttgtcgggg aaatcatcgt    6060
cctttccttg gctgctcgcc tgtgttgcca cctggattct gcgcgggacg tccttctgct    6120
acgtcccttc ggccctcaat ccagcggacc ttccttcccg cggcctgctg ccggctctgc    6180
ggcctcttcc gcgtcttcgc cttcgccctc agacgagtcg atctcccctt gggccgcct    6240 ccccgcatcg ataccgtcga cctcgatcga gacctagaaa aacatggagc aatcacaagt    6300
agcaatacag cagctaccaa tgctgattgt gcctggctag aagcacaaga ggaggaggag    6360
gtgggttttc cagtcacacc tcaggtacca agcatgggt aaagtactgt tctcatcaca    6420
tcatatcaag gttatatacc atcaatattg ccacagatgt tacttagcct tttaatattt    6480
ctctaattta gtgtatatgc aatgatagtt ctctgatttc tgagattgag tttctcatgt    6540
gtaatgatta tttagagttt ctcttttcatc tgttcaaatt tttgtctagt tttatttttt    6600
actgatttgt aagacttctt tttataatct gcatattaca attctcttta ctggggtgtt    6660
gcaaatattt tctgtcattc tatggcctga ctttcttaa tggttttta atttaaaaa      6720 taagtcttaa tattcatgca atctaattaa caatcttttc tttgtggtta ggactttgag    6780
tcataagaaa ttttcttcta cactgaagtc atgatggcat gcttctatat tattttctaa    6840
aagatttaaa gttttgcctt ctccatttag acttataatt cactggaatt ttttgtgtg    6900 tatggtatga catatgggtt ccctttatt ttttacatat aaatatattt ccctgttttt     6960
```

| | | | | |
|---|---|---|---|---|
| ctaaaaaaga | aaaagatcat | cattttccca | ttgtaaaatg | ccatatttt ttcataggtc | 7020 |
| acttacatat | atcaatgggt | ctgtttctga | gctctactct | attttatcag cctcactgtc | 7080 |
| tatccccaca | catctcatgc | tttgctctaa | atcttgatat | ttagtggaac attctttccc | 7140 |
| attttgttct | acaagaatat | ttttgttatt | gtcttttggg | cttctatata cattttagaa | 7200 |
| tgaggttggc | aagttctgta | gatcttagcc | acttttaaa | agaaaagggg ggactggaag | 7260 |
| ggctaattca | ctcccaacga | agacaagata | tccttgatct | gtggatctac cacacacaag | 7320 |
| gctacttccc | tgattggcag | aactacacac | cagggccagg | gatcagatat ccactgacct | 7380 |
| ttggatggtg | ctacaagcta | gtaccagttg | agcaagagaa | ggtagaagaa gccaatgaag | 7440 |
| gagagaacac | ccgcttgtta | caccctgtga | gcctgcatgg | gatggatgac ccggagagag | 7500 |
| aagtattaga | gtggaggttt | gacagccgcc | tagcatttca | tcacatggcc cgagagctgc | 7560 |
| atccggactg | tactgggtct | ctctggttag | accagatctg | agcctgggag ctctctggct | 7620 |
| aactagggaa | cccactgctt | aagcctcaat | aaagcttgcc | ttgagtgctt caagtagtgt | 7680 |
| gtgcccgtct | gttgtgtgac | tctggtaact | agagatccct | cagaccctt tagtcagtgt | 7740 |
| ggaaaatctc | tagcagcatg | tgagcaaaag | gccagcaaaa | ggccaggaac cgtaaaaagg | 7800 |
| ccgcgttgct | ggcgtttttc | cataggctcc | gcccccctga | cgagcatcac aaaaatcgac | 7860 |
| gctcaagtca | gaggtggcga | aacccgacag | gactataaag | ataccaggcg tttccccctg | 7920 |
| gaagctccct | cgtgcgctct | cctgttccga | ccctgccgct | taccggatac ctgtccgcct | 7980 |
| ttctcccttc | gggaagcgtg | gcgctttctc | atagctcacg | ctgtaggtat ctcagttcgg | 8040 |
| tgtaggtcgt | tcgctccaag | ctgggctgtg | tgcacgaacc | ccccgttcag cccgaccgct | 8100 |
| gcgccttatc | cggtaactat | cgtcttgagt | ccaacccggt | aagacacgac ttatcgccac | 8160 |
| tggcagcagc | cactggtaac | aggattagca | gagcgaggta | tgtaggcggt gctacagagt | 8220 |
| tcttgaagtg | gtggcctaac | tacggctaca | ctagaagaac | agtatttggt atctgcgctc | 8280 |
| tgctgaagcc | agttaccttc | ggaaaaagag | ttggtagctc | ttgatccggc aaacaaacca | 8340 |
| ccgctggtag | cggtggtttt | tttgtttgca | agcagcagat | tacgcgcaga aaaaaggat | 8400 |
| ctcaagaaga | tcctttgatc | ttttctacgg | ggtctgacgc | tcagtggaac gaaaactcac | 8460 |
| gttaagggat | tttggtcatg | agattatcaa | aaaggatctt | cacctagatc cttttaaatt | 8520 |
| aaaaatgaag | ttttaaatca | atctaaagta | tatatgagta | aacttggtct gacagttacc | 8580 |
| aatgcttaat | cagtgaggca | cctatctcag | cgatctgtct | atttcgttca tccatagttg | 8640 |
| cctgactccc | cgtcgtgtag | ataactacga | tacgggaggg | cttaccatct ggccccagtg | 8700 |
| ctgcaatgat | accgcgagac | ccacgctcac | cggctccaga | tttatcagca ataaaccagc | 8760 |
| cagccggaag | ggccgagcgc | agaagtggtc | ctgcaacttt | atccgcctcc atccagtcta | 8820 |
| ttaattgttg | ccgggaagct | agagtaagta | gttcgccagt | taatagtttg cgcaacgttg | 8880 |
| ttgccattgc | tacaggcatc | gtggtgtcac | gctcgtcgtt | tggtatggct tcattcagct | 8940 |
| ccggttccca | acgatcaagg | cgagttacat | gatccccat | gttgtgcaaa aaagcggtta | 9000 |
| gctccttcgg | tcctccgatc | gttgtcagaa | gtaagttggc | cgcagtgtta tcactcatgg | 9060 |
| ttatggcagc | actgcataat | tctcttactg | tcatgccatc | cgtaagatgc ttttctgtga | 9120 |
| ctggtgagta | ctcaaccaag | tcattctgag | aatagtgtat | gcggcgaccg agttgctctt | 9180 |
| gcccggcgtc | aatacgggat | aataccgcgc | cacatagcag | aactttaaaa gtgctcatca | 9240 |
| ttggaaaacg | ttcttcgggg | cgaaaactct | caaggatctt | accgctgttg agatccagtt | 9300 |
| cgatgtaacc | cactcgtgca | cccaactgat | cttcagcatc | ttttactttc accagcgttt | 9360 |

| | |
|---|---|
| ctgggtgagc aaaaacagga aggcaaaatg ccgcaaaaaa gggaataagg gcgacacgga | 9420 |
| aatgttgaat actcatactc ttccttttc aatattattg aagcatttat cagggttatt | 9480 |
| gtctcatgag cggatacata tttgaatgta tttagaaaaa taaacaaata ggggttccgc | 9540 |
| gcacatttcc ccgaaaagtg ccacctgac | 9569 |

<210> SEQ ID NO 10
<211> LENGTH: 9394
<212> TYPE: DNA
<213> ORGANISM: Artificial Sequence
<220> FEATURE:
<223> OTHER INFORMATION: Constructed plasmid vector
<220> FEATURE:
<221> NAME/KEY: misc_feature
<222> LOCATION: (7971)..(7971)
<223> OTHER INFORMATION: n=a ,t, c or g

<400> SEQUENCE: 10

| | |
|---|---|
| ttgtacaaag tggtgataac ctcgagggcg caattcgtcg agggacctaa taacttcgta | 60 |
| tagcatacat tatacgaagt tatacatgtt taagggttcc ggttccacta ggtacaattc | 120 |
| gatatcaagc ttatcgataa tcaacctctg gattacaaaa tttgtgaaag attgactggt | 180 |
| attcttaact atgttgctcc ttttacgcta tgtggatacg ctgctttaat gcctttgtat | 240 |
| catgctattg cttcccgtat ggctttcatt ttctcctcct tgtataaatc ctggttgctg | 300 |
| tctctttatg aggagttgtg gcccgttgtc aggcaacgtg gcgtggtgtg cactgtgttt | 360 |
| gctgacgcaa ccccccactgg ttggggcatt gccaccacct gtcagctcct ttccgggact | 420 |
| ttcgctttcc cctcctat tgccacggcg aactcatcg ccgcctgcct tgcccgctgc | 480 |
| tggacagggg ctcggctgtt gggcactgac aattccgtgg tgttgtcggg gaaatcatcg | 540 |
| tccttttcctt ggctgctcgc ctgtgttgcc acctggattc tgcgcgggac gtccttctgc | 600 |
| tacgtccctt cggccctcaa tccagcggac cttccttccc gcggcctgct gccggctctg | 660 |
| cggcctcttc cgcgtcttcg ccttcgccct cagacgagtc ggatctccct ttgggccgcc | 720 |
| tccccgcatc gataccgtcg acctcgatcg agacctagaa aaacatggag caatcacaag | 780 |
| tagcaataca gcagctacca atgctgattg tgcctggcta aagcacaag aggaggagga | 840 |
| ggtgggtttt ccagtcacac ctcaggtacc aagcatgggg taaagtactg ttctcatcac | 900 |
| atcatatcaa ggttatatac catcaatatt gccacagatg ttacttagcc ttttaatatt | 960 |
| tctctaattt agtgtatatg caatgatagt tctctgattt ctgagattga gtttctcatg | 1020 |
| tgtaatgatt atttagagtt tctctttcat ctgttcaaat ttttgtctag ttttattttt | 1080 |
| tactgatttg taagacttct ttttataatc tgcatattac aattctcttt actggggtgt | 1140 |
| tgcaaatatt ttctgtcatt ctatggcctg acttttctta atggttttt aattttaaaa | 1200 |
| ataagtctta atattcatgc aatctaatta caatcttttt ctttgtggtt aggactttga | 1260 |
| gtcataagaa attttctctc acactgaagt catgatggca tgcttctata ttatttttcta | 1320 |
| aaagatttaa agttttgcct tctccattta gactataat tcactggaat ttttttgtgt | 1380 |
| gtatggtatg acatatgggt tccctttat ttttacata taaatatatt tccctgtttt | 1440 |
| tctaaaaaag aaaaagatca tcattttccc attgtaaaat gccatatttt tttcataggt | 1500 |
| cacttacata tatcaatggg tctgtttctg agctctactc tattttatca gcctcactgt | 1560 |
| ctatccccac acatctcatg ctttgctcta aatcttgata tttagtggaa cattctttcc | 1620 |
| cattttgttc tacaagaata tttttgttat tgtcttttgg gcttctatat acattttaga | 1680 |

```
atgaggttgg caagttctgt agatcttagc cacttttaa aagaaaaggg gggactggaa      1740
gggctaattc actcccaacg aagacaagat atccttgatc tgtggatcta ccacacacaa      1800
ggctacttcc ctgattggca gaactacaca ccagggccag ggatcagata tccactgacc      1860
tttggatggt gctacaagct agtaccagtt gagcaagaga aggtagaaga agccaatgaa      1920
ggagagaaca cccgcttgtt acaccctgtg agcctgcatg ggatggatga cccggagaga      1980
gaagtattag agtggaggtt tgacagccgc ctagcatttc atcacatggc ccagagctg       2040
catccggact gtactgggtc tctctggtta gaccagatct gagcctggga gctctctggc      2100
taactaggga acccactgct taagcctcaa taaagcttgc cttgagtgct tcaagtagtg      2160
tgtgcccgtc tgttgtgtga ctctggtaac tagagatccc tcagacccct ttagtcagtg      2220
tggaaaatct ctagcagcat gtgagcaaaa ggccagcaaa aggccaggaa ccgtaaaaag      2280
gccgcgttgc tggcgttttt ccataggctc cgcccccctg acgagcatca aaaaatcga      2340
cgctcaagtc agaggtggcg aaacccgaca ggactataaa gataccaggc gtttccccct      2400
ggaagctccc tcgtgcgctc tcctgttccg accctgccgc ttaccggata cctgtccgcc      2460
tttctccctt cgggaagcgt ggcgctttct catagctcac gctgtaggta tctcagttcg      2520
gtgtaggtcg ttcgctccaa gctgggctgt gtgcacgaac cccccgttca gcccgaccgc      2580
tgcgccttat ccggtaacta tcgtcttgag tccaacccgg taagacacga cttatcgcca      2640
ctggcagcag ccactggtaa caggattagc agagcgaggt atgtaggcgg tgctacagag      2700
ttcttgaagt ggtggcctaa ctacggctac actagaagaa cagtatttgg tatctgcgct      2760
ctgctgaagc cagttacctt cggaaaaaga gttggtagct cttgatccgg caaacaaacc      2820
accgctggta gcggtggttt ttttgtttgc aagcagcaga ttacgcgcag aaaaaaagga      2880
tctcaagaag atcctttgat cttttctacg gggtctgacg ctcagtggaa cgaaaactca      2940
cgttaaggga ttttggtcat gagattatca aaaaggatct tcacctagat ccttttaaat      3000
taaaaatgaa gttttaaatc aatctaaagt atatatgagt aaacttggtc tgacagttac      3060
caatgcttaa tcagtgaggc acctatctca gcgatctgtc tatttcgttc atccatagtt      3120
gcctgactcc ccgtcgtgta gataactacg atacgggagg gcttaccatc tggccccagt      3180
gctgcaatga taccgcgaga cccacgctca ccggctccag atttatcagc aataaaccag      3240
ccagccggaa gggccgagcg cagaagtggt cctgcaactt tatccgcctc catccagtct      3300
attaattgtt gccgggaagc tagagtaagt agttcgccag ttaatagttt gcgcaacgtt      3360
gttgccattg ctacaggcat cgtggtgtca cgctcgtcgt ttggtatggc ttcattcagc      3420
tccggttccc aacgatcaag gcgagttaca tgatccccca tgttgtgcaa aaaagcggtt      3480
agctccttcg gtcctccgat cgttgtcaga agtaagttgg ccgcagtgtt atcactcatg      3540
gttatggcag cactgcataa ttctcttact gtcatgccat ccgtaagatg cttttctgtg      3600
actggtgagt actcaaccaa gtcattctga atagtgta tgcggcgacc gagttgctct       3660
tgcccggcgt caatacggga taataccgcg ccacatagca gaactttaaa agtgctcatc      3720
attggaaaac gttcttcggg gcgaaaactc tcaaggatct taccgctgtt gagatccagt      3780
tcgatgtaac ccactcgtgc acccaactga tcttcagcat cttttacttt caccagcgtt      3840
tctgggtgag caaaaacagg aaggcaaaat gccgcaaaaa agggaataag ggcgacacgg      3900
aaatgttgaa tactcatact cttccttttt caatattatt gaagcattta tcagggttat      3960
tgtctcatga gcggatacat atttgaatgt atttagaaaa ataaacaaat aggggttccg      4020
cgcacatttc cccgaaaagt gccacctgac gtcgacggat cgggagatct cccgatcccc      4080
```

```
tatggtgcac tctcagtaca atctgctctg atgccgcata gttaagccag tatctgctcc    4140
ctgcttgtgt gttggaggtc gctgagtagt gcgcgagcaa aatttaagct acaacaaggc    4200
aaggcttgac cgacaattgc atgaagaatc tgcttagggt taggcgtttt gcgctgcttc    4260
gcgatgtacg ggccagatat acgcgttgac attgattatt gactagttat taatagtaat    4320
caattacggg gtcattagtt catagcccat atatggagtt ccgcgttaca taacttacgg    4380
taaatggccc gcctggctga ccgcccaacg accccgccc attgacgtca ataatgacgt    4440
atgttcccat agtaacgcca tagggactt tccattgacg tcaatgggtg gagtatttac    4500
ggtaaactgc ccacttggca gtacatcaag tgtatcatat gccaagtacg ccccctattg    4560
acgtcaatga cggtaaatgg cccgcctggc attatgccca gtacatgacc ttatgggact    4620
ttcctacttg gcagtacatc tacgtattag tcatcgctat taccatggtg atgcggtttt    4680
ggcagtacat caatgggcgt ggatagcggt ttgactcacg gggatttcca agtctccacc    4740
ccattgacgt caatgggagt ttgttttggc accaaaatca acgggacttt ccaaaatgtc    4800
gtaacaactc cgccccattg acgcaaatgg gcggtaggcg tgtacggtgg gaggtctata    4860
taagcagcgc gttttgcctg tactgggtct ctctggttag accagatctg agcctgggag    4920
ctctctggct aactagggaa cccactgctt aagcctcaat aaagcttgcc ttgagtgctt    4980
caagtagtgt gtgcccgtct gttgtgtgac tctggtaact agagatccct cagacccttt    5040
tagtcagtgt ggaaaatctc tagcagtggc gcccgaacag ggacttgaaa gcgaaaggga    5100
aaccagagga gctctctcga cgcaggactc ggcttgctga agcgcgcacg gcaagaggcg    5160
aggggcggcg actggtgagt acgccaaaaa ttttgactag cggaggctag aaggagagag    5220
atgggtgcga gagcgtcagt attaagcggg ggagaattag atcgcgatgg gaaaaaattc    5280
ggttaaggcc agggggaaag aaaaaatata aattaaaaca tatagtatgg gcaagcaggg    5340
agctagaacg attcgcagtt aatcctggcc tgttagaaac atcagaaggc tgtagacaaa    5400
tactgggaca gctacaacca tcccttcaga caggatcaga agaacttaga tcattatata    5460
atacagtagc aaccctctat tgtgtgcatc aaaggataga gataaaagac accaaggaag    5520
ctttagacaa gatagaggaa gagcaaaaca aaagtaagac caccgcacag caagcggccg    5580
gccgcgctga tcttcagacc tggaggagga gatatgaggg acaattggag aagtgaatta    5640
tataaatata aagtagtaaa aattgaacca ttaggagtag cacccaccaa ggcaaagaga    5700
agagtggtgc agagagaaaa aagagcagtg ggaataggag ctttgttcct tgggttcttg    5760
ggagcagcag gaagcactat gggcgcagcg tcaatgacgc tgacggtaca ggccagacaa    5820
ttattgtctg gtatagtgca gcagcagaac aatttgctga gggctattga ggcgcaacag    5880
catctgttgc aactcacagt ctggggcatc aagcagctcc aggcaagaat cctggctgtg    5940
gaaagatacc taaaggatca acagctcctg gggatttggg gttgctctgg aaaactcatt    6000
tgcaccactg ctgtgccttg gaatgctagt tggagtaata atctctggaa cagatttgg    6060
aatcacacga cctggatgga gtgggacaga gaaattaaca attacacaag cttaatacac    6120
tccttaattg aagaatcgca aaaccagcaa gaaaagaatg aacaagaatt attggaatta    6180
gataaatggg caagtttgtg gaattggttt aacataacaa attggctgtg gtatataaaa    6240
ttattcataa tgatagtagg aggcttggta ggtttaagaa tagttttgc tgtactttct    6300
atagtgaata gagttaggca gggatattca ccattatcgt ttcagaccca cctcccaacc    6360
ccgaggggac ccgacaggcc cgaaggaata gaagaagaag gtggagagag agacagagac    6420
```

```
agatccattc gattagtgaa cggatcggca ctgcgtgcgc caattctgca gacaaatggc    6480
agtattcatc cacaatttta aaagaaaagg ggggattggg gggtacagtg caggggaaag    6540
aatagtagac ataatagcaa cagacataca aactaaagaa ttacaaaaac aaattacaaa    6600
aattcaaaat tttcgggttt attacaggga cagcagagat ccagtttggt tagtaccggg    6660
cccggtgctt tgctctgagc cagcccacca gtttggaatg actccttttt atgacttgaa    6720
ttttcaagta taaagtctag tgctaaattt aatttgaaca actgtatagt ttttgctggt    6780
tgggggaagg aaaaaaaatg gtggcagtgt ttttttcaga attagaagtg aaatgaaaat    6840
tgttgtgtgt gaggatttct aatgacatgt ggtggttgca tactgagtga agccggtgag    6900
cattctgcca tgtcaccccc tcgtgctcag taatgtactt tacagaaatc ctaaactcaa    6960
aagattgata taaccatgc ttcttgtgta tatccggtct cttctctggg tagtctcact    7020
cagcctgcat ttctgccagg gcccgctcta gtcgaggtcg acggtatcga taagctcgct    7080
tcacgagatt ccagcaggtc gagggaccta ataacttcgt atagcataca ttatacgaag    7140
ttatattaag ggttccaagc ttaagcggcc gcgtggataa ccgtattacc gccatgcatt    7200
agttattaat agtaatcaat tacggggtca ttagttcata gcccatatat ggagttccgc    7260
gttacataac ttacggtaaa tggcccgcct ggctgaccgc ccaacgaccc ccgcccattg    7320
acgtcaataa tgacgtatgt tcccatagta acgccaatag ggactttcca ttgacgtcaa    7380
tgggtggagt atttacggta aactgcccac ttggcagtac atcaagtgta tcatatgcca    7440
agtacgcccc ctattgacgt caatgacggt aaatggcccg cctggcatta tgcccagtac    7500
atgaccttat gggactttcc tacttggcag tacatctacg tattagtcat cgctattacc    7560
atggtgatgc ggttttggca gtacatcaat gggcgtggat agcggtttga ctcacgggga    7620
tttccaagtc tccaccccat tgacgtcaat gggagtttgt tttggcacca aaatcaacgg    7680
gactttccaa aatgtcgtaa caactccgcc ccattgacgc aaatgggcgg taggcgtgta    7740
cggtgggagg tctatataag cagagctggt ttagtgaacc gtcagatccg ctagcgctac    7800
cggctagaaa attgtccgct aaattctggc cgttttttggc ttttttgtta gacaggatcc    7860
gttatcacaa gtttgtacaa aaaagcaggc tctttaaagg aaccaattca gtcgactgga    7920
tccggtaccg aattcaaaga caactcagag ttcaccatgg gctccatcgg ngcagcaagc    7980
atggaatttt gttttgatgt attcaaggag ctcaaagtcc accatgccaa tgagaacatc    8040
ttctactgcc ccattgccat catgtcagct ctagccatgg tatacctggg tgcaaaagac    8100
agcaccagga cacaaataaa taaggttgtt cgctttgata aacttccagg attcggagac    8160
agtattgaag ctcagtgtgg cacatctgta aacgttcact cttcacttag agacatcctc    8220
aaccaaatca ccaaaccaaa tgatgtttat tcgttcagcc ttgccagtag actttatgct    8280
gaagagagat acccaatcct gccagaatac ttgcagtgtg tgaaggaact gtatagagga    8340
ggcttggaac ctatcaactt tcaaacagct gcagatcaag ccagagagct catcaattcc    8400
tgggtagaaa gtcagacaaa tggaattatc agaaatgtcc ttcagccaag ctccgtggat    8460
tctcaaactg caatggttct ggttaatgcc attgtcttca aaggactgtg ggagaaaaca    8520 tttaaggat aagacacaca agcaatgcct ttcagtgtga ctgagcaaga aagcaaacct    8580
gtgcagatga tgtaccagat tggtttattt agagtggcat caatggcttc tgagaaaatg    8640
aagatcctgg agcttccatt tgccagtggg acaatgagca tgttggtgct gttgcctgat    8700
gaagtctcag gccttgagca gcttgagagt ataatcaact ttgaaaaact gactgaatgg    8760
accagttcta atgttatgga agagaggaag atcaaagtgt acttacctcg catgaagatg    8820
```

```
gaggaaaaat acaacctcac atctgtctta atggctatgg gcattactga cgtgtttagc    8880
tcttcagcca atctgtctgg catctcctca gcagagagcc tgaagatatc tcaagctgtc    8940
catgcagcac atgcagaaat caatgaagca ggcagagagg tggtagggtc agcagaggct    9000
ggagtggatg ctgcaagcgt ctctgaagaa tttagggctg accatccatt cctcttctgt    9060
atcaagcaca tcgcaaccaa cgccgttctc ttctttggca gatgtgtttc cccttaaaaa    9120
gaagaaagct gaaaaactct gtcccttcca acaagaccca gagcactgta gtatcagggg    9180
taaaatgaaa agtatgttct ctgctgcatc cagacttcat aaaagctgga gcttaatcta    9240
gactggaggc ttgctgaagg ctgtatgctg tgagaactga attccatggg ttgttttggc    9300
cactgactga caacccatga ttcagttctc acaggacaca aggcctgtta ctagcactca    9360
catggaacaa atggcccatc tagacccagc tttc                                9394
```

```
<210> SEQ ID NO 11
<211> LENGTH: 986
<212> TYPE: PRT
<213> ORGANISM: Artificial Sequence
<220> FEATURE:
<223> OTHER INFORMATION: Mutated Sindbis virus glycoprotein

<400> SEQUENCE: 11

Met Ser Ala Ala Pro Leu Val Thr Ala Met Cys Leu Leu Gly Asn Val
1               5                   10                  15

Ser Phe Pro Cys Asp Arg Pro Pro Thr Cys Tyr Thr Arg Glu Pro Ser
                20                  25                  30

Arg Ala Leu Asp Ile Leu Glu Glu Asn Val Asn His Glu Ala Tyr Asp
            35                  40                  45

Thr Leu Leu Asn Ala Ile Leu Arg Cys Gly Ser Ser Gly Ser Val Ile
        50                  55                  60

Asp Asp Phe Thr Leu Thr Ser Pro Tyr Leu Gly Thr Cys Ser Tyr Cys
65                  70                  75                  80

His His Thr Val Pro Cys Phe Ser Pro Val Lys Ile Glu Gln Val Trp
                85                  90                  95

Asp Glu Ala Asp Asp Asn Thr Ile Arg Ile Gln Thr Ser Ala Gln Phe
            100                 105                 110

Gly Tyr Asp Gln Ser Gly Ala Ala Ser Ala Asn Lys Tyr Arg Tyr Met
        115                 120                 125

Ser Leu Lys Leu Met Tyr Pro Tyr Asp Val Pro Asp Tyr Ala Thr Val
130                 135                 140

Lys Glu Gly Thr Met Asp Asp Ile Lys Ile Ser Thr Ser Gly Pro Cys
145                 150                 155                 160

Arg Arg Leu Ser Tyr Lys Gly Tyr Phe Leu Leu Ala Lys Cys Pro Pro
                165                 170                 175

Gly Asp Ser Val Thr Val Ser Ile Val Ser Ser Asn Ser Ala Thr Ser
            180                 185                 190

Cys Thr Leu Ala Arg Lys Ile Lys Pro Lys Phe Val Gly Arg Glu Lys
        195                 200                 205

Tyr Asp Leu Pro Pro Val His Gly Lys Lys Ile Pro Cys Thr Val Tyr
    210                 215                 220

Asp Arg Leu Ala Ala Thr Thr Ala Gly Tyr Ile Thr Met His Arg Pro
225                 230                 235                 240

Arg Pro His Ala Tyr Thr Ser Tyr Leu Glu Glu Ser Ser Gly Lys Val
                245                 250                 255
```

```
Tyr Ala Lys Pro Pro Ser Gly Lys Asn Ile Thr Tyr Glu Cys Lys Cys
                260                 265                 270

Gly Asp Tyr Lys Thr Gly Thr Val Ser Thr Arg Thr Glu Ile Thr Gly
            275                 280                 285

Cys Thr Ala Ile Lys Gln Cys Val Ala Tyr Lys Ser Asp Gln Thr Lys
        290                 295                 300

Trp Val Phe Asn Ser Pro Asp Leu Ile Arg His Asp Asp His Thr Ala
305                 310                 315                 320

Gln Gly Lys Leu His Leu Pro Phe Lys Leu Ile Pro Ser Thr Cys Met
                325                 330                 335

Val Pro Val Ala His Ala Pro Asn Val Ile His Gly Phe Lys His Ile
            340                 345                 350

Ser Leu Gln Leu Asp Thr Asp His Leu Thr Leu Leu Thr Thr Arg Arg
        355                 360                 365

Leu Gly Ala Asn Pro Glu Pro Thr Thr Glu Trp Ile Val Gly Lys Thr
370                 375                 380

Val Arg Asn Phe Thr Val Asp Arg Asp Gly Leu Glu Tyr Ile Trp Gly
385                 390                 395                 400

Asn His Glu Pro Val Arg Val Tyr Ala Gln Glu Ser Ala Pro Gly Asp
                405                 410                 415

Pro His Gly Trp Pro His Glu Ile Val Gln His Tyr Tyr His Arg His
            420                 425                 430

Pro Val Tyr Thr Ile Leu Ala Val Ala Ser Ala Thr Val Ala Met Met
        435                 440                 445

Ile Gly Val Thr Val Ala Val Leu Cys Ala Cys Lys Ala Arg Arg Glu
        450                 455                 460

Cys Leu Thr Pro Tyr Ala Leu Ala Pro Asn Ala Val Ile Pro Thr Ser
465                 470                 475                 480

Leu Ala Leu Leu Cys Cys Val Arg Ser Ala Asn Ala Glu Thr Phe Thr
                485                 490                 495

Glu Thr Met Ser Tyr Leu Trp Ser Asn Ser Gln Pro Phe Phe Trp Val
            500                 505                 510

Gln Leu Cys Ile Pro Leu Ala Ala Phe Ile Val Leu Met Arg Cys Cys
        515                 520                 525

Ser Cys Cys Leu Pro Phe Leu Val Val Ala Gly Ala Tyr Leu Ala Lys
530                 535                 540

Val Asp Ala Tyr Glu His Ala Thr Thr Val Pro Asn Val Pro Gln Ile
545                 550                 555                 560

Pro Tyr Lys Ala Leu Val Glu Arg Ala Gly Tyr Ala Pro Leu Asn Leu
                565                 570                 575

Glu Ile Thr Val Met Ser Ser Glu Val Leu Pro Ser Thr Asn Gln Glu
            580                 585                 590

Tyr Ile Thr Cys Lys Phe Thr Thr Val Val Pro Ser Pro Lys Ile Lys
        595                 600                 605

Cys Cys Gly Ser Leu Glu Cys Gln Pro Ala Ala His Ala Gly Tyr Thr
610                 615                 620

Cys Lys Val Phe Gly Gly Val Tyr Pro Phe Met Trp Gly Gly Ala Gln
625                 630                 635                 640

Cys Phe Cys Asp Ser Glu Asn Ser Gln Met Ser Glu Ala Tyr Val Glu
                645                 650                 655

Leu Ser Ala Asp Cys Ala Ser Asp His Ala Gln Ala Ile Lys Val His
            660                 665                 670

Thr Ala Ala Met Lys Val Gly Leu Arg Ile Val Tyr Gly Asn Thr Thr
```

```
                675                 680                 685
Ser Phe Leu Asp Val Tyr Val Asn Gly Val Thr Pro Gly Thr Ser Lys
    690                 695                 700

Asp Leu Lys Val Ile Ala Gly Pro Ile Ser Ala Ser Phe Thr Pro Phe
705                 710                 715                 720

Asp His Lys Val Val Ile His Arg Gly Leu Val Tyr Asn Tyr Asp Phe
                725                 730                 735

Pro Glu Tyr Gly Ala Met Lys Pro Gly Ala Phe Gly Asp Ile Gln Ala
            740                 745                 750

Thr Ser Leu Thr Ser Lys Asp Leu Ile Ala Ser Thr Asp Ile Arg Leu
            755                 760                 765

Leu Lys Pro Ser Ala Lys Asn Val His Val Pro Tyr Thr Gln Ala Ser
    770                 775                 780

Ser Gly Phe Glu Met Trp Lys Asn Asn Ser Gly Arg Pro Leu Gln Glu
785                 790                 795                 800

Thr Ala Pro Phe Gly Cys Lys Ile Ala Val Asn Pro Leu Arg Ala Val
                805                 810                 815

Asp Cys Ser Tyr Gly Asn Ile Pro Ile Ser Ile Asp Ile Pro Asn Ala
                820                 825                 830

Ala Phe Ile Arg Thr Ser Asp Ala Pro Leu Val Ser Thr Val Lys Cys
            835                 840                 845

Glu Val Ser Glu Cys Thr Tyr Ser Ala Asp Phe Gly Gly Met Ala Thr
850                 855                 860

Leu Gln Tyr Val Ser Asp Arg Glu Gly Gln Cys Pro Val His Ser His
865                 870                 875                 880

Ser Ser Thr Ala Thr Leu Gln Glu Ser Thr Val His Val Leu Glu Lys
                885                 890                 895

Gly Ala Val Thr Val His Phe Ser Thr Ala Ser Pro Gln Ala Asn Phe
            900                 905                 910

Ile Val Ser Leu Cys Gly Lys Lys Thr Thr Cys Asn Ala Glu Cys Lys
            915                 920                 925

Pro Pro Ala Asp His Ile Val Ser Thr Pro His Lys Asn Asp Gln Glu
    930                 935                 940

Phe Gln Ala Ala Ile Ser Lys Thr Ser Trp Ser Trp Leu Phe Ala Leu
945                 950                 955                 960

Phe Gly Gly Ala Ser Ser Leu Leu Ile Ile Gly Leu Met Ile Phe Ala
                965                 970                 975

Cys Ser Met Met Leu Thr Ser Thr Arg Arg
                980                 985
```